(12) United States Patent
Wang et al.

(10) Patent No.: US 11,548,899 B2
(45) Date of Patent: Jan. 10, 2023

(54) FUSED 1,4-OXAZEPINES AND RELATED ANALOGS AS BET BROMODOMAIN INHIBITORS

(71) Applicant: THE REGENTS OF THE UNIVERSITY OF MICHIGAN, Ann Arbor, MI (US)

(72) Inventors: Shaomeng Wang, Superior Township, MI (US); Bing Zhou, Ann Arbor, MI (US); Yang Hu, Ann Arbor, MI (US); Chao-Yie Yang, Ann Arbor, MI (US); Chong Qin, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1050 days.

(21) Appl. No.: 16/077,844

(22) PCT Filed: Feb. 15, 2017

(86) PCT No.: PCT/US2017/017848
§ 371 (c)(1),
(2) Date: Aug. 14, 2018

(87) PCT Pub. No.: WO2017/142881
PCT Pub. Date: Aug. 24, 2017

(65) Prior Publication Data
US 2021/0188870 A1    Jun. 24, 2021

Related U.S. Application Data

(60) Provisional application No. 62/393,897, filed on Sep. 13, 2016, provisional application No. 62/295,271, filed on Feb. 15, 2016.

(51) Int. Cl.
| | |
|---|---|
| *C07D 495/14* | (2006.01) |
| *C07D 498/14* | (2006.01) |
| *C07D 498/04* | (2006.01) |
| *A61K 45/06* | (2006.01) |
| *A61P 35/04* | (2006.01) |

(52) U.S. Cl.
CPC ............ *C07D 495/14* (2013.01); *A61K 45/06* (2013.01); *A61P 35/04* (2018.01); *C07D 498/04* (2013.01); *C07D 498/14* (2013.01)

(58) Field of Classification Search
CPC .. C07D 495/14; C07D 498/04; C07D 498/14; A61P 35/04; A61K 45/06
USPC ....................................................... 514/220
See application file for complete search history.

(56) References Cited

U.S. PATENT DOCUMENTS

| | | | |
|---|---|---|---|
| 8,044,042 B2 | 10/2011 | Adachi et al. | |
| 8,114,995 B2 | 2/2012 | Hansen et al. | |
| 8,476,260 B2 | 7/2013 | Miyoshi et al. | |
| 8,557,984 B2 | 10/2013 | Bouillot et al. | |
| 8,580,957 B2 | 11/2013 | Demont et al. | |
| 2010/0286127 A1 | 11/2010 | Miyoshi et al. | |
| 2012/0059002 A1 | 3/2012 | Hansen et al. | |
| 2012/0157428 A1 | 6/2012 | Albrecht et al. | |
| 2012/0202799 A1 | 8/2012 | Crowe et al. | |
| 2012/0208800 A1 | 8/2012 | Chung et al. | |
| 2012/0252781 A1 | 10/2012 | Bailey et al. | |
| 2012/0273468 A1 | 11/2012 | Arjakine et al. | |
| 2013/0079335 A1 | 3/2013 | Bailey | |
| 2013/0184264 A1 | 7/2013 | Bradner et al. | |

(Continued)

FOREIGN PATENT DOCUMENTS

| | | |
|---|---|---|
| CA | 2265645 A1 | 3/1998 |
| WO | WO-1998/011111 A1 | 3/1998 |

(Continued)

OTHER PUBLICATIONS

Cancer [online], [retrieved on Jul. 6, 2007] Retrieved from the Internet, URL: http://www.nim.nih.gov/medlineplus/cancer.html (Year: 2007).*

(Continued)

*Primary Examiner* — Kristin A Vajda
(74) *Attorney, Agent, or Firm* — Marshall, Gerstein & Borun LLP

(57) ABSTRACT

The present disclosure provides fused 1,4-oxazepines and related analogs represented by Formula (I) and the pharmaceutically acceptable salts, hydrates, and solvates thereof, wherein $R^1$, $R^{2a}$, $R^{2b}$, $R^{3a}$, $R^{3b}$, $R^4$, $R^5$, A, and Y are as defined as set forth in the specification. The present disclosure is also directed to the use of compounds of Formula (I) to treat a condition or disorder responsive to inhibition of BET bromodomains such as cancer.

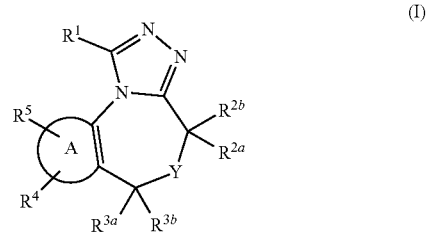

(I)

16 Claims, 2 Drawing Sheets

(56) References Cited

U.S. PATENT DOCUMENTS

| | | |
|---|---|---|
| 2013/0252331 A1 | 9/2013 | Bradner et al. |
| 2013/0281399 A1 | 10/2013 | McLure et al. |
| 2013/0281450 A1 | 10/2013 | Pratt et al. |
| 2013/0331382 A1 | 12/2013 | Hubbard et al. |
| 2014/0005169 A1 | 1/2014 | Albrecht et al. |
| 2014/0011862 A1 | 1/2014 | Bradner et al. |
| 2014/0213575 A1 | 7/2014 | Schmees et al. |
| 2014/0256706 A1 | 9/2014 | Wang et al. |
| 2018/0050021 A1 | 2/2018 | Ciulli et al. |
| 2021/0106688 A1 | 4/2021 | Phillips et al. |
| 2021/0251988 A1 | 8/2021 | Zhou et al. |
| 2021/0276996 A1 | 9/2021 | Gray et al. |
| 2021/0277018 A1 | 9/2021 | Gray et al. |
| 2021/0284654 A1 | 9/2021 | Yamazaki et al. |
| 2021/0300941 A1 | 9/2021 | Gray et al. |
| 2021/0309660 A1 | 10/2021 | Blaquiere et al. |
| 2022/0089570 A1 | 3/2022 | Crew et al. |

FOREIGN PATENT DOCUMENTS

| | | |
|---|---|---|
| WO | WO-2006/129623 A1 | 12/2006 |
| WO | WO-2008/092231 A1 | 8/2008 |
| WO | WO-2009/084693 A1 | 7/2009 |
| WO | WO-2009093269 A1 | 7/2009 |
| WO | WO-2009/158404 A1 | 12/2009 |
| WO | WO-2010/011653 A1 | 1/2010 |
| WO | WO-2010/123975 A1 | 10/2010 |
| WO | WO-2011/054843 A1 | 5/2011 |
| WO | WO-2011/054844 A1 | 5/2011 |
| WO | WO-2011/054845 A1 | 5/2011 |
| WO | WO-2011/054846 A1 | 5/2011 |
| WO | WO-2011/054848 A1 | 5/2011 |
| WO | WO-2011/054864 A1 | 5/2011 |
| WO | WO-2011/143651 A1 | 11/2011 |
| WO | WO-2011/143660 A2 | 11/2011 |
| WO | WO-2011/143669 A2 | 11/2011 |
| WO | WO-2011/161031 A1 | 12/2011 |
| WO | WO-2012/075383 | 6/2012 |
| WO | WO-2012/075456 A1 | 6/2012 |
| WO | WO-2012/116170 A1 | 8/2012 |
| WO | WO-2012/151512 A2 | 11/2012 |
| WO | WO-2012/174487 | 12/2012 |
| WO | WO-2013/024104 | 2/2013 |
| WO | WO-2013/027168 | 2/2013 |
| WO | WO-2013/030150 | 3/2013 |
| WO | WO-2013/033268 | 3/2013 |
| WO | WO-2013064231 A1 | 5/2013 |
| WO | WO-2013/097601 A1 | 7/2013 |
| WO | WO-2014/164596 A1 | 10/2014 |

OTHER PUBLICATIONS

Lala et al., Role of nitric oxide in tumor progression: Lessons from experimental tumors, Cancer and Metastasis Reviews (1998), 17, 91-106 (Year: 1998).*

Golub et al., Molecular Classification of Cancer: Class Discovery and Class Prediction by Gene Expression Monitoring, Science (1999), vol. 286, 531-537 (Year: 1999).*

Delmore, J. E., et al., "BET Bromodomain Inhibition as a Therapeutic Strategy to Target c-Myc." *Cell,* vol. 146, No. 6 (2011), pp. 904-917.

International Search Report for PCT Patent Application No. PCT/US2017/017848, dated Apr. 6, 2017.

De Lera Ruiz, M., et al., "Bicyclic and Tricyclic Heterocycle Derivatives as Histamine H3 Receptor Antagonists for the Treatment of Obesity." *Bioorganic & Medicinal Chemistry Letters,* vol. 23, No. 21 (2013), pp. 6004-6009.

Seal, J., et al., "Identification of a Novel Series of BET Family Bromodomain Inhibitors: Binding Mode and Profile of I-BET151 (GSK1210151A)." *Bioorganic & Medicinal Chemistry Letters,* vol. 22, No. 8 (2012), pp. 2968-2972.

* cited by examiner

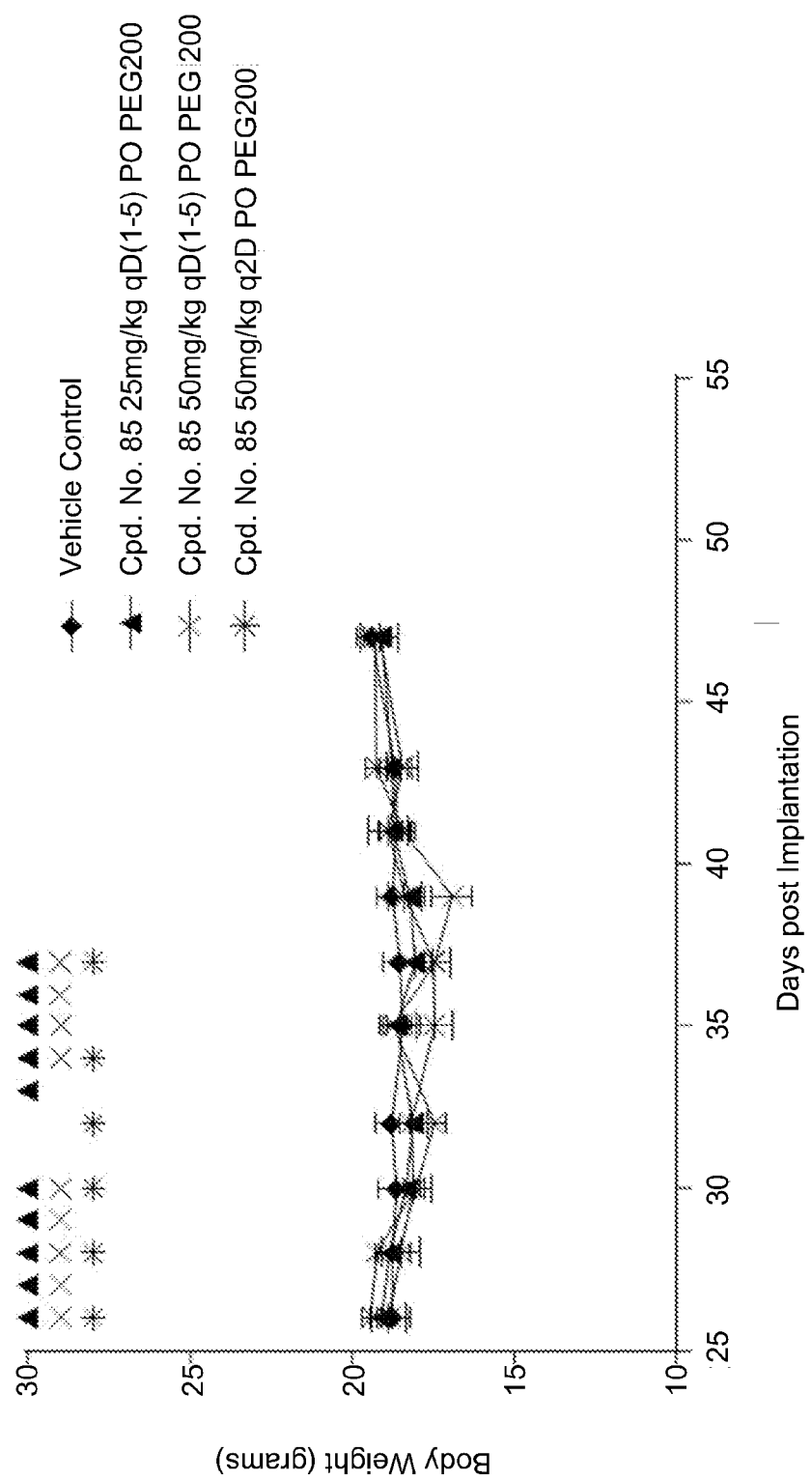

FUSED 1,4-OXAZEPINES AND RELATED ANALOGS AS BET BROMODOMAIN INHIBITORS

BACKGROUND OF THE INVENTION

Field of the Invention

The present disclosure provides BET bromodomain inhibitors and therapeutic methods of treating conditions and diseases wherein inhibition of one or more BET bromodomains provides a benefit.

Background Art

The genomes of eukaryotic organisms are highly organized within the nucleus of the cell. The long strands of duplex DNA are wrapped around an octamer of histone proteins (usually comprising two copies of histones H2A, H2B, H3, and H4) to form a nucleosome, which then is further compressed to form a highly condensed chromatin structure. A range of different condensation states are possible, and the tightness of this structure varies during the cell cycle. The chromatin structure plays a critical role in regulating gene transcription, which cannot occur efficiently from highly condensed chromatin. The chromatin structure is controlled by a series of post translational modifications to histone proteins, notably histones H3 and H4. These modifications include acetylation, methylation, phosphorylation, ubiquitinylation, and SUMOylation.

Histone acetylation usually is associated with the activation of gene transcription, as the modification loosens the interaction of the DNA and the histone octamer by changing the electrostatics. In addition to this physical change, specific proteins bind to acetylated lysine residues within histones to read the epigenetic code. Bromodomains are small (about 110 amino acid) distinct domains within proteins that bind to acetylated lysine resides commonly, but not exclusively, in the context of histones. There is a family of about 50 proteins known to contain bromodomains, which have a range of functions within the cell.

The BET family of bromodomain-containing proteins ("BET bromodomains") includes four proteins, i.e., BRD2, BRD3, BRD4, and BRD-t, which contain tandem bromodomains capable of binding to two acetylated lysine residues in close proximity, thereby increasing the specificity of the interaction. BRD2 and BRD3 associate with histones along actively transcribed genes and may be involved in facilitating transcriptional elongation, while BRD4 may be involved in the recruitment of the pTEF-β complex to inducible genes, resulting in phosphorylation of RNA polymerase and increased transcriptional output. BRD4 or BRD3 also may fuse with NUT (nuclear protein in testis) forming novel fusion oncogenes, BRD4-NUT or BRD3-NUT, in a highly malignant form of epithelial neoplasia. Data suggests that BRD-NUT fusion proteins contribute to carcinogenesis. BRD-t is uniquely expressed in the testes and ovary. All family members have been reported to have some function in controlling or executing aspects of the cell cycle, and have been shown to remain in complex with chromosomes during cell division, which suggests a role in the maintenance of epigenetic memory. In addition, some viruses make use of these proteins to tether their genomes to the host cell chromatin as part of the process of viral replication.

A discussion of BET proteins can be found in WO 2012/075456, WO 2012/075383, and WO 2011/054864. A discussion of BET bromodomain inhibitors, e.g., I-BET-151 and I-BET-762, can be found in Delmore et al., Cell 146: 904-917 (2011) and Seal et al., Bioorg. Med. Chem. Lett. 22:2968-2972 (2012). Small molecule inhibitors of BET bromodomains have therapeutic potential for the treatment of many diseases and conditions in which BET bromodomains have a role, including cancer. BET bromodomain inhibitors are disclosed in the following U.S. patents: U.S. Pat. Nos. 8,044,042, 8,476,260, 8,114,995, 8,557,984, and 8,580,957; the following U.S. patent application publications: US 20120059002, US 20120208800, US 2012202799, US 2012252781, US 20130252331, US 20140011862, US 20130184264, US 2013079335, US 20140011862, US 20140005169, US 20130331382, US 20130281450, US 20130281399, US 20120157428, US 20100286127, and US 20140256706; and the following international applications: WO 1998011111, WO 2006129623, WO 2008092231, WO 2009084693, WO 2009158404, WO 2010123975, WO 2011054843, WO 2011054844, WO 2011054845, WO 2011054846, WO 2011054848, WO 2011143651, WO 2011143660, WO 2011143669, WO 2011161031, WO 2012075383, WO 2012116170, WO 2012151512, WO 2012174487, WO 2013024104, WO 2013027168, WO 2013030150, WO 2013033268, WO 2013097601, and WO 2014164596.

BRIEF SUMMARY OF THE INVENTION

In one aspect, the present disclosure provides fused 1,4-oxazepines and related analogs represented by any one of Formulae I-XII, below, and the pharmaceutically acceptable salts, hydrates, and solvates thereof, collectively referred to herein as "Compounds of the Disclosure." Compounds of the Disclosure are inhibitors of BET bromodomains that bind to BET bromodomains and function as antagonists of BET bromodomains and/or synthetic intermediates that can be used to prepare inhibitors of BET bromodomains. Compounds of the Disclosure that inhibit BET bromodomains are useful in treating diseases or conditions wherein inhibition of BET bromodomains, e.g., BRD2, BRD3, BRD4, BRD-t, or an isoform or mutant thereof, provides a benefit.

In another aspect, the present disclosure provides methods of treating a condition or disease by administering a therapeutically effective amount of a Compound of the Disclosure to an individual, e.g., a human, in need thereof. The disease or condition of interest is treatable by inhibition of BET bromodomains, for example, a cancer, a chronic autoimmune disorder, an inflammatory condition, a proliferative disorder, sepsis, or a viral infection. Also provided are methods of preventing the proliferation of unwanted proliferating cells, such as cancer, in a subject comprising administering a therapeutically effective amount of a Compound of the Disclosure to a subject at risk of developing a condition characterized by unwanted proliferating cells. In some embodiments, the Compounds of the Disclosure reduce the proliferation of unwanted cells by inducing apoptosis in those cells.

In another aspect, the present disclosure provides a method of inhibiting BET bromodomains in an individual, comprising administering to the individual an effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating diseases or conditions wherein inhibition of BET bromodomains provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in treatment of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure, e.g., compounds having any one of Formulae I-XII.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF DRAWINGS

FIG. 2 is a line graph showing animal weight following administration of Cpd. No. 85 in mice.

DETAILED DESCRIPTION OF THE INVENTION

Figure 1:
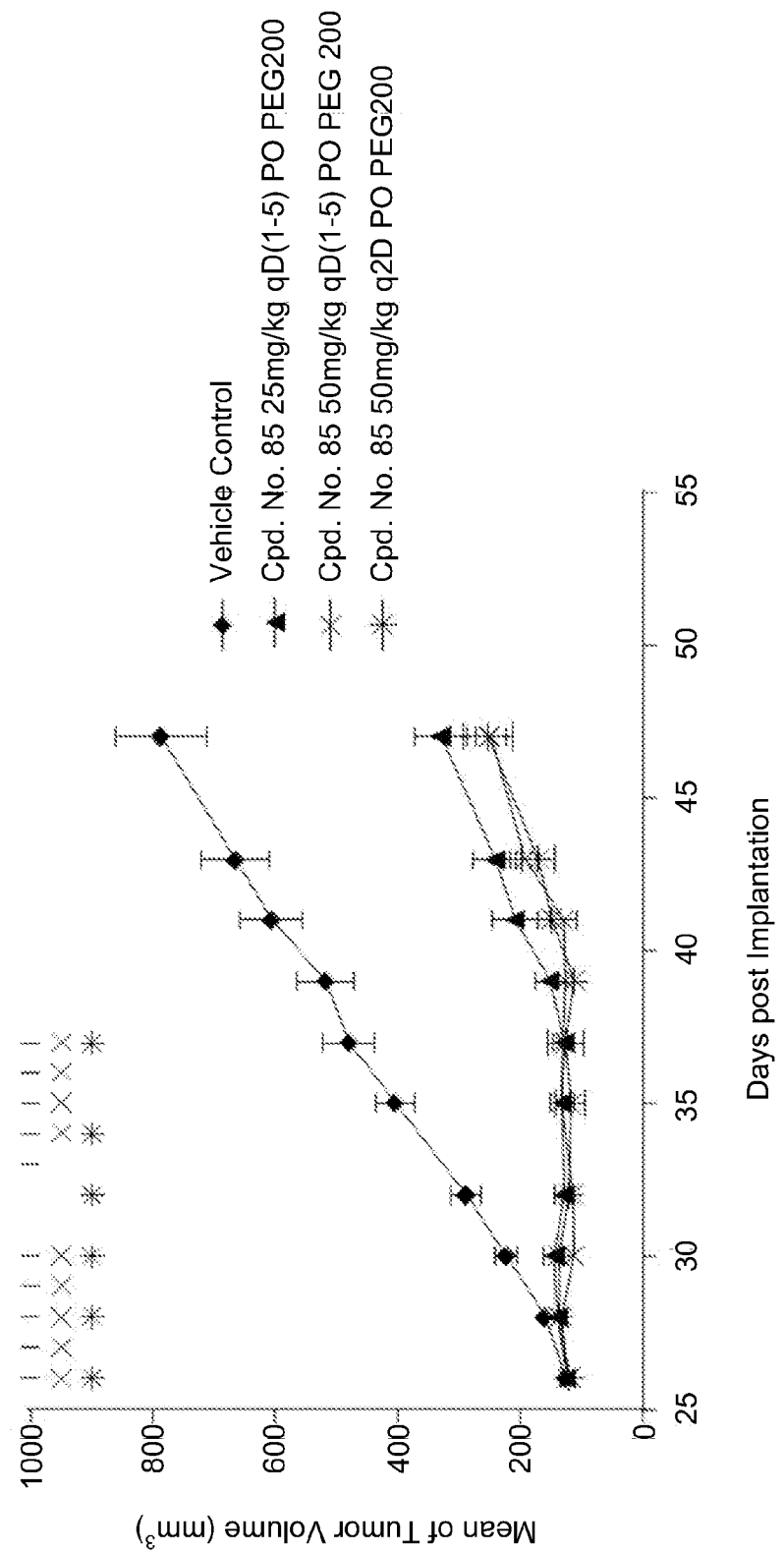
FIG. 1 is a line graph showing in vivo antitumor activity of Cpd. No. 85 in the MDA-MB-231 xenograft tumor growth model in mice.

Compounds of the Disclosure are inhibitors of BET bromodomain proteins and/or synthetic intermediates used to prepare inhibitors of BET bromodomain proteins.

In one embodiment, Compounds of the Disclosure are compounds represented by Formula I:

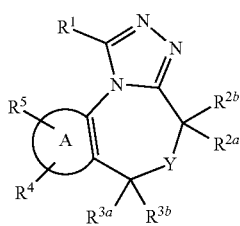

I and the pharmaceutically acceptable salts, hydrates, and solvates thereof, wherein:

$R^1$ is selected from the group consisting of hydrogen and optionally substituted $C_{1-4}$ alkyl;

$R^{2a}$ and $R^{2b}$ are each independently selected from the group consisting of hydrogen, optionally substituted $C_{1-4}$ alkyl, and (alkoxycarbonyl)alkyl, or $R^{2a}$ and $R^{2b}$ together with the carbon atom to which they are attached form a 3- to 6-membered cycloalkyl;

$R^{3a}$ and $R^{3b}$ are each independently selected from the group consisting of hydrogen and optionally substituted $C_{1-4}$ alkyl; or $R^{3a}$ and $R^{3b}$ together with the carbon atom to which they are attached form an optionally substituted 3- to 6-membered cycloalkyl;

$R^4$ and $R^5$ are each independently selected from the group consisting of hydrogen, halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, —$NR^{6a}R^{6b}$, —$OR^7$, —$SR^{8a}$, —$S(=O)R^{8b}$, —$S(=O)_2R^{8c}$, —$C(=O)R^9$, (heteroaryl)alkyl, and alkoxyalkyl;

$R^{6a}$ and $R^{6b}$ are each independently selected from the group consisting of hydrogen, optionally substituted $C_{1-6}$ alkyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, alkylcarbonyl, arylcarbonyl, alkoxycarbonyl, alkylsulfonyl, arylsulfonyl, and carboxamido; or $R^{6a}$ and $R^{6b}$ taken together with the nitrogen atom to which they are attached form an optionally substituted 4- to 8-membered heterocyclo;

$R^7$ is selected from the group consisting of hydrogen, optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl, alkylcarbonyl, and carboxamido;

$R^{8a}$ is selected from the group consisting of optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

$R^{8b}$ is selected from the group consisting of optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

$R^{8c}$ is selected from the group consisting of optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and amino;

$R^9$ selected from the group consisting of hydrogen, optionally substituted $C_{1-4}$ alkyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, alkoxy, and amino;

Y is selected from the group consisting of —O—, —S—, and —$NR^{10}$—;

$R^{10}$ is selected from the group consisting of hydrogen, optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, $(C_{3-6}$ cycloalkyl)$C_{1-4}$ alkyl, aralkyl, (alkoxycarbonyl)alkyl, —$C(=O)R^{11}$, —$SO_2R^{12}$, —$C(=O)$—$OR^{13}$, and —$C(=O)$—$NR^{14a}R^{14b}$;

$R^{11}$ is selected from the group consisting of optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and aralkyl;

$R^{12}$ is selected from the group consisting of optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and aralkyl;

$R^{13}$ is selected from the group consisting of optionally substituted $C_{1-6}$ alkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, and aralkyl;

$R^{14a}$ and $R^{14b}$ are each independently selected from the group consisting of hydrogen, optionally substituted $C_{1-6}$ alkyl, optionally substituted $C_{6-14}$ aryl, optionally substituted $C_{3-12}$ cycloalkyl, 3- to 14-membered heterocyclo, optionally substituted 5- to 14-membered heteroaryl, and aralkyl; or $R^{14a}$ and $R^{14b}$ taken together with the nitrogen atom to which they are attached form an optionally substituted 4- to 8-membered heterocyclo;

Ⓐ is a fused thienyl or fused phenyl group, wherein the fused phenyl group is additionally substituted with $R^{15}$, and $R^{15}$ is selected from the group consisting of hydrogen, halogen, optionally substituted $C_{1-4}$ alkyl, and alkoxy.

In another embodiment, Compounds of the Disclosure are compounds represented by Formula I, and the pharmaceutically acceptable salts, hydrates, and solvates thereof, wherein $R^4$ is selected from the group consisting of halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, —$NR^{6a}R^{6b}$, —$OR^7$, —$SR^{8a}$, —$S(=O)R^{8b}$, —$S(=O)_2R^{8c}$, —$C(=O)R^9$, (heteroaryl)alkyl, and alkoxyalkyl; and $R^5$ is selected from the group consisting of hydrogen, halogen, and optionally substituted $C_{1-4}$ alkyl.

In another embodiment, Compounds of the Disclosure are compounds represented by Formula I, and the pharmaceutically acceptable salts, hydrates, and solvates thereof, wherein $R^4$ is selected from the group consisting of hydrogen, halogen, and optionally substituted $C_{1-4}$ alkyl; and $R^5$ is selected from the group consisting of halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, optionally substituted 5- to 14-membered heteroaryl, —$NR^{6a}R^{6b}$, —$OR^7$, —$SR^{8a}$, —$S(=O)R^{8b}$, —$S(=O)_2R^{8c}$, —$C(=O)R^9$, (heteroaryl)alkyl, and alkoxyalkyl.

In another embodiment, Compounds of the Disclosure are compounds represented by Formula II:

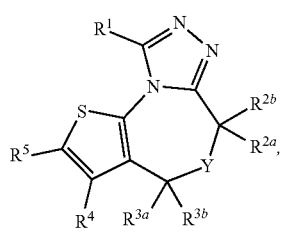

II and the pharmaceutically acceptable salts, hydrates, and solvates thereof, wherein $R^1$, $R^{2a}$, $R^{2b}$, $R^{3a}$, $R^{3b}$, $R^4$, $R^5$, and Y are as defined in connection with Formula I.

In another embodiment, Compounds of the Disclosure are compounds represented by Formula III:

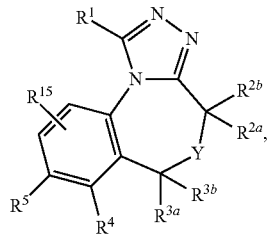

III and the pharmaceutically acceptable salts, hydrates, and solvates thereof, wherein $R^1$, $R^{2a}$, $R^{2b}$, $R^{3a}$, $R^{3b}$, $R^4$, $R^5$, $R^{15}$, and Y are as defined in connection with Formula I. In another embodiment, $R^{15}$ is hydrogen.

In another embodiment, Compounds of the Disclosure are compounds represented by any one of Formulae I-III, and the pharmaceutically acceptable salts, hydrates, and solvates thereof, wherein $R^{3a}$ and $R^{3b}$ are hydrogen.

In another embodiment, Compounds of the Disclosure are compounds represented by any one of Formulae I-III, and the pharmaceutically acceptable salts, hydrates, and solvates thereof, wherein $R^{2a}$ and $R^{2b}$ are taken with the carbon atom to which they are attached form a 3- to 6-membered cycloalkyl, and $R^{3a}$ and $R^b$ are hydrogen. In another embodiment, $R^{2a}$ and $R^{2b}$ are taken with the carbon atom to which they are attached form a cyclopropyl group.

In another embodiment, Compounds of the Disclosure are compounds represented by any one of Formulae I-III, and the pharmaceutically acceptable salts, hydrates, and solvates thereof, wherein $R^{2a}$ and $R^{2b}$ are each independently selected from the group consisting of hydrogen and $C_{1-4}$ alkyl, and $R^{3a}$ and $R^{3b}$ are hydrogen. In another embodiment, $R^{2a}$ and $R^{2b}$ are hydrogen.

In another embodiment, Compounds of the Disclosure are compounds represented by any one of Formulae I-III, and the pharmaceutically acceptable salts, hydrates, and solvates thereof, wherein $R^1$ is $C_{1-4}$ alkyl. In another embodiment, $R^1$ is methyl.

In another embodiment, Compounds of the Disclosure are compounds represented by Formula IV

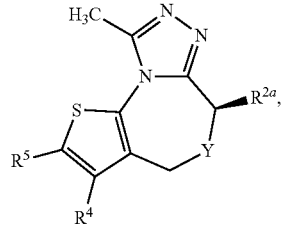

IV and the pharmaceutically acceptable salts, hydrates, and solvates thereof, wherein $R^{2a}$ is selected from the group consisting of $C_{1-4}$ alkyl and (alkoxycarbonyl)alkyl; and $R^4$, $R^5$, and Y are as defined in connection with Formula I. In another embodiment, $R^{2a}$ is $C_{1-4}$ alkyl. In another embodiment, $R^{2a}$ is methyl.

In another embodiment, Compounds of the Disclosure are compounds represented by Formula V:

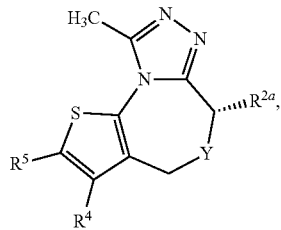

and the pharmaceutically acceptable salts, hydrates, and solvates thereof, wherein $R^{2a}$ is selected from the group consisting of $C_{1-4}$ alkyl and (alkoxycarbonyl)alkyl; and $R^4$, $R^5$, and Y are as defined in connection with Formula I. In another embodiment, $R^{2a}$ is $C_{1-4}$ alkyl. In another embodiment, $R^{2a}$ is methyl.

In another embodiment, Compounds of the Disclosure are compounds represented by Formula VI:

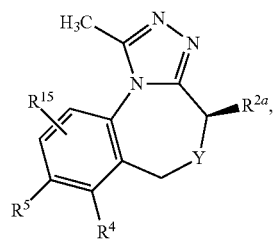

and the pharmaceutically acceptable salts, hydrates, and solvates thereof, wherein $R^{2a}$ is selected from the group consisting of $C_{1-4}$ alkyl and (alkoxycarbonyl)alkyl; and $R^4$, $R^5$, $R^1$, and Y are as defined in connection with Formula I. In another embodiment, $R^{2a}$ is $C_{1-4}$ alkyl. In another embodiment, $R^{2a}$ is methyl. In another embodiment, $R^1$ is hydrogen.

In another embodiment, Compounds of the Disclosure are compounds represented by Formula VII:

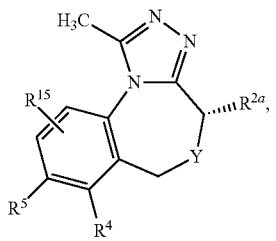

and the pharmaceutically acceptable salts, hydrates, and solvates thereof, wherein $R^{2a}$ is selected from the group consisting of $C_{1-4}$ alkyl and (alkoxycarbonyl)alkyl; and $R^4$, $R^5$, $R^1$, and Y are as defined in connection with Formula I. In another embodiment, $R^{2a}$ is $C_{1-4}$ alkyl. In another embodiment, $R^{2a}$ is methyl. In another embodiment, $R^{15}$ is hydrogen.

In another embodiment, Compounds of the Disclosure are compounds represented by any one of Formulae I-VII, and the pharmaceutically acceptable salts, hydrates, and solvates thereof, wherein $R^5$ is selected from the group consisting of hydrogen, halogen, $C_{1-4}$ alkyl, optionally substituted $C_{2-4}$ alkynyl, and substituted 5- to 14-membered heteroaryl. In another embodiment, $R^5$ is selected from the group consisting of hydrogen, halogen, and $C_{1-4}$ alkyl.

In another embodiment, Compounds of the Disclosure are compounds represented by any one of Formulae I-VII, and the pharmaceutically acceptable salts, hydrates, and solvates thereof, wherein $R^4$ is selected from the group consisting of halogen, $C_{1-4}$ alkyl, optionally $C_{2-4}$ alkenyl, optionally substituted $C_{2-4}$ alkynyl, aralkyl, optionally substituted $C_{6-14}$ aryl, optionally substituted $C_{3-12}$ cycloalkyl, 3- to 14-membered heterocyclo, optionally substituted 5- to 14-membered heteroaryl, —$NR^{6a}R^{6b}$, —$OR^7$, —$SR^{8a}$, —$S(=O)R^{8b}$, —$S(=O)_2R^{8c}$, —$C(=O)R^9$, (heteroaryl)alkyl, and alkoxyalkyl. In another embodiment, $R^4$ is —$NR^{6a}R^{6b}$. In another embodiment, $R^{6a}$ is selected from the group consisting of optionally substituted $C_{6-14}$ aryl and optionally substituted 5- to 14-membered heteroaryl, and $R^{6b}$ is hydrogen. In another embodiment, $R^4$ is —$OR^7$. In another embodiment, $R^7$ is selected from the group consisting of hydrogen and optionally substituted $C_{6-14}$ aryl. In another embodiment, $R^4$ is —$S(=O)_2R^{8c}$. In another embodiment, $R^{8c}$ is optionally substituted $C_{6-14}$ aryl. In another embodiment, $R^4$ is —$C(=O)R^9$. In another embodiment, $R^9$ is optionally substituted $C_{6-14}$ aryl. In another embodiment, $R^4$ is optionally substituted $C_{3-7}$ cycloalkyl. In another embodiment, $R^4$ is optionally substituted $C_{3-7}$ cycloalkyl selected from the group consisting of:

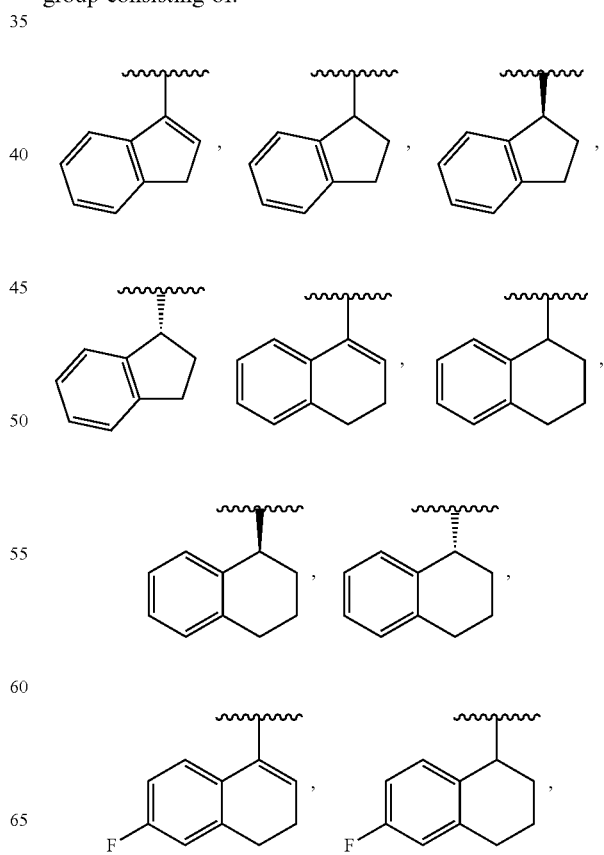

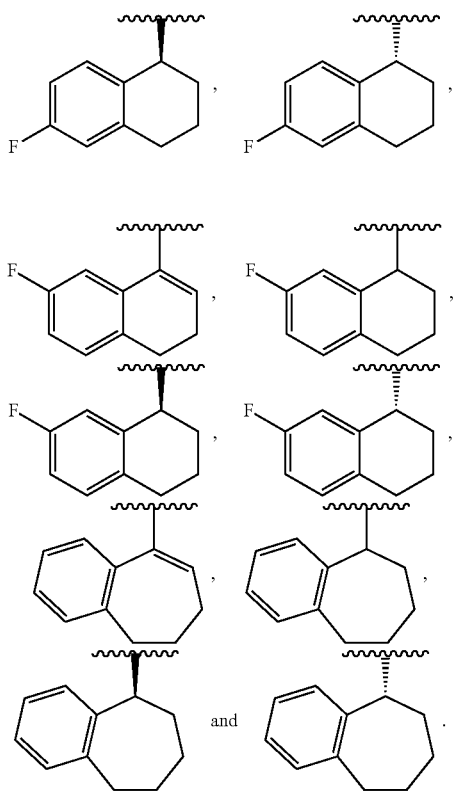

In another embodiment, $R^4$ is optionally substituted $C_{3-7}$ cycloalkyl selected from the group consisting of:

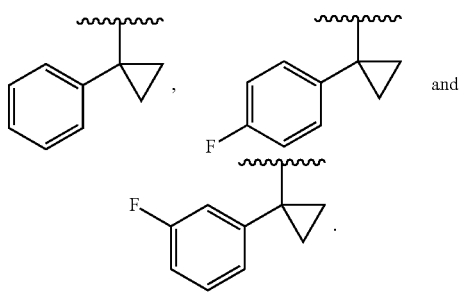

In another embodiment, R is aralkyl.

In another embodiment, Compounds of the Disclosure are compounds represented by any one of Formulae I-VII, and the pharmaceutically acceptable salts, hydrates, and solvates thereof, wherein Y is —$NR^{10}$. In another embodiment, $R^{10}$ is selected from the group consisting of hydrogen, $C_{1-6}$ alkyl, optionally substituted $C_{3-12}$ cycloalkyl, ($C_{3-6}$ cycloalkyl)$C_{1-4}$ alkyl, (alkoxycarbonyl)alkyl —C(=O)$R^{11}$, —$SO_2R^{12}$, —C(=O)—$OR^1$, and —C(=O)—$NR^{14a}R^{14b}$. In another embodiment, $R^{10}$ is hydrogen. In another embodiment, $R^{10}$ is methyl.

In another embodiment, Compounds of the Disclosure are compounds represented by any one of Formulae I-VII, and the pharmaceutically acceptable salts, hydrates, and solvates thereof, wherein Y is —O—.

In another embodiment, Compounds of the Disclosure are compounds represented by Formula VIII:

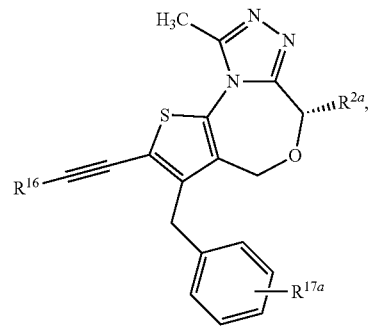

VIII and the pharmaceutically acceptable salts, hydrates, and solvates thereof, wherein:

$R^{2a}$ is selected from the group consisting of hydrogen and $C_{1-3}$ alkyl;

$R^{16}$ is selected from the group consisting of hydroxyalkyl, optionally substituted aryl, and optionally substituted heteroaryl; and $R^{17a}$ is selected from the group consisting of hydrogen and halo.

In another embodiment, Compounds of the Disclosure are compounds represented by Formula VIII, or a pharmaceutically acceptable salt or hydrate thereof, wherein:

$R^{2a}$ is selected from the group consisting of hydrogen and $C_{1-3}$ alkyl;

$R^{16}$ is selected from the group consisting of optionally substituted alkyl, optionally substituted aryl, and optionally substituted heteroaryl; and $R^{17a}$ is selected from the group consisting of hydrogen and halo.

In another embodiment, Compounds of the Disclosure are compounds represented by Formula VIII, or a pharmaceutically acceptable salt or hydrate thereof, wherein:

$R^{2a}$ is selected from the group consisting of hydrogen and $C_{1-3}$ alkyl;

$R^{16}$ is optionally substituted heteroaryl; and $R^{17a}$ is selected from the group consisting of hydrogen and halo.

In another embodiment, Compounds of the Disclosure are compounds represented by Formula IX:

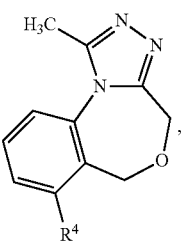

IX and the pharmaceutically acceptable salts, hydrates, and solvates thereof, wherein $R^4$ is optionally substituted cycloalkyl.

In another embodiment, Compounds of the Disclosure are compounds represented by Formula X:

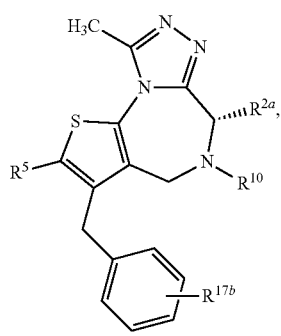

X and the pharmaceutically acceptable salts, hydrates, and solvates thereof, wherein:

$R^{2a}$ is selected from the group consisting of hydrogen and $C_{1-3}$ alkyl;

$R^5$ is selected from the group consisting of hydrogen and $C_{1-3}$ alkyl;

$R^{10}$ is selected from the group consisting of hydrogen and $C_{1-3}$ alkyl; and $R^{17b}$ is selected from the group consisting of hydrogen and halo.

In another embodiment, Compounds of the Disclosure are compounds represented by Formula XI:

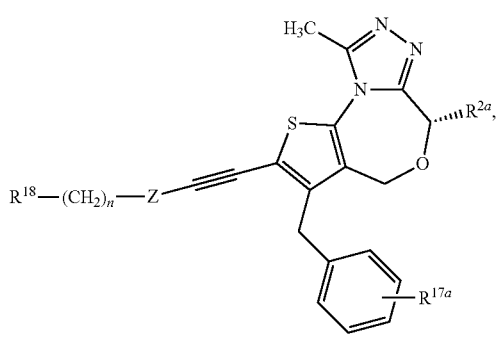

XI and the pharmaceutically acceptable salts, hydrates, and solvates thereof, wherein:

$R^{2a}$ is selected from the group consisting of hydrogen and $C_{1-3}$ alkyl;

Z is heteroarylenyl;

$R^{17a}$ is selected from the group consisting of hydrogen and halo;

$R^{18}$ is selected from the group consisting of —C≡CH, —CHO, —CO$_2$H, —OH, and halo; and n is 0, 1, 2, 3, 4, 5, or 6.

In another embodiment, Compounds of the Disclosure are compounds represented by Formula XI, and the pharmaceutically acceptable salts, hydrates, and solvates thereof, wherein $R^{18}$ is —CHO. In another embodiment, Compounds of the Disclosure are compounds represented by Formula XI, and the pharmaceutically acceptable salts, hydrates, and solvates thereof, wherein $R^{18}$ is —C≡CH.

In another embodiment, Compounds of the Disclosure are compounds represented by Formula XII:

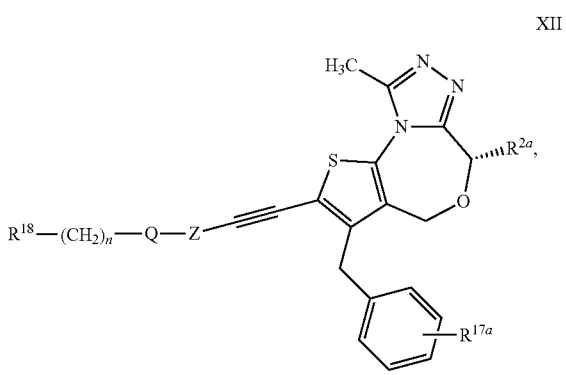

XII and the pharmaceutically acceptable salts, hydrates, and solvates thereof, wherein:

$R^{2a}$ is selected from the group consisting of hydrogen and $C_{1-3}$ alkyl;

Z is heteroarylenyl;

Q is selected from the group consisting of —O— and —N($R^{2c}$);

$R^{2c}$ is selected from the group consisting of hydrogen and $C_{1-3}$ alkyl;

$R^{17a}$ is selected from the group consisting of hydrogen and halo;

$R^{18}$ is selected from the group consisting of —C≡CH, —CHO, —CO$_2$H, —OH, and halo; and n is 2, 3, 4, 5, or 6.

In another embodiment, Compounds of the Disclosure are compounds represented by Formula XII, and the pharmaceutically acceptable salts, hydrates, and solvates thereof, wherein $R^{18}$ is —CHO. In another embodiment, Compounds of the Disclosure are compounds represented by Formula XII, and the pharmaceutically acceptable salts, hydrates, and solvates thereof, wherein $R^{18}$ is —C≡CH. In another embodiment, Compounds of the Disclosure are compounds represented by Formula XII, and the pharmaceutically acceptable salts, hydrates, and solvates thereof, wherein Q is —O—. In another embodiment, Compounds of the Disclosure are compounds represented by Formula XII, and the pharmaceutically acceptable salts, hydrates, and solvates thereof, wherein Q is —N(H)—.

In another embodiment, Compounds of the Disclosure are compounds of Table 1, and the pharmaceutically acceptable salts, hydrates, and solvates thereof.

TABLE 1

| Cpd. No. | Structure | Name |
|---|---|---|
| 1 | 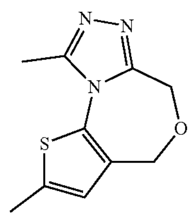 | 2,9-dimethyl-4H,6H-thieno[2,3-e][1,2,4]triazolo[3,4-c][1,4]oxazepine |
| 2 | 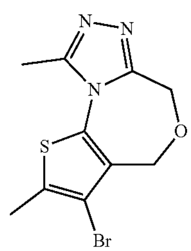 [SMILES: Cc1sc2c(c1Br)COCc1nnc(C)n1-2] | 3-bromo-2,9-dimethyl-4H,6H-thieno[2,3-e][1,2,4]triazolo[3,4-c][1,4]oxazepine |
| 3 | 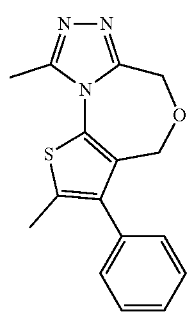 [SMILES: Cc1sc2c(c1-c1ccccc1)COCc1nnc(C)n1-2] | 2,9-dimethyl-3-phenyl-4H,6H-thieno[2,3-e][1,2,4]triazolo[3,4-c][1,4]oxazepine |
| 4 | 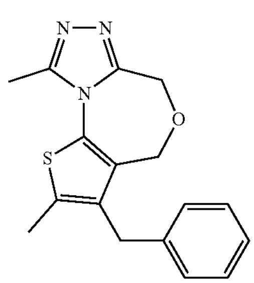 [SMILES: Cc1sc2c(c1Cc1ccccc1)COCc1nnc(C)n1-2] | 3-benzyl-2,9-dimethyl-4H,6H-thieno[2,3-e][1,2,4]triazolo[3,4-c][1,4]oxazepine |
| 5 | 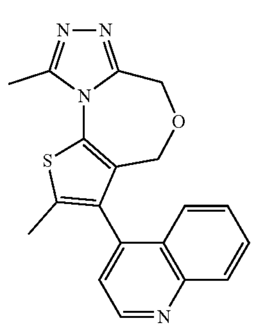 [SMILES: Cc1sc2c(c1-c1ccnc3ccccc13)COCc1nnc(C)n1-2] | 2,9-dimethyl-3-(quinolin-4-yl)-4H,6H-thieno[2,3-e][1,2,4]triazolo[3,4-c][1,4]oxazepine |

TABLE 1-continued

| Cpd. No. | Structure | Name |
|---|---|---|
| 6 | 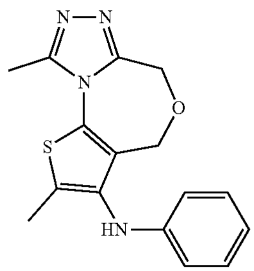 [SMILES: Cc1sc2c(c1Nc1ccccc1)COCc1nnc(C)n1-2] | 2,9-dimethyl-N-phenyl-4H,6H-thieno[2,3-e][1,2,4]triazolo[3,4-c][1,4]oxazepin-3-amine |
| 7 | 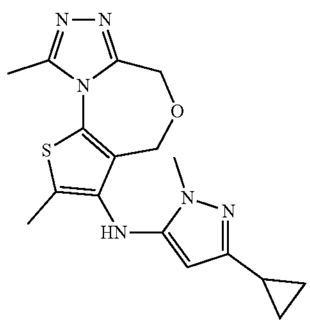 [SMILES: Cc1sc2c(c1Nc1cc(C3CC3)nn1C)COCc1nnc(C)n1-2] | N-(3-cyclopropyl-1-methyl-1H-pyrazol-5-yl)-2,9-dimethyl-4H,6H-thieno[2,3-e][1,2,4]triazolo[3,4-c][1,4]oxazepin-3-amine |
| 8 | 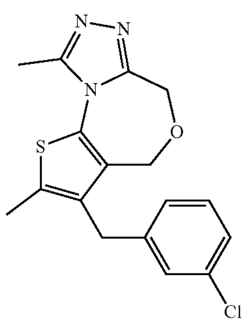 [SMILES: Cc1sc2c(c1Cc1cccc(Cl)c1)COCc1nnc(C)n1-2] | 3-(3-chlorobenzyl)-2,9-dimethyl-4H,6H-thieno[2,3-e][1,2,4]triazolo[3,4-c][1,4]oxazepine |
| 9 | 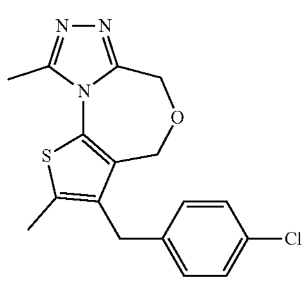 [SMILES: Cc1sc2c(c1Cc1ccc(Cl)cc1)COCc1nnc(C)n1-2] | 3-(4-chlorobenzyl)-2,9-dimethyl-4H,6H-thieno[2,3-e][1,2,4]triazolo[3,4-c][1,4]oxazepine |
| 10 | 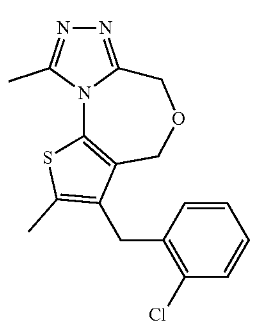 [SMILES: Cc1sc2c(c1Cc1ccccc1Cl)COCc1nnc(C)n1-2] | 3-(2-chlorobenzyl)-2,9-dimethyl-4H,6H-thieno[2,3-e][1,2,4]triazolo[3,4-c][1,4]oxazepine |

TABLE 1-continued

| Cpd. No. | Structure | Name |
|---|---|---|
| 12 | 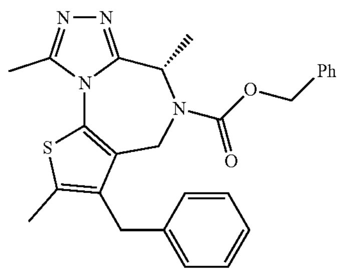 [SMILES: Cc1sc2c(c1Cc1ccccc1)CN(C(=O)OCc1ccccc1)[C@@H](C)c1nnc(C)n1-2] | benzyl (S)-3-benzyl-2,6,9-trimethyl-4H-thieno[3,2-f][1,2,4]triazolo[4,3-a][1,4]diazepine-5(6H)-carboxylate |
| 13 | 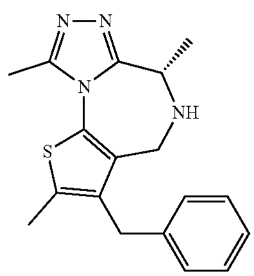 [SMILES: Cc1sc2c(c1Cc1ccccc1)CN[C@@H](C)c1nnc(C)n1-2] | (S)-3-benzyl-2,6,9-trimethyl-5,6-dihydro-4H-thieno[3,2-f][1,2,4]triazolo[4,3-a][1,4]diazepine |
| 14 | 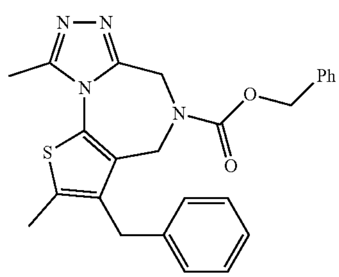 [SMILES: Cc1sc2c(c1Cc1ccccc1)CN(C(=O)OCc1ccccc1)Cc1nnc(C)n1-2] | benzyl 3-benzyl-2,9-dimethyl-4H-thieno[3,2-f][1,2,4]triazolo[4,3-a][1,4]diazepine-5(6H)-carboxylate |
| 15 | 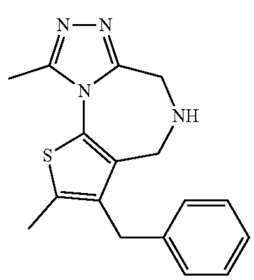 [SMILES: Cc1sc2c(c1Cc1ccccc1)CNCc1nnc(C)n1-2] | 3-benzyl-2,9-dimethyl-5,6-dihydro-4H-thieno[3,2-f][1,2,4]triazolo[4,3-a][1,4]diazepine |
| 16 | 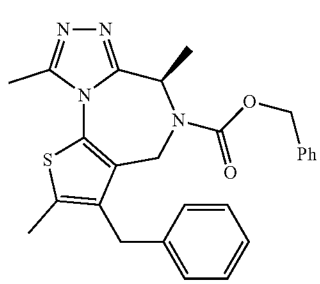 [SMILES: Cc1sc2c(c1Cc1ccccc1)CN(C(=O)OCc1ccccc1)[C@H](C)c1nnc(C)n1-2] | benzyl (R)-3-benzyl-2,6,9-trimethyl-4H-thieno[3,2-f][1,2,4]triazolo[4,3-a][1,4]diazepine-5(6H)-carboxylate |

TABLE 1-continued

| Cpd. No. | Structure | Name |
|---|---|---|
| 17 | 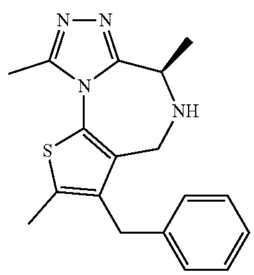 [SMILES: Cc1sc2c(c1Cc1ccccc1)CN[C@H](C)c1nnc(C)n1-2] | (R)-3-benzyl-2,6,9-trimethyl-5,6-dihydro-4H-thieno[3,2-f][1,2,4]triazolo[4,3-a][1,4]diazepine |
| 18 | 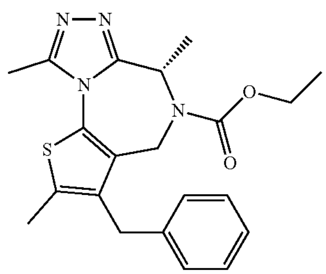 [SMILES: CCOC(=O)N1Cc2c(sc(C)c2Cc2ccccc2)-n2c(C)nnc2[C@@H]1C] | ethyl (S)-3-benzyl-2,6,9-trimethyl-4H-thieno[3,2-f][1,2,4]triazolo[4,3-a][1,4]diazepine-5(6H)-carboxylate |
| 19 | 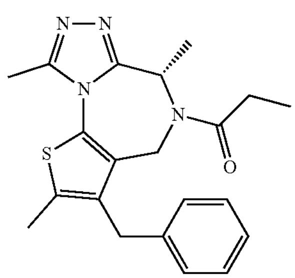 [SMILES: CCC(=O)N1Cc2c(sc(C)c2Cc2ccccc2)-n2c(C)nnc2[C@@H]1C] | (S)-1-(3-benzyl-2,6,9-trimethyl-4H-thieno[3,2-f][1,2,4]triazolo[4,3-a][1,4]diazepin-5(6H)-yl)propan-1-one |
| 20 | 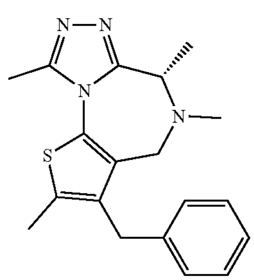 [SMILES: Cc1sc2c(c1Cc1ccccc1)CN(C)[C@@H](C)c1nnc(C)n1-2] | (S)-3-benzyl-2,5,6,9-tetramethyl-5,6-dihydro-4H-thieno[3,2-f][1,2,4]triazolo[4,3-a][1,4]diazepine |
| 21 | 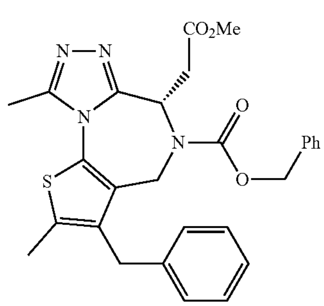 [SMILES: COC(=O)C[C@H]1c2nnc(C)n2-c2sc(C)c(Cc3ccccc3)c2CN1C(=O)OCc1ccccc1] | benzyl (S)-3-benzyl-6-(2-methoxy-2-oxoethyl)-2,9-dimethyl-4H-thieno[3,2-f][1,2,4]triazolo[4,3-a][1,4]diazepine-5(6H)-carboxylate |

TABLE 1-continued

| Cpd. No. | Structure | Name |
|---|---|---|
| 22 | 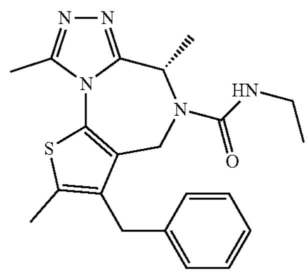 [SMILES: CCNC(=O)N1Cc2c(sc(C)c2Cc2ccccc2)-n2c(C)nnc2[C@@H]1C] | (S)-3-benzyl-N-ethyl-2,6,9-trimethyl-4H-thieno[3,2-f][1,2,4]triazolo[4,3-a][1,4]diazepine-5(6H)-carboxamide |
| 23 | 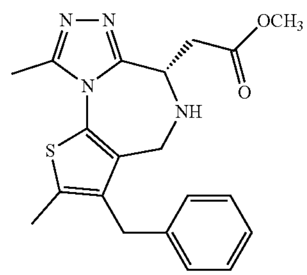 [SMILES: COC(=O)C[C@@H]1NCc2c(sc(C)c2Cc2ccccc2)-n2c(C)nnc21] | methyl (S)-2-(3-benzyl-2,9-dimethyl-5,6-dihydro-4H-thieno[3,2-f][1,2,4]triazolo[4,3-a][1,4]diazepin-6-yl)acetate |
| 24 | 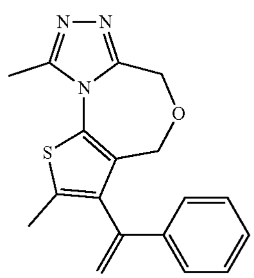 [SMILES: C=C(c1ccccc1)c1c(C)sc2c1COCc1nnc(C)n1-2] | 2,9-dimethyl-3-(1-phenylvinyl)-4H,6H-thieno[2,3-e][1,2,4]triazolo[3,4-c][1,4]oxazepine |
| 25 | 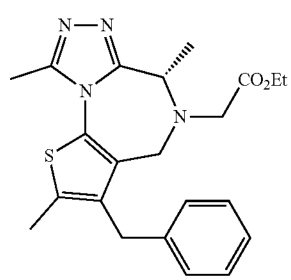 [SMILES: CCOC(=O)CN1Cc2c(sc(C)c2Cc2ccccc2)-n2c(C)nnc2[C@@H]1C] | ethyl (S)-2-(3-benzyl-2,6,9-trimethyl-4H-thieno[3,2-f][1,2,4]triazolo[4,3-a][1,4]diazepin-5(6H)-yl)acetate |
| 26 | 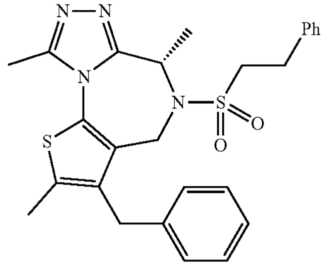 [SMILES: Cc1sc2c(c1Cc1ccccc1)CN(S(=O)(=O)CCc1ccccc1)[C@@H](C)c1nnc(C)n1-2] | (S)-3-benzyl-2,6,9-trimethyl-5-(phenethylsulfonyl)-5,6-dihydro-4H-thieno[3,2-f][1,2,4]triazolo[4,3-a][1,4]diazepine |

TABLE 1-continued

| Cpd. No. | Structure | Name |
|---|---|---|
| 27 | 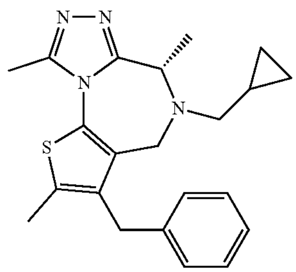 [SMILES: Cc1sc2c(c1Cc1ccccc1)CN(CC1CC1)[C@@H](C)c1nnc(C)n1-2] | (S)-3-benzyl-5-(cyclopropylmethyl)-2,6,9-trimethyl-5,6-dihydro-4H-thieno[3,2-f][1,2,4]triazolo[4,3-a][1,4]diazepine |
| 28 | 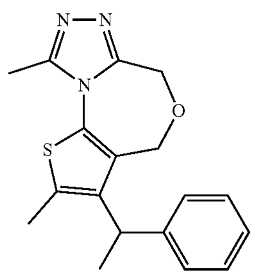 [SMILES: Cc1sc2c(c1C(C)c1ccccc1)COCc1nnc(C)n1-2] | 2,9-dimethyl-3-(1-phenylethyl)-4H,6H-thieno[2,3-e][1,2,4]triazolo[3,4-c][1,4]oxazepine |
| 29 | 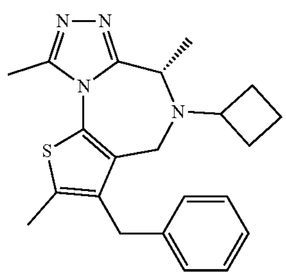 [SMILES: Cc1sc2c(c1Cc1ccccc1)CN(C1CCC1)[C@@H](C)c1nnc(C)n1-2] | (S)-3-benzyl-5-cyclobutyl-2,6,9-trimethyl-5,6-dihydro-4H-thieno[3,2-f][1,2,4]triazolo[4,3-a][1,4]diazepine |
| 30 | 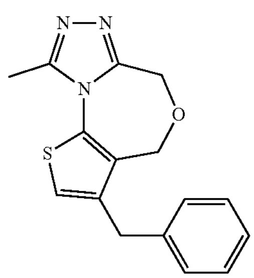 [SMILES: Cc1nnc2n1-c1scc(Cc3ccccc3)c1COC2] | 3-benzyl-9-methyl-4H,6H-thieno[2,3-e][1,2,4]triazolo[3,4-c][1,4]oxazepine |
| 31 | 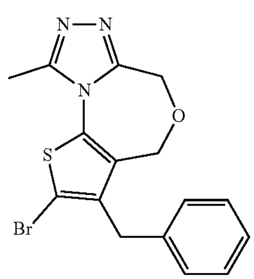 [SMILES: Cc1nnc2n1-c1sc(Br)c(Cc3ccccc3)c1COC2] | 3-benzyl-2-bromo-9-methyl-4H,6H-thieno[2,3-e][1,2,4]triazolo[3,4-c][1,4]oxazepine |

TABLE 1-continued

| Cpd. No. | Structure | Name |
|---|---|---|
| 32 | 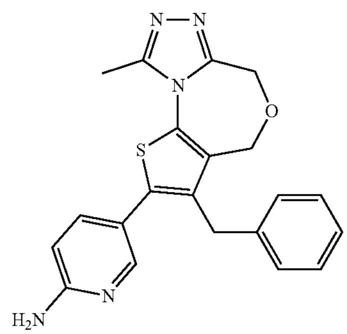 [SMILES: Cc1nnc2n1-c1sc(-c3ccc(N)nc3)c(Cc3ccccc3)c1COC2] | 5-(3-benzyl-9-methyl-4H,6H-thieno[2,3-e][1,2,4]triazolo[3,4-c][1,4]oxazepin-2-yl)pyridin-2-amine |
| 33 | 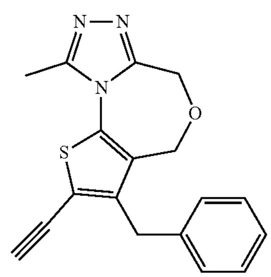 [SMILES: C#Cc1sc2c(c1Cc1ccccc1)COCc1nnc(C)n1-2] | 3-benzyl-2-ethynyl-9-methyl-4H,6H-thieno[2,3-e][1,2,4]triazolo[3,4-c][1,4]oxazepine |
| 34 | 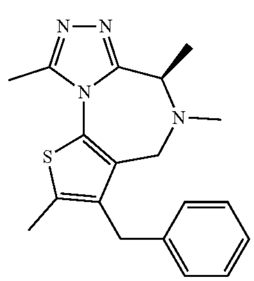 [SMILES: Cc1sc2c(c1Cc1ccccc1)CN(C)[C@H](C)c1nnc(C)n1-2] | (R)-3-benzyl-2,5,6,9-tetramethyl-5,6-dihydro-4H-thieno[3,2-f][1,2,4]triazolo[4,3-a][1,4]diazepine |
| 35 | 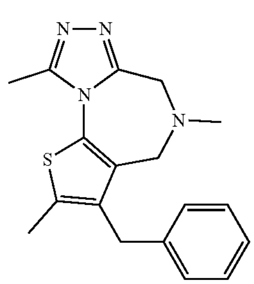 [SMILES: Cc1sc2c(c1Cc1ccccc1)CN(C)Cc1nnc(C)n1-2] | 3-benzyl-2,5,9-trimethyl-5,6-dihydro-4H-thieno[3,2-f][1,2,4]triazolo[4,3-a][1,4]diazepine |
| 36 | 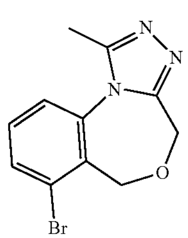 [SMILES: Cc1nnc2n1-c1cccc(Br)c1COC2] | 7-bromo-1-methyl-4H,6H-benzo[e][1,2,4]triazolo[3,4-c][1,4]oxazepine |

TABLE 1-continued

| Cpd. No. | Structure | Name |
|---|---|---|
| 37 | 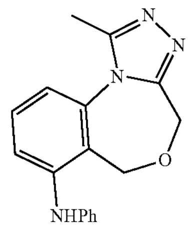 | 1-methyl-N-phenyl-4H,6H-benzo[e][1,2,4]triazolo[3,4-c][1,4]oxazepin-7-amine |
| 38 | 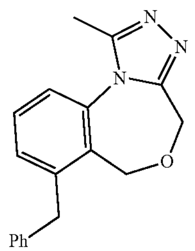 [SMILES: Cc1nnc2n1-c1cccc(Cc3ccccc3)c1COC2] | 7-benzyl-1-methyl-4H,6H-benzo[e][1,2,4]triazolo[3,4-c][1,4]oxazepine |
| 39 | 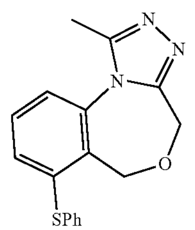 | 1-methyl-7-(phenylthio)-4H,6H-benzo[e][1,2,4]triazolo[3,4-c][1,4]oxazepine |
| 40 | 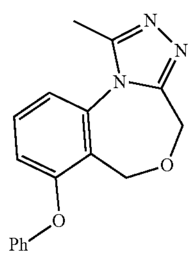 [SMILES: Cc1nnc2n1-c1cccc(Oc3ccccc3)c1COC2] | 1-methyl-7-phenoxy-4H,6H-benzo[e][1,2,4]triazolo[3,4-c][1,4]oxazepine |
| 41 | 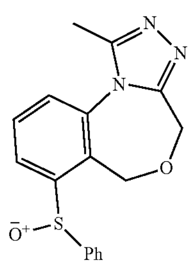 | 7-(($\lambda^1$-oxidanyl)(phenyl)-$\lambda^3$-sulfanyl)-1-methyl-4H,6H-benzo[e][1,2,4]triazolo[3,4-c][1,4]oxazepine |
| 42 | 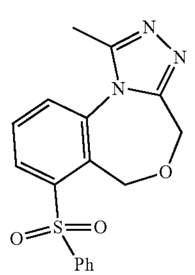 [SMILES: Cc1nnc2n1-c1cccc(S(=O)(=O)c3ccccc3)c1COC2] | 1-methyl-7-(phenylsulfonyl)-4H,6H-benzo[e][1,2,4]triazolo[3,4-c][1,4]oxazepine |

TABLE 1-continued

| Cpd. No. | Structure | Name |
|---|---|---|
| 43 | 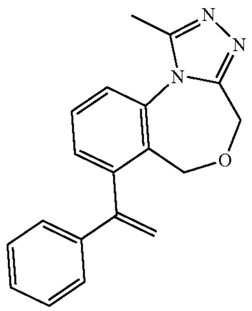 [SMILES: C=C(c1ccccc1)c1cccc2c1COCc1nnc(C)n1-2] | 1-methyl-7-(1-phenylvinyl)-4H,6H-benzo[e][1,2,4]triazolo[3,4-c][1,4]oxazepine |
| 44 | 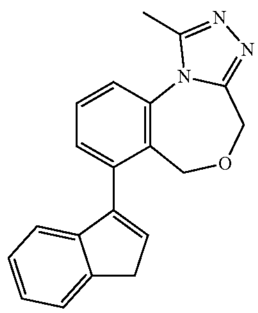 [SMILES: Cc1nnc2n1-c1cccc(C3=CCc4ccccc43)c1COC2] | 7-(1H-inden-3-yl)-1-methyl-4H,6H-benzo[e][1,2,4]triazolo[3,4-c][1,4]oxazepine |
| 45 | 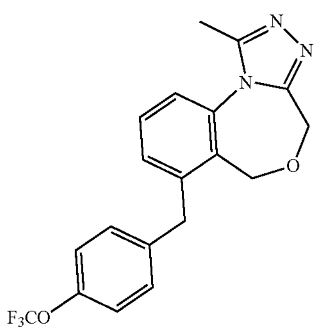 [SMILES: Cc1nnc2n1-c1cccc(Cc3ccc(OC(F)(F)F)cc3)c1COC2] | 1-methyl-7-(4-(trifluoromethoxy)benzyl)-4H,6H-benzo[e][1,2,4]triazolo[3,4-c][1,4]oxazepine |
| 46 | 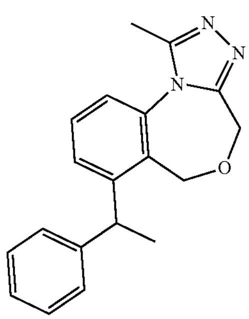 [SMILES: Cc1nnc2n1-c1cccc(C(C)c3ccccc3)c1COC2] | 1-methyl-7-(1-phenylethyl)-4H,6H-benzo[e][1,2,4]triazolo[3,4-c][1,4]oxazepine |
| 47 | 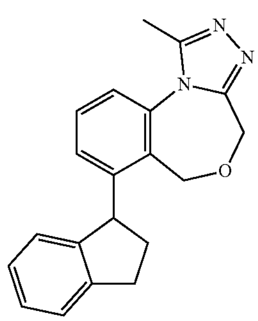 [SMILES: Cc1nnc2n1-c1cccc(C3CCc4ccccc43)c1COC2] | 7-(2,3-dihydro-1H-inden-1-yl)-1-methyl-4H,6H-benzo[e][1,2,4]triazolo[3,4-c][1,4]oxazepine |

TABLE 1-continued

| Cpd. No. | Structure | Name |
|---|---|---|
| 48 | 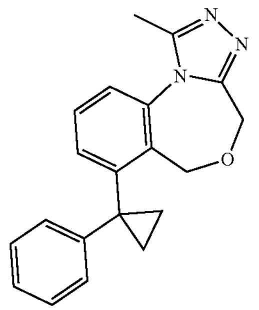 [SMILES: Cc1nnc2n1-c1cccc(C3(c4ccccc4)CC3)c1COC2] | 1-methyl-7-(1-phenylcyclopropyl)-4H,6H-benzo[e][1,2,4]triazolo[3,4-c][1,4]oxazepine |
| 49 | 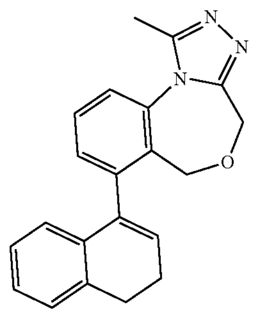 [SMILES: Cc1nnc2n1-c1cccc(C3=CCCc4ccccc43)c1COC2] | 7-(3,4-dihydronaphthalen-1-yl)-1-methyl-4H,6H-benzo[e][1,2,4]triazolo[3,4-c][1,4]oxazepine |
| 50 | 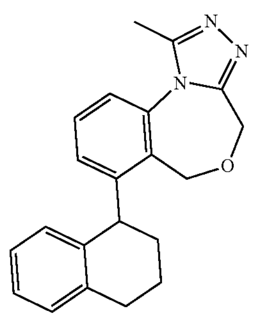 [SMILES: Cc1nnc2n1-c1cccc(C3CCCc4ccccc43)c1COC2] | 1-methyl-7-(1,2,3,4-tetrahydronaphthalen-1-yl)-4H,6H-benzo[e][1,2,4]triazolo[3,4-c][1,4]oxazepine |
| 51 | 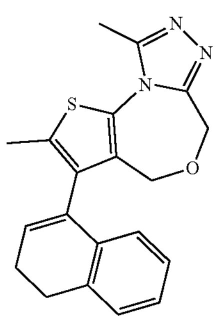 [SMILES: Cc1sc2c(c1C1=CCCc3ccccc31)COCc1nnc(C)n1-2] | 3-(3,4-dihydronaphthalen-1-yl)-2,9-dimethyl-4H,6H-thieno[2,3-e][1,2,4]triazolo[3,4-c][1,4]oxazepine |
| 52 | 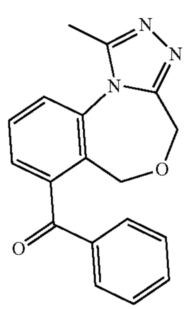 [SMILES: Cc1nnc2n1-c1cccc(C(=O)c3ccccc3)c1COC2] | (1-methyl-4H,6H-benzo[e][1,2,4]triazolo[3,4-c][1,4]oxazepin-7-yl)(phenyl)methanone |

TABLE 1-continued

| Cpd. No. | Structure | Name |
| --- | --- | --- |
| 53 | 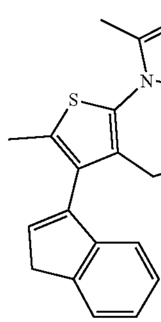 | 3-(1H-inden-3-yl)-2,9-dimethyl-4H,6H-thieno[2,3-e][1,2,4]triazolo[3,4-c][1,4]oxazepine |
| 54 | 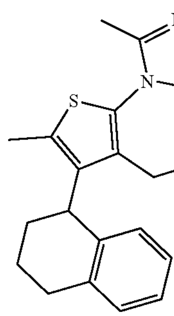 | 2,9-dimethyl-3-(1,2,3,4-tetrahydronaphthalen-1-yl)-4H,6H-thieno[2,3-e][1,2,4]triazolo[3,4-c][1,4]oxazepine |
| 55 | 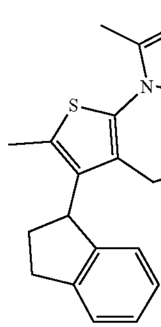 | 3-(2,3-dihydro-1H-inden-1-yl)-2,9-dimethyl-4H,6H-thieno[2,3-e][1,2,4]triazolo[3,4-c][1,4]oxazepine |
| 56 | 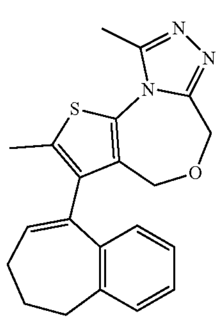 [SMILES: Cc1sc2c(c1C1=CCCCc3ccccc31)COCc1nnc(C)n1-2] | 3-(6,7-dihydro-5H-benzo[7]annulen-9-yl)-2,9-dimethyl-4H,6H-thieno[2,3-e][1,2,4]triazolo[3,4-c][1,4]oxazepine |

TABLE 1-continued

| Cpd. No. | Structure | Name |
|---|---|---|
| 57 | 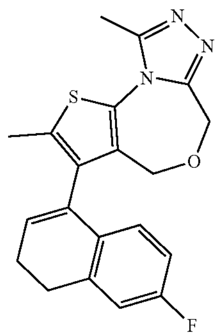 [SMILES: Cc1sc2c(c1C1=CCCc3cc(F)ccc31)COCc1nnc(C)n1-2] | 3-(6-fluoro-3,4-dihydronaphthalen-1-yl)-2,9-dimethyl-4H,6H-thieno[2,3-e][1,2,4]triazolo[3,4-c][1,4]oxazepine |
| 58 | 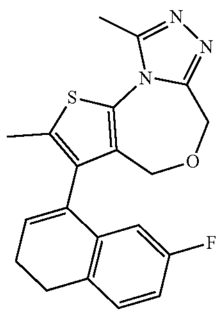 [SMILES: Cc1sc2c(c1C1=CCCc3ccc(F)cc31)COCc1nnc(C)n1-2] | 3-(7-fluoro-3,4-dihydronaphthalen-1-yl)-2,9-dimethyl-4H,6H-thieno[2,3-e][1,2,4]triazolo[3,4-c][1,4]oxazepine |
| 59 | 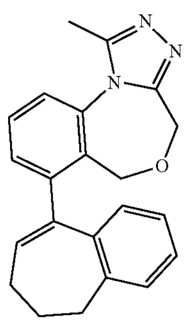 [SMILES: Cc1nnc2n1-c1cccc(C3=CCCCc4ccccc43)c1COC2] | 7-(6,7-dihydro-5H-benzo[7]annulen-9-yl)-1-methyl-4H,6H-benzo[e][1,2,4]triazolo[3,4-c][1,4]oxazepine |
| 60 | 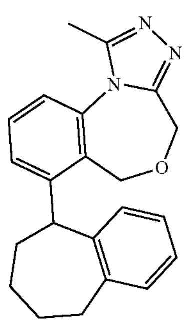 [SMILES: Cc1nnc2n1-c1cccc(C3CCCCc4ccccc43)c1COC2] | 1-methyl-7-(6,7,8,9-tetrahydro-5H-benzo[7]annulen-5-yl)-4H,6H-benzo[e][1,2,4]triazolo[3,4-c][1,4]oxazepine |
| 61 | 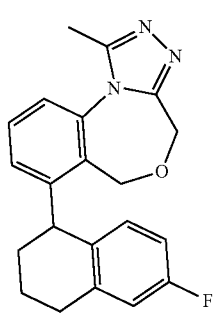 [SMILES: Cc1nnc2n1-c1cccc(C3CCCc4cc(F)ccc43)c1COC2] | 7-(6-fluoro-1,2,3,4-tetrahydronaphthalen-1-yl)-1-methyl-4H,6H-benzo[e][1,2,4]triazolo[3,4-c][1,4]oxazepine |

TABLE 1-continued

| Cpd. No. | Structure | Name |
|---|---|---|
| 62 | 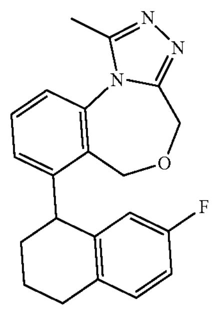 [SMILES: Cc1nnc2n1-c1cccc(C3CCCc4ccc(F)cc43)c1COC2] | 7-(7-fluoro-1,2,3,4-tetrahydronaphthalen-1-yl)-1-methyl-4H,6H-benzo[e][1,2,4]triazolo[3,4-c][1,4]oxazepine |
| 63 | 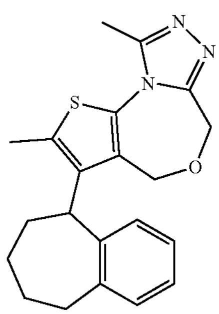 [SMILES: Cc1sc2c(c1C1CCCCc3ccccc31)COCc1nnc(C)n1-2] | 2,9-dimethyl-3-(6,7,8,9-tetrahydro-5H-benzo[7]annulen-5-yl)-4H,6H-thieno[2,3-e][1,2,4]triazolo[3,4-c][1,4]oxazepine |
| 64 | 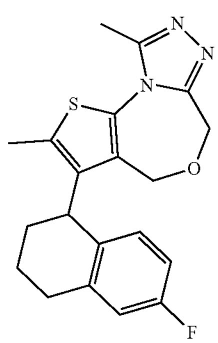 [SMILES: Cc1sc2c(c1C1CCCc3cc(F)ccc31)COCc1nnc(C)n1-2] | 3-(6-fluoro-1,2,3,4-tetrahydronaphthalen-1-yl)-2,9-dimethyl-4H,6H-thieno[2,3-e][1,2,4]triazolo[3,4-c][1,4]oxazepine |
| 65 | 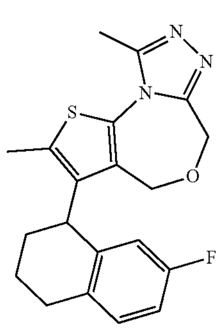 [SMILES: Cc1sc2c(c1C1CCCc3ccc(F)cc31)COCc1nnc(C)n1-2] | 3-(7-fluoro-1,2,3,4-tetrahydronaphthalen-1-yl)-2,9-dimethyl-4H,6H-thieno[2,3-e][1,2,4]triazolo[3,4-c][1,4]oxazepine |

TABLE 1-continued

| Cpd. No. | Structure | Name |
|---|---|---|
| 66 | 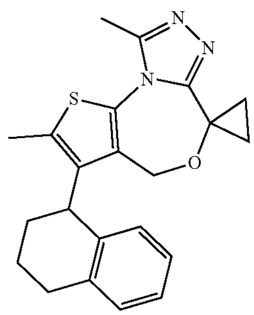 [SMILES: Cc1sc2c(c1C1CCCc3ccccc31)COC1(CC1)c1nnc(C)n1-2] | 2',9'-dimethyl-3'-(1,2,3,4-tetrahydronaphthalen-1-yl)-4'H-spiro[cyclopropane-1,6'-thieno[2,3-e][1,2,4]triazolo[3,4-c][1,4]oxazepine] |
| 67 | 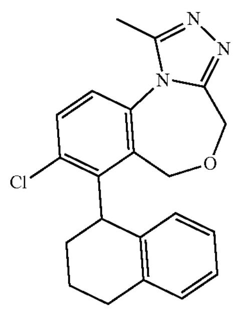 [SMILES: Cc1nnc2n1-c1ccc(Cl)c(C3CCCc4ccccc43)c1COC2] | 8-chloro-1-methyl-7-(1,2,3,4-tetrahydronaphthalen-1-yl)-4H,6H-benzo[e][1,2,4]triazolo[3,4-c][1,4]oxazepine |
| 68 | 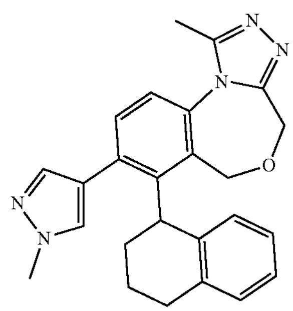 [SMILES: Cc1nnc2n1-c1ccc(-c3cnn(C)c3)c(C3CCCc4ccccc43)c1COC2] | 1-methyl-8-(1-methyl-1H-pyrazol-4-yl)-7-(1,2,3,4-tetrahydronaphthalen-1-yl)-4H,6H-benzo[e][1,2,4]triazolo[3,4-c][1,4]oxazepine |
| 69 | 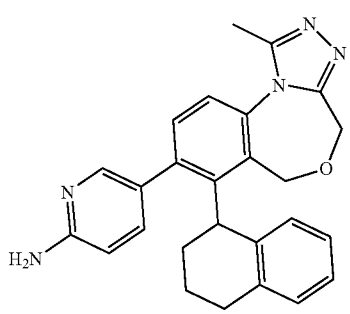 [SMILES: Cc1nnc2n1-c1ccc(-c3ccc(N)nc3)c(C3CCCc4ccccc43)c1COC2] | 5-(1-methyl-7-(1,2,3,4-tetrahydronaphthalen-1-yl)-4H,6H-benzo[e][1,2,4]triazolo[3,4-c][1,4]oxazepin-8-yl)pyridin-2-amine |
| 70 | 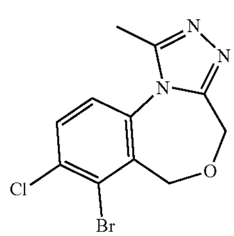 [SMILES: Cc1nnc2n1-c1ccc(Cl)c(Br)c1COC2] | 7-bromo-8-chloro-1-methyl-4H,6H-benzo[e][1,2,4]triazolo[3,4-c][1,4]oxazepine |

TABLE 1-continued

| Cpd. No. | Structure | Name |
|---|---|---|
| 71 | 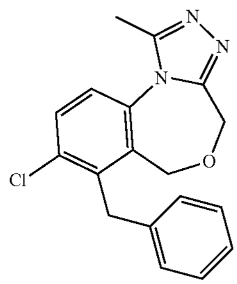 [SMILES: Cc1nnc2n1-c1ccc(Cl)c(Cc3ccccc3)c1COC2] | 7-benzyl-8-chloro-1-methyl-4H,6H-benzo[e][1,2,4]triazolo[3,4-c][1,4]oxazepine |
| 72 | 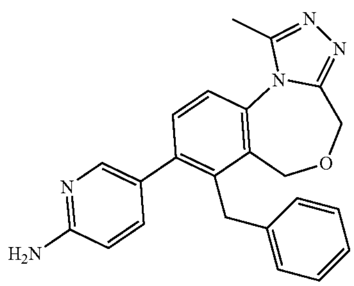 [SMILES: Cc1nnc2n1-c1ccc(-c3ccc(N)nc3)c(Cc3ccccc3)c1COC2] | 5-(7-benzyl-1-methyl-4H,6H-benzo[e][1,2,4]triazolo[3,4-c][1,4]oxazepin-8-yl)pyridin-2-amine |
| 73 | 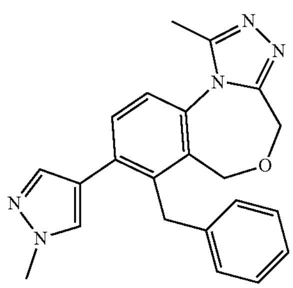 [SMILES: Cc1nnc2n1-c1ccc(-c3cnn(C)c3)c(Cc3ccccc3)c1COC2] | 7-benzyl-1-methyl-8-(1-methyl-1H-pyrazol-4-yl)-4H,6H-benzo[e][1,2,4]triazolo[3,4-c][1,4]oxazepine |
| 74 | 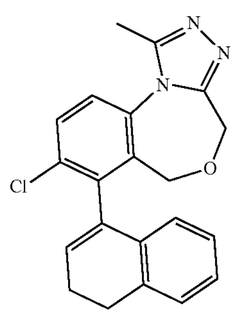 [SMILES: Cc1nnc2n1-c1ccc(Cl)c(C3=CCCc4ccccc43)c1COC2] | 8-chloro-7-(3,4-dihydronaphthalen-1-yl)-1-methyl-4H,6H-benzo[e][1,2,4]triazolo[3,4-c][1,4]oxazepine |
| 75 | 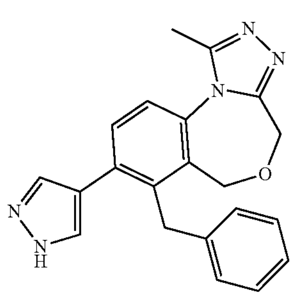 [SMILES: Cc1nnc2n1-c1ccc(-c3cn[nH]c3)c(Cc3ccccc3)c1COC2] | 7-benzyl-1-methyl-8-(1H-pyrazol-4-yl)-4H,6H-benzo[e][1,2,4]triazolo[3,4-c][1,4]oxazepine |

TABLE 1-continued

| Cpd. No. | Structure | Name |
|---|---|---|
| 76 | 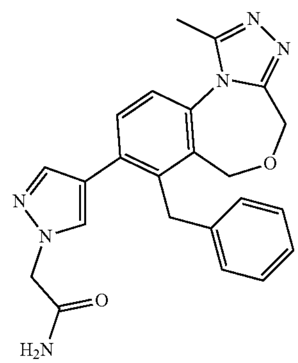 [SMILES: Cc1nnc2n1-c1ccc(-c3cnn(CC(N)=O)c3)c(Cc3ccccc3)c1COC2] | 2-(4-(7-benzyl-1-methyl-4H,6H-benzo[e][1,2,4]triazolo[3,4-c][1,4]oxazepin-8-yl)-1H-pyrazol-1-yl)acetamide |
| 77 | 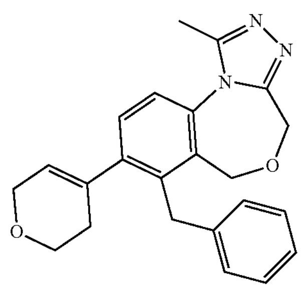 [SMILES: Cc1nnc2n1-c1ccc(C3=CCOCC3)c(Cc3ccccc3)c1COC2] | 7-benzyl-8-(3,6-dihydro-2H-pyran-4-yl)-1-methyl-4H,6H-benzo[e][1,2,4]triazolo[3,4-c][1,4]oxazepine |
| 78 | 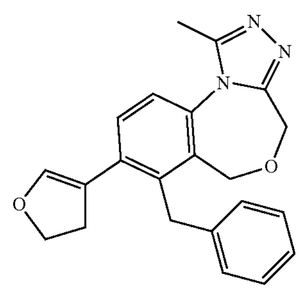 [SMILES: Cc1nnc2n1-c1ccc(C3=COCC3)c(Cc3ccccc3)c1COC2] | 7-benzyl-8-(4,5-dihydrofuran-3-yl)-1-methyl-4H,6H-benzo[e][1,2,4]triazolo[3,4-c][1,4]oxazepine |
| 79 | 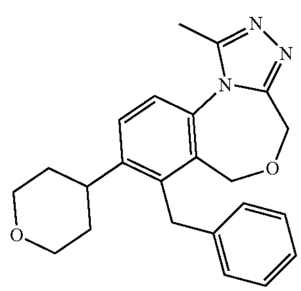 [SMILES: Cc1nnc2n1-c1ccc(C3CCOCC3)c(Cc3ccccc3)c1COC2] | 7-benzyl-1-methyl-8-(tetrahydro-2H-pyran-4-yl)-4H,6H-benzo[e][1,2,4]triazolo[3,4-c][1,4]oxazepine |
| 80 | 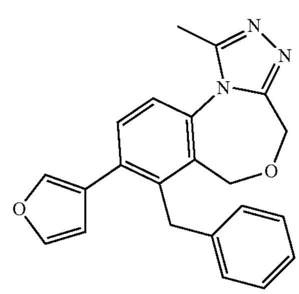 [SMILES: Cc1nnc2n1-c1ccc(-c3ccoc3)c(Cc3ccccc3)c1COC2] | 7-benzyl-8-(furan-3-yl)-1-methyl-4H,6H-benzo[e][1,2,4]triazolo[3,4-c][1,4]oxazepine |

TABLE 1-continued

| Cpd. No. | Structure | Name |
|---|---|---|
| 81 | 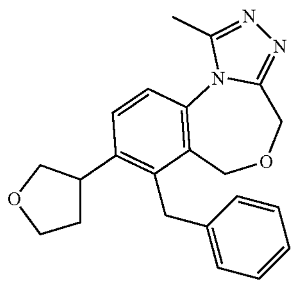 [SMILES: Cc1nnc2n1-c1ccc(C3CCOC3)c(Cc3ccccc3)c1COC2] | 7-benzyl-1-methyl-8-(tetrahydrofuran-3-yl)-4H,6H-benzo[e][1,2,4]triazolo[3,4-c][1,4]oxazepine |
| 82 | 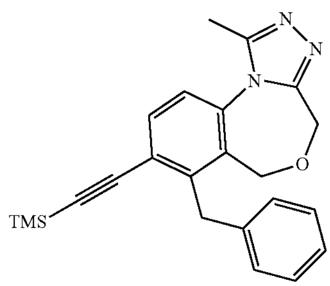 [SMILES: Cc1nnc2n1-c1ccc(C#C[Si](C)(C)C)c(Cc3ccccc3)c1COC2] | 7-benzyl-1-methyl-8-((trimethylsilyl)ethynyl)-4H,6H-benzo[e][1,2,4]triazolo[3,4-c][1,4]oxazepine |
| 83 | 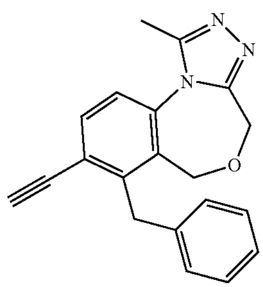 [SMILES: C#Cc1ccc2c(c1Cc1ccccc1)COCc1nnc(C)n1-2] | 7-benzyl-8-ethynyl-1-methyl-4H,6H-benzo[e][1,2,4]triazolo[3,4-c][1,4]oxazepine |
| 84 | 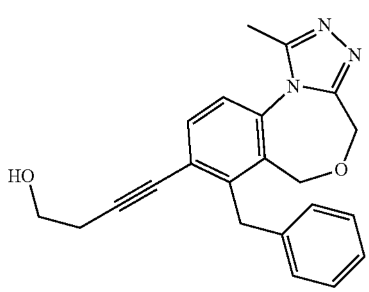 [SMILES: Cc1nnc2n1-c1ccc(C#CCCO)c(Cc3ccccc3)c1COC2] | 4-(7-benzyl-1-methyl-4H,6H-benzo[e][1,2,4]triazolo[3,4-c][1,4]oxazepin-8-yl)but-3-yn-1-ol |
| 85 | 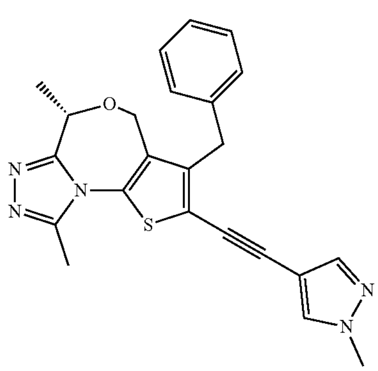 [SMILES: Cc1nnc2n1-c1sc(C#Cc3cnn(C)c3)c(Cc3ccccc3)c1CO[C@H]2C] | (S)-3-benzyl-6,9-dimethyl-2-((1-methyl-1H-pyrazol-4-yl)ethynyl)-4H,6H-thieno[2,3-e][1,2,4]triazolo[3,4-c][1,4]oxazepine |

TABLE 1-continued

| Cpd. No. | Structure | Name |
|---|---|---|
| 86 | 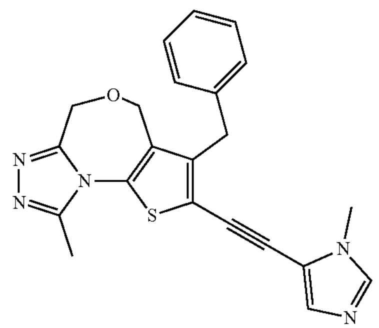 [SMILES: Cc1nnc2n1-c1sc(C#Cc3cncn3C)c(Cc3ccccc3)c1COC2] | 3-benzyl-9-methyl-2-((1-methyl-1H-imidazol-5-yl)ethynyl)-4H,6H-thieno[2,3-e][1,2,4]triazolo[3,4-c][1,4]oxazepine |
| 87 | 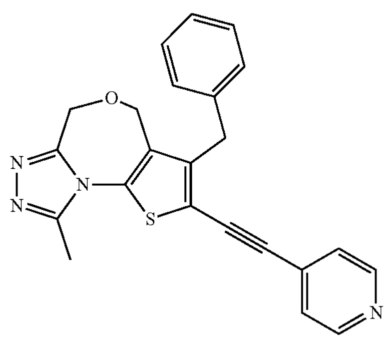 [SMILES: Cc1nnc2n1-c1sc(C#Cc3ccncc3)c(Cc3ccccc3)c1COC2] | 3-benzyl-9-methyl-2-(pyridin-4-ylethynyl)-4H,6H-thieno[2,3-e][1,2,4]triazolo[3,4-c][1,4]oxazepine |
| 88 | 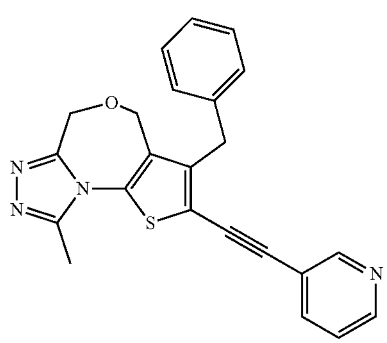 [SMILES: Cc1nnc2n1-c1sc(C#Cc3cccnc3)c(Cc3ccccc3)c1COC2] | 3-benzyl-9-methyl-2-(pyridin-3-ylethynyl)-4H,6H-thieno[2,3-e][1,2,4]triazolo[3,4-c][1,4]oxazepine |
| 89 | 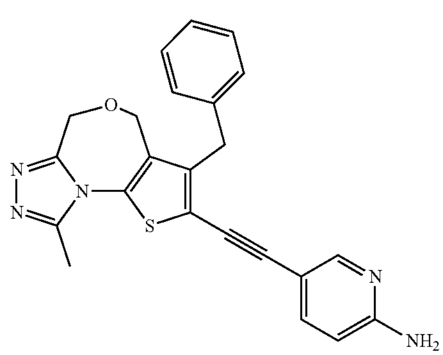 [SMILES: Cc1nnc2n1-c1sc(C#Cc3ccc(N)nc3)c(Cc3ccccc3)c1COC2] | 5-((3-benzyl-9-methyl-4H,6H-thieno[2,3-e][1,2,4]triazolo[3,4-c][1,4]oxazepin-2-yl)ethynyl)pyridin-2-amine |

TABLE 1-continued

| Cpd. No. | Structure | Name |
|---|---|---|
| 90 | 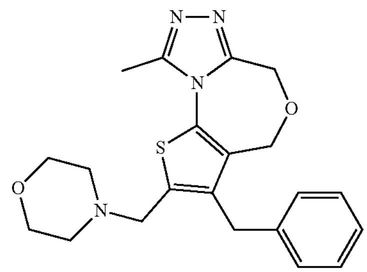 [SMILES: Cc1nnc2n1-c1sc(CN3CCOCC3)c(Cc3ccccc3)c1COC2] | 3-benzyl-9-methyl-2-(morpholinomethyl)-4H,6H-thieno[2,3-e][1,2,4]triazolo[3,4-c][1,4]oxazepine |
| 91 | 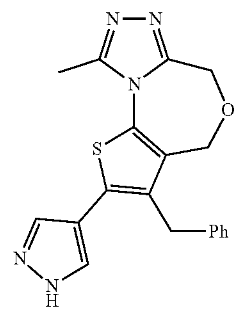 [SMILES: Cc1nnc2n1-c1sc(-c3cn[nH]c3)c(Cc3ccccc3)c1COC2] | 3-benzyl-9-methyl-2-(1H-pyrazol-4-yl)-4H,6H-thieno[2,3-e][1,2,4]triazolo[3,4-c][1,4]oxazepine |
| 92 | 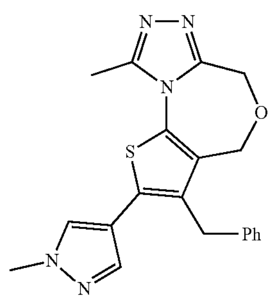 [SMILES: Cc1nnc2n1-c1sc(-c3cnn(C)c3)c(Cc3ccccc3)c1COC2] | 3-benzyl-9-methyl-2-(1-methyl-1H-pyrazol-4-yl)-4H,6H-thieno[2,3-e][1,2,4]triazolo[3,4-c][1,4]oxazepine |
| 93 | 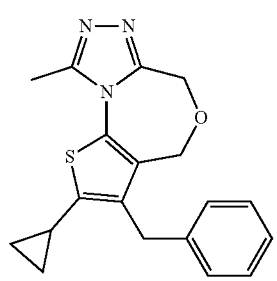 [SMILES: Cc1nnc2n1-c1sc(C3CC3)c(Cc3ccccc3)c1COC2] | 3-benzyl-2-cyclopropyl-9-methyl-4H,6H-thieno[2,3-e][1,2,4]triazolo[3,4-c][1,4]oxazepine |
| 94 | 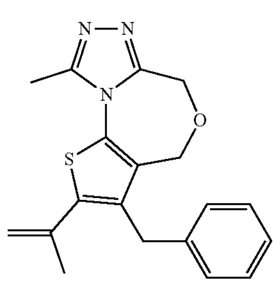 [SMILES: C=C(C)c1sc2c(c1Cc1ccccc1)COCc1nnc(C)n1-2] | 3-benzyl-9-methyl-2-(prop-1-en-2-yl)-4H,6H-thieno[2,3-e][1,2,4]triazolo[3,4-c][1,4]oxazepine |

TABLE 1-continued

| Cpd. No. | Structure | Name |
|---|---|---|
| 95 | 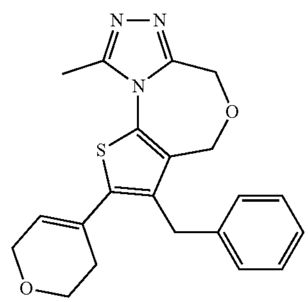 [SMILES: Cc1nnc2n1-c1sc(C3=CCOCC3)c(Cc3ccccc3)c1COC2] | 3-benzyl-2-(3,6-dihydro-2H-pyran-4-yl)-9-methyl-4H,6H-thieno[2,3-e][1,2,4]triazolo[3,4-c][1,4]oxazepine |
| 96 | 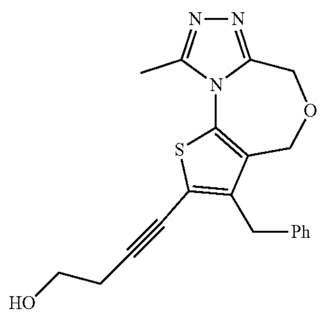 [SMILES: Cc1nnc2n1-c1sc(C#CCCO)c(Cc3ccccc3)c1COC2] | 4-(3-benzyl-9-methyl-4H,6H-thieno[2,3-e][1,2,4]triazolo[3,4-c][1,4]oxazepin-2-yl)but-3-yn-1-ol |
| 97 | 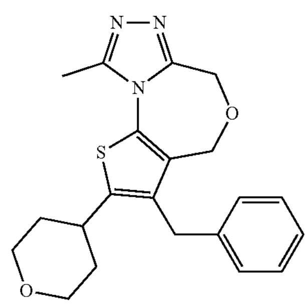 [SMILES: Cc1nnc2n1-c1sc(C3CCOCC3)c(Cc3ccccc3)c1COC2] | 3-benzyl-9-methyl-2-(tetrahydro-2H-pyran-4-yl)-4H,6H-thieno[2,3-e][1,2,4]triazolo[3,4-c][1,4]oxazepine |
| 98 | 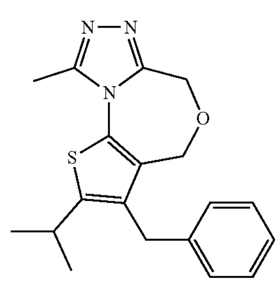 [SMILES: Cc1nnc2n1-c1sc(C(C)C)c(Cc3ccccc3)c1COC2] | 3-benzyl-2-isopropyl-9-methyl-4H,6H-thieno[2,3-e][1,2,4]triazolo[3,4-c][1,4]oxazepine |
| 99 | 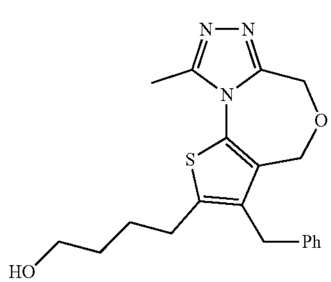 [SMILES: Cc1nnc2n1-c1sc(CCCCO)c(Cc3ccccc3)c1COC2] | 4-(3-benzyl-9-methyl-4H,6H-thieno[2,3-e][1,2,4]triazolo[3,4-c][1,4]oxazepin-2-yl)butan-1-ol |

TABLE 1-continued

| Cpd. No. | Structure | Name |
|---|---|---|
| 100 | 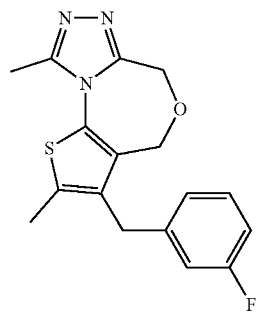 [SMILES: Cc1sc2c(c1Cc1cccc(F)c1)COCc1nnc(C)n1-2] | 3-(3-fluorobenzyl)-2,9-dimethyl-4H,6H-thieno[2,3-e][1,2,4]triazolo[3,4-c][1,4]oxazepine |
| 101 | 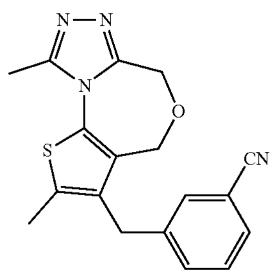 [SMILES: Cc1sc2c(c1Cc1cccc(C#N)c1)COCc1nnc(C)n1-2] | 3-((2,9-dimethyl-4H,6H-thieno[2,3-e][1,2,4]triazolo[3,4-c][1,4]oxazepin-3-yl)methyl)benzonitrile |
| 102 | 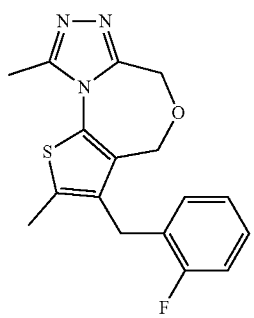 [SMILES: Cc1sc2c(c1Cc1ccccc1F)COCc1nnc(C)n1-2] | 3-(2-fluorobenzyl)-2,9-dimethyl-4H,6H-thieno[2,3-e][1,2,4]triazolo[3,4-c][1,4]oxazepine |
| 103 | 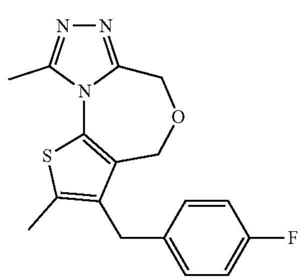 [SMILES: Cc1sc2c(c1Cc1ccc(F)cc1)COCc1nnc(C)n1-2] | 3-(4-fluorobenzyl)-2,9-dimethyl-4H,6H-thieno[2,3-e][1,2,4]triazolo[3,4-c][1,4]oxazepine |
| 104 | 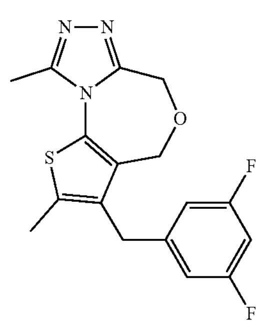 [SMILES: Cc1sc2c(c1Cc1cc(F)cc(F)c1)COCc1nnc(C)n1-2] | 3-(3,5-difluorobenzyl)-2,9-dimethyl-4H,6H-thieno[2,3-e][1,2,4]triazolo[3,4-c][1,4]oxazepine |

TABLE 1-continued

| Cpd. No. | Structure | Name |
|---|---|---|
| 105 | 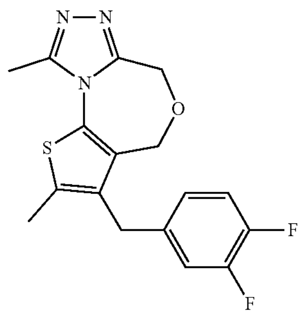 [SMILES: Cc1sc2c(c1Cc1ccc(F)c(F)c1)COCc1nnc(C)n1-2] | 3-(3,4-difluorobenzyl)-2,9-dimethyl-4H,6H-thieno[2,3-e][1,2,4]triazolo[3,4-c][1,4]oxazepine |
| 106 | 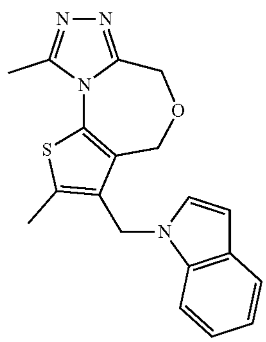 [SMILES: Cc1sc2c(c1Cn1ccc3ccccc31)COCc1nnc(C)n1-2] | 3-((1H-indol-1-yl)methyl)-2,9-dimethyl-4H,6H-thieno[2,3-e][1,2,4]triazolo[3,4-c][1,4]oxazepine |
| 107 | 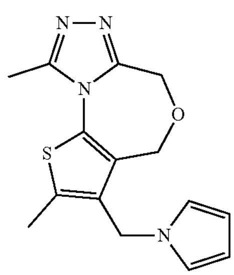 [SMILES: Cc1sc2c(c1Cn1cccc1)COCc1nnc(C)n1-2] | 3-((1H-pyrrol-1-yl)methyl)-2,9-dimethyl-4H,6H-thieno[2,3-e][1,2,4]triazolo[3,4-c][1,4]oxazepine |
| 108 | 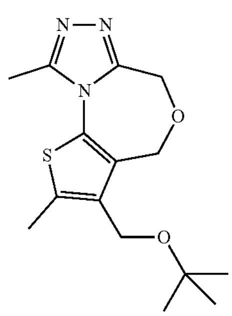 [SMILES: Cc1sc2c(c1COC(C)(C)C)COCc1nnc(C)n1-2] | 3-(tert-butoxymethyl)-2,9-dimethyl-4H,6H-thieno[2,3-e][1,2,4]triazolo[3,4-c][1,4]oxazepine |
| 109 | 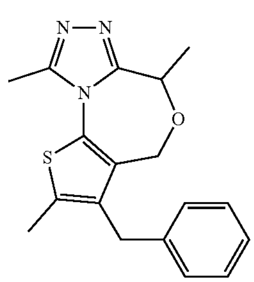 [SMILES: Cc1sc2c(c1Cc1ccccc1)COC(C)c1nnc(C)n1-2] | 3-benzyl-2,6,9-trimethyl-4H,6H-thieno[2,3-e][1,2,4]triazolo[3,4-c][1,4]oxazepine |

TABLE 1-continued

| Cpd. No. | Structure | Name |
|---|---|---|
| 110 | 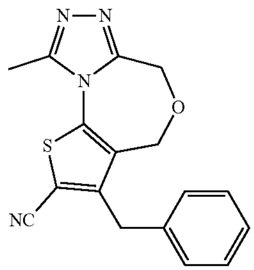 [SMILES: Cc1nnc2n1-c1sc(C#N)c(Cc3ccccc3)c1COC2] | 3-benzyl-9-methyl-4H,6H-thieno[2,3-e][1,2,4]triazolo[3,4-c][1,4]oxazepine-2-carbonitrile |
| 111 | 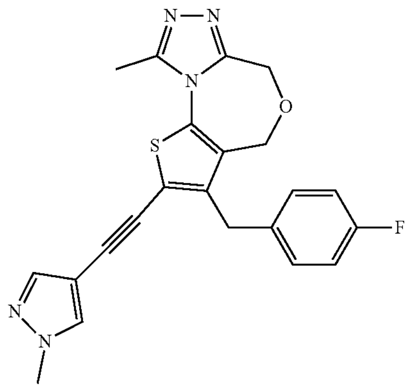 [SMILES: Cc1nnc2n1-c1sc(C#Cc3cnn(C)c3)c(Cc3ccc(F)cc3)c1COC2] | 3-(4-fluorobenzyl)-9-methyl-2-((1-methyl-1H-pyrazol-4-yl)ethynyl)-4H,6H-thieno[2,3-e][1,2,4]triazolo[3,4-c][1,4]oxazepine |
| 112 | 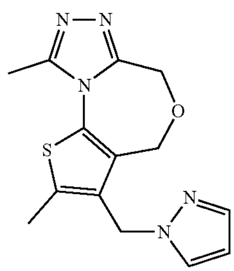 [SMILES: Cc1sc2c(c1Cn1cccn1)COCc1nnc(C)n1-2] | 3-((1H-pyrazol-1-yl)methyl)-2,9-dimethyl-4H,6H-thieno[2,3-e][1,2,4]triazolo[3,4-c][1,4]oxazepine |
| 113 | 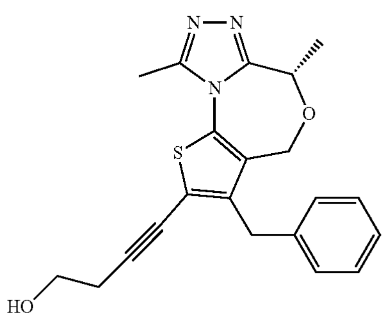 [SMILES: Cc1nnc2n1-c1sc(C#CCCO)c(Cc3ccccc3)c1CO[C@H]2C] | (S)-4-(3-benzyl-6,9-dimethyl-4H,6H-thieno[2,3-e][1,2,4]triazolo[3,4-c][1,4]oxazepin-2-yl)but-3-yn-1-ol |
| 114 | 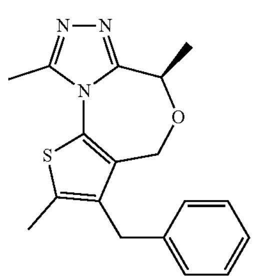 [SMILES: Cc1sc2c(c1Cc1ccccc1)CO[C@H](C)c1nnc(C)n1-2] | (R)-3-benzyl-2,6,9-trimethyl-4H,6H-thieno[2,3-e][1,2,4]triazolo[3,4-c][1,4]oxazepine |

TABLE 1-continued

| Cpd. No. | Structure | Name |
|---|---|---|
| 115 | 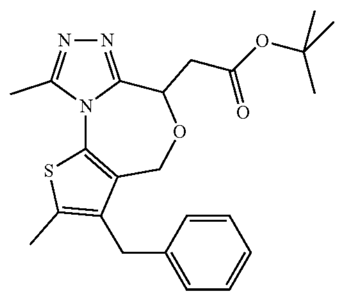 [SMILES: Cc1sc2c(c1Cc1ccccc1)COC(CC(=O)OC(C)(C)C)c1nnc(C)n1-2] | tert-butyl 2-(3-benzyl-2,9-dimethyl-4H,6H-thieno[2,3-e][1,2,4]triazolo[3,4-c][1,4]oxazepin-6-yl)acetate |
| 116 | 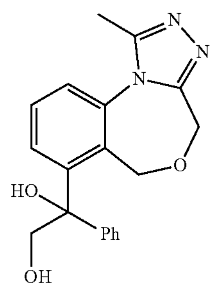 [SMILES: Cc1nnc2n1-c1cccc(C(O)(CO)c3ccccc3)c1COC2] | 1-(1-methyl-4H,6H-benzo[e][1,2,4]triazolo[3,4-c][1,4]oxazepin-7-yl)-1-phenylethane-1,2-diol |
| 117 | 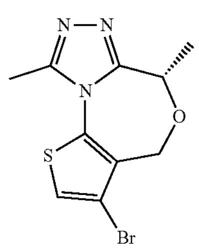 | (S)-3-bromo-6,9-dimethyl-4H,6H-thieno[2,3-e][1,2,4]triazolo[3,4-c][1,4]oxazepine |
| 118 | 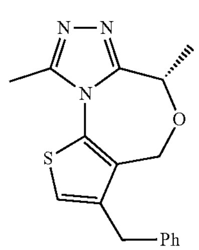 | (S)-3-benzyl-6,9-dimethyl-4H,6H-thieno[2,3-e][1,2,4]triazolo[3,4-c][1,4]oxazepine |
| 119 | 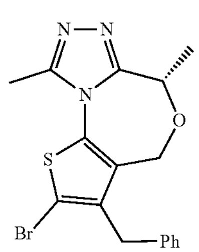 | (S)-3-benzyl-2-bromo-6,9-dimethyl-4H,6H-thieno[2,3-e][1,2,4]triazolo[3,4-c][1,4]oxazepine |

TABLE 1-continued

| Cpd. No. | Structure | Name |
|---|---|---|
| 120 | 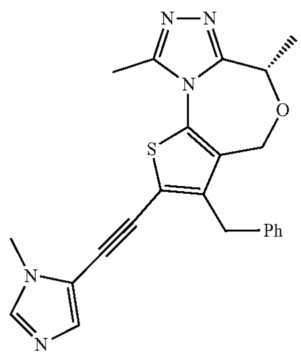 [SMILES: Cc1nnc2n1-c1sc(C#Cc3cncn3C)c(Cc3ccccc3)c1CO[C@H]2C] | (S)-3-benzyl-6,9-dimethyl-2-((1-methyl-1H-imidazol-5-yl)ethynyl)-4H,6H-thieno[2,3-e][1,2,4]triazolo[3,4-c][1,4]oxazepine |
| 121 | 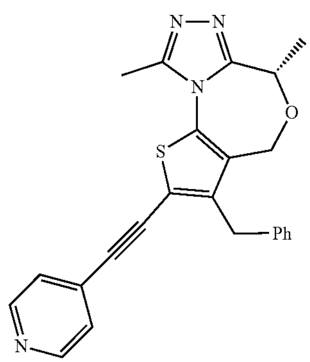 [SMILES: Cc1nnc2n1-c1sc(C#Cc3ccncc3)c(Cc3ccccc3)c1CO[C@H]2C] | (S)-3-benzyl-6,9-dimethyl-2-(pyridin-4-ylethynyl)-4H,6H-thieno[2,3-e][1,2,4]triazolo[3,4-c][1,4]oxazepine |
| 122 | 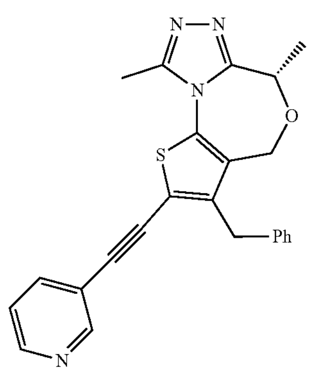 [SMILES: Cc1nnc2n1-c1sc(C#Cc3cccnc3)c(Cc3ccccc3)c1CO[C@H]2C] | (S)-3-benzyl-6,9-dimethyl-2-(pyridin-3-ylethynyl)-4H,6H-thieno[2,3-e][1,2,4]triazolo[3,4-c][1,4]oxazepine |
| 123 | 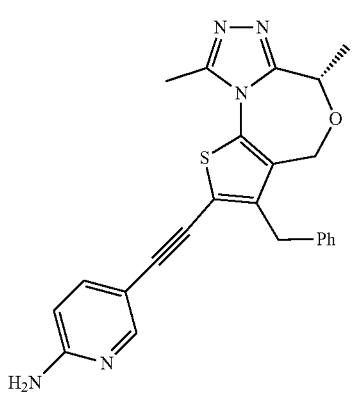 [SMILES: Cc1nnc2n1-c1sc(C#Cc3ccc(N)nc3)c(Cc3ccccc3)c1CO[C@H]2C] | (S)-5-((3-benzyl-6,9-dimethyl-4H,6H-thieno[2,3-e][1,2,4]triazolo[3,4-c][1,4]oxazepin-2-yl)ethynyl)pyridin-2-amine |

TABLE 1-continued

| Cpd. No. | Structure | Name |
|---|---|---|
| 124 | 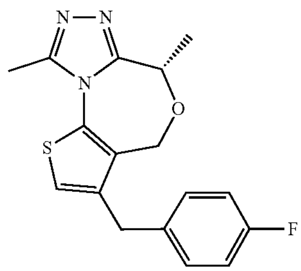 [SMILES: Cc1nnc2n1-c1scc(Cc3ccc(F)cc3)c1CO[C@H]2C] | (S)-3-(4-fluorobenzyl)-6,9-dimethyl-4H,6H-thieno[2,3-e][1,2,4]triazolo[3,4-c][1,4]oxazepine |
| 125 | 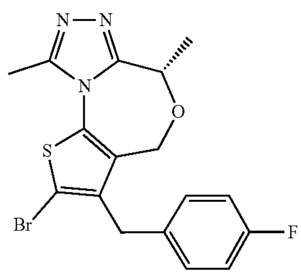 [SMILES: Cc1nnc2n1-c1sc(Br)c(Cc3ccc(F)cc3)c1CO[C@H]2C] | (S)-2-bromo-3-(4-fluorobenzyl)-6,9-dimethyl-4H,6H-thieno[2,3-e][1,2,4]triazolo[3,4-c][1,4]oxazepine |
| 126 | 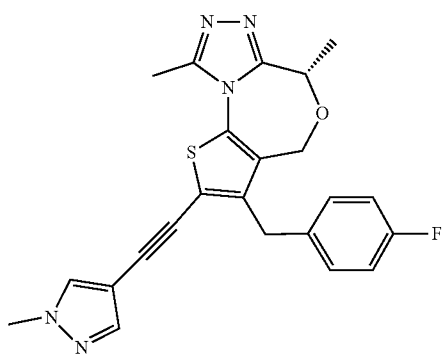 [SMILES: Cc1nnc2n1-c1sc(C#Cc3cnn(C)c3)c(Cc3ccc(F)cc3)c1CO[C@H]2C] | (S)-3-(4-fluorobenzyl)-6,9-dimethyl-2-((1-methyl-1H-pyrazol-4-yl)ethynyl)-4H,6H-thieno[2,3-e][1,2,4]triazolo[3,4-c][1,4]oxazepine |
| 127 | 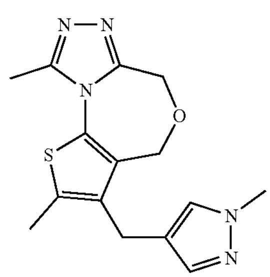 | 2,9-dimethyl-3-((1-methyl-1H-pyrazol-4-yl)methyl)-4H,6H-thieno[2,3-e][1,2,4]triazolo[3,4-c][1,4]oxazepine |
| 128 | 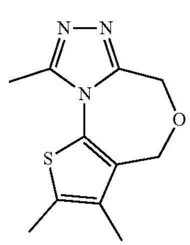 [SMILES: Cc1sc2c(c1C)COCc1nnc(C)n1-2] | 2,3,9-trimethyl-4H,6H-thieno[2,3-e][1,2,4]triazolo[3,4-c][1,4]oxazepine |

TABLE 1-continued

| Cpd. No. | Structure | Name |
|---|---|---|
| 129 | 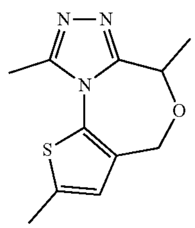 | 2,6,9-trimethyl-4H,6H-thieno[2,3-e][1,2,4]triazolo[3,4-c][1,4]oxazepine |
| 130 | 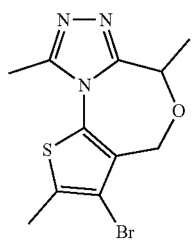 | 3-bromo-2,6,9-trimethyl-4H,6H-thieno[2,3-e][1,2,4]triazolo[3,4-c][1,4]oxazepine |
| 131 | 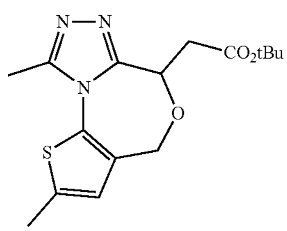 [SMILES: Cc1cc2c(s1)-n1c(C)nnc1C(CC(=O)OC(C)(C)C)OC2] | tert-butyl 2-(2,9-dimethyl-4H,6H-thieno[2,3-e][1,2,4]triazolo[3,4-c][1,4]oxazepin-6-yl)acetate |
| 132 | 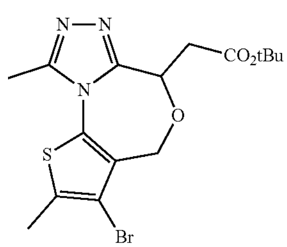 [SMILES: Cc1sc2c(c1Br)COC(CC(=O)OC(C)(C)C)c1nnc(C)n1-2] | tert-butyl 2-(3-bromo-2,9-dimethyl-4H,6H-thieno[2,3-e][1,2,4]triazolo[3,4-c][1,4]oxazepin-6-yl)acetate |
| 133 | 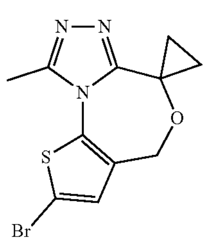 [SMILES: Cc1nnc2n1-c1sc(Br)cc1COC21CC1] | 2'-bromo-9'-methyl-4'H-spiro[cyclopropane-1,6'-thieno[2,3-e][1,2,4]triazolo[3,4-c][1,4]oxazepine] |
| 134 | 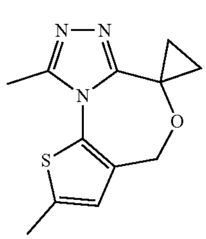 [SMILES: Cc1cc2c(s1)-n1c(C)nnc1C1(CC1)OC2] | 2',9'-dimethyl-4'H-spiro[cyclopropane-1,6'-thieno[2,3-e][1,2,4]triazolo[3,4-c][1,4]oxazepine] |

TABLE 1-continued

| Cpd. No. | Structure | Name |
|---|---|---|
| 135 | 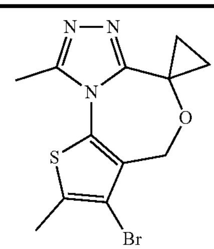 | 3'-bromo-2',9'-dimethyl-4'H-spiro[cyclopropane-1,6'-thieno[2,3-e][1,2,4]triazolo[3,4-c][1,4]oxazepine] |
| 136 | 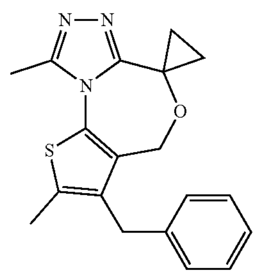 [SMILES: Cc1sc2c(c1Cc1ccccc1)COC1(CC1)c1nnc(C)n1-2] | 3'-benzyl-2',9'-dimethyl-4'H-spiro[cyclopropane-1,6'-thieno[2,3-e][1,2,4]triazolo[3,4-c][1,4]oxazepine] |
| 137 | 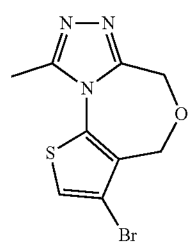 | 3-bromo-9-methyl-4H,6H-thieno[2,3-e][1,2,4]triazolo[3,4-c][1,4]oxazepine |
| 138 | 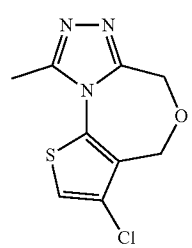 | 3-chloro-9-methyl-4H,6H-thieno[2,3-e][1,2,4]triazolo[3,4-c][1,4]oxazepine |
| 139 | 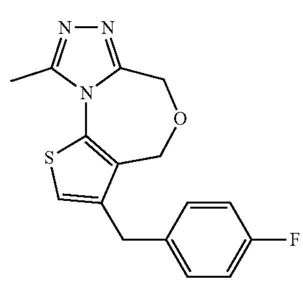 [SMILES: Cc1nnc2n1-c1scc(Cc3ccc(F)cc3)c1COC2] | 3-(4-fluorobenzyl)-9-methyl-4H,6H-thieno[2,3-e][1,2,4]triazolo[3,4-c][1,4]oxazepine |
| 140 | 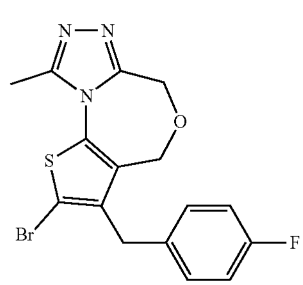 [SMILES: Cc1nnc2n1-c1sc(Br)c(Cc3ccc(F)cc3)c1COC2] | 2-bromo-3-(4-fluorobenzyl)-9-methyl-4H,6H-thieno[2,3-e][1,2,4]triazolo[3,4-c][1,4]oxazepine |

TABLE 1-continued

| Cpd. No. | Structure | Name |
|---|---|---|
| 141 | 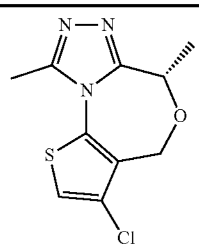 | (S)-3-chloro-6,9-dimethyl-4H,6H-thieno[2,3-e][1,2,4]triazolo[3,4-c][1,4]oxazepine |
| 144 | 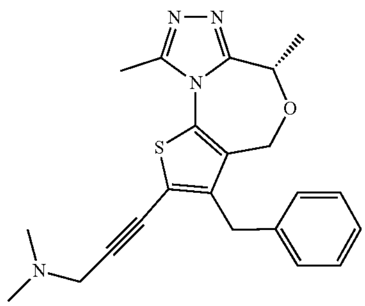 | (S)-3-(3-benzyl-6,9-dimethyl-4H,6H-thieno[2,3-e][1,2,4]triazolo[3,4-c][1,4]oxazepin-2-yl)-N,N-dimethylprop-2-yn-1-amine |
| 145 | 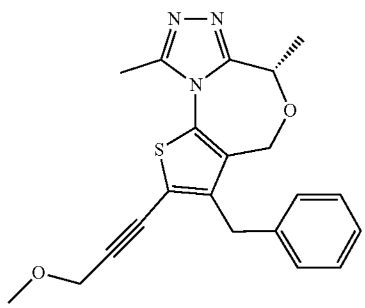 [SMILES: COCC#Cc1sc2c(c1Cc1ccccc1)CO[C@@H](C)c1nnc(C)n1-2] | (S)-3-benzyl-2-(3-methoxyprop-1-yn-1-yl)-6,9-dimethyl-4H,6H-thieno[2,3-e][1,2,4]triazolo[3,4-c][1,4]oxazepine |
| 146 | 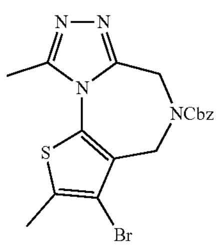 [SMILES: Cc1sc2c(c1Br)CN(C(=O)OCc1ccccc1)Cc1nnc(C)n1-2] | benzyl 3-bromo-2,9-dimethyl-4H-thieno[3,2-f][1,2,4]triazolo[4,3-a][1,4]diazepine-5(6H)-carboxylate |
| 147 | 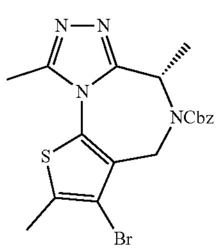 | benzyl (S)-3-bromo-2,6,9-trimethyl-4H-thieno[3,2-f][1,2,4]triazolo[4,3-a][1,4]diazepine-5(6H)-carboxylate |
| 148 | 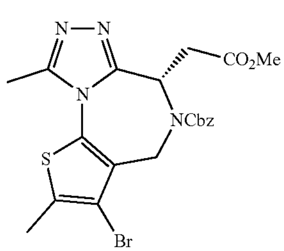 [SMILES: COC(=O)C[C@H]1c2nnc(C)n2-c2sc(C)c(Br)c2CN1C(=O)OCc1ccccc1] | benzyl (S)-3-bromo-6-(2-methoxy-2-oxoethyl)-2,9-dimethyl-4H-thieno[3,2-f][1,2,4]triazolo[4,3-a][1,4]diazepine-5(6H)-carboxylate |

TABLE 1-continued

| Cpd. No. | Structure | Name |
|---|---|---|
| 149 | 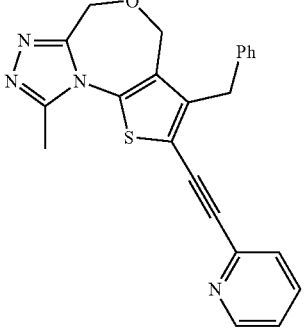 | 3-benzyl-9-methyl-2-(pyridin-2-ylethynyl)-4H,6H-thieno[2,3-e][1,2,4]triazolo[3,4-c][1,4]oxazepine |
| 150 | 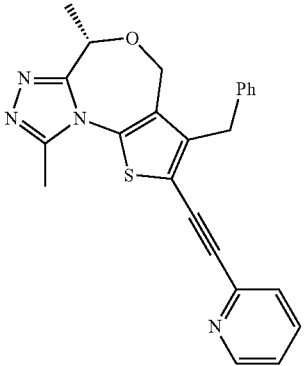 [SMILES: Cc1nnc2n1-c1sc(C#Cc3ccccn3)c(Cc3ccccc3)c1CO[C@H]2C] | (S)-3-benzyl-6,9-dimethyl-2-(pyridin-2-ylethynyl)-4H,6H-thieno[2,3-e][1,2,4]triazolo[3,4-c][1,4]oxazepine |
| 151 | 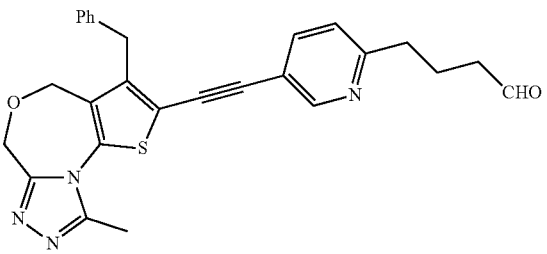 [SMILES: Cc1nnc2n1-c1sc(C#Cc3ccc(CCCC=O)nc3)c(Cc3ccccc3)c1COC2] | 4-(5-((3-benzyl-9-methyl-4H,6H-thieno[2,3-e][1,2,4]triazolo[3,4-c][1,4]oxazepin-2-yl)ethynyl)pyridin-2-yl)butanal |
| 152 | 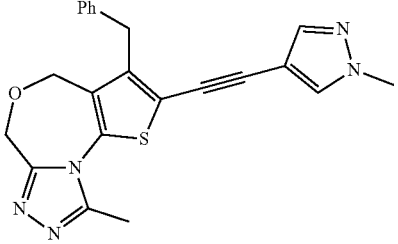 [SMILES: Cc1nnc2n1-c1sc(C#Cc3cnn(C)c3)c(Cc3ccccc3)c1COC2] | 3-benzyl-9-methyl-2-((1-methyl-1H-pyrazol-4-yl)ethynyl)-4H,6H-thieno[2,3-e][1,2,4]triazolo[3,4-c][1,4]oxazepine |
| 153 | 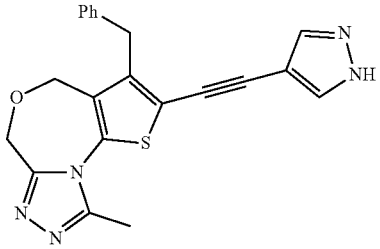 [SMILES: Cc1nnc2n1-c1sc(C#Cc3cn[nH]c3)c(Cc3ccccc3)c1COC2] | 2-((1H-pyrazol-4-yl)ethynyl)-3-benzyl-9-methyl-4H,6H-thieno[2,3-e][1,2,4]triazolo[3,4-c][1,4]oxazepine |

TABLE 1-continued

| Cpd. No. | Structure | Name |
|---|---|---|
| 154 | 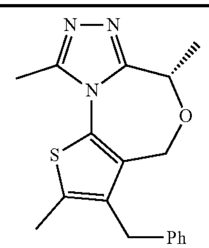 | (S)-3-benzyl-2,6,9-trimethyl-4H,6H-thieno[2,3-e][1,2,4]triazolo[3,4-c][1,4]oxazepine |

Compounds of the Disclosure inhibit BET bromodomains and are useful in the treatment of a variety of diseases and conditions. In particular, Compounds of the Disclosure are useful in methods of treating a disease or condition wherein inhibition of BET bromodomains provides a benefit, for example, cancers and proliferative diseases. Methods of the disclosure comprise administering a therapeutically effective amount of a Compound of the Disclosure to an individual in need thereof. The present methods also encompass administering a second therapeutic agent to the individual in addition to the Compound of the Disclosure. The second therapeutic agent is selected from drugs known as useful in treating the disease or condition afflicting the individual in need thereof, e.g., a chemotherapeutic agent and/or radiation known as useful in treating a particular cancer.

Salts, hydrates, and solvates of the Compounds of the Disclosure can also be used in the methods disclosed herein. The present disclosure further includes all possible stereoisomers and geometric isomers of Compounds of the Disclosure to include both racemic compounds and optically active isomers. When a Compound of the Disclosure is desired as a single enantiomer, it can be obtained either by resolution of the final product or by stereospecific synthesis from either isomerically pure starting material or use of achiral auxiliary reagent, for example, see Z. Ma et al., *Tetrahedron: Asymmetry,* 8(6), pages 883-888 (1997). Resolution of the final product, an intermediate, or a starting material can be achieved by any suitable method known in the art. Additionally, in situations where tautomers of the Compounds of the Disclosure are possible, the present disclosure is intended to include all tautomeric forms of the compounds.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with an acid having a suitable cation. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1):Article 12 (2004), and A. L. Bingham et al., *Chem.*

Commun. 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure provides Compounds of the Disclosure as BET bromodomain inhibitors for the treatment of a variety of diseases and conditions wherein inhibition of BET bromodomains has a beneficial effect. Compounds of the Disclosure typically have a binding affinity ($IC_{50}$) to BET bromodomains of less than 100 µM, e.g., less than 50 µM, less than 25 µM, and less than 5 µM, less than about 1 µM, less than about 0.5 µM, or less than about 0.1 µM. In one embodiment, the present disclosure relates to a method of treating an individual suffering from a disease or condition wherein inhibition of the BET bromodomains provides a benefit comprising administering a therapeutically effective amount of a Compound of the Disclosure to an individual in need thereof.

Since Compounds of the Disclosure are inhibitors of one or more BET bromodomains, a number of diseases and conditions mediated by BET bromodomain proteins can be treated by employing these compounds. The present disclosure is thus directed generally to a method for treating a condition or disorder responsive to inhibition of BRD2, BRD3, BRD4, BRD-t, or an isoform or mutant thereof, in an animal, e.g., a human, suffering from, or at risk of suffering from, the condition or disorder, the method comprising administering to the animal an effective amount of one or more Compounds of the Disclosure.

The present disclosure is further directed to a method of inhibiting BET bromodomains in an animal in need thereof, said method comprising administering to the animal an effective amount of at least one Compound of the Disclosure.

In another embodiment, the disclosure is directed to a method of treating a patient, comprising administering to the patient a therapeutically effective amount of a Compound of the Disclosure, or a pharmaceutically acceptable salt or hydrate thereof, wherein the patient has cancer, a chronic autoimmune disorder, an inflammatory condition, a proliferative disorder, sepsis, or a viral infection.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent useful in the treatment of diseases and conditions wherein inhibition of BET bromodomains provides a benefit, packaged separately or together, and an insert having instructions for using these active agents.

In one embodiment, a Compound of the Disclosure is administered in conjunction with a second therapeutic agent useful in the treatment of a disease or condition wherein inhibition of BET bromodomains provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human patient is treated with a Compound of the Disclosure, or a pharmaceutical composition comprising a Compound of the Disclosure, wherein the compound is administered in an amount sufficient to inhibit BET bromodomain activity in the patient.

In one embodiment, the disease to be treated by the Compound of the Disclosure is cancer. Examples of treatable cancers include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In another embodiment, the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the BET bromodomain inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a Compound of the Disclosure, or a composition containing the same, can be from about 1 ng/kg to about 200 mg/kg, about 1 μg/kg to about 100 mg/kg, or about 1 mg/kg to about 50 mg/kg. The dosage of a composition can be at any dosage including, but not limited to, about 1 g/kg. The dosage of a composition may be at any dosage including, but not limited to, about 1 μg/kg, about 10 μg/kg, about 25 μg/kg, about 50 μg/kg, about 75 ag/kg, about 100 g/kg, about 125 ag/kg, about 150 ag/kg, about 175 μg/kg, about 200 g/kg, about 225 μg/kg, about 250 μg/kg, about 275 μg/kg, about 300 g/kg, about 325 g/kg, about 350 μg/kg, about 375 μg/kg, about 400 μg/kg, about 425 g/kg, about 450 g/kg, about 475 μg/kg, about 500 μg/kg, about 525 μg/kg, about 550 g/kg, about 575 g/kg, about 600 μg/kg, about 625 μg/kg, about 650 μg/kg, about 675 g/kg, about 700 g/kg, about 725 μg/kg, about 750 μg/kg, about 775 μg/kg, about 800 g/kg, about 825 g/kg, about 850 μg/kg, about 875 μg/kg, about 900 μg/kg, about 925 μg/kg, about 950 g/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketokonazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DM, cetuximab, bevacizumab, rituximab, PR064553, and 2C4. The term "antibody" includes intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransylcytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidineamine derivatives, such as imatinib, SU101, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, CI-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or $CDCl_{2-5}$, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a present BET bromodomain inhibitor, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a present BET bromodomain inhibitor also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution.

The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

The term "BET bromodomain" as used herein means one or more of BRD2, BRD3, BRD4, and BRD-t, or an isoform or mutant thereof.

The term "a disease or condition wherein inhibition of BET bromodomains provides a benefit" pertains to a condition in which at least one of BRD2, BRD3, BRD4, or BRD-t, and/or an action of at least one of BRD2, BRD3, BRD4, and BRD-t, is important or necessary, e.g., for the onset, progress, expression of that disease or condition, or a disease or a condition which is known to be treated by a BET bromodomain inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a BET bromodomain for any particular cell type, for example, by assays which conveniently can be used to assess the activity of particular compounds.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, a Compound of the Disclosure is a potent inhibitor of BET bromodomains and can be used in treating diseases and conditions wherein inhibition of BET bromodomains provides a benefit.

As used herein, the terms "treat," "treating," "treatment," refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a Compound of the Disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce BET bromodomain signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

In the present disclosure, the term "leaving group" refers to an atom or group of atoms that becomes detached from an atom or group of atoms in what is considered to be the residual or main part of the molecule in a specified reaction. Non-limiting exemplary leaving groups include —Cl, —I, —Br, —OTf, —OMs, and —OTs.

In the present disclosure, the term "halo" as used by itself or as part of another group refers to —Cl, —F, —Br, or —I.

In the present disclosure, the term "nitro" as used by itself or as part of another group refers to —NO$_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, and so on. In one embodiment, the alkyl group is a straight chain $C_{1-10}$ alkyl. In another embodiment, the alkyl group is a branched chain $C_{3-10}$ alkyl. In another embodiment, the alkyl group is a straight chain $C_{1-6}$ alkyl. In another embodiment, the alkyl group is a branched chain $C_{3-6}$ alkyl. In another embodiment, the alkyl group is a straight chain $C_{1-4}$ alkyl. In another embodiment, the alkyl group is a branched chain $C_{3-4}$ alkyl group. In another embodiment, the alkyl group is a straight or branched chain $C_{3-4}$ alkyl group. Non-limiting exemplary $C_{1-10}$ alkyl groups include methyl, ethyl, propyl, isopropyl, butyl, sec-butyl, tert-butyl, isobutyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl.

In the present disclosure, the term "optionally substituted alkyl" as used by itself or as part of another group refers to an alkyl that is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, and cycloalkyl. In another embodiment, the optionally substituted alkyl is substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, cycloalkyl, and —CHO. In one embodiment, the optionally substituted alkyl is substituted with two substituents. In another embodiment, the optionally substituted alkyl is substituted with one substituent. Non-limiting exemplary substituted alkyl groups include —$CH_2CH_2NO_2$, —$CH_2SO_2CH_3$, $CH_2CH_2CO_2H$, —$CH_2CH_2SO_2CH_3$, —$CH_2CH_2COPh$, and —$CH_2C_6H_{11}$. Non-limiting exemplary substituted alkyl groups also include —$CH_2CH_2CHO$, —$CH_2CH_2CH_2CHO$, and —$CH_2CH_2CH_2CH_2CHO$.

In the present disclosure, the term "cycloalkyl" as used by itself or as part of another group refers to unsubstituted saturated and partially unsaturated, e.g., containing one or two double bonds, cyclic aliphatic hydrocarbons containing one to three rings having from three to twelve carbon atoms, i.e., $C_{3-12}$ cycloalkyl, or the number of carbons designated. In one embodiment, the cycloalkyl group has two rings. In one embodiment, the cycloalkyl group has one ring. In another embodiment, the cycloalkyl is saturated. In another embodiment, the cycloalkyl is unsaturated. In another embodiment, the cycloalkyl group is a $C_{3-8}$ cycloalkyl group. In another embodiment, the cycloalkyl group is a $C_{3-7}$ cycloalkyl group. In another embodiment, the cycloalkyl group is a $C_{5-7}$ cycloalkyl group. In another embodiment, the cycloalkyl group is a $C_{3-6}$ cycloalkyl group. The term "cycloalkyl" includes groups wherein a ring —$CH_2$— is replaced with a —C(=O)—. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, cyclohexenyl, and cyclopentanone.

In the present disclosure, the term "optionally substituted cycloalkyl" as used by itself or as part of another group refers to a cycloalkyl that is either unsubstituted or substituted with one, two, or three substituents independently chosen from halo, nitro, cyano, hydroxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted cycloalkyl is substituted with two substituents. In another embodiment, the optionally substituted cycloalkyl is substituted with one substituent. In another embodiment, the optionally substituted cycloalkyl is substituted with one optionally substituted phenyl, e.g.,

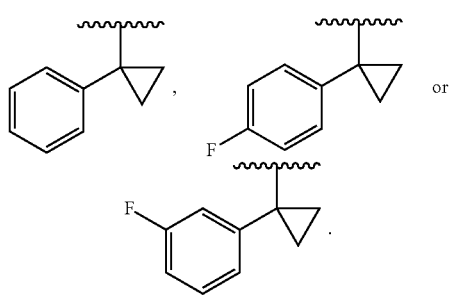

The term optionally substituted cycloalkyl includes cycloalkyl groups having a fused optionally substituted aryl, e.g., phenyl, or fused optionally substituted heteroaryl, e.g., pyridyl. An optionally substituted cycloalkyl having a fused optionally substituted aryl or fused optionally substituted heteroaryl group may be attached to the remainder of the molecule at any available carbon atom on the cycloalkyl ring. In one embodiment, the optionally substituted cycloalkyl group is a 5-, 6-, or 7-membered cycloalkyl group having a fused phenyl group, wherein the phenyl optionally substituted with one, two, or three substituents. Non-limiting examples include:

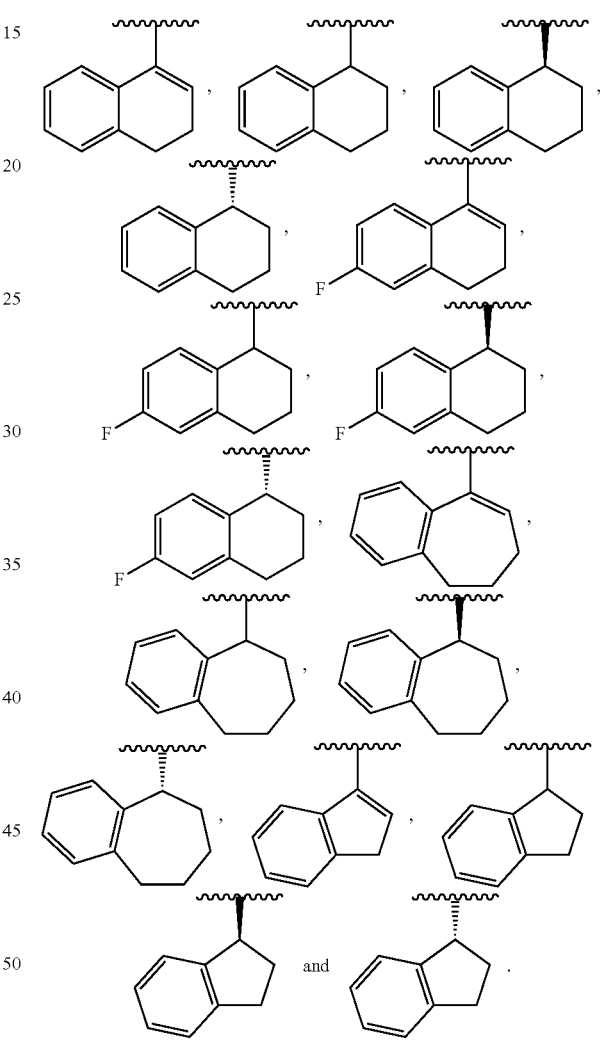

In the present disclosure, the term "alkenyl" as used by itself or as part of another group refers to an alkyl containing one, two or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group refers to an alkenyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, heteroaryl, and optionally substituted heterocyclo.

In the present disclosure, the term "alkynyl" as used by itself or as part of another group refers to an alkyl containing one to three carbon-to-carbon triple bonds. In one embodiment, the alkynyl has one carbon-to-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part of another group refers to an alkynyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, optionally substituted aryl, optionally substituted heteroaryl, heterocyclo, and —Si(R)$_3$, wherein R is selected from the group consisting of alkyl and aryl.

In the present disclosure, the term "haloalkyl" as used by itself or as part of another group refers to an alkyl substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "hydroxyalkyl" as used by itself or as part of another group refers to an alkyl substituted with one two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups, e.g.,

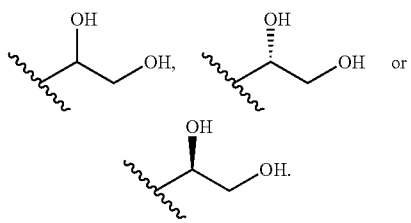

In another embodiment, the hydroxyalkyl group is a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

In the present disclosure, the term "(cycloalkyl)alkyl," as used by itself or as part of another group refers to an alkyl substituted with an optionally substituted cycloalkyl group. In one embodiment, the (cycloalkyl) alkyl, is a "($C_{3-6}$ cycloalkyl)$C_{1-4}$ alkyl," i.e., a $C_{1-4}$ alkyl substituted with an unsubstituted or substituted $C_{3-6}$ cycloalkyl. Non-limiting exemplary (cycloalkyl) alkyl groups include

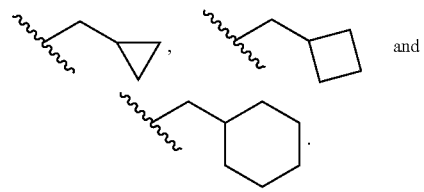

In the present disclosure, the term "alkoxy" as used by itself or as part of another group refers to an optionally substituted alkyl, optionally substituted cycloalkyl, optionally substituted alkenyl, or optionally substituted alkynyl attached to a terminal oxygen atom. In one embodiment, the alkoxy group is a $C_{1-6}$ alkyl attached to a terminal oxygen atom. In another embodiment, the alkoxy group is chosen from a $C_{1-4}$ alkyl attached to a terminal oxygen atom, e.g., methoxy, ethoxy, tert-butoxy, —OCH$_2$CH$_2$C≡CH, and —OCH$_2$CH$_2$CH$_2$C≡CH.

In the present disclosure, the term "alkylthio" as used by itself or as part of another group refers to a sulfur atom substituted by an optionally substituted alkyl group. In one embodiment, the alkylthio group is a $C_{1-4}$ alkylthio group. Non-limiting exemplary alkylthio groups include —SCH$_3$, and —SCH$_2$CH$_3$.

In the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

In the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryl" as used by itself or as part of another group refers to unsubstituted monocyclic or bicyclic aromatic ring systems having from six to fourteen carbon atoms, i.e., a $C_{6-14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is a phenyl or naphthyl.

In the present disclosure, the term "optionally substituted aryl" as used herein by itself or as part of another group refers to an aryl that is either unsubstituted or substituted with one to five substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl includes phenyl groups having fused optionally substituted cycloalkyl and fused optionally substituted heterocyclo rings. An optionally substituted aryl having a fused optionally substituted cycloalkyl and fused optionally substituted heterocyclo is attached to the remainder of the molecule at any available carbon atom on the aryl ring. Non-limiting examples include:

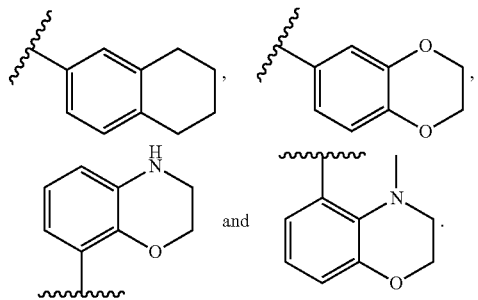

In the present disclosure, the term "aryloxy" as used by itself or as part of another group refers to an optionally substituted aryl attached to a terminal oxygen atom. A non-limiting exemplary aryloxy group is PhO—.

In the present disclosure, the term "aralkyloxy" as used by itself or as part of another group refers to an aralkyl group attached to a terminal oxygen atom. A non-limiting exemplary aralkyloxy group is PhCH$_2$O—.

In the present disclosure, the term "heteroalkyl" as used by itself or part of another group refers to stable straight or branched chain hydrocarbon radicals containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. In one embodiment, the heteroalkyl contains one oxygen and one nitrogen atom. In one embodiment, the heteroalkyl contains two nitrogen atoms. Non-limiting exemplary heteroalkyl groups include —CH$_2$OCH$_2$CH$_2$OCH$_3$, —OCH$_2$CH$_2$OCH$_2$CH$_2$OCH$_3$, —CH$_2$NHCH$_2$CH$_2$OCH$_2$, —OCH$_2$CH$_2$NH$_2$, —NHCH$_2$CH$_2$N(H)CH$_3$, —NHCH$_2$CH$_2$OCH$_3$ and —OCH$_2$CH$_2$OCH$_3$.

In the present disclosure, the term "heteroaryl" or "heteroaromatic" refers to unsubstituted monocyclic and bicyclic aromatic ring systems having 5 to 14 ring atoms, i.e., a 5- to 14-membered heteroaryl, wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl is a 5- or 6-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), or indazolyl (e.g., 1H-indazol-3-yl). The term "heteroaryl" also includes possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group refers to a heteroaryl that is either unsubstituted or substituted with one to four substituents, e.g., one or two substituents, independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted heteroaryl has one substituent. Any available carbon or nitrogen atom can be substituted. Non-limiting exemplary substituted 5-membered heteroaryl groups include, but are not limited to:

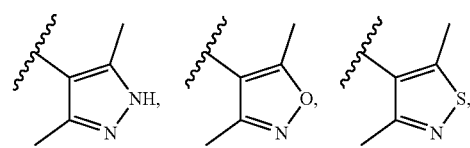

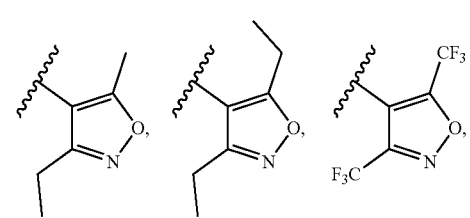

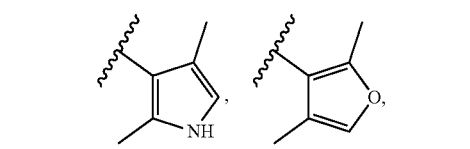

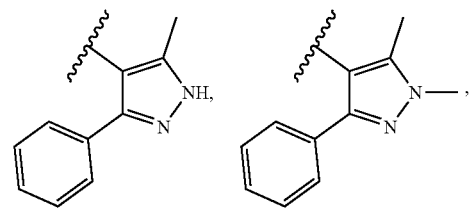

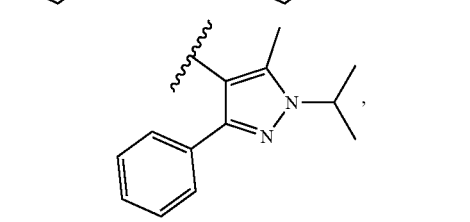

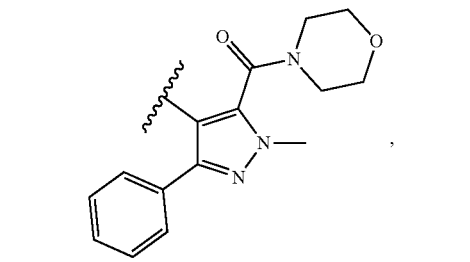

-continued

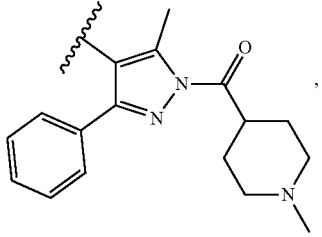

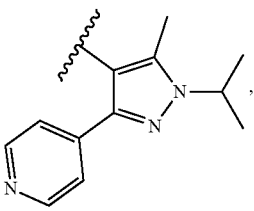

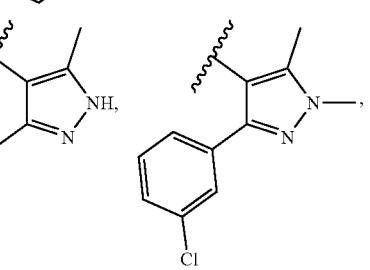

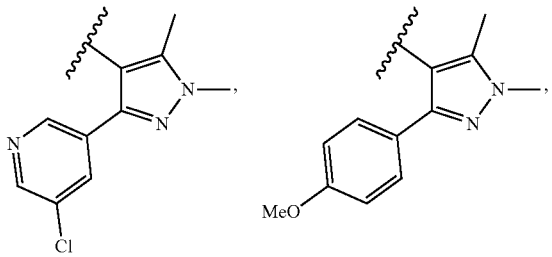

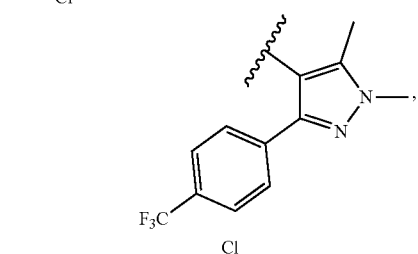

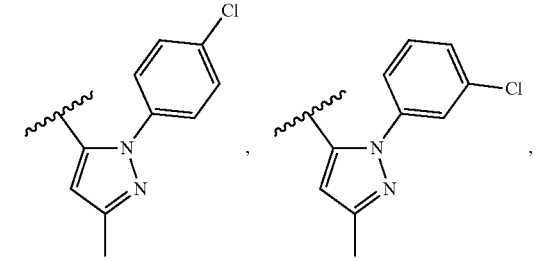

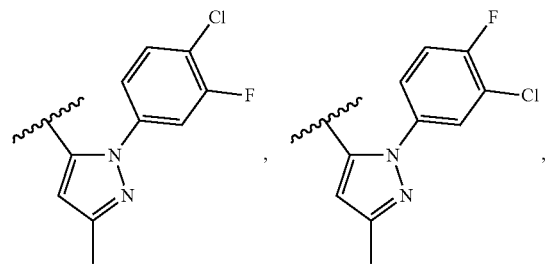

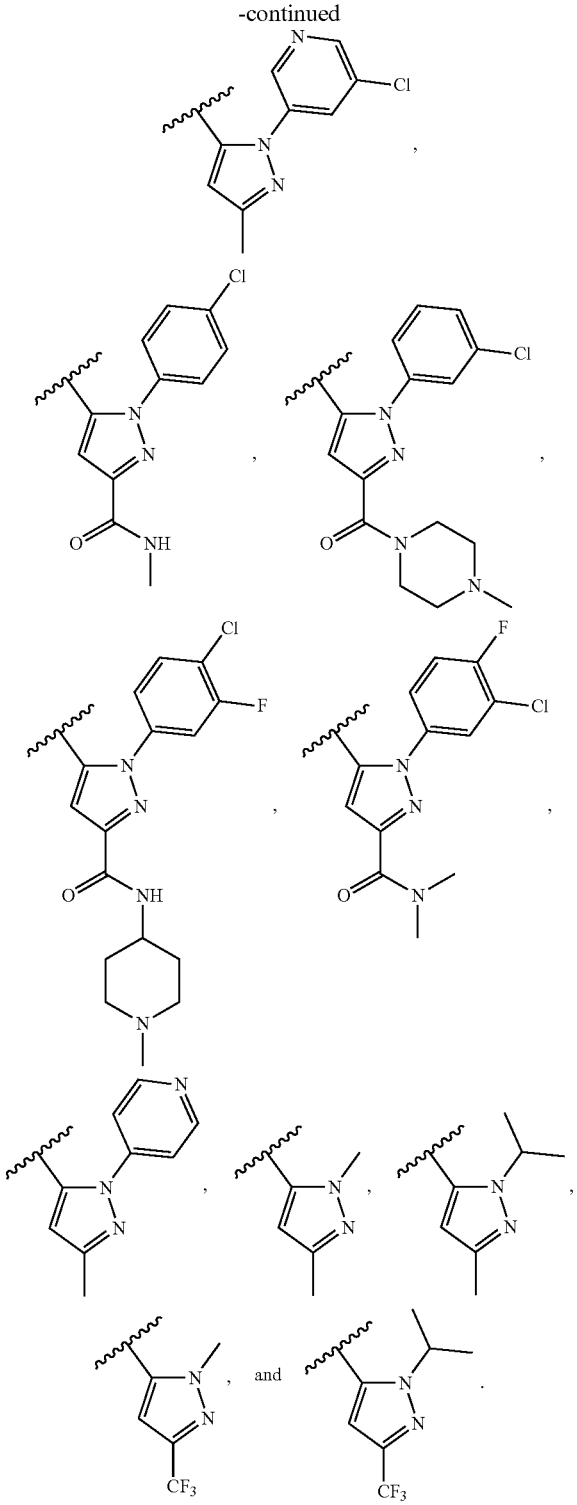

The term optionally substituted heteroaryl includes heteroaryl groups having a fused optionally substituted cycloalkyl or fused optionally substituted heterocyclo group. An optionally substituted heteroaryl having a fused optionally substituted cycloalkyl or fused optionally substituted heterocyclo group may be attached to the remainder of the molecule at any available carbon atom on the heteroaryl ring. Non-limiting examples include:

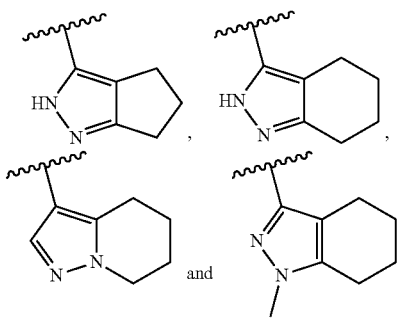

In the present disclosure, the term "heteroarylenyl" as used herein by itself or part of another group refers to a divalent form of an optionally substituted heteroaryl group. In one embodiment, the heteroarylenyl is a 5-membered heteroarylenyl. Non-limiting examples of a 5-membered heteroarylenyl-include:

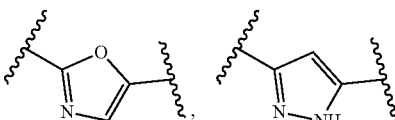
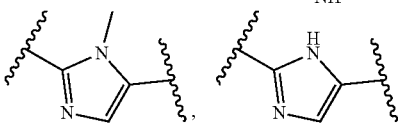
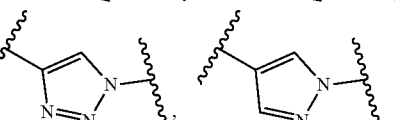
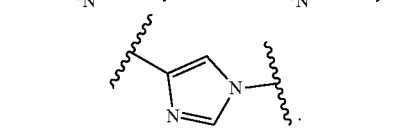

In one embodiment, the heteroarylenyl is a 6-membered heteroarylenyl. Non-limiting examples of a 6-membered heteroarylenyl include:

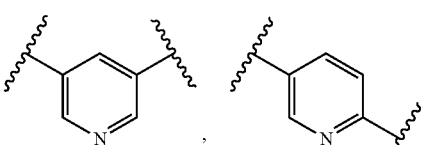
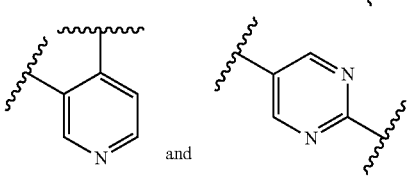

In the present disclosure, the term "heterocycle" or "heterocyclo" as used by itself or as part of another group refers to unsubstituted saturated and partially unsaturated, e.g., containing one or two double bonds, cyclic groups containing one, two, or three rings having from three to fourteen ring members, i.e., a 3- to 14-membered heterocyclo, wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" includes groups wherein a ring —CH$_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" also include a groups having fused optionally substituted aryl groups, e.g., indolinyl, chroman-4-yl. In one embodiment, the heterocyclo group is chosen from a 5- or 6-membered cyclic group containing one ring and one or two oxygen and/or nitrogen atoms. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group refers to a heterocyclo that is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, alkoxycarbonyl, CF$_3$C(=O)—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. Substitution may occur on any available carbon or nitrogen atom, or both. Non-limiting exemplary substituted heterocyclo groups include:

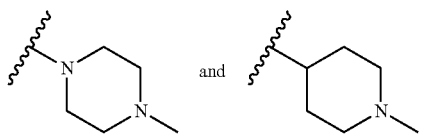

In the present disclosure, the term "amino" as used by itself or as part of another group refers to —NR$^{7a}$R$^{7b}$, wherein R$^{7a}$ and R$^{7b}$ are each independently hydrogen, optionally substituted alkyl, alkynyl, haloalkyl, hydroxyalkyl, optionally substituted cycloalkyl, optionally substituted aryl, optionally substituted heterocyclo, or optionally substituted heteroaryl, or R$^{7a}$ and R$^{7b}$ are taken together to form a 3- to 8-membered optionally substituted heterocyclo. Non-limiting exemplary amino groups include —NH$_2$ and —N(H)(CH$_3$).

In the present disclosure, the term "(amino)alkyl" as used by itself or as part of another group refers to an alkyl group substituted with an amino group. Non-limiting exemplary amino alkyl groups include —CH$_2$CH$_2$NH$_2$, —CH$_2$CH$_2$N(H)CH$_3$, —CH$_2$CH$_2$N(CH$_3$)$_2$, and —CH$_2$N(H)cyclopropyl.

In the present disclosure, the term "carboxamido" as used by itself or as part of another group refers to a radical of formula —C(=O)NR$^{9a}$R$^{9b}$, wherein R$^{9a}$ and R$^{9b}$ are each independently hydrogen, optionally substituted alkyl, hydroxyalkyl, optionally substituted cycloalkyl, optionally substituted aryl, optionally substituted heterocyclo, or optionally substituted heteroaryl, or R$^{9a}$ and R$^{9b}$ taken together with the nitrogen to which they are attached form a 3- to 8-membered optionally substituted heterocyclo group. In one embodiment, R$^{9a}$ and R$^{9b}$ are each independently hydrogen or optionally substituted alkyl. In one embodiment, R$^{9a}$ and R$^{9b}$ are taken together to taken together with the nitrogen to which they are attached form a 3- to 8-membered optionally substituted heterocyclo group. Non-limiting exemplary carboxamido groups include, but are not limited to, —CONH$_2$, —CON(H)CH$_3$, —CON(CH$_3$)$_2$, —CON(H)Ph,

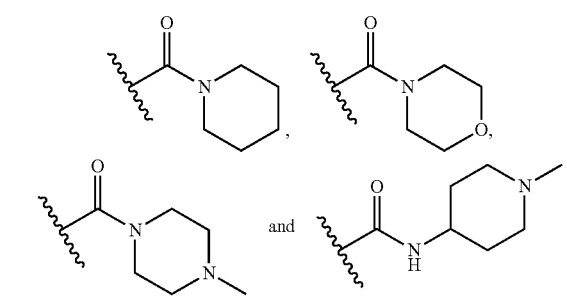

In the present disclosure, the term "sulfonamido" as used by itself or as part of another group refers to a radical of the formula —SO$_2$NR$^{8a}$R$^{8b}$, wherein R$^{8a}$ and R$^{8b}$ are each independently hydrogen, optionally substituted alkyl, or optionally substituted aryl, or R$^{8a}$ and R$^{8b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

In the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

In the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

In the present disclosure, the term "alkoxycarbonyl" as used by itself or as part of another group refers to a carbonyl group, i.e., —C(=O)—, substituted by an alkoxy group. In one embodiment, the alkoxy is a C$_{1-4}$ alkoxy. Non-limiting exemplary alkoxycarbonyl groups include —C(=O)OMe, —C(=O)OEt, and —C(=O)OtBu.

In the present disclosure, the term "(alkoxycarbonyl)alkyl" as used by itself or as part of another group refers to an alkyl group substituted by an alkoxycarbonyl group. Non-limiting exemplary (alkoxycarbonyl)alkyl groups include —CH$_2$C(=O)OMe, —CH$_2$C(=O)OEt, and —CH$_2$C(=O)OtBu.

In the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

In the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

In the present disclosure, the term "mercaptoalkyl" as used by itself or as part of another group refers to any of the above-mentioned alkyl groups substituted by a —SH group.

In the present disclosure, the term "carboxy" as used by itself or as part of another group refers to a radical of the formula —COOH.

In the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

In the present disclosure, the terms "aralkyl" or "arylalkyl" as used by themselves or as part of another group refers to an alkyl substituted with one, two, or three optionally substituted aryl groups. In one embodiment, the optionally substituted aralkyl group is a C$_{1-4}$ alkyl substituted with one optionally substituted C$_5$ or C$_6$ aryl group. In one embodiment, the optionally substituted aralkyl group is a C$_1$ or C$_2$ alkyl substituted with one optionally substituted aryl group. In one embodiment, the optionally substituted aralkyl group is a C$_1$ or C$_2$ alkyl substituted with one optionally substituted phenyl group. Non-limiting exemplary optionally substituted aralkyl groups include benzyl, phenethyl, —CHPh$_2$, —CH$_2$(4-F-Ph), —CH$_2$(4-Me-Ph), —CH$_2$(4-CF$_3$-Ph), and —CH(4-F-Ph)$_2$.

In the present disclosure, the terms "(heterocyclo)alkyl" as used by itself or part of another group refers to an alkyl substituted with an optionally substituted heterocyclo group. In one embodiment, the (heterocyclo)alkyl is a C$_{1-4}$ alkyl substituted with one optionally substituted heterocyclo group. Non-limiting exemplary (heterocyclo)alkyl groups include:

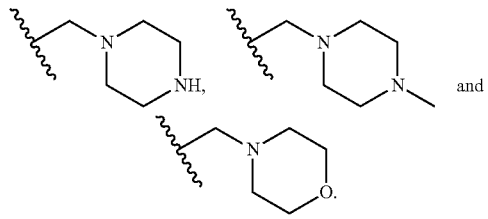

In the present disclosure, the term "(carboxamido)alkyl" as used by itself or as part of another group refers to an alkyl substituted with one or two carboxamido groups. In one embodiment, the (carboxamido)alkyl is a C$_{1-4}$ alkyl substituted with one carboxamido group, i.e., a (carboxamido)C$_{1-4}$ alkyl. In another embodiment, the (carboxamido)alkyl is a C$_{1-4}$ alkyl substituted with two carboxamido groups. Non-limiting exemplary (carboxamido)alkyl groups include —CH$_2$CONH$_2$, —C(H)CH$_3$—CONH$_2$, —CH$_2$CON(H)CH$_3$, and —CH(CO$_2$NH$_2$)CH$_2$CH$_2$CO$_2$NH$_2$.

In the present disclosure, the term "(heteroaryl)alkyl" as used by itself or as part of another group refers to an alkyl substituted with an optionally substituted heteroaryl group. In one embodiment, the (heteroaryl)alkyl is a C$_{1-4}$ alkyl substituted with one optionally substituted heteroaryl group. In another embodiment, the (heteroaryl)alkyl is a C$_1$ alkyl substituted with one optionally substituted heteroaryl group Non-limiting exemplary (heteroaryl)alkyl groups include:

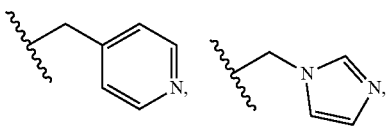

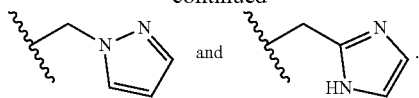

EXAMPLES

Example 1

Synthesis of N-(3-bromo-2-formylphenyl)-2-chloroacetamide (ZBC43)

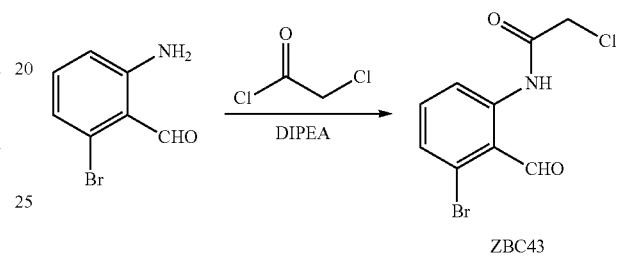

A solution of 2-amino-6-bromobenzaldehyde (50 mg) in DCM (10 mL) was cooled to 0° C. and DIPEA (37 μL) was added slowly. Then 2-chloroacetyl chloride (17 μL) was added dropwise. After stirring at 0° C. for 30 min, the reaction was diluted with DCM, washed with brine, dried, and concentrated on a rotary evaporator. The remaining residues were purified by flash column chromatography on silica gel to afford ZBC43 in 42 mg. ESI-MS calculated for C$_9$H$_8$BrClNO$_2$ [M+H]$^+$=275.9; Observed: 276.0. $^1$H NMR (400 MHz, CDCl$_3$) δ 12.32 (s, 1H), 10.51 (s, 1H), 8.78-8.70 (m, 1H), 7.49-7.40 (m, 2H), 4.22 (s, 2H).

Example 2

Synthesis of N-(3-bromo-2-(hydroxymethyl)phenyl)-2-chloroacetamide(ZBC44)

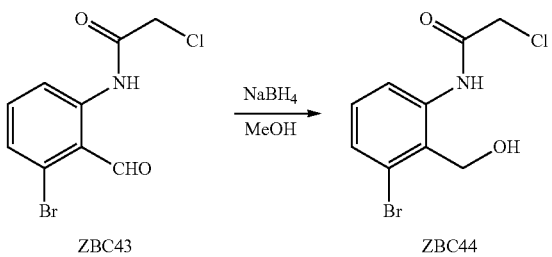 [SMILES: "MeOH" ; O=Cc1c(Br)cccc1NC(=O)CCl ; "NaBH4" ; O=C(CCl)Nc1cccc(Br)c1CO]

A solution of ZBC43 (600 mg) in methanol (30 mL) was cooled to 0° C. and NaBH$_4$ (157 mg) was added slowly. After 30 min, the reaction was finished and the solvent was evaporated under vacuum. The remaining residues was dissolved in ethyl acetate and washed with saturated aqueous sodium bicarbonate. The aqueous layer was extracted with ethyl acetate. The organic layers were combined and washed with brine, dried over anhydrous sodium sulfate, and concentrated on a rotary evaporator. The remaining residues were purified by flash column chromatography on silica gel to afford ZBC44 in 560 mg.

Example 3

Synthesis of 6-bromo-3,5-dihydrobenzo[e][1,4] oxazepin-2(1H)-one (ZBC45)

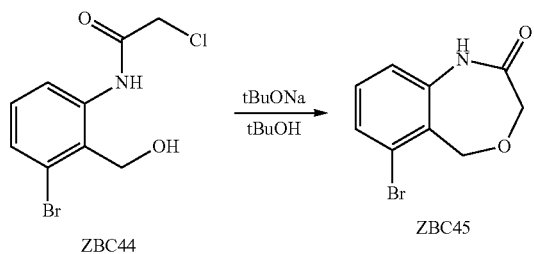 [SMILES: "tBuONa" ; "tBuOH" ; O=C(CCl)Nc1cccc(Br)c1CO ; O=C1COCc2c(Br)cccc2N1]

A suspension of NaOtBu (3 g) in tBuOH (50 mL) was heated at 80° C. until it turns into a clear solution. Then ZBC44 (4.8 g) was added in one portion and the reaction is heated at 80° C. for 15 min. The reaction mixture was cooled, poured into ice-water, and extracted with ethyl acetate. The organic layers were combined and washed with brine, dried over anhydrous sodium sulfate, and concentrated on a rotary evaporator. The remaining residues were purified by flash column chromatography on silica gel to afford ZBC45 in 3.7 g. ESI-MS calculated for $C_9H_9BrNO_2$ [M+H]$^+$=241.98; Observed: 242.14. $^1$H NMR (400 MHz, DMSO) δ 10.29 (s, 1H), 7.39-7.26 (m, 1H), 7.26-7.11 (m, 2H), 4.89 (s, 2H), 4.42 (s, 2H).

Example 4

Synthesis of 7-bromo-1-methyl-4,6-dihydrobenzo[e][1,2,4]triazolo[3,4-c][1,4]oxazepine (Cpd. No. 36)

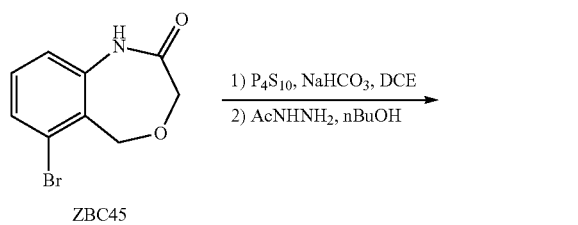

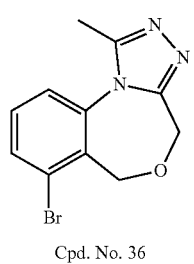

Cpd. No. 36

A suspension of $P_4S_{10}$ (147 mg, 0.66 mmol) and NaHCO$_3$ (70 mg, 0.66 mmol) in 1,2-DCE (5 mL) was stirred for 10 min prior to the addition of ZBC45 (85 mg). The reaction mixture was stirred at 65° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The remaining residues were dissolved in nBuOH (10 ml) and AcNHNH$_2$ (100 mg) was added. The reaction mixture was stirred at 120° C. for 2 h. The reaction mixture was cooled, poured into ice-water, and extracted with ethyl acetate. The organic layers were combined and washed with brine, dried over anhydrous sodium sulfate, and concentrated on a rotary evaporator. The residues were purified by reverse phase HPLC. Cpd. No. 36 was isolated in 45 mg as a salt of CF$_3$CO$_2$H. ESI-MS calculated for $C_{11}H_{11}BrN_3O$ [M+H]$^+$=280.00; Observed: 280.42. $^1$H NMR (400 MHz, MeOD) δ 7.93 (d, J=8.0 Hz, 1H), 7.72 (d, J=7.4 Hz, 1H), 7.62 (t, J=8.1 Hz, 1H), 4.75 (s, 2H), 4.66 (s, 2H), 2.73 (s, 3H).

Example 5

Synthesis of 1-methyl-N-phenyl-4,6-dihydrobenzo[e][1,2,4]triazolo[3,4-c][1,4]oxazepin-7-amine (Cpd. No. 37)

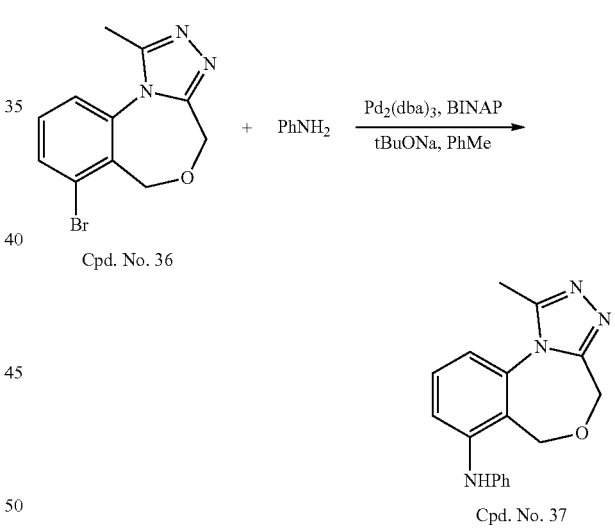

Pd$_2$(dba)$_3$ (18 mg) and BINAP (26 mg) were mixed in anhydrous toluene. And the mixture was heated at reflux for 3-4 minutes. This mixture was transferred into a round-bottom flask containing Cpd. No. 36 (60 mg), PhNH2 (88 mg), tBuONa (60 mg), and toluene (2 mL). The mixture was heated at reflux for overnight before quenching with methanol. The reaction mixture was filtered and the mixture was purified by HPLC to yield Cpd. No. 37 as a CF$_3$CO$_2$H salt in 1.7 mg. ESI-MS calculated for $C_{17}H_{17}N_4O$ [M+H]$^+$=293.14; Observed: 293.45. $^1$H NMR (400 MHz, MeOD) δ 7.52 (t, J=8.1 Hz, 1H), 7.42 (d, J=8.3 Hz, 1H), 7.28 (t, J=7.6 Hz, 2H), 7.21 (d, J=7.8 Hz, 1H), 7.06 (d, J=8.5 Hz, 2H), 6.96 (td, J=7.4, 1.0 Hz, 1H), 4.67 (s, 2H), 4.58 (s, 2H), 2.73 (s, 3H).

Example 6

Synthesis of 7-benzyl-1-methyl-4,6-dihydrobenzo[e][1,2,4]triazolo[3,4-c][1,4]oxazepine (Cpd. No. 38)

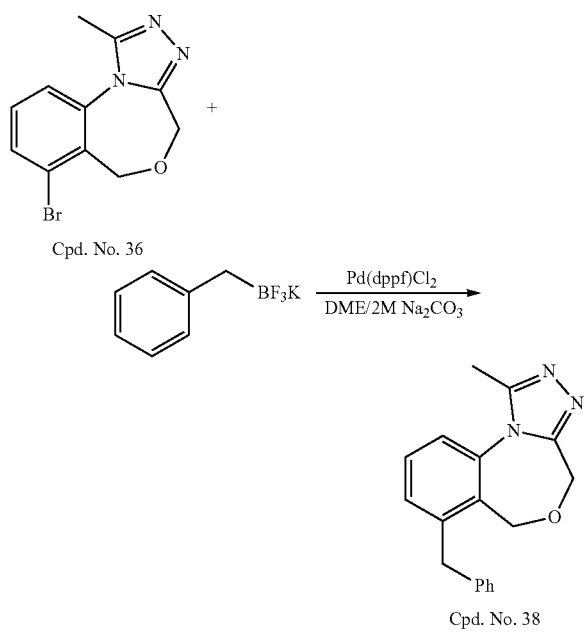

To a round-bottom flask was charged with Cpd. No. 36 (28 mg, 0.1 mmol), potassium benzyltrifluoroborate (40 mg, 0.2 mmol), Pd(dppf)Cl$_2$ (8 mg). Under N$_2$ atmosphere, DME (3 mL) and a solution of Na$_2$CO$_3$ (2.0 M, 1 mL) was added. The reaction mixture was heated at 100° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The residues were purified by reverse phase HPLC. Cpd. No. 38 was isolated in 20 mg as a salt of CF$_3$CO$_2$H. ESI-MS calculated for C$_{18}$H$_{18}$N$_3$O [M+H]$^+$=292.14; Observed: 292.56. $^1$H NMR (400 MHz, MeOD) δ 7.69-7.65 (m, 1H), 7.62-7.54 (m, 2H), 7.29 (t, J=7.3 Hz, 2H), 7.20 (m, 3H), 4.59 (brs, 4H), 4.28 (s, 2H), 2.77 (s, 3H).

Example 7

Synthesis of 1-methyl-7-(phenylthio)-4,6-dihydrobenzo[e][1,2,4]triazolo[3,4-c][1,4]oxazepine (Cpd. No. 39)

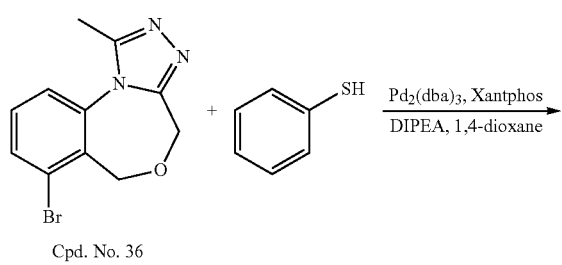

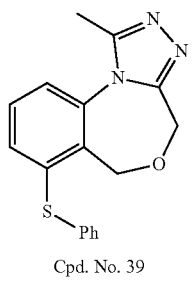

To a round-bottom flask containing Cpd. No. 36 (30 mg), DIPEA (56 µL), and 1,4-dioxane (4 mL) under N$_2$, Pd$_2$(dba)$_3$ (10 mg), Xantphos (12 mg) and PhSH (14 mg) was added. And the mixture was heated at reflux for 4 hour. The reaction mixture was filtered and the mixture was purified by HPLC to yield Cpd. No. 39 as a CF$_3$CO$_2$H salt in 12 mg. ESI-MS calculated for C$_{17}$H$_{16}$N$_3$OS [M+H]$^+$=310.10; Observed: 310.44. $^1$H NMR (400 MHz, MeOD) δ 7.65-7.61 (m, 2H), 7.54-7.50 (m, 1H), 7.42-7.33 (m, 5H), 4.80 (s, 2H), 4.64 (s, 2H), 2.77 (s, 3H).

Example 8

Synthesis of 1-methyl-7-(phenylsulfinyl)-4,6-dihydrobenzo[e][1,2,4]triazolo[3,4-c][1,4]oxazepine (Cpd. No. 41)

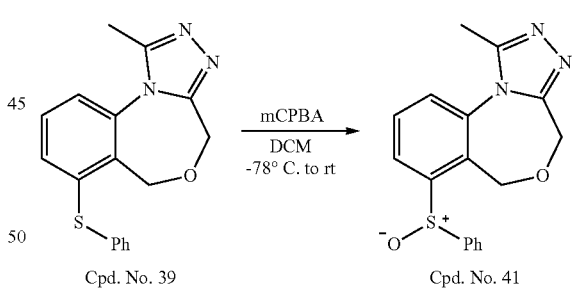

To a round-bottom flask containing Cpd. No. 39 (30 mg) in DCM (4 mL) at −78° C., mCPBA (16 mg) was added. The mixture was allowed to warm to room temperature and was stirred at rt for 2 hour. The reaction mixture was filtered and the mixture was purified by HPLC to yield Cpd. No. 41 as a CF$_3$CO$_2$H salt in 23 mg. ESI-MS calculated for C$_{17}$H$_{16}$N$_3$O$_2$S [M+H]$^+$=326.09; Observed: 326.35. $^1$H NMR (400 MHz, MeOD) δ 8.22 (d, J=8.0 Hz, 1H), 7.96 (td, J=8.0, 1.1 Hz, 1H), 7.87 (d, J=8.0 Hz, 1H), 7.78 (m, 2H), 7.60-7.53 (m, 3H), 4.98 (d, J=13.3 Hz, 1H), 4.73 (d, J=13.5 Hz, 1H), 4.64 (d, J=13.4 Hz, 1H), 4.28 (d, J=13.4 Hz, 1H), 2.72 (s, 3H).

Example 9

Synthesis of 1-methyl-7-(phenylsulfonyl)-4,6-dihydrobenzo[e][1,2,4]triazolo[3,4-c][1,4]oxazepine (Cpd. No. 42)

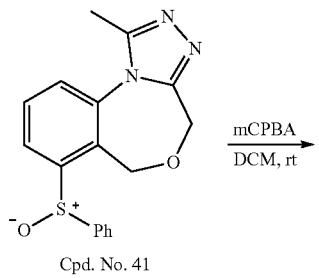

Cpd. No. 41

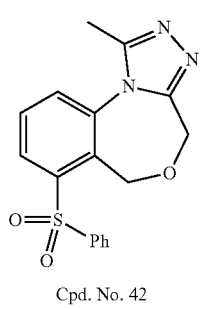

Cpd. No. 42

To a round-bottom flask containing Cpd. No. 41 (30 mg) in DCM (4 mL) at rt, mCPBA (32 mg) was added. The mixture was allowed to warm to room temperature and was stirred at rt for 5 hour. The reaction mixture was filtered and the mixture was purified by HPLC to yield Cpd. No. 42 as a $CF_3CO_2H$ salt in 17 mg. ESI-MS calculated for $C_{17}H_{16}N_3O_3S$ $[M+H]^+$=342.09; Observed: 342.46.

Example 10

Synthesis of 1-methyl-7-(1-phenylvinyl)-4,6-dihydrobenzo[e][1,2,4]triazolo[3,4-c][1,4]oxazepine (Cpd. No. 43)

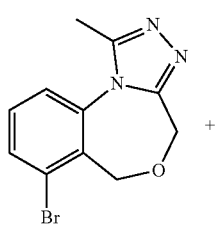

Cpd. No. 36

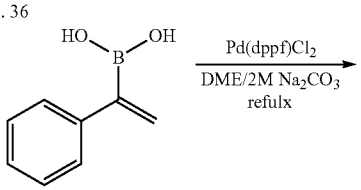

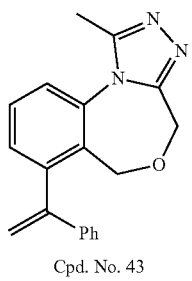

Cpd. No. 43

To a round-bottom flask containing Cpd. No. 36 (28 mg, 0.1 mmol), (1-phenylvinyl)boronic acid (30 mg), Pd(dppf)Cl$_2$ (8 mg), under N$_2$ atmosphere, dimethoxyethane (DME) (6 mL) and a solution of Na$_2$CO$_3$ (2.0 M, 2 mL) was added. The reaction mixture was heated at 100° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The residues were purified by reverse phase HPLC. Cpd. No. 43 was isolated in 17 mg as a salt of CF$_3$CO$_2$H. ESI-MS calculated for $C_{19}H_{18}N_3O$ $[M+H]^+$=304.14; Observed: 304.45. $^1$H NMR (400 MHz, MeOD) δ 7.80-7.68 (m, 2H), 7.52 (dd, J=6.8, 1.7 Hz, 1H), 7.42-7.25 (m, 5H), 6.01 (s, 1H), 5.36 (s, 1H), 4.63 (s, 2H), 4.44 (s, 2H), 2.79 (s, 3H).

Example 11

Synthesis of 7-(1H-inden-3-yl)-1-methyl-4,6-dihydrobenzo[e][1,2,4]triazolo[3,4-c][1,4]oxazepine (Cpd. No. 44)

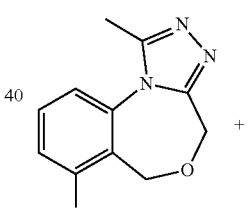

Cpd. No. 36

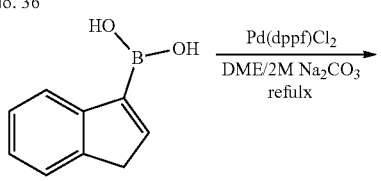

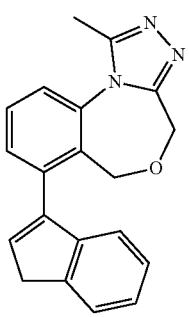

Cpd. No. 44

To a round-bottom flask containing Cpd. No. 36 (28 mg, 0.1 mmol), (1H-inden-3-yl)boronic acid (30 mg), Pd(dppf)Cl$_2$(8 mg), under N$_2$ atmosphere, DME (6 mL) and a solution of Na$_2$CO$_3$ (2.0 M, 2 mL) was added. The reaction mixture was heated at 100° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The residues were purified by reverse phase HPLC. Cpd. No. 44 was isolated in 19 mg as a salt of CF$_3$CO$_2$H. ESI-MS calculated for C$_{20}$H$_{18}$N$_3$O [M+H]$^+$=316.14; Observed: 316.63. $^1$H NMR (400 MHz, MeOD) δ 7.84-7.71 (m, 3H), 7.61-7.56 (m, 1H), 7.34-7.19 (m, 3H), 6.68 (s, 1H), 4.76 (s, 2H), 4.48 (s, 2H), 3.65 (s, 2H), 2.82 (s, 3H).

Example 12

Synthesis of 1-methyl-7-(4-(trifluoromethoxy)benzyl)-4,6-dihydrobenzo[e][1,2,4]triazolo[3,4-c][1,4]oxazepine (Cpd. No. 45)

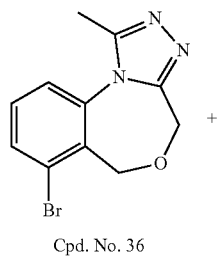

Cpd. No. 36

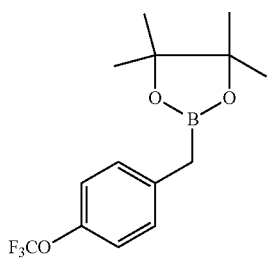

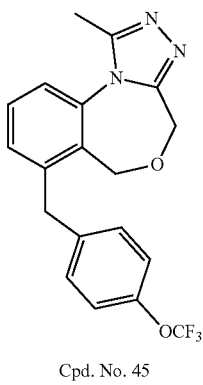

Cpd. No. 45

To a round-bottom flask containing Cpd. No. 36 (28 mg, 0.1 mmol), 4,4,5,5-tetramethyl-2-(4-(trifluoromethoxy)benzyl)-1,3,2-dioxaborolane (55 mg), Pd(dppf)Cl$_2$ (8 mg) under N$_2$ atmosphere, DME (6 mL) and a solution of Na$_2$CO$_3$ (2.0 M, 2 mL) was added. The reaction mixture was heated at 100° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The residues were purified by reverse phase HPLC. Cpd. No. 45 was isolated in 20 mg as a salt of CF$_3$CO$_2$H. ESI-MS calculated for C$_{19}$H$_{17}$F$_3$N$_3$O$_2$ [M+H]$^+$=376.12; Observed: 376.34. $^1$H NMR (400 MHz, MeOD) δ 7.69 (t, J=7.8 Hz, 1H), 7.61 (t, J=8.5 Hz, 2H), 7.30 (d, J=8.5 Hz, 2H), 7.21 (d, J=8.6 Hz, 2H), 4.59 (brs, 4H), 4.32 (s, 2H), 2.77 (s, 3H).

Example 13

Synthesis of 1-methyl-7-(1-phenylethyl)-4,6-dihydrobenzo[e][1,2,4]triazolo[3,4-c][1,4]oxazepine (Cpd. No. 46)

Cpd. No. 43

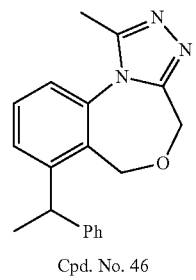

Cpd. No. 46

Cpd. No. 43 (20 mg) was dissolved in a mixture of methanol (4.0 mL). Then 10% Pd/C (4 mg) was added and the reaction mixture was stirred under H$_2$ (1 atm) at room temperature for 10 h. The mixture was filtered and the filtrate was concentrated on a rotary evaporator. The residues were purified by reverse phase HPLC. Cpd. No. 46 was isolated in 16 mg as a salt of CF$_3$CO$_2$H. ESI-MS calculated for C$_{19}$H$_2$N$_3$O [M+H]+=306.16; Observed: 306.41. $^1$H NMR (400 MHz, MeOD) δ 7.64 (t, J=7.8 Hz, 1H), 7.57-7.49 (m, 2H), 7.35-7.15 (m, 5H), 4.67 (q, J=7.1 Hz, 1H), 4.53 (brs, 4H), 2.65 (s, 3H), 1.71 (d, J=6.8 Hz, 3H).

Example 14

Synthesis of 7-(2,3-dihydro-1H-inden-1-yl)-1-methyl-4,6-dihydrobenzo[e][1,2,4]triazolo[3,4-c][1,4]oxazepine (Cpd. No. 47)

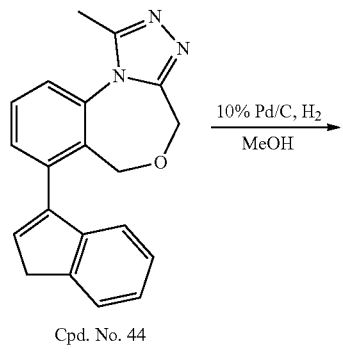

Cpd. No. 44 (20 mg) was dissolved in a mixture of methanol (4.0 mL). Then 10% Pd/C (4 mg) was added and the reaction mixture was stirred under $H_2$ (1 atm) at room temperature for 10 h. The mixture was filtered and the filtrate was concentrated on a rotary evaporator. The residues were purified by reverse phase HPLC. Cpd. No. 47 was isolated in 14 mg as a salt of $CF_3CO_2H$. ESI-MS calculated for $C_2H_2N_3O$ $[M+H]^+=318.16$; Observed: 318.24.

Example 15

Synthesis of 1-methyl-7-(1-phenylcyclopropyl)-4,6-dihydrobenzo[e][1,2,4]triazolo[3,4-c][1,4]oxazepine (Cpd. No. 48)

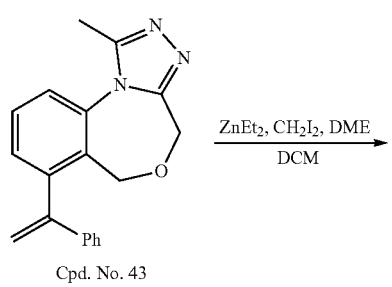

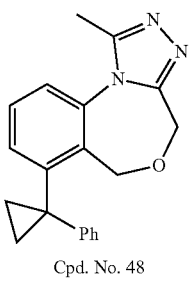

Cpd. No. 48

To a solution of $ZnEt_2$ (0.15 mL, 1 M in hexane) in DCM (2 mL) at −40° C., was added $CH_2I_2$ (25 μL). The mixture was stirred at −40° C. for 1 h. Then $CCl_3COOH$ (1 mg) and DME (10 μL) was added. The mixture was stirred at −15° C. for 1 h, then Cpd. No. 43 (10 mg) in DCM (2 mL) was added and the mixture was stirred at rt overnight. Then water (0.5 mL) was added to the mixture. The mixture was filtered and the filtrate was concentrated on a rotary evaporator. The residues were purified by reverse phase HPLC to yield Cpd. No. 48 in 1 mg as a salt of $CF_3CO_2H$. ESI-MS calculated for $C_{20}H_{20}N_3O$ $[M+H]^+=318.16$; Observed: 318.44. $^1$H NMR (400 MHz, MeOD) δ 7.80 (dd, J=7.7, 1.1 Hz, 1H), 7.72 (t, J=7.9 Hz, 1H), 7.64-7.60 (m, 1H), 7.22 (t, J=7.6 Hz, 2H), 7.12 (t, J=7.3 Hz, 1H), 7.04-6.99 (m, 1H), 4.60 (s, 2H), 4.55 (s, 2H), 2.69 (s, 3H), 1.50 (m, 4H).

Example 17

Synthesis of 2-(3,4-dihydronaphthalen-1-yl)-4,4,5,5-tetramethyl-1,3,2-dioxaborolane (ZBC71)

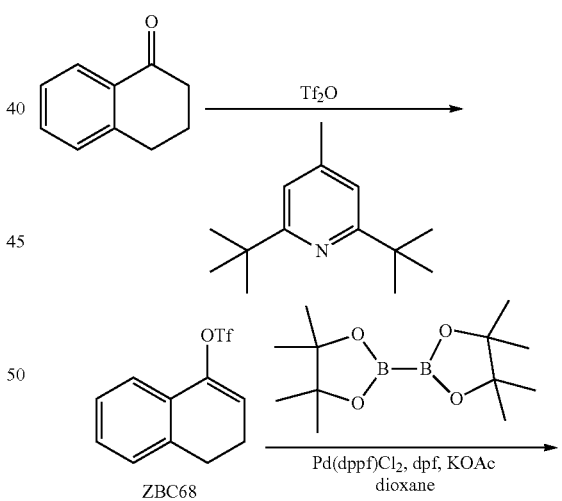

To a round-bottom flask containing 3,4-dihydronaphthalen-1(2H)-one (3 g) in DCE (70 mL) under N₂ atmosphere, Tf₂O (4.1 mL) and 2,6-di-tert-butyl-4-methylpyridine (6.3 g) was added. The mixture was stirred at rt overnight. Then hexane (200 mL) was added. The mixture was filtered and the filtrate was concentrated on a rotary evaporator to give ZBC68. To a round-bottom flask containing Pd(dppf)Cl₂ (1.7 g), dppf (1.2 g), KOAc (3.1 g), 4,4,4',4',5,5,5',5'-octamethyl-2,2'-bi(1,3,2-dioxaborolane) (5.4 g) in dioxane (100 mL) under N₂ atmosphere, ZBC68 in dioxane (50 mL) was added. The reaction mixture was heated at 100° C. overnight. The mixture was filtered and the filtrate was concentrated on a rotary evaporator. The residues were purified by flash column chromatography on silica gel to afford ZBC71 in 2.1 g. ESI-MS calculated for C₁₆H₂₂BO₂ [M+H]⁺=257.17; Observed: 257.32. ¹H NMR (400 MHz, CDCl₃) δ 7.78 (d, J=7.6 Hz, 1H), 7.22 (td, J=7.6, 1.4 Hz, 1H), 7.18-7.09 (m, 2H), 6.98 (t, J=4.5 Hz, 1H), 2.77 (t, J=8.0 Hz, 2H), 2.34 (td, J=8.0, 4.7 Hz, 2H), 1.37 (s, 12H).

Example 18

Synthesis of 7-(3,4-dihydronaphthalen-1-yl)-1-methyl-4,6-dihydrobenzo[e][1,2,4]triazolo[3,4-c][1,4]oxazepine (Cpd. No. 49)

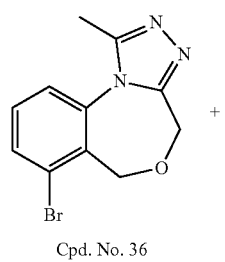

Cpd. No. 36

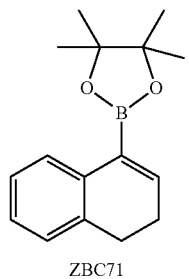

ZBC71

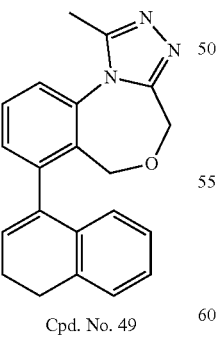

Cpd. No. 49

To a round-bottom flask containing Cpd. No. 36 (28 mg, 0.1 mmol), ZBC71 (55 mg), Pd(dppf)Cl₂ (8 mg) under N₂ atmosphere, DME (6 mL) and a solution of Na₂CO₃ (2.0 M, 2 mL) was added. The reaction mixture was heated at 100° C. for 4 h. The reaction was cooled, taken up with saturated NaHCO₃, extracted with DCM. The organic layers were combined and washed with brine, dried over anhydrous sodium sulfate, and concentrated on a rotary evaporator. The residues were purified by reverse phase HPLC to yield Cpd. No. 49 in 18 mg as a salt of CF₃CO₂H. ESI-MS calculated for C₂₁H₂₀N₃O [M+H]⁺=330.16; Observed: 330.43. ¹H NMR (400 MHz, MeOD) δ 7.81-7.69 (m, 2H), 7.55 (dd, J=7.2, 1.3 Hz, 1H), 7.24 (d, J=7.4 Hz, 1H), 7.17 (t, J=7.4 Hz, 1H), 7.07 (t, J=7.5 Hz, 1H), 6.60 (d, J=7.6 Hz, 1H), 6.11 (t, J=4.5 Hz, 1H), 4.75 (d, J=13.3 Hz, 1H), 4.61 (d, J=13.3 Hz, 1H), 4.41 (s, 2H), 2.93 (t, J=8.0 Hz, 2H), 2.84 (s, 3H), 2.50 (m, 2H).

Example 19

Synthesis of 1-methyl-7-(1,2,3,4-tetrahydronaphthalen-1-yl)-4,6-dihydrobenzo[e][1,2,4]triazolo[3,4-c][1,4]oxazepine (Cpd. No. 50)

Cpd. No. 49 (20 mg) was dissolved in a mixture of methanol (4.0 mL). Then 10% Pd/C (4 mg) was added and the reaction mixture was stirred under H₂ (1 atm) at room temperature for 10 h. The mixture was filtered and the filtrate was concentrated on a rotary evaporator. The residues were purified by reverse phase HPLC to yield Cpd. No. 50 in 14 mg as a salt of CF₃CO₂H. ESI-MS calculated for C₂₁H₂₂N₃O [M+H]+=332.17; Observed: 332.45. ¹H NMR (400 MHz, MeOD) δ 7.60-7.54 (m 2H), 7.25-7.11 (m, 3H), 7.04 (t, J=7.2 Hz, 1H), 6.75 (d, J=7.4 Hz, 1H), 4.80-4.55 (m, 5H), 3.00-2.88 (m, 2H), 2.77 (s, 3H), 2.30-2.20 (m, 1H), 2.07-1.76 (m, 3H).

Example 20

Synthesis of 1-(1-methyl-4,6-dihydrobenzo[e][1,2,4]triazolo[3,4-c][1,4]oxazepin-7-yl)-1-phenylethane-1,2-diol (Cpd. No. 116)

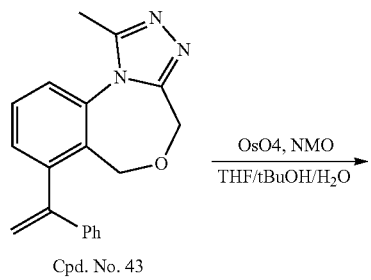

Cpd. No. 43

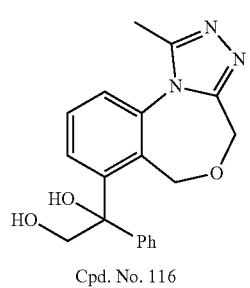

Cpd. No. 116

To a round-bottom flask containing Cpd. No. 43 (100 mg) in THF (6 mL), tBuOH (6 mL), and H$_2$O (2 mL), NMO (58 mg) and a solution of OSO$_4$ (2.5% wt in tBuOH, 0.4 mL) was added. The reaction mixture was heated at 100° C. for 8 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC to yield Cpd. No. 116 in 60 mg as a salt of CF$_3$CO$_2$H. ESI-MS calculated for C$_{19}$H$_{20}$N$_3$O$_3$ [M+H]$^+$=338.15; Observed: 338.43.

Example 21

Synthesis of (1-methyl-4,6-dihydrobenzo[e][1,2,4]triazolo[3,4-c][1,4]oxazepin-7-yl)(phenyl)methanone (Cpd. No. 52)

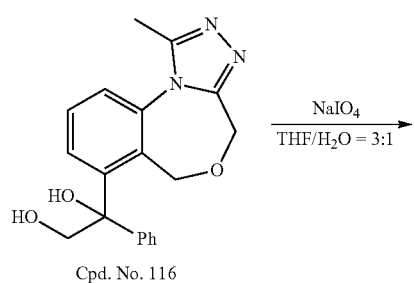

Cpd. No. 116

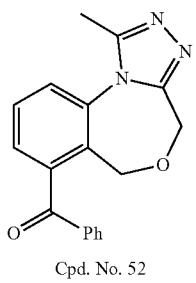

Cpd. No. 52

To a round-bottom flask containing Cpd. No. 116 (80 mg) in THF (9 mL) and H$_2$O (3 mL), NaIO$_4$ (51 mg) was added. The reaction mixture was stirred at room temperature for 8 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC to yield Cpd. No. 52 in 63 mg as a salt of CF$_3$CO$_2$H. ESI-MS calculated for C$_{18}$H$_{16}$N$_3$O$_2$ [M+H]$^+$=306.12; Observed: 306.36. $^1$H NMR (400 MHz, MeOD) δ 7.95-7.83 (m, 4H), 7.75-7.68 (m, 2H), 7.57 (t, J=7.6 Hz, 2H), 4.73 (s, 2H), 4.46 (s, 2H), 2.82 (s, 3H).

Example 22

Synthesis of 2-(6,7-dihydro-5H-benzo[7]annulen-9-yl)-4,4,5,5-tetramethyl-1,3,2-dioxaborolane (ZBC92)

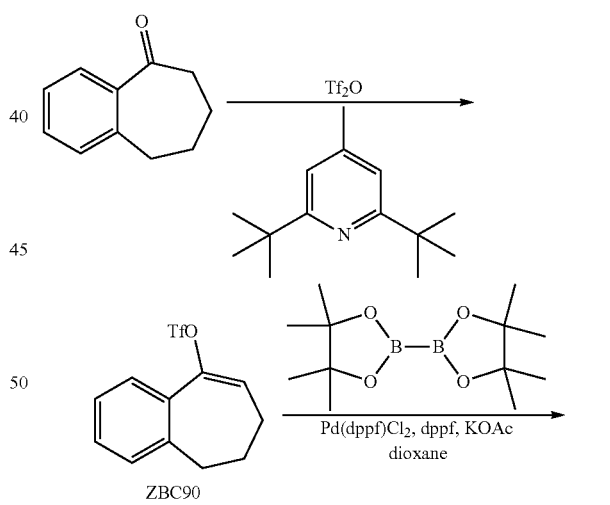

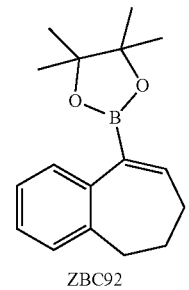

ZBC92

To a round-bottom flask containing 6,7,8,9-tetrahydro-5H-benzo[7]annulen-5-one (3 g) in DCE (70 mL) under N₂ atmosphere, Tf₂O (4.1 mL) and 2,6-di-tert-butyl-4-methylpyridine (6.3 g) was added. The mixture was stirred at rt overnight. Then hexane (200 mL) was added. The mixture was filtered and the filtrate was concentrated on a rotary evaporator to give ZBC90. To a round-bottom flask containing Pd(dppf)Cl₂ (1.7 g), dppf (1.2 g), KOAc (3.1 g), 4,4,4',4',5,5,5',5'-octamethyl-2,2'-bi(1,3,2-dioxaborolane) (5.4 g) in dioxane (100 mL) under N₂ atmosphere, ZBC90 in dioxane (50 mL) was added. The reaction mixture was heated at 100° C. overnight. The mixture was filtered and the filtrate was concentrated on a rotary evaporator. The residues were purified by flash column chromatography on silica gel to afford ZBC92 in 1.3 g. ESI-MS calculated for $C_{17}H_{24}BO_2$ [M+H]⁺=271.18; Observed: 271.32.

Example 23

Synthesis of 7-(6,7-dihydro-5H-benzo[7]annulen-9-yl)-1-methyl-4,6-dihydrobenzo[e][1,2,4]triazolo[3,4-c][1,4]oxazepine (Cpd. No. 59)

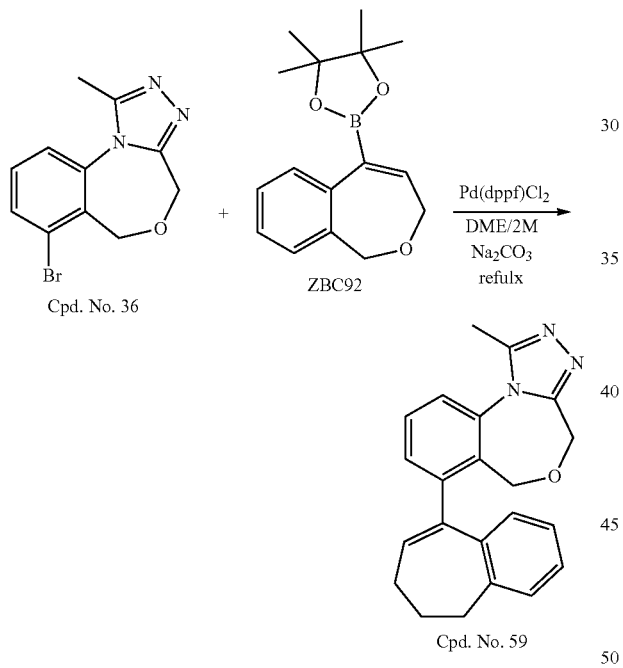

To a round-bottom flask containing Cpd. No. 36 (28 mg, 0.1 mmol), ZBC92 (55 mg), Pd(dppf)Cl₂ (8 mg) under N₂ atmosphere, DME (6 mL) and a solution of Na₂CO₃ in water (2.0 M, 2 mL) was added. The reaction mixture was heated at 100° C. for 4 h. The reaction was cooled, taken up with saturated NaHCO₃, extracted with DCM. The organic layers were combined and washed with brine, dried over anhydrous sodium sulfate, and concentrated on a rotary evaporator. The residues were purified by reverse phase HPLC to yield Cpd. No. 59 in 10 mg as a salt of CF₃CO₂H. ESI-MS calculated for $C_{22}H_{22}N_3O$ [M+H]⁺=344.17; Observed: 344.45. ¹H NMR (400 MHz, MeOD) δ 7.72-7.63 (m, 2H), 7.46 (dd, J=7.1, 1.5 Hz, 1H), 7.33 (d, J=7.5 Hz, 1H), 7.22 (td, J=7.4, 1.3 Hz, 1H), 7.15 (td, J=7.5, 1.3 Hz, 1H), 6.75 (d, J=7.6 Hz, 1H), 6.38 (t, J=6.9 Hz, 1H), 4.60 (s, 2H), 4.39 (s, 2H), 2.86-2.76 (m, 5H), 2.34-2.23 (m, 2H), 2.13 (m, 2H).

Example 24

Synthesis of 1-methyl-7-(6,7,8,9-tetrahydro-5H-benzo[7]annulen-5-yl)-4,6-dihydrobenzo[e][1,2,4]triazolo[3,4-c][1,4]oxazepine (Cpd. No. 60)

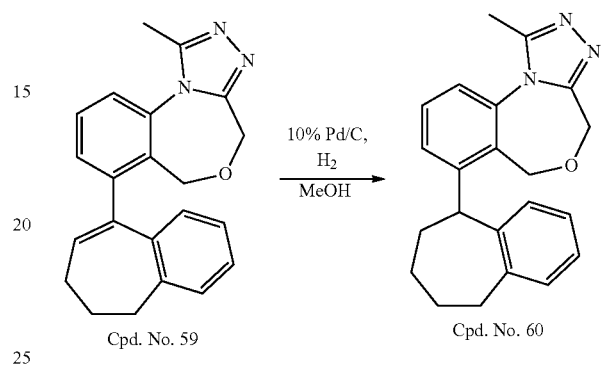

Cpd. No. 59 (20 mg) was dissolved in a mixture of methanol (4.0 mL). Then 10% Pd/C (4 mg) was added and the reaction mixture was stirred under H₂ (1 atm) at room temperature for 10 h. The mixture was filtered and the filtrate was concentrated on a rotary evaporator. The residues were purified by reverse phase HPLC to yield Cpd. No. 60 in 10 mg as a salt of CF₃CO₂H. ESI-MS calculated for $C_{22}H_{24}N_3O$ [M+H]⁺=346.19; Observed: 346.43. ¹H NMR (400 MHz, MeOD) δ 7.76 (t, J=7.9 Hz, 1H), 7.64 (dd, J=16.4, 7.9 Hz, 2H), 7.18 (d, J=7.4 Hz, 1H), 7.07 (t, J=7.4 Hz, 1H), 6.93 (t, J=7.6 Hz, 1H), 6.33 (d, J=7.7 Hz, 1H), 4.74-4.66 (m, 2H), 4.42 (m, 2H), 4.19-4.07 (m, 1H), 3.16 (t, J=12.7 Hz, 1H), 2.91 (dd, J=14.0, 6.3 Hz, 1H), 2.71 (s, 3H), 2.37-1.89 (m, 5H), 1.45 (m, 1H).

Example 25

Synthesis of 3-(3,4-dihydronaphthalen-1-yl)-2,9-dimethyl-4,6-dihydrothieno[2,3-e][1,2,4]triazolo[3,4-c][1,4]oxazepine (Cpd. No. 51)

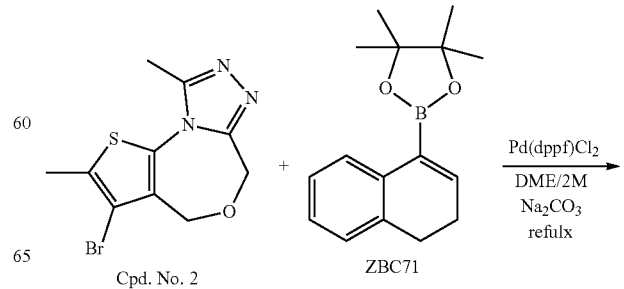

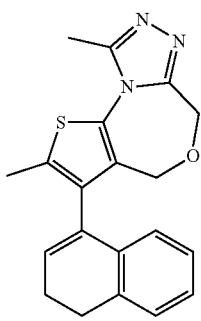

Cpd. No. 51

To a round-bottom flask containing Cpd. No. 2 (30 mg, 0.1 mmol), ZBC71 (55 mg), Pd(dppf)Cl$_2$ (8 mg) under N$_2$ atmosphere, DME (6 mL) and a solution of Na$_2$CO$_3$ in water (2.0 M, 2 mL) was added. The reaction mixture was heated at 100° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The residues were purified by reverse phase HPLC to yield Cpd. No. 51 in 20 mg as a salt of CF$_3$CO$_2$H. ESI-MS calculated for C$_{20}$H$_{20}$N$_3$OS [M+H]$^+$=350.13; Observed: 350.53.

Example 26

Synthesis of 3-(1H-inden-3-yl)-2,9-dimethyl-4,6-dihydrothieno[2,3-e][1,2,4]triazolo[3,4-c][1,4]oxazepine (Cpd. No. 53)

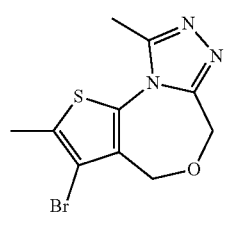

Cpd. No. 2

+

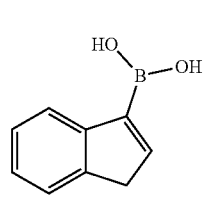

Pd(dppf)Cl$_2$
DME/2M
Na$_2$CO$_3$
refulx

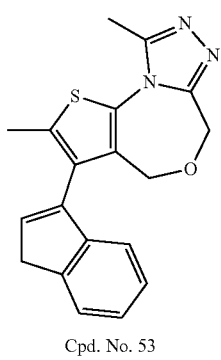

Cpd. No. 53

To a round-bottom flask containing Cpd. No. 2 (30 mg, 0.1 mmol), (1H-inden-3-yl)boronic acid (30 mg), Pd(dppf)Cl$_2$ (8 mg), under N$_2$ atmosphere, DME (6 mL) and a solution of Na$_2$CO$_3$ (2.0 M, 2 mL) was added. The reaction mixture was heated at 100° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The residues were purified by reverse phase HPLC. Cpd. No. 53 was isolated in 14 mg as a salt of CF$_3$CO$_2$H. ESI-MS calculated for C$_9$H$_{18}$N$_3$OS [M+H]=336.11; Observed: 336.48. $^1$H NMR (400 MHz, MeOD) δ 7.62-7.54 (m, 1H), 7.32-7.23 (m, 2H), 7.13-7.08 (m, 1H), 6.59 (s, 1H), 4.83 (s, 2H), 4.70 (d, J=15.1 Hz, 1H), 4.60 (d, J=15.1 Hz, 1H), 3.63 (s, 2H), 2.86 (s, 3H), 2.38 (s, 3H).

Example 27

Synthesis of 2,9-dimethyl-3-(1,2,3,4-tetrahydronaphthalen-1-yl)-4,6-dihydrothieno[2,3-e][1,2,4]triazolo[3,4-c][1,4]oxazepine (Cpd. No. 54)

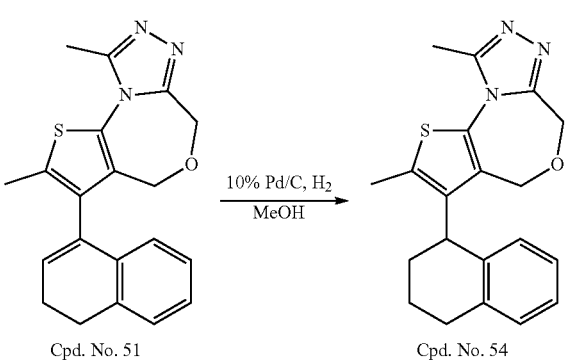 [SMILES: "MeOH" ; Cc1sc2c(c1C1=CCCc3ccccc31)COCc1nnc(C)n1-2 ; Cc1sc2c(c1C1CCCc3ccccc31)COCc1nnc(C)n1-2]

Cpd. No. 51           Cpd. No. 54

Cpd. No. 51 (20 mg) was dissolved in a mixture of methanol (4.0 mL). Then 10% Pd/C (4 mg) was added and the reaction mixture was stirred under H$_2$ (1 atm) at room temperature for 10 h. The mixture was filtered and the filtrate was concentrated on a rotary evaporator. The residues were purified by reverse phase HPLC to yield Cpd. No. 54 in 6 mg as a salt of CF$_3$CO$_2$H. ESI-MS calculated for C$_{20}$H$_{22}$N$_3$OS [M+H]+=352.14; Observed: 352.33.

Example 28

Synthesis of 3-(2,3-dihydro-1H-inden-1-yl)-2,9-dimethyl-4,6-dihydrothieno[2,3-e][1,2,4]triazolo[3,4-c][1,4]oxazepine (Cpd. No. 55)

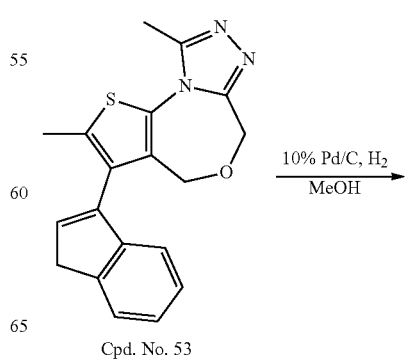

10% Pd/C, H$_2$
MeOH

Cpd. No. 53

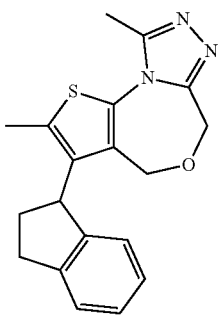

Cpd. No. 55

Cpd. No. 53 (20 mg) was dissolved in a mixture of methanol (4.0 mL). Then 10% Pd/C (4 mg) was added and the reaction mixture was stirred under H$_2$ (1 atm) at room temperature for 10 h. The mixture was filtered and the filtrate was concentrated on a rotary evaporator. The residues were purified by reverse phase HPLC to yield Cpd. No. 55 in 5 mg as a salt of CF$_3$CO$_2$H. ESI-MS calculated for C$_{19}$H$_2$N$_3$OS [M+H]+=338.13; Observed: 338.54.

Example 29

Synthesis of 3-(6,7-dihydro-5H-benzo[7]annulen-9-yl)-2,9-dimethyl-4,6-dihydrothieno[2,3-e][1,2,4]triazolo[3,4-c][1,4]oxazepine (Cpd. No. 56)

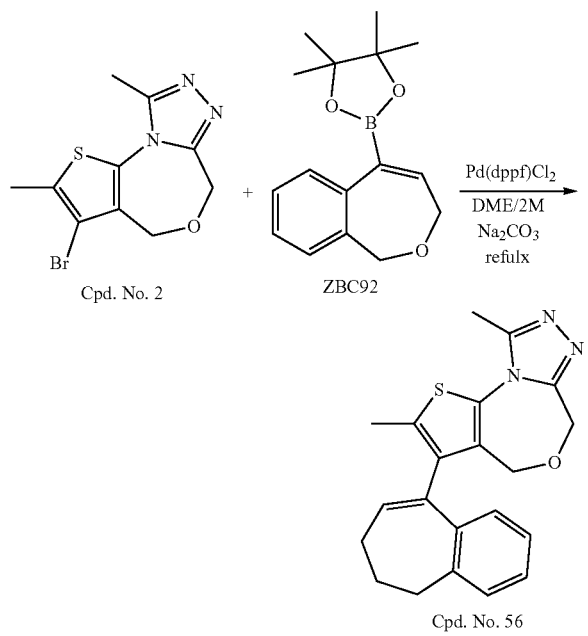

Cpd. No. 56

To a round-bottom flask containing Cpd. No. 2 (30 mg, 0.1 mmol), ZBC92 (65 mg), Pd(dppf)Cl$_2$ (8 mg) under N$_2$ atmosphere, DME (6 mL) and a solution of Na$_2$CO$_3$ in water (2.0 M, 2 mL) was added. The reaction mixture was heated at 100° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The residues were purified by reverse phase HPLC to yield Cpd. No. 56 in 11 mg as a salt of CF$_3$CO$_2$H. ESI-MS calculated for C$_{21}$H$_{22}$N$_3$OS [M+H]+=364.14; Observed: 364.43.

Example 30

Synthesis of 2-(6-fluoro-3,4-dihydronaphthalen-1-yl)-4,4,5,5-tetramethyl-1,3,2-dioxaborolane (ZBC93)

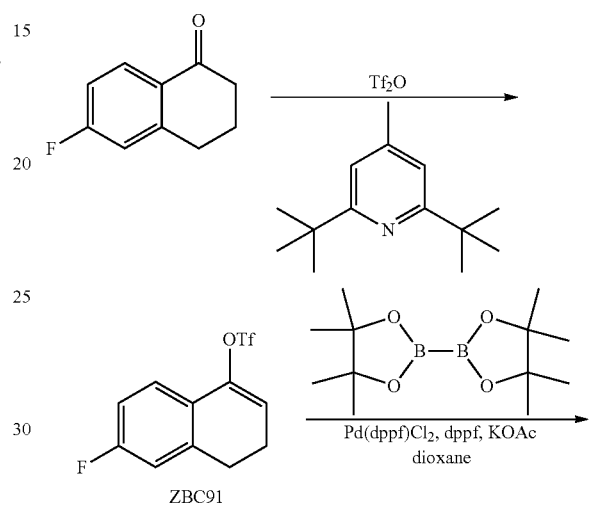

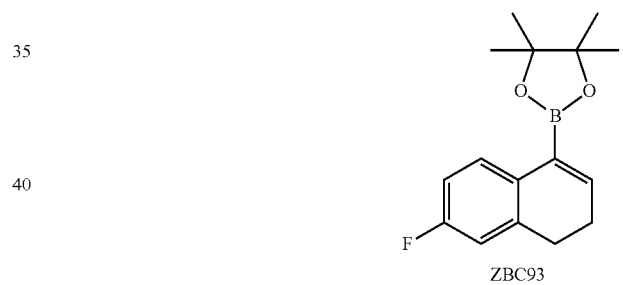

ZBC93

To a round-bottom flask containing 6-fluoro-3,4-dihydronaphthalen-1(2H)-one (3 g) in DCE (70 mL) under N$_2$ atmosphere, Tf$_2$O (4.1 mL) and 2,6-di-tert-butyl-4-methylpyridine (6.3 g) was added. The mixture was stirred at rt overnight. Then hexane (200 mL) was added. The mixture was filtered and the filtrate was concentrated on a rotary evaporator to give ZBC91 which was used directly without purification. To a round-bottom flask containing Pd(dppf)Cl$_2$ (1.7 g), dppf (1.2 g), KOAc (3.1 g), and 4,4,4',4',5,5,5',5'-octamethyl-2,2'-bi(1,3,2-dioxaborolane) (5.4 g) in dioxane (100 mL) under N$_2$ atmosphere, ZBC91 in dioxane (50 mL) was added. The reaction mixture was heated at 100° C. overnight. The mixture was filtered and the filtrate was concentrated on a rotary evaporator. The residues were purified by flash column chromatography on silica gel to afford ZBC93 in 1.4 g. ESI-MS calculated for C$_{16}$H$_{21}$BFO$_2$ [M+H]+=275.16; Observed: 275.35. $^1$H NMR (400 MHz, CDCl$_3$) δ 7.75-7.69 (m, 1H), 6.96-6.78 (m, 3H), 2.73 (t, J=8.1 Hz, 2H), 2.31 (td, J=8.0, 4.9 Hz, 2H), 1.35 (s, 12H).

Example 31

Synthesis of 2-(7-fluoro-3,4-dihydronaphthalen-1-yl)-4,4,5,5-tetramethyl-1,3,2-dioxaborolane (ZBC95-2)

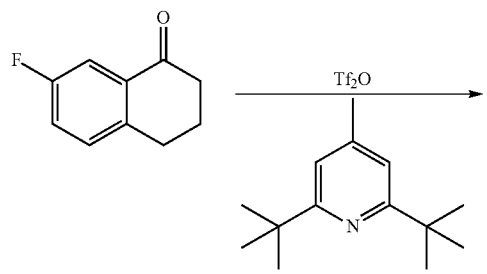

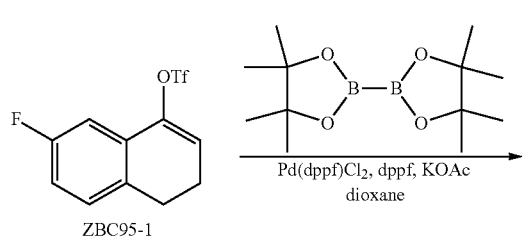

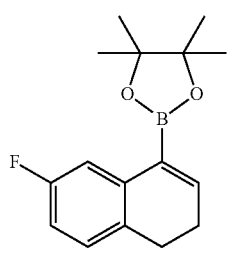

To a round-bottom flask containing 7-fluoro-3,4-dihydronaphthalen-1(2H)-one (3 g) in DCE (70 mL) under N₂ atmosphere, Tf₂O (4.1 mL) and 2,6-di-tert-butyl-4-methylpyridine (6.3 g) was added. The mixture was stirred at rt overnight. Then hexane (200 mL) was added. The mixture was filtered and the filtrate was concentrated on a rotary evaporator to give ZBC95-1 which was used directly without purification. To a round-bottom flask containing Pd(dppf)Cl₂ (1.7 g), dppf (1.2 g), KOAc (3.1 g), and 4,4,4',4',5,5,5',5'-octamethyl-2,2'-bi(1,3,2-dioxaborolane) (5.4 g) in dioxane (100 mL) under N₂ atmosphere, ZBC95-1 in dioxane (50 mL) was added. The reaction mixture was heated at 100° C. overnight. The mixture was filtered and the filtrate was concentrated on a rotary evaporator. The residues were purified by flash column chromatography on silica gel to afford ZBC95-2 in 1.0 g. ESI-MS calculated for $C_{16}H_{21}BFO_2$ [M+H]⁺=275.16; Observed: 275.22.

Example 32

Synthesis of 3-(6-fluoro-3,4-dihydronaphthalen-1-yl)-2,9-dimethyl-4,6-dihydrothieno[2,3-e][1,2,4]triazolo[3,4-c][1,4]oxazepine (Cpd. No. 57)

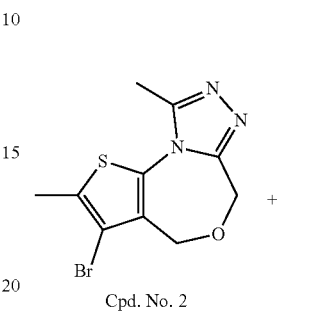

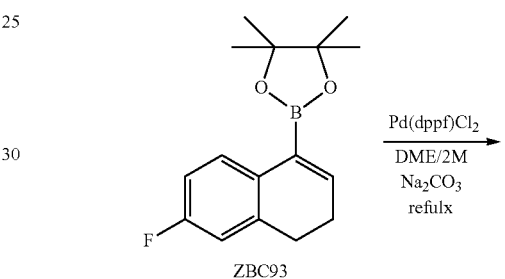

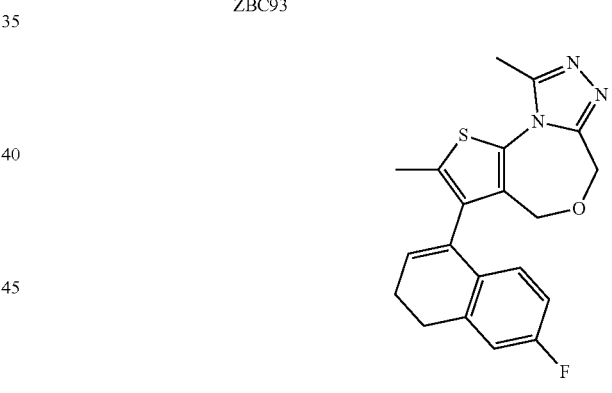

To a round-bottom flask containing Cpd. No. 2 (30 mg, 0.1 mmol), ZBC93 (70 mg), Pd(dppf)Cl₂ (8 mg) under N₂ atmosphere, DME (6 mL) and a solution of Na₂CO₃ in water (2.0 M, 2 mL) was added. The reaction mixture was heated at 100° C. for 4 h. The reaction was cooled, taken up with saturated NaHCO₃, extracted with DCM. The organic layers were combined and washed with brine, dried over anhydrous sodium sulfate, and concentrated on a rotary evaporator. The residues were purified by reverse phase HPLC to yield Cpd. No. 57 in 20 mg as a salt of CF₃CO₂H. ESI-MS calculated for $C_{20}H_{19}FN_3OS$ [M+H]⁺=368.12; Observed: 368.44. ¹H NMR (400 MHz, MeOD) δ 7.00 (dd, J=9.2, 2.5 Hz, 1H), 6.83 (td, J=8.6, 2.5 Hz, 1H), 6.69 (dd, J=8.4, 5.8 Hz, 1H), 6.04 (t, J=4.5 Hz, 1H), 4.80 (s, 2H), 4.71 (d, J=15.3 Hz, 1H), 4.48 (d, J=15.3 Hz, 1H), 2.92 (t, J=8.0 Hz, 2H), 2.87 (s, 3H), 2.55-2.43 (m, 2H), 2.35 (s, 3H).

Example 33

Synthesis of 3-(7-fluoro-3,4-dihydronaphthalen-1-yl)-2,9-dimethyl-4,6-dihydrothieno[2,3-e][1,2,4]triazolo[3,4-c][1,4]oxazepine (Cpd. No. 58)

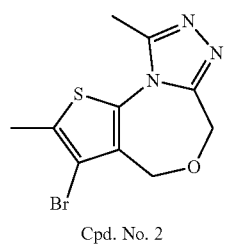

Cpd. No. 2

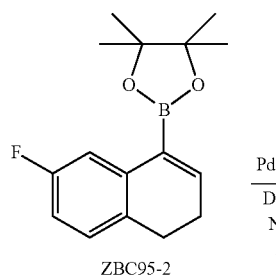

ZBC95-2

Pd(dppf)Cl₂
———————→
DME/2M
Na₂CO₃
reflux

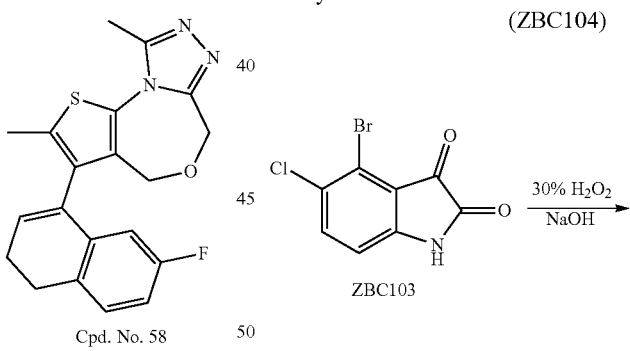

Cpd. No. 58

To a round-bottom flask containing Cpd. No. 2 (30 mg, 0.1 mmol), ZBC95-2 (70 mg), Pd(dppf)Cl₂ (8 mg) under N₂ atmosphere, DME (6 mL) and a solution of Na₂CO₃ in water (2.0 M, 2 mL) was added. The reaction mixture was heated at 100° C. for 4 h. The reaction was cooled, taken up with saturated NaHCO₃, extracted with DCM. The organic layers were combined and washed with brine, dried over anhydrous sodium sulfate, and concentrated on a rotary evaporator. The residues were purified by reverse phase HPLC to yield Cpd. No. 58 in 21 mg as a salt of CF₃CO₂H. ESI-MS calculated for $C_{20}H_{19}FN_3OS$ [M+H]⁺=368.12; Observed: 368.34. ¹H NMR (400 MHz, MeOD) δ 7.28-7.22 (m, 1H), 6.91 (t, J=8.5 Hz, 1H), 6.40 (d, J=9.8 Hz, 1H), 6.17 (t, J=4.4 Hz, 1H), 4.81 (s, 2H), 4.71 (d, J=15.3 Hz, 1H), 4.49 (d, J=15.3 Hz, 1H), 2.93-2.81 (m, 5H), 2.56-2.46 (m, 2H), 2.36 (d, J=1.1 Hz, 3H).

Example 34

Synthesis of 4-bromo-5-chloroindoline-2,3-dione (ZBC103)

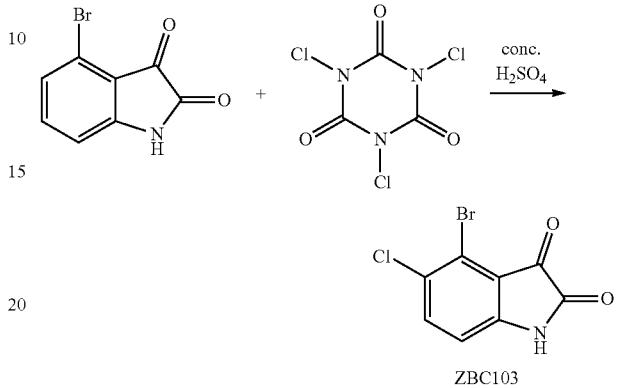

To a mixture of 4-bromoisatin (3 g) and trichloroisocyanuric acid (1.4 g) in an ice bath, 10 mL of conc. H₂SO₄ was added dropwise over a 5 minute period with magnetic stirring. The mixture was kept in an ice bath under stirring for 15 minutes. The mixture was then poured over cracked ice. The crystals were collected and washed with cold water to afford 3.1 g of ZBC103 as an orange solid.

Example 35

Synthesis of 6-amino-2-bromo-3-chlorobenzoic acid (ZBC104)

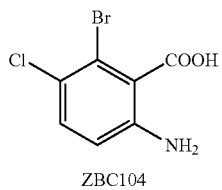

To a 250 mL round bottom flask, ZBC103 (3 g) and 2N NaOH (40 mL) were added and the reaction vessel was cooled to 0° C. Then 30% hydrogen peroxide (4 mL) was slowly added. The reaction mixture was stirred at 0° C. for 3 h. Subsequently, the reaction mixture was acidified with 2N HCl at 0° C. to afford the solid compound. The solid material was collected by filtration and dried to obtain the title compound. ESI-MS calculated for $C_7H_6BrClNO_2$ [M+H]⁺=249.9; Observed: 250.11.

Example 36

Synthesis of (6-amino-2-bromo-3-chlorophenyl)methanol (ZBC105-1)

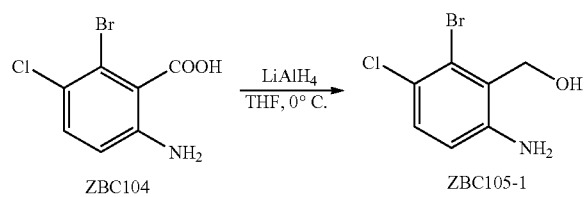 [SMILES: Nc1ccc(Cl)c(Br)c1C(=O)O ; "THF, 0° C." ; "LiAlH4" ; Nc1ccc(Cl)c(Br)c1CO]

To a 250 mL round bottom flask, ZBC104 (170 mg) and THF (40 mL) were added and the reaction vessel was cooled to 0° C. Then LiAlH$_4$ (60 mg) was slowly added. The reaction mixture was stirred at 0° C. for 3 h. Then 2 N NaOH (15 mL) was added. After 30 min, the solvent was evaporated under vacuum. The remaining residues was dissolved in ethyl acetate and washed with saturated aqueous sodium bicarbonate. The aqueous layer was extracted with ethyl acetate. The organic layers were combined and washed with brine, dried over anhydrous sodium sulfate, and concentrated on a rotary evaporator. The remaining residues were purified by flash column chromatography on silica gel to afford ZBC105-1 in 120 mg. ESI-MS calculated for C$_7$H$_8$BrClNO [M+H]$^+$=235.94; Observed: 236.05. $^1$H NMR (400 MHz, CDCl$_3$) δ 7.21 (d, J=8.6 Hz, 1H), 6.62 (d, J=8.6 Hz, 1H), 4.97 (s, 2H).

Example 37

Synthesis of N-(3-bromo-4-chloro-2-(hydroxymethyl)phenyl)-2-chloroacetamide (ZBC107)

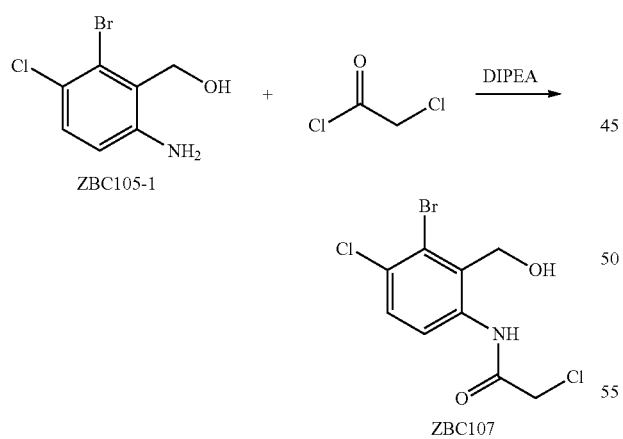

A solution of ZBC105-1 (50 mg) in DCM (10 mL) was cooled to 0° C. and DIPEA (37 μL) was added slowly. Then 2-chloroacetyl chloride (17 μL) was added dropwise. After stirring at 0° C. for 30 min, the reaction was diluted with DCM, washed with brine, dried, and concentrated on a rotary evaporator. The remaining residues were purified by flash column chromatography on silica gel to afford ZBC107 in 44 mg. ESI-MS calculated for C$_9$H$_9$BrCl$_2$NO$_2$ [M+H]$^+$=311.9; Observed: 312.1.

Example 38

Synthesis of 6-bromo-7-chloro-3,5-dihydrobenzo[e][1,4]oxazepin-2(1H)-one (ZBC109)

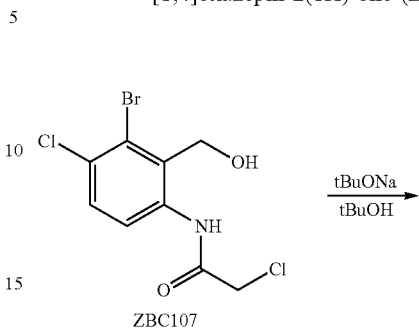

A suspension of NaOtBu (1 g) in tBuOH (50 mL) was heated at 80° C. until it turns into a clear solution. Then ZBC107 (1.6 g) was added in one portion and the reaction is heated at 80° C. for 15 min. The reaction mixture was cooled, poured into ice-water, and extracted with ethyl acetate. The organic layers were combined and washed with brine, dried over anhydrous sodium sulfate, and concentrated on a rotary evaporator. The remaining residues were purified by flash column chromatography on silica gel to afford ZBC109 in 1.1 g. ESI-MS calculated for C$_9$H$_8$BrClNO$_2$ [M+H]$^+$=275.9; Observed: 276.1.

Example 39

Synthesis of 7-bromo-8-chloro-1-methyl-4,6-dihydrobenzo[e][1,2,4]triazolo[3,4-c][1,4]oxazepine (Cpd. No. 70)

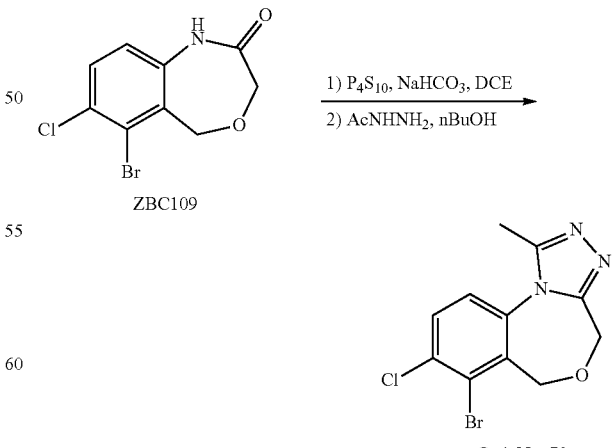

A suspension of P$_4$S$_{10}$ (147 mg, 0.66 mmol) and NaHCO$_3$ (70 mg, 0.66 mmol) in 1,2-DCE (5 mL) was stirred for 10 min prior to the addition of ZBC109 (85 mg). The reaction mixture was stirred at 65° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The remaining residues were dissolved in nBuOH (10 ml) and AcNHNH$_2$ (135 mg) was added. The reaction mixture was stirred at 120° C. for 2 h. The reaction mixture was cooled, poured into ice-water, and extracted with ethyl acetate. The organic layers were combined and washed with brine, dried over anhydrous sodium sulfate, and concentrated on a rotary evaporator. The residues were purified by reverse phase HPLC to yield Cpd. No. 70 in 60 mg as a salt of CF$_3$CO$_2$H. ESI-MS calculated for C$_{11}$H$_{10}$BrClN$_3$O [M+H]$^+$=313.9; Observed: 314.3. $^1$H NMR (400 MHz, MeOD) δ 7.90 (d, J=8.6 Hz, 1H), 7.72 (d, J=8.6 Hz, 1H), 4.80 (s, 2H), 4.68 (s, 2H), 2.71 (s, 3H).

Example 40

Synthesis of 7-benzyl-8-chloro-1-methyl-4,6-dihydrobenzo[e][1,2,4]triazolo[3,4-c][1,4]oxazepine (Cpd. No. 71)

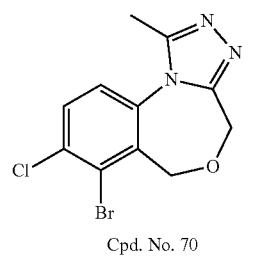

Cpd. No. 70

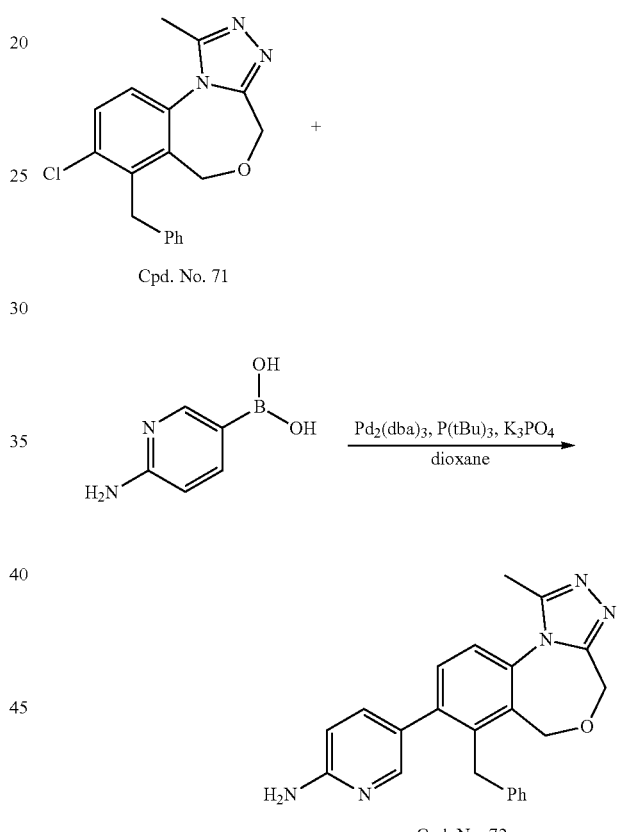

To a round-bottom flask was charged with Cpd. No. 70 (31 mg, 0.1 mmol), boroate salt (40 mg, 0.2 mmol), Pd(dppf)Cl$_2$ (8 mg). Under N$_2$ atmosphere, DME (3 mL) and a solution of Na$_2$CO$_3$ (2.0 M, 1 mL) was added. The reaction mixture was heated at 100° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The residues were purified by reverse phase HPLC to yield Cpd. No. 71 in 21 mg as a salt of CF$_3$CO$_2$H. ESI-MS calculated for C$_{18}$H$_{17}$ClN$_3$O [M+H]$^+$=326.1; Observed: 326.4. $^1$H NMR (400 MHz, MeOD) δ 7.85 (d, J=8.6 Hz, 1H), 7.67 (d, J=8.6 Hz, 1H), 7.28 (t, J=7.6 Hz, 2H), 7.20 (t, J=7.0 Hz, 1H), 7.14 (d, J=7.9 Hz, 2H), 4.64 (s, 2H), 4.57 (s, 2H), 4.47 (s, 2H), 2.80 (s, 3H).

Example 41

Synthesis of 5-(7-benzyl-1-methyl-4,6-dihydrobenzo[e][1,2,4]triazolo[3,4-c][1,4]oxazepin-8-yl)pyridin-2-amine (Cpd. No. 72)

To a round-bottom flask containing Cpd. No. 71 (31 mg, 0.1 mmol), (6-aminopyridin-3-yl)boronic acid (43 mg), Pd$_2$(dba)$_3$ (20 mg), tritertbutylphosphine tetrafluoroborate (12 mg) and K$_3$PO$_4$ (60 mg), dioxane (5 mL) and water (100 μL) were added. The reaction mixture was heated at 100° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC to yield Cpd. No. 72 in 10 mg as a salt of CF$_3$CO$_2$H. ESI-MS calculated for C$_{23}$H$_{22}$N$_5$O [M+H]$^+$=384.1; Observed: 384.3. $^1$H NMR (400 MHz, MeOD) δ 7.93 (t, J=7.9 Hz, 1H), 7.81 (d, J=8.5 Hz, 1H), 7.74 (d, J=8.5 Hz, 1H), 7.60 (d, J=6.4 Hz, 1H), 7.17-7.11 (m, 2H), 7.07 (t, J=7.5 Hz, 2H), 7.01 (d, J=8.4 Hz, 1H), 6.93 (t, J=6.7 Hz, 1H), 4.73 (s, 2H), 4.70 (s, 2H), 4.33 (s, 2H), 2.73 (s, 3H).

Example 42

Synthesis of 7-benzyl-1-methyl-8-(1-methyl-1H-pyrazol-4-yl)-4,6-dihydrobenzo[e][1,2,4]triazolo[3,4-c][1,4]oxazepine (Cpd. No. 73)

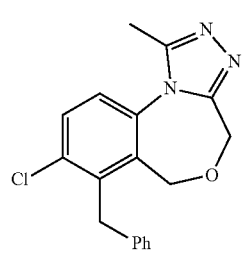

Cpd. No. 71

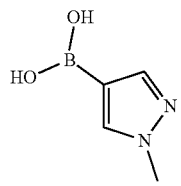 Pd$_2$(dba)$_3$, P(tBu)$_3$, K$_3$PO$_4$ / dioxane →

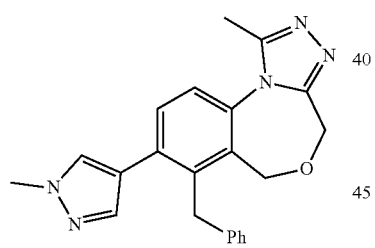

Cpd. No. 73

To a round-bottom flask containing Cpd. No. 71 (31 mg, 0.1 mmol), (1-methyl-1H-pyrazol-4-yl)boronic acid (46 mg), Pd$_2$(dba)$_3$ (20 mg), tritertbutylphosphine tetrafluoroborate (12 mg) and K$_3$PO$_4$ (60 mg), dioxane (5 mL) and water (100 μL) were added. The reaction mixture was heated at 100° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC to yield Cpd. No. 73 in 8 mg as a salt of CF$_3$CO$_2$H. ESI-MS calculated for C$_{22}$H$_{22}$N$_5$O [M+H]$^+$=372.18; Observed: 372.4. $^1$H NMR (400 MHz, MeOD) δ 7.77 (d, J=8.3 Hz, 1H), 7.69 (d, J=8.4 Hz, 1H), 7.59 (s, 1H), 7.43 (s, 1H), 7.30 (t, J=7.5 Hz, 2H), 7.22 (t, J=7.2 Hz, 1H), 7.02 (d, J=7.5 Hz, 2H), 4.65 (s, 2H), 4.52 (s, 2H), 4.38 (s, 2H), 3.90 (s, 3H), 2.85 (s, 3H).

Example 43

Synthesis of 8-chloro-7-(3,4-dihydronaphthalen-1-yl)-1-methyl-4,6-dihydrobenzo[e][1,2,4]triazolo[3,4-c][1,4]oxazepine (Cpd. No. 74)

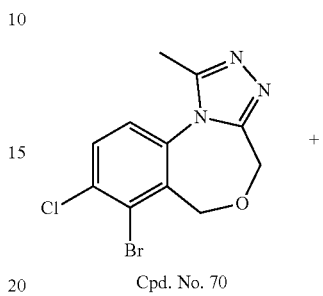

Cpd. No. 70

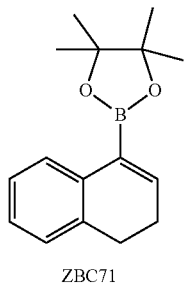 Pd(dppf)Cl$_2$ / DME/2M Na$_2$CO$_3$ →

ZBC71

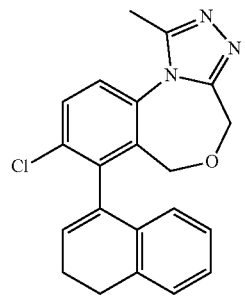

Cpd. No. 74

To a round-bottom flask was charged with Cpd. No. 70 (31 mg, 0.1 mmol), ZBC71 (60 mg), Pd(dppf)Cl$_2$ (8 mg). Under N$_2$ atmosphere, DME (6 mL) and a solution of Na$_2$CO$_3$ (2.0 M, 2 mL) was added. The reaction mixture was heated at 100° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The residues were purified by reverse phase HPLC to yield Cpd. No. 74 in 14 mg as a salt of CF$_3$CO$_2$H. ESI-MS calculated for C$_{21}$H$_{19}$CN$_3$O [M+H]$^+$=364.1; Observed: 364.4. $^1$H NMR (400 MHz, MeOD) δ 7.84 (d, J=8.6 Hz, 1H), 7.74 (d, J=8.6 Hz, 1H), 7.25 (d, J=7.3 Hz, 1H), 7.20-7.15 (m, 1H), 7.06 (t, J=7.5 Hz, 1H), 6.49 (d, J=7.6 Hz, 1H), 6.07 (t, J=4.5 Hz, 1H), 4.77 (d, J=13.4 Hz, 1H), 4.60 (d, J=13.4 Hz, 1H), 4.41 (s, 2H), 3.05-2.88 (m, 2H), 2.79 (s, 3H), 2.58-2.48 (m, 2H).

Example 44

Synthesis of 7-benzyl-1-methyl-8-(1H-pyrazol-4-yl)-4,6-dihydrobenzo[e][1,2,4]triazolo[3,4-c][1,4]oxazepine (Cpd. No. 75)

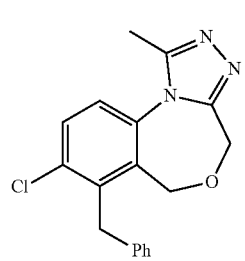

Cpd. No. 71

+

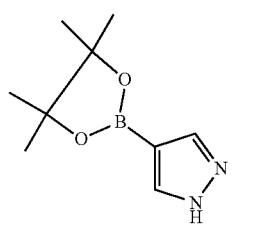

$\xrightarrow{\text{Pd}_2(\text{dba})_3, \text{P(tBu)}_3, \text{K}_3\text{PO}_4}{\text{dioxane}}$

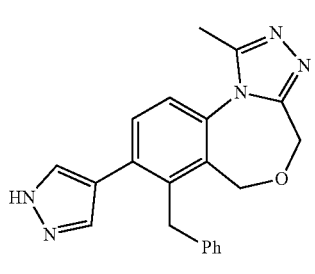

Cpd. No. 75

To a round-bottom flask containing Cpd. No. 71 (31 mg, 0.1 mmol), 4-(4,4,5,5-tetramethyl-1,3,2-dioxaborolan-2-yl)-1H-pyrazole (60 mg), Pd$_2$(dba)$_3$ (20 mg), tritertbutylphosphine tetrafluoroborate (12 mg) and K$_3$PO$_4$ (60 mg), dioxane (5 mL) and water (100 µL) were added. The reaction mixture was heated at 100° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC to yield Cpd. No. 75 in 4 mg as a salt of CF$_3$CO$_2$H. ESI-MS calculated for C$_{21}$H$_{20}$N$_5$O [M+H]$^+$=358.1; Observed: 358.3. $^1$H NMR (400 MHz, MeOD) δ 7.75 (d, J=8.2 Hz, 1H), 7.66 (d, J=8.3 Hz, 1H), 7.57 (s, 2H), 7.30 (t, J=7.6 Hz, 2H), 7.22 (t, J=7.2 Hz, 1H), 7.02 (d, J=7.8 Hz, 2H), 4.62 (s, 2H), 4.46 (s, 2H), 4.36 (s, 2H), 2.74 (s, 3H).

Example 45

Synthesis of 2-(4-(7-benzyl-1-methyl-4,6-dihydrobenzo[e][1,2,4]triazolo[3,4-c][1,4]oxazepin-8-yl)-1H-pyrazol-1-yl)acetamide (Cpd. No. 76)

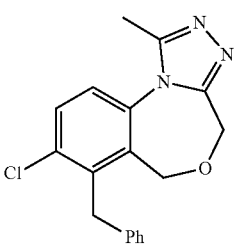

Cpd. No. 71

+

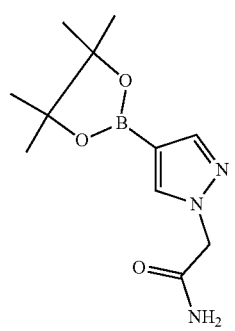

$\xrightarrow{\text{Pd}_2(\text{dba})_3, \text{P(tBu)}_3, \text{K}_3\text{PO}_4}{\text{dioxane}}$

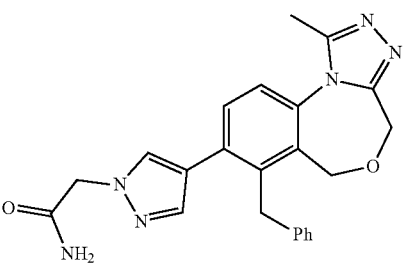

Cpd. No. 76

To a round-bottom flask containing Cpd. No. 71 (31 mg, 0.1 mmol), 2-(4-(4,4,5,5-tetramethyl-1,3,2-dioxaborolan-2-yl)-1H-pyrazol-1-yl)acetamide (60 mg), Pd$_2$(dba)$_3$ (20 mg), tritertbutylphosphine tetrafluoroborate (12 mg) and K$_3$PO$_4$ (60 mg), dioxane (5 mL) and water (100 µL) were added. The reaction mixture was heated at 100° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC to yield Cpd. No. 76 in 5 mg as a salt of CF$_3$CO$_2$H. ESI-MS calculated for C$_{23}$H$_{23}$N$_6$O$_2$ [M+H]$^+$=415.18; Observed: 415.5.

Example 46

Synthesis of 7-benzyl-8-(3,6-dihydro-2H-pyran-4-yl)-1-methyl-4,6-dihydrobenzo[e][1,2,4]triazolo[3,4-c][1,4]oxazepine (Cpd. No. 77)

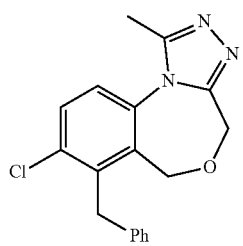

Cpd. No. 71

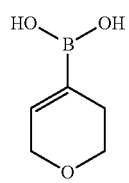

$\xrightarrow{\text{Pd}_2(\text{dba})_3,\ \text{P(tBu)}_3,\ \text{K}_3\text{PO}_4}{\text{dioxane}}$

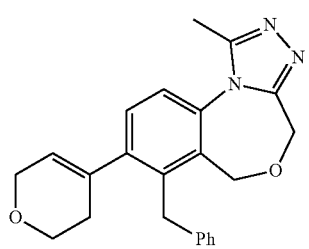

Cpd. No. 77

To a round-bottom flask containing Cpd. No. 71 (31 mg, 0.1 mmol), (3,6-dihydro-2H-pyran-4-yl)boronic acid (60 mg), Pd$_2$(dba)$_3$ (20 mg), tritertbutylphosphine tetrafluoroborate (12 mg) and K$_3$PO$_4$ (60 mg), dioxane (5 mL) and water (100 µL) were added. The reaction mixture was heated at 100° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC to yield Cpd. No. 77 in 6 mg as a salt of CF$_3$CO$_2$H. ESI-MS calculated for C$_{23}$H$_{24}$N$_3$O$_2$ [M+H]$^+$=374.18; Observed: 374.5.

Example 47

Synthesis of 7-benzyl-8-(4,5-dihydrofuran-3-yl)-1-methyl-4,6-dihydrobenzo[e][1,2,4]triazolo[3,4-c][1,4]oxazepine (Cpd. No. 78)

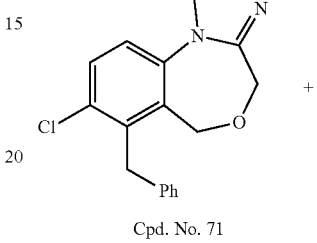

Cpd. No. 71

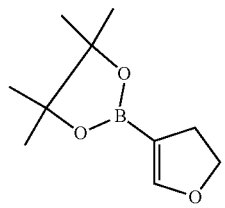

$\xrightarrow{\text{Pd}_2(\text{dba})_3,\ \text{P(tBu)}_3,\ \text{K}_3\text{PO}_4}{\text{dioxane}}$

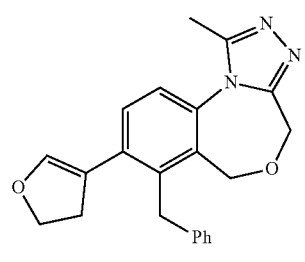

Cpd. No. 78

To a round-bottom flask containing Cpd. No. 71 (31 mg, 0.1 mmol), 2-(4,5-dihydrofuran-3-yl)-4,4,5,5-tetramethyl-1,3,2-dioxaborolane (60 mg), Pd$_2$(dba)$_3$ (20 mg), tritertbutylphosphine tetrafluoroborate (12 mg) and K$_3$PO$_4$ (60 mg), dioxane (5 mL) and water (100 µL) were added. The reaction mixture was heated at 100° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC to yield Cpd. No. 78 in 8 mg as a salt of CF$_3$CO$_2$H. ESI-MS calculated for C$_{22}$H$_{22}$N$_3$O$_2$ [M+H]$^+$=360.17; Observed: 360.4.

Example 48

Synthesis of 7-benzyl-1-methyl-8-(tetrahydro-2H-pyran-4-yl)-4,6-dihydrobenzo[e][1,2,4]triazolo[3,4-c][1,4]oxazepine (Cpd. No. 79)

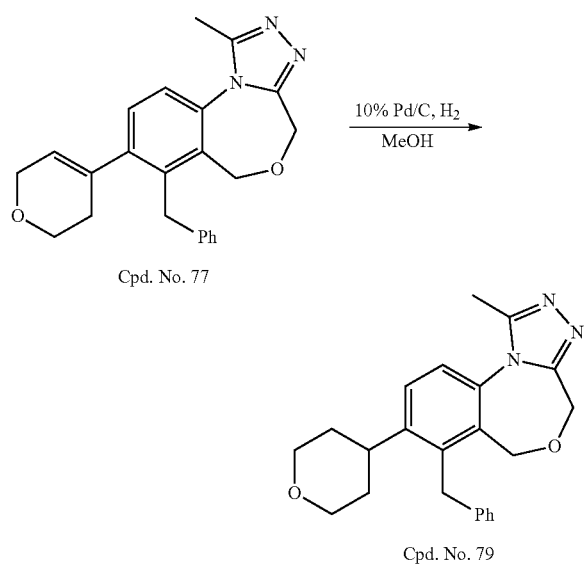

Cpd. No. 77 (20 mg) was dissolved in a mixture of methanol (4.0 mL). Then 10% Pd/C (4 mg) was added and the reaction mixture was stirred under $H_2$ (1 atm) at room temperature for 10 h. The mixture was filtered and the filtrate was concentrated on a rotary evaporator. The residues were purified by reverse phase HPLC to yield Cpd. No. 79 in 11 mg as a salt of $CF_3CO_2H$. ESI-MS calculated for $C_{23}H_{26}N_3O_2$ [M+H]$^+$=376.20; Observed: 376.4.

Example 49

Synthesis of 7-benzyl-8-(furan-3-yl)-1-methyl-4,6-dihydrobenzo[e][1,2,4]triazolo[3,4-c][1,4]oxazepine (Cpd. No. 80)

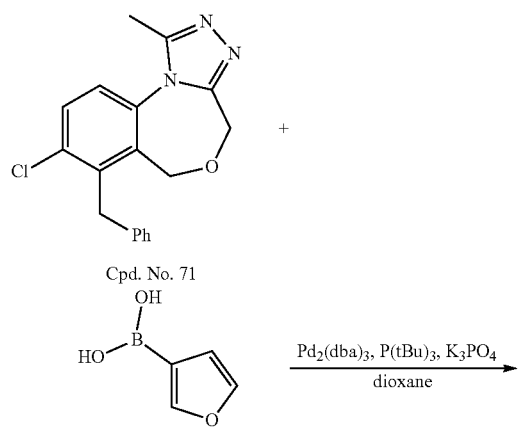

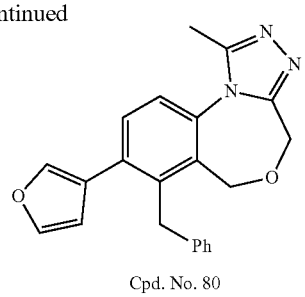

To a round-bottom flask containing Cpd. No. 71 (31 mg, 0.1 mmol), furan-3-ylboronic acid (60 mg), $Pd_2(dba)_3$ (20 mg), tritertbutylphosphine tetrafluoroborate (12 mg) and $K_3PO_4$ (60 mg), dioxane (5 mL) and water (100 µL) were added. The reaction mixture was heated at 100° C. for 10 h. The reaction was cooled, taken up with saturated $NaHCO_3$, extracted with EtOAc. The organic layers were combined and washed with brine, dried over anhydrous sodium sulfate, and concentrated on a rotary evaporator. The residues were purified by reverse phase HPLC to yield Cpd. No. 80 in 15 mg as a salt of $CF_3CO_2H$. ESI-MS calculated for $C_{22}H_{20}N_3O_2$ [M+H]$^+$=358.15; Observed: 358.5. $^1$H NMR (400 MHz, MeOD) δ 7.74 (d, J=8.3 Hz, 1H), 7.67 (d, J=8.3 Hz, 1H), 7.57 (t, J=1.6 Hz, 1H), 7.47 (s, 1H), 7.29 (t, J=7.4 Hz, 2H), 7.21 (t, J=7.3 Hz, 1H), 7.01 (d, J=7.5 Hz, 2H), 6.47 (s, 1H), 4.62 (s, 2H), 4.47 (s, 2H), 4.37 (s, 2H), 2.77 (s, 3H).

Example 50

Synthesis of 7-benzyl-1-methyl-8-(tetrahydrofuran-3-yl)-4,6-dihydrobenzo[e][1,2,4]triazolo[3,4-c][1,4]oxazepine (Cpd. No. 81)

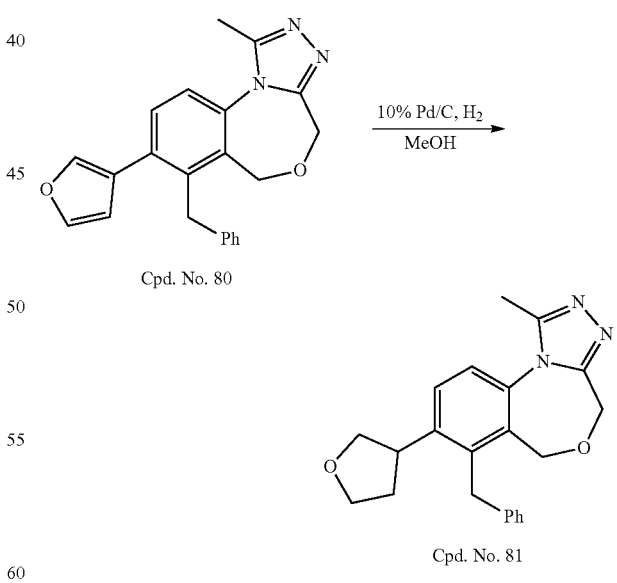

Cpd. No. 80 (20 mg) was dissolved in a mixture of methanol (4.0 mL). Then 10% Pd/C (4 mg) was added and the reaction mixture was stirred under $H_2$ (1 atm) at room temperature for 10 h. The mixture was filtered and the filtrate was concentrated on a rotary evaporator. The residues were purified by reverse phase HPLC to yield Cpd. No. 81 in 10 mg as a salt of CF$_3$CO$_2$H. ESI-MS calculated for C$_{22}$H$_{24}$N$_3$O$_2$ [M+H]$^+$=362.18; Observed: 362.4. $^1$H NMR (400 MHz, MeOD) δ 7.74 (d, J=8.5 Hz, 1H), 7.63 (d, J=8.5 Hz, 1H), 7.29 (t, J=7.4 Hz, 2H), 7.21 (t, J=7.3 Hz, 1H), 7.07 (d, J=7.1 Hz, 2H), 4.62 (s, 2H), 4.51 (s, 2H), 4.42 (s, 2H), 4.07 (td, J=8.3, 4.9 Hz, 1H), 3.90-3.79 (m, 2H), 3.78-3.67 (m, 2H), 2.72 (s, 3H), 2.24 (m, 1H), 1.93 (m, 1H).

Example 51

Synthesis of 7-benzyl-1-methyl-8-((trimethylsilyl)ethynyl)-4,6-dihydrobenzo[e][1,2,4]triazolo[3,4-c][1,4]oxazepine (Cpd. No. 82)

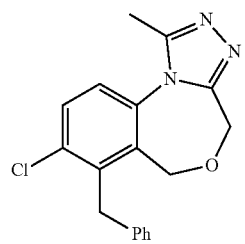

Cpd. No. 71

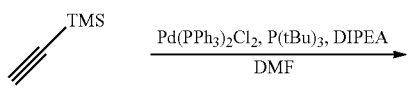

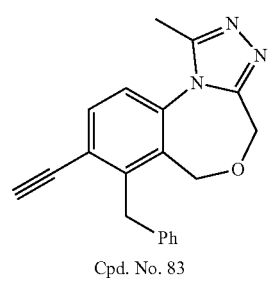

Cpd. No. 82

To a round-bottom flask containing Cpd. No. 71 (15 mg, 0.05 mmol), ethynyltrimethylsilane (15 μL), Pd(PPh$_3$)$_2$Cl$_2$ (10 mg), tritertbutylphosphine tetrafluoroborate (7 mg) and DIPEA (0.5 mL), DMF (0.5 mL) were added. The reaction mixture was heated at 80° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC to yield Cpd. No. 82 in 4 mg as a salt of CF$_3$CO$_2$H. ESI-MS calculated for C$_{23}$H$_{26}$N$_3$OSi [M+H]$^+$=388.18; Observed: 388.3.

Example 52

Synthesis of 7-benzyl-8-ethynyl-1-methyl-4,6-dihydrobenzo[e][1,2,4]triazolo[3,4-c][1,4]oxazepine (Cpd. No. 83)

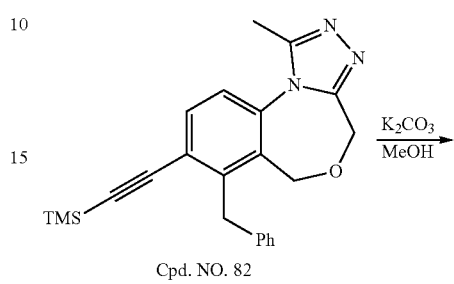

Cpd. NO. 82

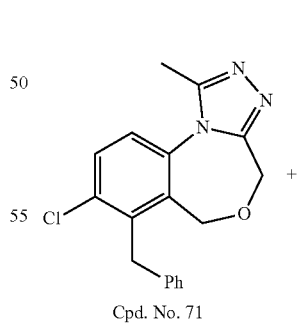

Cpd. No. 83

To a round-bottom flask containing Cpd. No. 82 (15 mg), and K$_2$CO$_3$ (1 mg), MeOH (1 mL) were added. The reaction mixture was stirred at rt for 2 h. The mixture were purified by reverse phase HPLC to yield Cpd. No. 83 in 3 mg as a salt of CF$_3$CO$_2$H. ESI-MS calculated for C$_{20}$H$_{18}$N$_3$O [M+H]$^+$=316.14; Observed: 316.4.

Example 53

Synthesis of 4-(7-benzyl-1-methyl-4,6-dihydrobenzo[e][1,2,4]triazolo[3,4-c][1,4]oxazepin-8-yl)but-3-yn-1-ol (Cpd. No. 84)

Cpd. No. 71

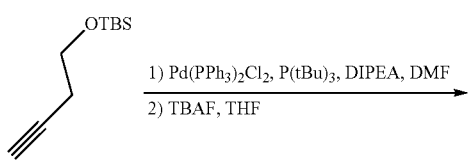

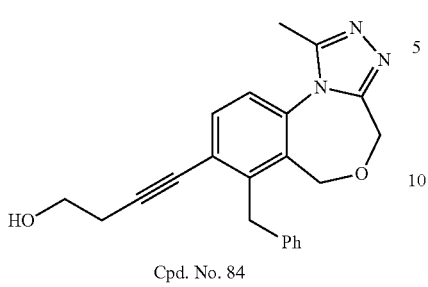

Cpd. No. 84

To a round-bottom flask containing Cpd. No. 71 (15 mg), (but-3-yn-1-yloxy)(tert-butyl)dimethylsilane (44 mg), Pd(PPh$_3$)$_2$Cl$_2$ (12 mg), tri tert butylphosphine tetrafluoroborate (10 mg), Cs$_2$CO$_3$ (33 mg) and DIPEA (0.2 mL), DMF (0.3 mL) were added. The reaction mixture was heated at 100° C. for 4 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC to yield the intermediate which was dissolved in THF (3 mL). Then TBAF (1 M/L in THF, 0.06 mL) was added and the mixture was stirred for 15 min at room temperature. The mixture was purified by reverse phase HPLC to yield Cpd. No. 84 in 4 mg as a salt of CF$_3$CO$_2$H. ESI-MS calculated for C$_{22}$H$_{22}$N$_3$O$_2$[M+H]$^+$=360.17; Observed: 360.5.

Example 54

Synthesis of methyl 2-amino-4-bromothiophene-3-carboxylate

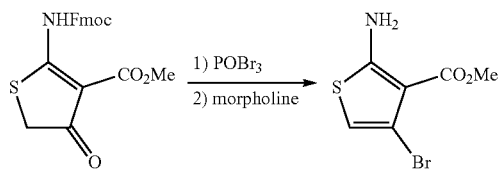

To a suspension of methyl 2-((((9H-fluoren-9-yl)methoxy)carbonyl)amino)-4-oxo-4,5-dihydrothiophene-3-carboxylate (3.1 g) in dioxane (20 mL) was added POBr$_3$ (2.7 g) and the reaction mixture was heated to reflux for 1 hour. The reaction mixture was cooled and poured into the mixture of ice-water. The reaction mixture was extracted with EtOAc (3×200 mL). The combined organic layers were washed with brine, dried over Na$_2$SO$_4$ and concentrated. The residue was dissolved in DCM (30 mL) and morpholine (5 g) was added and the reaction mixture was stirred overnight. The reaction mixture was filtered and rinsed with small amount of Et$_2$O. The filtrate was evaporated under vacuum and the residue was chromatographed on silica gel (pure DCM) to afford 2-amino-4-bromothiophene-3-carboxylate as a white solid (0.9 g).

Example 55

Synthesis of (S)-methyl 4-bromo-2-(2-((tert-butyldiphenylsilyl)oxy)propanamido)thiophene-3-carboxylate (ZBC180)

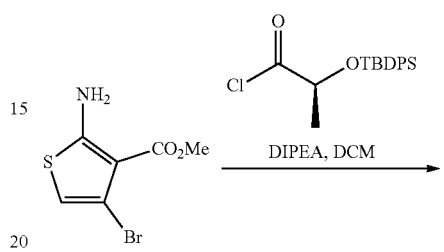

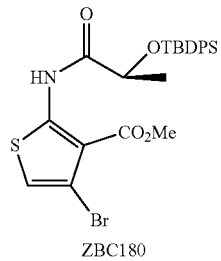

ZBC180

A solution of 2-amino-4-bromothiophene-3-carboxylate (50 mg) in DCM (10 mL) was cooled to 0° C. and DIPEA (37 µL) was added slowly. Then (S)-2-((tert-butyldiphenylsilyl)oxy)propanoyl chloride (60 mg) was added. After stirring at 0° C. for 30 min, the reaction was diluted with DCM, washed with brine, dried, and concentrated on a rotary evaporator. The remaining residues were purified by flash column chromatography on silica gel to afford ZBC180 in 56 mg. ESI-MS calculated for C$_{25}$H$_{29}$BrNO$_4$SSi [M+H]$^+$=546.07; Observed: 546.3.

Example 56

Synthesis of (S)-methyl 4-bromo-2-(2-((tert-butyldiphenylsilyl)oxy)propanethioamido)thiophene-3-carboxylate (ZBC181)

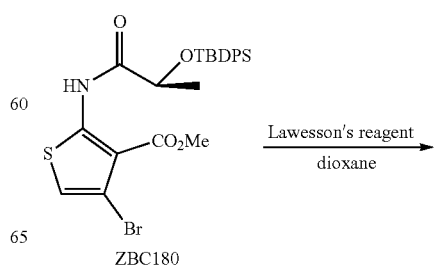

ZBC180

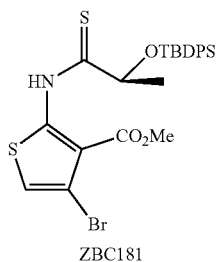

ZBC181

The mixture of ZBC180 (80 mg) and Lawesson's reagent (35 mg) in dioxane (10 mL) was heated at 80° C. overnight. Then the mixture was concentrated on a rotary evaporator and directly purified by flash column chromatography on silica gel to afford ZBC181 in 50 mg. ESI-MS calculated for $C_{25}H_{29}BrNO_3S_2Si$ $[M+H]^+$=562.05; Observed: 562.3.

Example 57

Synthesis of (S)-methyl 4-bromo-2-(3-(1-((tert-butyldiphenylsilyl)oxy)ethyl)-5-methyl-4H-1,2,4-triazol-4-yl)thiophene-3-carboxylate (ZBC183)

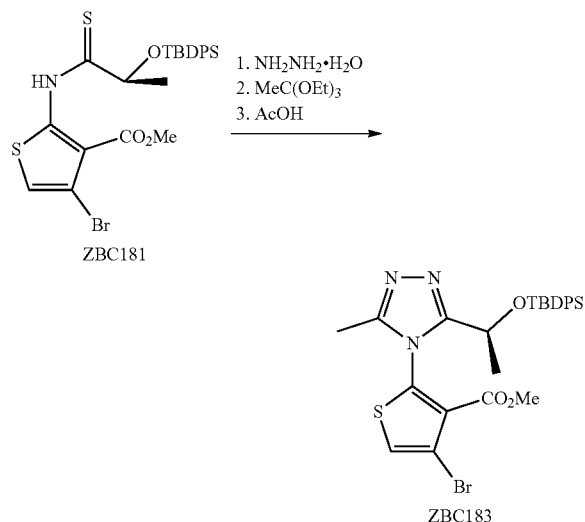

To a solution of ZBC181 (5.1 g, 9.2 mmol) in THF (10 mL) was added hydrazine monohydrate (0.89 mL, 18.4 mmol, 2 eq) at 0° C. and the reaction mixture was allowed to warm to r.t. The reaction mixture was stirred for 4 h prior to being concentrated in vacuum. The residue was taken up in DCM and washed with water and brine. The organic layer was separated, dried and concentrated. The residue was taken up in ethanol (10 mL) and triethyl orthoacetate (5 mL, 27.6 mmol, 3 eq) was added. The reaction mixture was heated at reflux for 1 h. All volatiles were removed under vacuum and the residue was dissolved in AcOH (10 mL). The solution was heated at reflux for 1 h prior to the removal of the solvent under vacuum. The residue was chromatographed on silica gel to give ZBC183 in 2.3 g. ESI-MS calculated for $C_{27}H_{31}BrN_3O_3SSi$ $[M+H]^+$=584.10; Observed: 584.3.

Example 58

Synthesis of (S)-4-(4-bromo-3-(chloromethyl)thiophen-2-yl)-3-(1-((tert-butyldiphenylsilyl)oxy)ethyl)-5-methyl-4H-1,2,4-triazole (ZBC184)

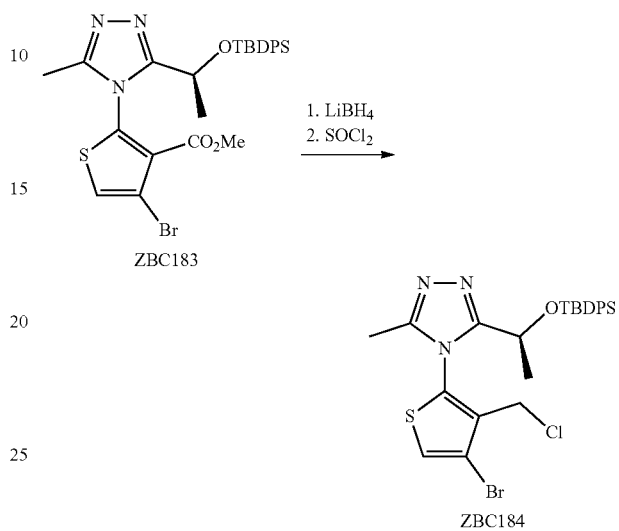

To a solution of ZBC183 (2.5 g, 4.3 mmol) in THF (30 mL) at 0° C. was added a solution of $LiBH_4$ (2 M in THF, 3.3 mL, 6.5 mmol, 1.5 eq). MeOH (3 mL) was added and the reaction mixture was allowed to warm to r.t. and stirred for 12 h. All volatiles were removed and the residue was taken up in EtOAc. The organic layer was washed with water and brine prior to being dried and concentrated. The residue was dissolved in DCM (20 mL) and cooled to 0° C. Thionyl chloride (0.94 mL, 12.9 mmol, 3 eq) was added and the reaction mixture was allowed to warm to r.t. After 1 h, all the volatiles were removed and the residue was taken up in EtOAc and washed with 1 M $Na_2CO_3$. The organic layer was washed with brine, dried and concentrated. The residue was chromatographed on silica gel (ethyl acetate/triethylamine 25:1) to give title compound in 1.8 gram. ESI-MS calculated for $C_{26}H_{30}BrClN_3OSSi$ $[M+H]^+$=574.07; Observed: 574.3.

Example 59

Synthesis of (S)-3-bromo-6,9-dimethyl-4,6-dihydrothieno[2,3-e][1,2,4]triazolo[3,4-c][1,4]oxazepine (Cpd. No. 117)

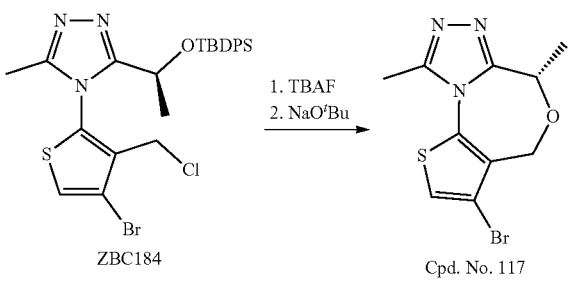

To a solution of ZBC184 (1.9 g, 3.3 mmol) in THF (10 mL) at 0° C. was added a solution of TBAF (3.6 mL, 3.6 mmol, 1M in THF). The solution was stirred for 1 h prior to being added to a hot solution of NaOtBu (634 mg, 6.6 mmol, 2 eq) in ᵗBuOH (40 mL) at 80° C. The reaction mixture was stirred for 5 min prior to the removal of the solvent under vacuum. The residue was taken up in EtOAc and water. The organic layer was washed with brine, dried and concentrated. The residue was purified through HPLC to afford TFA salt of Cpd. No. 117 (704 mg). ESI-MS calculated for $C_{10}H_{11}BrN_3OS$ [M+H]$^+$=299.98; Observed: 300.3. $^1$H NMR (400 MHz, MeOD) δ 7.67 (s, 1H), 5.04 (d, J=15.8 Hz, 1H), 4.88 (d, J=15.8 Hz, 1H), 4.80 (q, J=6.5 Hz, 1F), 2.81 (s, 311), 1.72 (d, J=6.5 Hz, 3H).

Example 60

Synthesis of (S)-3-benzyl-6,9-dimethyl-4,6-dihydrothieno[2,3-e][1,2,4]triazolo[3,4-c][1,4]oxazepine (Cpd. No. 118)

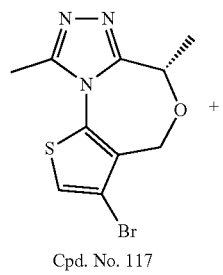

Cpd. No. 117

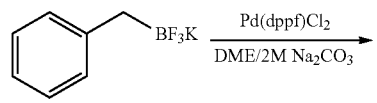

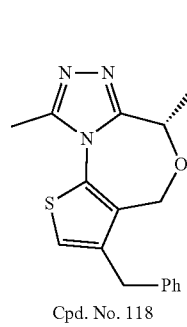

Cpd. No. 118

To a round-bottom flask containing Cpd. No. 117 (30 mg, 0.1 mmol), potassium benzyltrifluoroborate (40 mg, 0.2 mmol), Pd(dppf)Cl$_2$ (8 mg), DME (3 mL) and a solution of Na$_2$CO$_3$ in water (2.0 M, 1 mL) was added under N$_2$ atmosphere. The reaction mixture was heated at 100° C. for 4 h. The reaction was cooled, taken up with saturated NaHCO$_3$, extracted with DCM. The organic layers were combined and washed with brine, dried over anhydrous sodium sulfate, and concentrated on a rotary evaporator. The residues were purified by reverse phase HPLC. Cpd. No. 118 was isolated in 21 mg as a salt of CF$_3$CO$_2$H. ESI-MS calculated for $C_{17}H_{18}N_3OS$ [M+H]$^+$=312.11; Observed: 312.4. $^1$H NMR (400 MHz, MeOD) δ 7.33 (t, J=7.3 Hz, 2H), 7.28-7.21 (m, 3H), 7.18 (s, 1H), 4.98 (d, J=15.6 Hz, 1H), 4.76-4.69 (m, 2H), 3.99-3.86 (m, 2H), 2.85 (s, 3H), 1.68 (d, J=6.6 Hz, 3H).

Example 61

Synthesis of (S)-3-benzyl-2-bromo-6,9-dimethyl-4,6-dihydrothieno[2,3-e][1,2,4]triazolo[3,4-c][1,4]oxazepine (Cpd. No. 119)

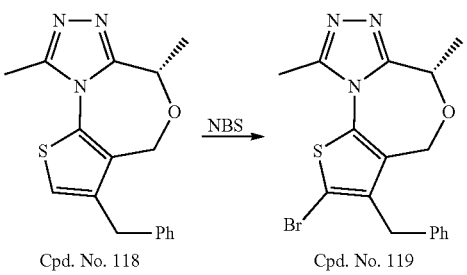

Cpd. No. 118     Cpd. No. 119

To a solution of Cpd. No. 118 (240 mg, 0.57 mmol) in AcOH (4 mL) was added NBS (101 mg, 0.57 mmol, 1 eq). The reaction mixture was stirred for 1 h prior to the addition of water (2 mL) and methanol (2 mL). All volatiles were removed under vacuum and the residue was purified by reverse phase HPLC to afford Cpd. No. 119 (240 mg) as a salt of CF$_3$CO$_2$H. ESI-MS calculated for $C_7H_{17}BrN_3OS$ [M+H]$^+$=390.02; Observed: 390.3.

Example 62

Synthesis of (S)-3-benzyl-6,9-dimethyl-2-((1-methyl-1H-pyrazol-4-yl)ethynyl)-4,6-dihydrothieno[2,3-e][1,2,4]triazolo[3,4-c][1,4]oxazepine (Cpd. No. 85)

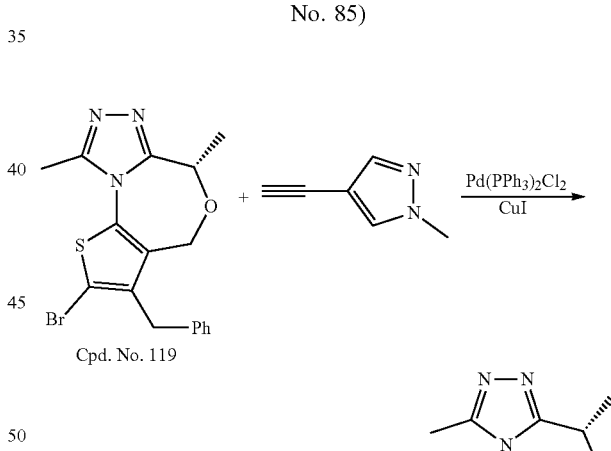

Cpd. No. 119

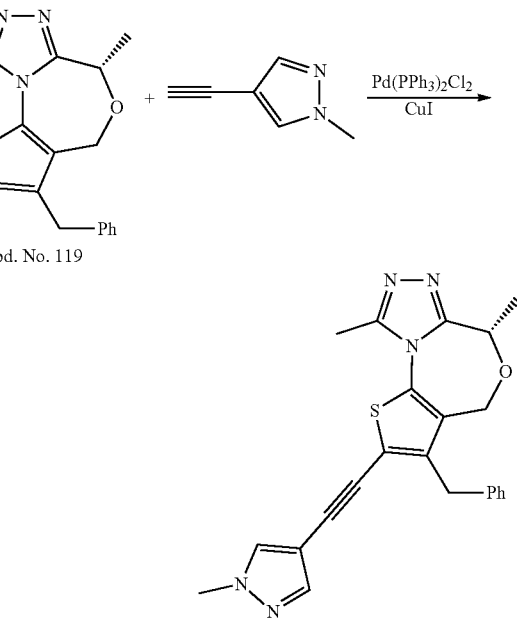

Cpd. No. 85

To a round-bottom flask containing Cpd. No. 119 (25 mg), 4-ethynyl-1-methyl-1H-pyrazole (16 mg), Pd(PPh$_3$)Cl$_2$ (13.5 mg) and CuI (7.3 mg), Et$_3$N (0.5 mL) and THF (1 mL) was added under N$_2$ atmosphere. The reaction mixture was heated at 60° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC. Cpd. No. 85 was isolated in 18 mg as a salt of CF$_3$CO$_2$H. ESI-MS calculated for C$_{23}$H$_{22}$N$_5$OS [M+H]$^+$=416.15; Observed: 416.2. $^1$H NMR (400 MHz, MeOD) δ 7.87 (s, 1H), 7.63 (s, 1H), 7.34-7.17 (m, 5H), 4.82 (d, J=15.2 Hz, 1H), 4.65-4.51 (m, 2H), 4.16-3.99 (m, 2H), 3.90 (s, 3H), 2.72 (s, 3H), 1.63 (d, J=6.5 Hz, 3H).

Example 63

Synthesis of 3-benzyl-9-methyl-2-((1-methyl-H-imidazol-5-yl)ethynyl)-4,6-dihydrothieno[2,3-e][1,2,4]triazolo[3,4-c][1,4]oxazepine (Cpd. No. 86)

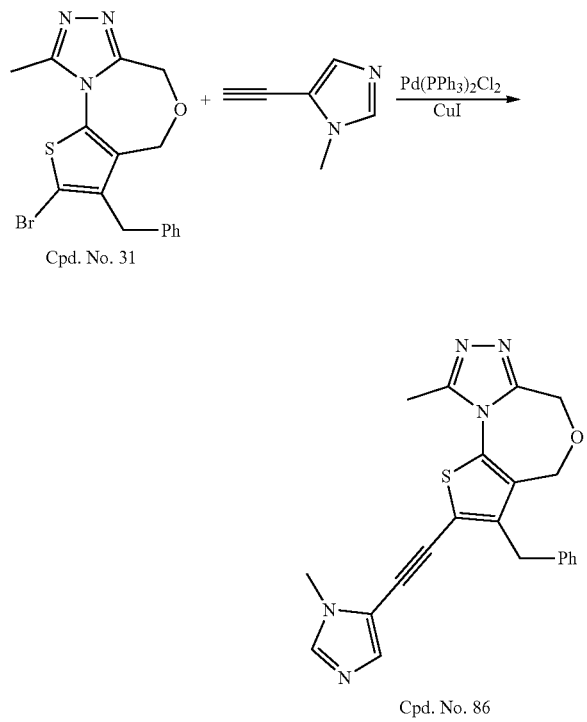

Cpd. No. 86

To a round-bottom flask containing Cpd. No. 31 (25 mg), 5-ethynyl-1-methyl-1H-imidazole (16 mg), Pd(PPh$_3$)Cl$_2$ (13.5 mg) and CuI (7.3 mg), Et$_3$N (0.5 mL) and THF (1 mL) was added under N$_2$ atmosphere. The reaction mixture was heated at 60° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC. Cpd. No. 86 was isolated in 10 mg as a salt of CF$_3$CO$_2$H. ESI-MS calculated for C$_{22}$H$_{20}$N$_5$OS [M+H]$^+$=402.13; Observed: 402.3. H NMR (400 MHz, MeOD) δ 8.97 (s, 1H), 7.93 (s, 1H), 7.37-7.28 (m, 2H), 7.27-7.21 (m, 3H), 4.77 (s, 2H), 4.75 (s, 2H), 4.19 (s, 2H), 3.88 (s, 3H), 2.79 (s, 3H).

Example 64

Synthesis of 3-benzyl-9-methyl-2-(pyridin-4-ylethynyl)-4,6-dihydrothieno[2,3-e][1,2,4]triazolo[3,4-c][1,4]oxazepine (Cpd. No. 87)

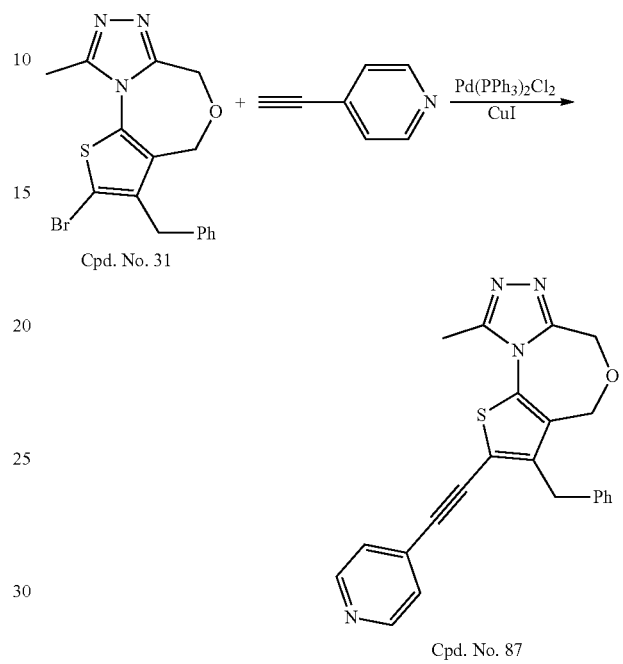

Cpd. No. 87

To a round-bottom flask containing Cpd. No. 31 (25 mg), 4-ethynylpyridine (16 mg), Pd(PPh$_3$)Cl$_2$(13.5 mg) and CuI (7.3 mg), Et$_3$N (0.5 mL) and THF (1 mL) was added under N$_2$ atmosphere. The reaction mixture was heated at 60° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC. Cpd. No. 87 was isolated in 10 mg as a salt of CF$_3$CO$_2$H. ESI-MS calculated for C$_{23}$H$_{19}$N$_4$OS [M+H]$^+$=399.12; Observed: 399.4. $^1$H NMR (400 MHz, MeOD) δ 8.83 (brs, 2H), 7.85 (brs, 2H), 7.46-7.16 (m, 5H), 4.77 (s, 4H), 4.23 (s, 2H), 2.79 (s, 3H).

Example 65

Synthesis of 3-benzyl-9-methyl-2-(pyridin-3-ylethynyl)-4,6-dihydrothieno[2,3-e][1,2,4]triazolo[3,4-c][1,4]oxazepine (Cpd. No. 88)

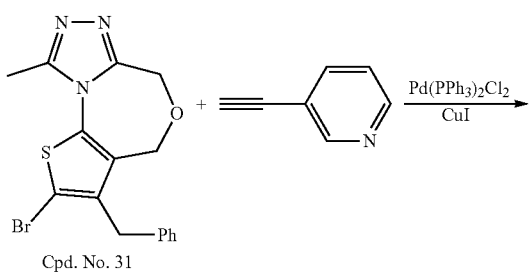

Cpd. No. 31

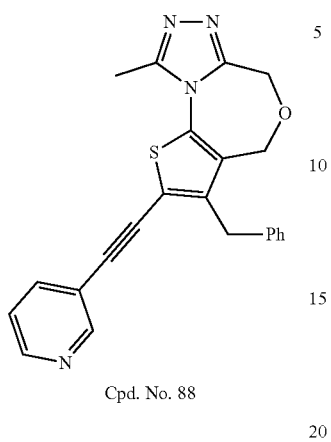

Cpd. No. 88

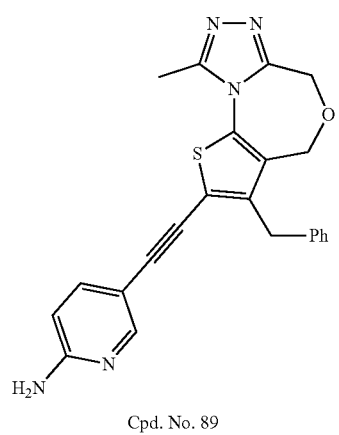

Cpd. No. 89

To a round-bottom flask containing Cpd. No. 31 (25 mg), 3-ethynylpyridine (16 mg), Pd(PPh$_3$)Cl$_2$ (13.5 mg) and CuI (7.3 mg), Et$_3$N (0.5 mL) and THF (1 mL) was added under N$_2$ atmosphere. The reaction mixture was heated at 60° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC. Cpd. No. 88 was isolated in 16 mg as a salt of CF$_3$CO$_2$H. ESI-MS calculated for C$_{23}$H$_{19}$N$_4$OS [M+H]$^+$=399.12; Observed: 399.3.

Example 66

Synthesis of 5-((3-benzyl-9-methyl-4,6-dihydrothieno[2,3-e][1,2,4]triazolo[3,4-c][1,4]oxazepin-2-yl)ethynyl)pyridin-2-amine (Cpd. No. 89)

To a round-bottom flask containing Cpd. No. 31 (25 mg), 5-ethynylpyridin-2-amine (16 mg), Pd(PPh$_3$)Cl$_2$ (13.5 mg) and CuI (7.3 mg), Et$_3$N (0.5 mL) and THF (1 mL) was added under N$_2$ atmosphere. The reaction mixture was heated at 60° C. for 10 h. The reaction was cooled, taken up with saturated NaHCO$_3$, extracted with EtOAc. The organic layers were combined and washed with brine, dried over anhydrous sodium sulfate, and concentrated on a rotary evaporator. The residues were purified by reverse phase HPLC. Cpd. No. 89 was isolated in 16 mg as a salt of CF$_3$CO$_2$H. ESI-MS calculated for C$_{23}$H$_{20}$N$_5$OS [M+H]$^+$=414.13; Observed: 414.3. $^1$H NMR (400 MHz, MeOD) δ 8.10 (d, J=1.8 Hz, 1H), 7.96 (dd, J=9.3, 2.0 Hz, 1H), 7.37-7.21 (m, 5H), 7.05 (d, J=9.3 Hz, 1H), 4.75 (s, 2H), 4.73 (s, 2H), 4.16 (s, 2H), 2.78 (s, 3H).

Example 67

Synthesis of (S)-3-benzyl-6,9-dimethyl-2-((1-methyl-H-imidazol-5-yl)ethynyl)-4,6-dihydrothieno[2,3-e][1,2,4]triazolo[3,4-c][1,4]oxazepine (Cpd. No. 120)

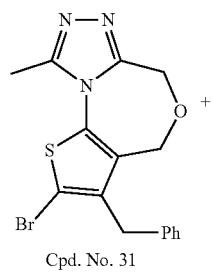

Cpd. No. 31

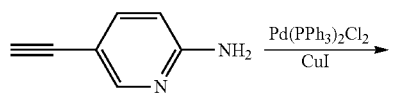

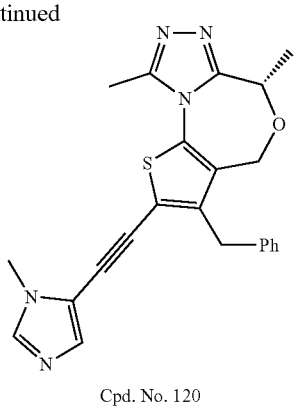

Cpd. No. 120

To a round-bottom flask containing Cpd. No. 119 (25 mg), 5-ethynyl-1-methyl-1H-imidazole (16 mg), Pd(PPh₃)Cl₂ (13.5 mg) and CuI (7.3 mg), Et₃N (0.5 mL) and THF (1 mL) was added under N₂ atmosphere. The reaction mixture was heated at 60° C. for 10 h. The reaction was cooled, taken up with saturated NaHCO₃, extracted with EtOAc. The organic layers were combined and washed with brine, dried over anhydrous sodium sulfate, and concentrated on a rotary evaporator. The residues were purified by reverse phase HPLC. Cpd. No. 120 was isolated in 13 mg as a salt of CF₃CO₂H. ESI-MS calculated for $C_{23}H_{22}N_5OS$ [M+H]⁺=416.15; Observed: 416.4. ¹H NMR (400 MHz, MeOD) δ 9.00 (s, 1H), 7.95 (s, 1H), 7.39-7.18 (m, 5H), 4.90 (d, J=15.3 Hz, 1H), 4.75-4.59 (m, 2H), 4.19 (q, J=15.9 Hz, 2H), 3.89 (s, 3H), 2.80 (s, 3H), 1.66 (d, J=6.5 Hz, 3H).

Example 68

Synthesis of (S)-3-benzyl-6,9-dimethyl-2-(pyridin-4-ylethynyl)-4,6-dihydrothieno[2,3-e][1,2,4]triazolo[3,4-c][1,4]oxazepine (Cpd. No. 121)

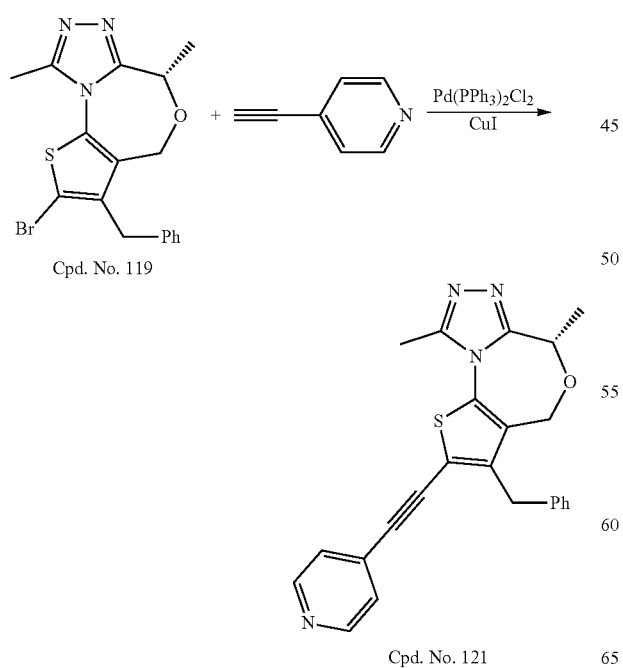

To a round-bottom flask containing Cpd. No. 119 (25 mg), 4-ethynylpyridine (16 mg), Pd(PPh₃)Cl₂ (13.5 mg) and CuI (7.3 mg), Et₃N (0.5 mL) and THF (1 mL) was added under N₂ atmosphere. The reaction mixture was heated at 60° C. for 10 h. The reaction was cooled, taken up with saturated NaHCO₃, extracted with EtOAc. The organic layers were combined and washed with brine, dried over anhydrous sodium sulfate, and concentrated on a rotary evaporator. The residues were purified by reverse phase HPLC. Cpd. No. 121 was isolated in 17 mg as a salt of CF₃CO₂H. ESI-MS calculated for $C_{24}H_{21}N_4OS$ [M+H]⁺=413.14; Observed: 413.2. ¹H NMR (400 MHz, MeOD) δ 8.81 (brs, 2H), 8.02 (d, J=5.6 Hz, 2H), 7.38-7.21 (m, 5H), 4.92 (d, J=15.2 Hz, 1H), 4.73-4.65 (m, 2H), 4.25 (q, J=15.7 Hz, 2H), 2.82 (s, 3H), 1.67 (d, J=6.5 Hz, 3H).

Example 69

Synthesis of (S)-3-benzyl-6,9-dimethyl-2-(pyridin-3-ylethynyl)-4,6-dihydrothieno[2,3-e][1,2,4]triazolo[3,4-c][1,4]oxazepine (Cpd. No. 122)

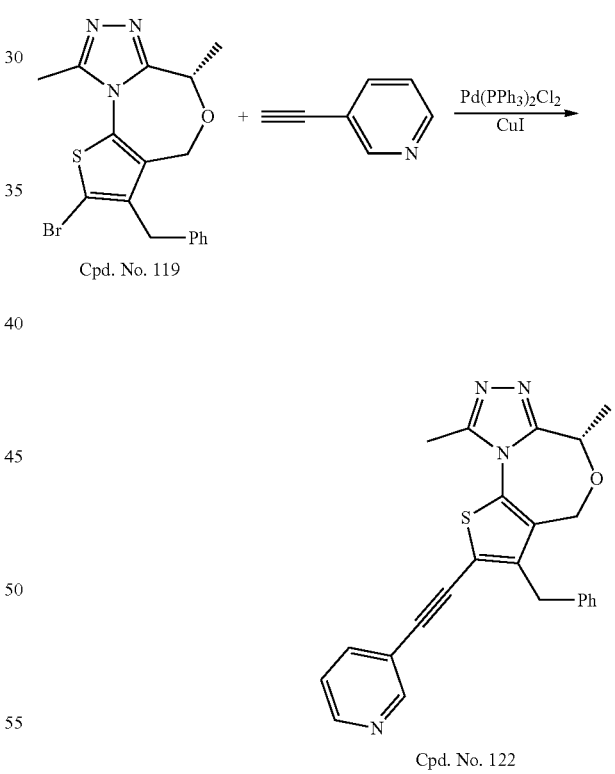

To a round-bottom flask containing Cpd. No. 119 (25 mg), 3-ethynylpyridine (16 mg), Pd(PPh₃)Cl₂ (13.5 mg) and CuI (7.3 mg), Et₃N (0.5 mL) and THF (1 mL) was added under N₂ atmosphere. The reaction mixture was heated at 60° C. for 10 h. The reaction was cooled, taken up with saturated NaHCO₃, extracted with EtOAc. The organic layers were combined and washed with brine, dried over anhydrous sodium sulfate, and concentrated on a rotary evaporator. The residues were purified by reverse phase HPLC. Cpd. No. 122 was isolated in 17 mg as a salt of CF₃CO₂H. ESI-MS calculated for $C_{24}H_{21}N_4OS$ [M+H]⁺=413.14; Observed: 413.2. ¹H NMR (400 MHz, MeOD) δ 8.88 (brs, 1H), 8.71 (brs, 1H), 8.31 (d, J=8.1 Hz, 1H), 7.78 (dd, J=7.9, 5.4 Hz, 1H), 7.36-7.20 (m, 5H), 4.91 (d, J=15.6 Hz, 1H), 4.76-4.62 (m, 2H), 4.22 (q, J=15.7 Hz, 2H), 2.84 (s, 3H), 1.66 (d, J=6.5 Hz, 2H).

Example 70

Synthesis of (S)-5-((3-benzyl-6,9-dimethyl-4,6-dihydrothieno[2,3-e][1,2,4]triazolo[3,4-c][1,4]oxazepin-2-yl)ethynyl)pyridin-2-amine (Cpd. No. 123)

HPLC. Cpd. No. 123 was isolated in 10 mg as a salt of CF₃CO₂H. ESI-MS calculated for $C_{24}H_{22}N_5OS$ [M+H]⁺=428.15; Observed: 428.4. ¹H NMR (400 MHz, MeOD) δ 8.10 (d, J=2.0 Hz, 1H), 7.95 (dd, J=9.2, 1.8 Hz, 1H), 7.36-7.19 (m, 5H), 7.05 (d, J=9.3 Hz, 1H), 4.88 (d, J=15.4 Hz, 1H), 4.71-4.59 (m, 2H), 4.15 (q, J=15.8 Hz, 2H), 2.80 (s, 3H), 1.65 (d, J=6.5 Hz, 3H).

Example 71

Synthesis of (S)-3-(4-fluorobenzyl)-6,9-dimethyl-4,6-dihydrothieno[2,3-e][1,2,4]triazolo[3,4-c][1,4]oxazepine (Cpd. No. 124)

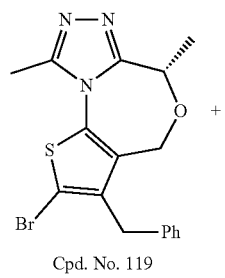

Cpd. No. 119

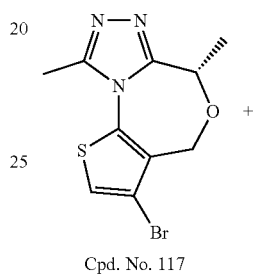

Cpd. No. 117

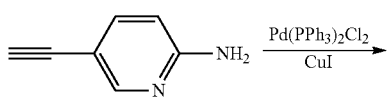

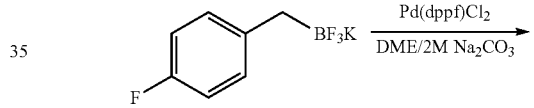

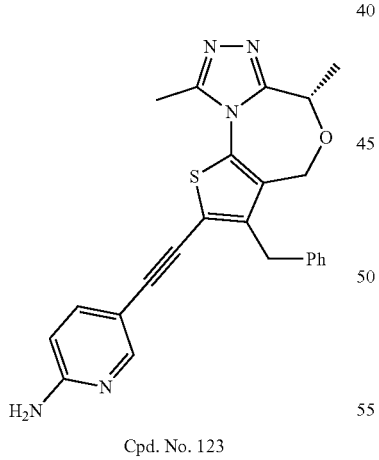

Cpd. No. 123

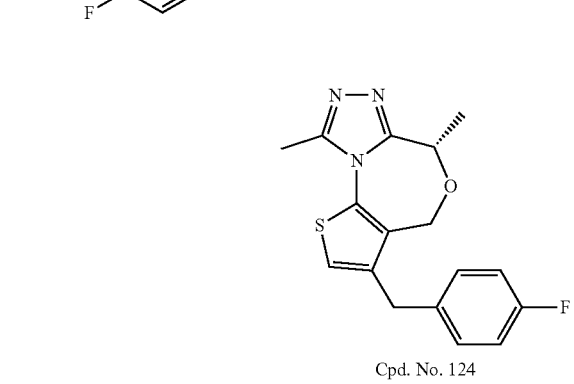

Cpd. No. 124

To a round-bottom flask containing Cpd. No. 119 (25 mg), 5-ethynylpyridin-2-amine (16 mg), Pd(PPh₃)Cl₂ (13.5 mg) and CuI (7.3 mg), Et₃N (0.5 mL) and THF (1 mL) was added under N₂ atmosphere. The reaction mixture was heated at 60° C. for 10 h. The reaction was cooled, taken up with saturated NaHCO₃, extracted with EtOAc. The organic layers were combined and washed with brine, dried over anhydrous sodium sulfate, and concentrated on a rotary evaporator. The residues were purified by reverse phase To a round-bottom flask containing Cpd. No. 117 (30 mg, 0.1 mmol), potassium 4-fluorobenzyltrifluoroborate (40 mg, 0.2 mmol), Pd(dppf)Cl₂(8 mg), DME (3 mL) and a solution of Na₂CO₃ in water (2.0 M, 1 mL) was added under N₂ atmosphere. The reaction mixture was heated at 100° C. for 4 h. The reaction was cooled, taken up with saturated NaHCO₃, extracted with DCM. The organic layers were combined and washed with brine, dried over anhydrous sodium sulfate, and concentrated on a rotary evaporator. The residues were purified by reverse phase HPLC. Cpd. No. 124 was isolated in 21 mg as a salt of CF₃CO₂H. ESI-MS calculated for $C_{17}H_{17}FN_3OS$ [M+H]+=330.10, Observed: 330.2. ¹H NMR (400 MHz, MeOD) δ 7.28-7.22 (m, 2H), 7.15 (s, 1H), 7.10-7.03 (m, 2H), 4.95 (dd, J=15.4 Hz, 1H), 4.75-4.66 (m, 2H), 4.00-3.85 (m, 2H), 2.81 (s, 3H), 1.68 (d, J=6.5 Hz, 3H).

Example 72

Synthesis of (S)-2-bromo-3-(4-fluorobenzyl)-6,9-dimethyl-4,6-dihydrothieno[2,3-e][1,2,4]triazolo[3,4-c][1,4]oxazepine (Cpd. No. 125)

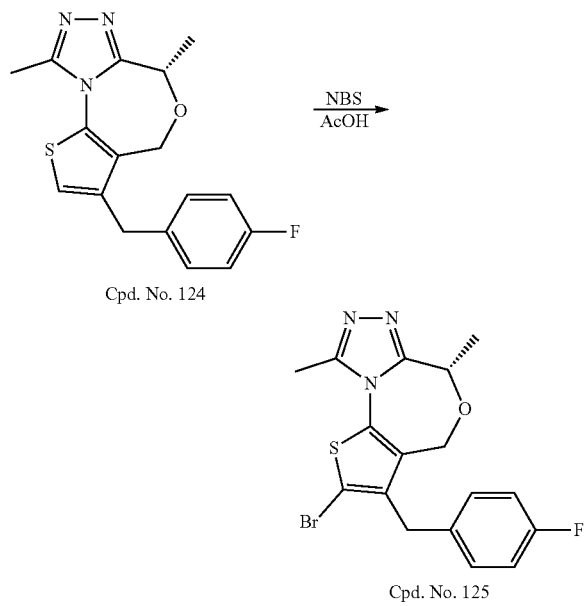

Cpd. No. 124

Cpd. No. 125

To a solution of Cpd. No. 124 (240 mg, 0.57 mmol) in AcOH (4 mL) was added NBS (101 mg, 0.57 mmol, 1 eq). The reaction mixture was stirred for 1 h. All volatiles were removed under vacuum and the residue was purified by reverse phase HPLC to afford Cpd. No. 125 (180 mg) as a salt of $CF_3CO_2H$. ESI-MS calculated for $C_{17}H_{16}BrFN_3OS$ $[M+H]^+=408.01$; Observed: 408.1.

Example 73

Synthesis of (S)-3-(4-fluorobenzyl)-6,9-dimethyl-2-((1-methyl-1H-pyrazol-4-yl)ethynyl)-4,6-dihydrothieno[2,3-e][1,2,4]triazolo[3,4-c][1,4]oxazepine (Cpd. No. 126)

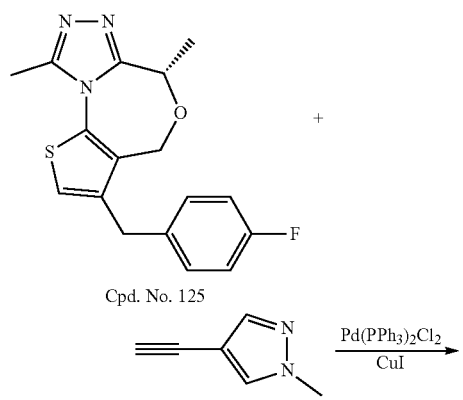

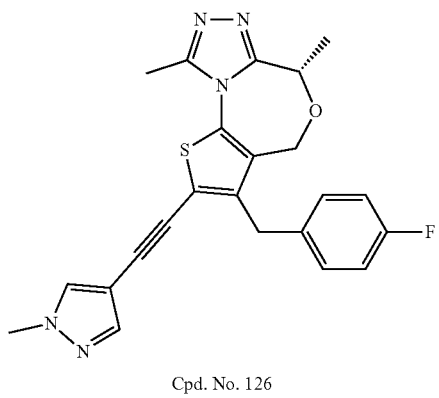

Cpd. No. 126

To a round-bottom flask containing Cpd. No. 125 (25 mg), 4-ethynyl-1-methyl-1H-pyrazole (16 mg), $Pd(PPh_3)Cl_2$ (13.5 mg) and CuI (7.3 mg), $Et_3N$ (0.5 mL) and THF (1 mL) was added under $N_2$ atmosphere. The reaction mixture was heated at 60° C. for 10 h. The reaction was cooled, taken up with saturated $NaHCO_3$, extracted with EtOAc. The organic layers were combined and washed with brine, dried over anhydrous sodium sulfate, and concentrated on a rotary evaporator. The residues were purified by reverse phase HPLC. Cpd. No. 126 was isolated in 18 mg as a salt of $CF_3CO_2H$. ESI-MS calculated for $C_{23}H_{21}FN_5OS$ $[M+H]^+=434.1$; Observed: 434.3. $^1$H NMR (400 MHz, MeOD) δ 7.90 (s, 1H), 7.66 (s, 1H), 7.29-7.24 (m, 2H), 7.08-7.02 (m, 2H), 4.85 (d, J=15.1 Hz, 1H), 4.64 (q, J=6.3 Hz, 1H), 4.58 (d, J=15.1 Hz, 1H), 4.08 (q, J=15.6 Hz, 3H), 3.92 (s, 3H), 2.74 (s, 3H), 1.65 (d, J=6.4 Hz, 3H).

Example 74

Synthesis of 3-bromo-2,9-dimethyl-4H,6H-thieno[2,3-e][1,2,4]triazolo[3,4-c][1,4]oxazepine (Cpd. No. 2)

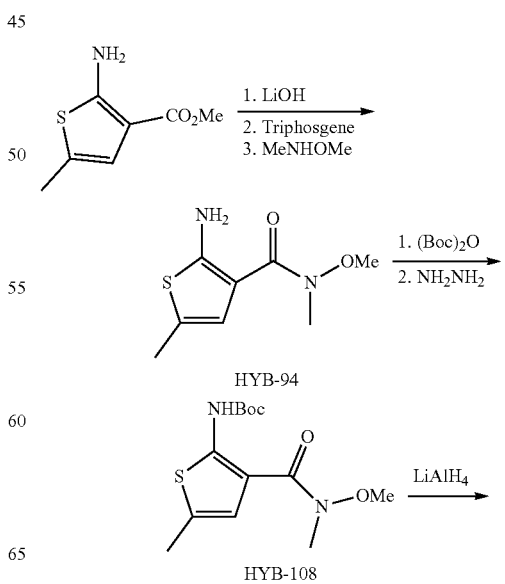

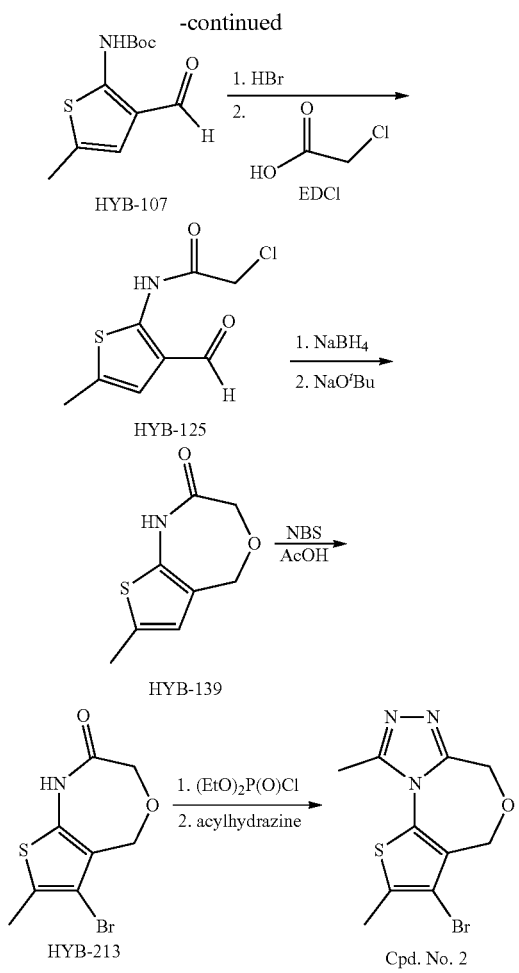

Example 74-A

Synthesis of 2-amino-N-methoxy-N,5-dimethylthiophene-3-carboxamide

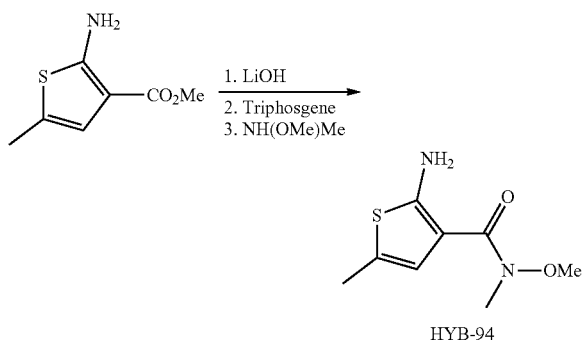

Step 1: 2-Amino-5-methyl-thiophene-3-carboxylic acid methyl ester (17.1 g, 100 mmol) was placed in a 1 L round-bottom flask equipped with a stir bar and dissolved in a mixture of THF (150 mL) and MeOH (100 mL). A solution of lithium hydroxide monohydrate (21 g, 500 mmol) in 250 mL of water was added to the flask with stirring. The flask was equipped with a condenser and the mixture was heated at 85° C. for 12 h. After cooling, the THF and MeOH were evaporated. The remaining solution was cooled at 0° C. and acidified to pH 4 with slow addition of 6 M HCl (~83 mL). The precipitate were filtered and washed with water. The wet solid were dissolved in EtOAc, washed with brine, and the organic layer was dried (Na$_2$SO$_4$), filtered and concentrated to give 12.8 g (82%) of 2-amino-5-methyl thiophene-3-carboxylic acid which was used without further purification.

Step 2: A round bottom flask containing a solution of 2-amino-5-methyl thiophene-3-carboxylic acid (12.8 g, 82 mmol, 1 equiv.) in dry THF (100 mL) was immersed into an oil bath. Triphosgene (8.2 g, 28 mmol, 0.34 equiv.) was added portionwise (exothermic reaction) and the reaction was heated at 40-50° C. for 3 hr. After cooling, hexanes (200 mL) was added. The precipitate was filtered to give the isatoic anhydride product (14.5 g, 97%).

Step 3: To a solution of N,O-dimethylhydroxylamine hydrochloride (11.5 g, 119 mmol) in 90% aqueous ethanol (40 mL) was added triethylamine (16.5 mL, 119 mmol). after 10 min of stirring at 25° C., isatoic anhydride product (14.5 g, 79 mmol) was added in portions. The reaction was then heated at reflux for 1.5 h and poured into an equal volume of ice and saturated sodium bicarbonate. The ethanol was then removed by rotary evaporation, the resulting aqueous mixture was extracted with ethyl acetate (3×150 mL) and the combined extract were washed with brine, dried, and concentrated to an oil. The oil was chromatographed on silica gel (1:2 ethyl acetate/hexanes) to give HYB-94 as a pale yellow oil: (9.5 g, 59%). $^1$H NMR (400 MHz, CDCl$_3$) δ 6.83 (s, 1H), 6.14 (br, s, 2H), 3.68 (s, 3H), 3.29 (s, 3H), 2.29 (s, 3H). ESI-MS: 201.62.

Example 74-B

Synthesis of tert-butyl (3-(methoxy(methyl)carbamoyl)-5-methylthiophen-2-yl)carbamate

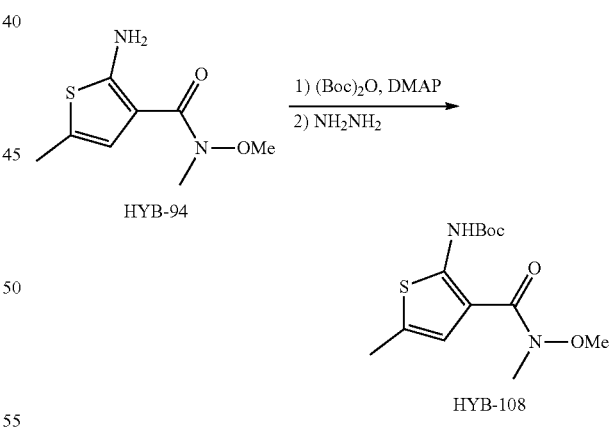

To a solution of HYB-94 (4.2 g, 21 mmol) in CH$_3$CN (50 mL) was added Boc$_2$O (7.3 g, 33.6 mmol, 1.6 eq) and DMAP (2.56 g, 21 mmol, 1 eq) and the mixture was stirred for 10 min during which time yellow precipitate was observed. Then tert-butanol (3.2 mL, 33.6 mmol, 1.6 eq) was added and the reaction mixture was heated at reflux overnight. The reaction mixture was cooled to 40° C., N$_2$H$_4$·H$_2$O (1 mL, 21 mmol, 1.0 eq) was added to the mixture and continued to stir at 40° C. for 3 h. The solvent was removed and the mixture was taken up in ethyl acetate (50 mL) and washed with water and then, dried (Na$_2$SO$_4$), filtered and then concentrated The oil was chromatographed on silica gel (1:4 ethyl acetate/hexanes) to give HYB-108 as a pale yellow oil: (6.4 g, 99%). ¹H NMR (400 MHz, CDCl₃) δ 10.77 (s, 1H), 7.03 (s, 1H), 3.68 (s, 3H), 3.34 (s, 3H), 2.38 (s, 3H), 1.52 (s, 9H).

Example 74-C

Synthesis of tert-butyl(3-formyl-5-methylthiophen-2-yl)carbamate

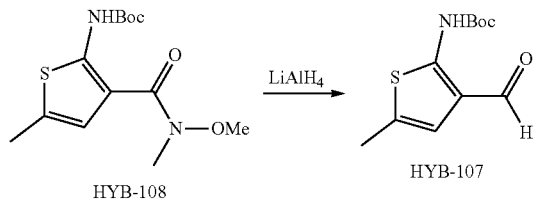 [SMILES: CON(C)C(=O)c1cc(C)sc1NC(=O)OC(C)(C)C ; "LiAlH4" ; Cc1cc(C=O)c(NC(=O)OC(C)(C)C)s1]

A solution of HYB-108 (6.4 g, 21 mmol) in Et₂O (100 mL) was cooled to 0° C. and LiAlH₄ (718 mg, 19 mmol) was added slowly and the reaction mixture was allowed to warm to r.t. Then the mixture was cooled to 0° C. and quenched with Na—K tartrate solution. The mixture was taken up in ethyl acetate (50 mL) and washed with brine (20 mL), dried, filtered and then concentrated to an oil that was chromatographed on silica gel (1:8 ethyl acetate/hexanes) to give HYB-107 as a yellow solid: (3.0 g, 59%). ¹H NMR (400 MHz, CDCl₃) δ 10.46 (s, 1H), 9.69 (s, 1H), 6.75 (s, 1H), 2.39 (s, 3H), 1.56 (s, 9H).

Example 74-D

Synthesis of 2-chloro-N-(3-formyl-5-methylthiophen-2-yl)acetamide

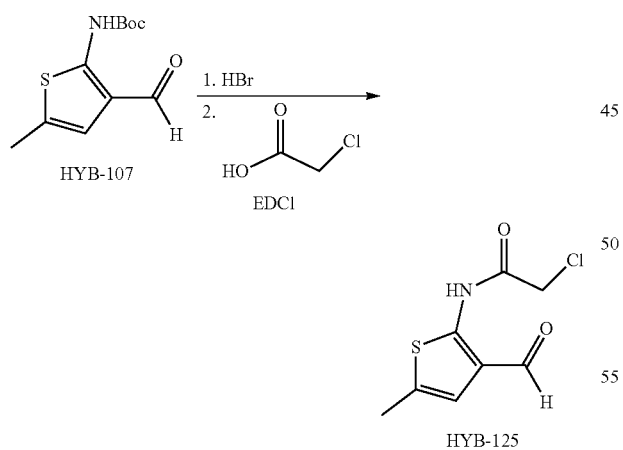

Step 1: A solution of 33% HBr in acetic acid (7.3 mL) was cooled to 0° C. A cold solution of HYB-107 (1 g, 4 mmol) in DCM (1 mL) was added and the reaction mixture turned red immediately. The reaction mixture was immediately poured into ice-water (50 g each) and was taken up in ethyl acetate. The organic layer was separated, washed successively with 10% NaOH (40 mL), NaHCO₃ (40 mL), and brine (40 mL). After drying, the organic solution was passed through a short pad of silica gel, then concentrated. The residue was dissolved in dichloromethane for next step.

Step 2: The solution prepared above was cooled to 0° C., and 2-chloroacetic acid (1.5 eq) and EDCI (1.5 eq) were successively added. Then DMAP (0.1 eq) was added and the reaction mixture was allowed to warm to r.t. and stirred overnight. The reaction was diluted with DCM, washed with brine and dried. The residue was chromatographed on silica gel (1:4 ethyl acetate/hexanes) to give HYB-125 as a solid: (640 mg, 45% over two steps). ¹H NMR (400 MHz, CDCl₃) δ 12.18 (s, 1H), 9.81 (s, 1H), 6.88 (s, 1H), 4.29 (s, 2H), 2.45 (s, 3H).

Example 74-E

Synthesis of 7-methyl-1,5-dihydrothieno[2,3-e][1,4]oxazepin-2(3H)-one

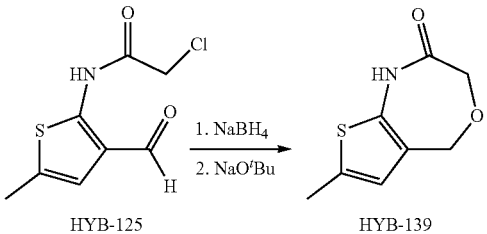

Step 1: A solution of HYB-125 (600 mg, 2.8 mmol) in methanol was cooled to 0° C. and NaBH₄ (157 mg, 4.1 mmol, 1.5 eq) was added slowly. After 30 min, the reaction was finished and the solvent was evaporated under vacuum. The residue was taken up in EtOAc, washed with water, brine, dried and concentrated. The solid was triturated with 1:2 ethyl acetate/hexanes, filtered to give a solid (400 mg, 64% yield).

Step 2: A suspension of NaOᵗBu (5.5 mmol, 3 eq) in ᵗBuOH (10 mL) was heated at 80° C. until it turns into a clear solution. Then the solid prepared above (400 mg, 1.8 mmol) was added in one portion and the reaction is finished in 5 min. The reaction mixture was cooled and poured into ice-water, extracted with ethyl acetate. The organic layer was washed with brine (20 mL), dried, filtered and then concentrated to an oil that was chromatographed on silica gel (1:2 ethyl acetate/hexanes) to give HYB-139: ¹H NMR (400 MHz, CDCl₃) δ 8.00 (s, 1H), 6.23 s, 1H), 4.79 (s, 2H), 4.40 (s, 2H), 2.37 (s, 3H).

Example 74-F

Synthesis of 6-bromo-7-methyl-1,5-dihydrothieno[2,3-e][1,4]oxazepin-2(3H)-one

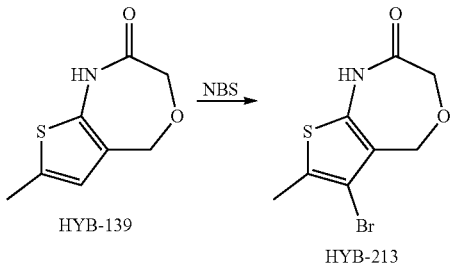

To a solution of HYB-139 (130 mg, 0.7 mmol) in acetic acid (2 mL) was added NBS (126 mg, 0.7 mmol). The reaction was stirred for 2 h. The precipitate was filtered to give 85 mg (60%) of HYB-213. H NMR (400 MHz, CDCl$_3$) δ 8.22 (s, 1H), 4.75 (s, 2H), 4.40 (s, 2H), 2.32 (s, 3H).

Example 74-G

Synthesis of 3-bromo-2,9-dimethyl-4H,6H-thieno[2,3-e][1,2,4]triazolo[3,4-c][1,4]oxazepine

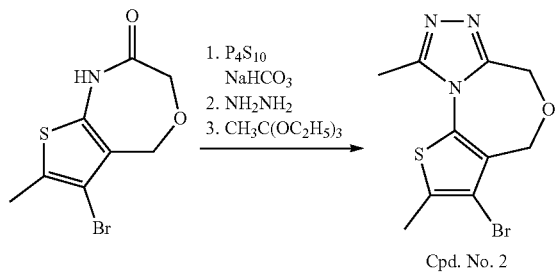 [SMILES: Cc1sc2c(c1Br)COCC(=O)N2 ; Cc1sc2c(c1Br)COCc1nnc(C)n1-2]

Cpd. No. 2

Step 1: A suspension of P$_4$S$_{10}$ (147 mg, 0.66 mmol, 2 eq) and Na$_2$CO$_3$ (70 mg, 0.66 mmol, 2 eq) in 1,2-DCE (5 mL) was stirred for 10 min prior to the addition of HYB-213 (85 mg, 0.33 mmol). The reaction mixture was stirred at 65° C. for 4 h. The reaction was cooled, taken up with saturated NaHCO$_3$, extracted with DCM. The organic layer was separated, dried, and concentrated to give a crude product.

Step 2: To a solution of crude in THF was added hydrazine monohydrate (33 mg, 0.66 mmol) and the reaction turned yellow. After 1 h, the solvent was removed and the residue was taken up with DCM, washed with water and brine, dried, and concentrated to give a crude product.

Step 3: The above crude was taken up in ethanol, triethylorthoacetate (0.18 mL, 0.99 mmol, 3 eq) was added and the reaction was heated reflux until all starting material is consumed. After evaporation of the solvent, the residue solid was triturated with hexanes to give Cpd. No. 2 (40 mg, 40%). $^1$H NMR (400 MHz, CDCl$_3$) δ 4.95 (s, 2H), 4.93 (s, 2H), 2.93 (s, 3H), 2.50 (s, 3H). ESI-MS: 300.11.

Example 75

Synthesis of 3-benzyl-2,9-dimethyl-4H,6H-thieno[2,3-e][1,2,4]triazolo[3,4-c][1,4]oxazepine (Cpd No. 4) and 2,9-dimethyl-4H,6H-thieno[2,3-e][1,2,4]triazolo[3,4-c][1,4]oxazepine (Cpd. No. 1)

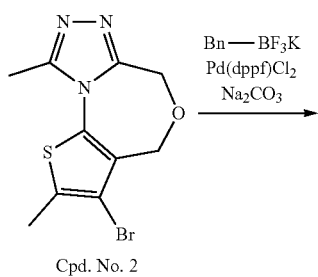

Cpd. No. 2

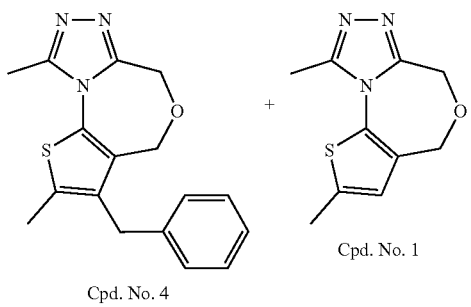

Cpd. No. 4

Cpd. No. 1

To a round-bottom flask was charged with HYB-149 (0.1 mmol), potassium benzyltrifluoroborate (40 mg, 0.2 mmol), Pd(dppf)Cl$_2$ (8 mg). Under N$_2$ atmosphere, dioxane (2 mL) and a solution of Na$_2$CO$_3$ (2.0 M, 1 mL) was added. The reaction mixture was heated at 100° C. for 4 h prior to being taken up in EtOAc and water. The organic layer was separated, evaporated to give a crude mixture which was purified via HPLC. Major product Cpd No. 4 (70% yield): $^1$H NMR (400 MHz, CDCl$_3$) δ 7.51-7.21 (m, 4H), 7.07 (d, J=7.2 Hz, 2H), 4.82 (s, 2H), 4.72 (s, 2H), 3.88 (s, 2H), 2.96 (s, 3H), 2.52 (s, 3H). ESI-MS: 312.20. Minor side product Cpd. No. 1: $^1$H NMR (400 MHz, CDCl$_3$) δ 6.55 (s, 1H), 4.93 (s, 2H), 4.87 (s, 2H), 2.84 (s, 3H), 2.53 (s, 3H).

Example 76

Synthesis of 2,9-dimethyl-3-phenyl-4H,6H-thieno[2,3-e][1,2,4]triazolo[3,4-c][1,4]oxazepine (Cpd. No. 3)

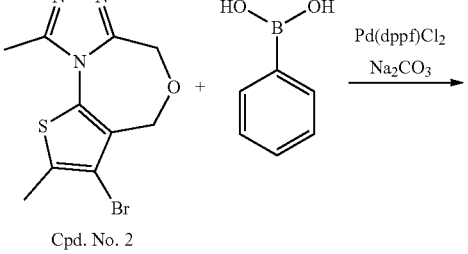

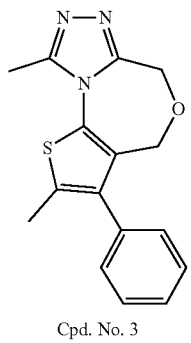

Cpd. No. 3

To a round-bottom flask was charged with Cpd. No. 2 (10 mg, 0.033 mmol), phenylboronic acid (8 mg, 2 eq), Pd(dppf)Cl₂ (3 mg). Under N₂ atmosphere, dioxane (1 mL) and a solution of Na₂CO₃ (2.0 M, 0.5 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 3 (90% yield). ¹H NMR (400 MHz, CDCl₃) δ 7.58-7.41 (m, 3H), 7.26-7.18 (m, 2H), 4.87 (s, 2H), 4.59 (s, 2H), 2.93 (s, 3H), 2.39 (s, 3H). ESI-MS: 298.17.

Example 77

Synthesis of 2,9-dimethyl-3-(quinolin-4-yl)-4H,6H-thieno[2,3-e][1,2,4]triazolo[3,4-c][1,4]oxazepine (Cpd. No. 5)

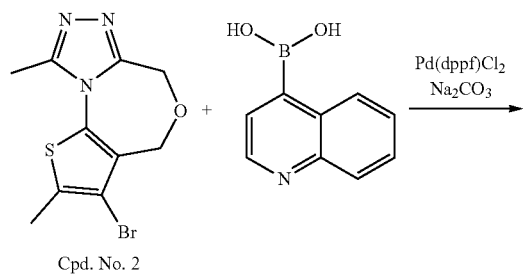

Cpd. No. 2

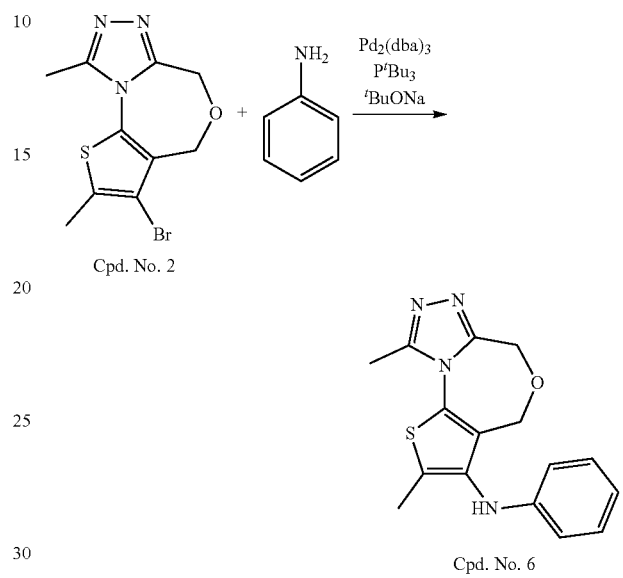

Cpd. No. 5

To a round-bottom flask was charged with Cpd. No. 2 (10 mg, 0.033 mmol), quinolin-4-ylboronic acid (12 mg, 2 eq), Pd(dppf)Cl₂ (3 mg). Under N₂ atmosphere, dioxane (1 mL) and a solution of Na₂CO₃ (2.0 M, 0.5 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 5 (80% yield). ¹H NMR (400 MHz, CDCl₃) δ 9.39 (d, J=5.2 Hz, 2H), 8.61 (d, J=8.6 Hz, 1H), 8.12 (ddd, J=8.5, 7.0, 1.3 Hz, 1H), 7.92-7.85 (m, 1H), 7.85-7.78 (m, 1H), 7.74 (d, J=5.2 Hz, 1H), 4.95 (d, J=14.3 Hz, 1H), 4.88 (d, J=14.3 Hz, 1H), 4.47 (d, J=15.2 Hz, 1H), 4.35 (d, J=15.2 Hz, 1H), 2.94 (s, 2H), 2.32 (s, 3H). ESI-MS: 349.10.

Example 78

Synthesis of 2,9-dimethyl-N-phenyl-4H,6H-thieno[2,3-e][1,2,4]triazolo[3,4-c][1,4]oxazepin-3-amine (Cpd. No. 6)

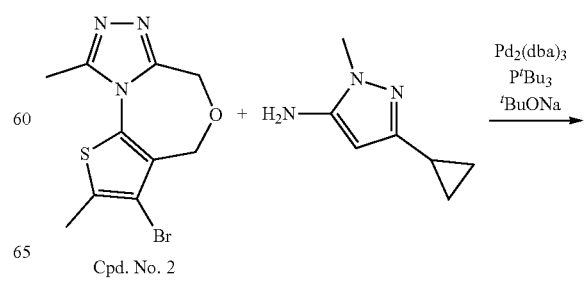

To a round-bottom flask was charged with Cpd. No. 2 (10 mg, 0.033 mmol), aniline (6 mg, 2 eq), Pd₂(dba)₃ (5.3 mg), a solution of PᵗBu₃ (0.2 eq) in toluene, and NaOᵗBu (10 mg, 3 eq). Under N₂ atmosphere, toluene (1 mL) was added. The reaction mixture was heated at 100° C. for 12 h prior to being taken up in EtOAc and water. The organic layer was separated, evaporated to give a crude mixture which was purified via HPLC to provide the TFA salt of Cpd. No. 6 (50% yield). ¹H NMR (400 MHz, MeOD) δ 7.15 (t, J=7.9 Hz, 2H), 6.72 (t, J=7.3 Hz, 1H), 6.59 (d, J=7.9 Hz, 2H), 4.80 (s, 2H), 4.74 (s, 2H), 2.83 (s, 3H), 2.33 (s, 3H). ESI-MS 313.22.

Example 79

Synthesis of N-(3-cyclopropyl-1-methyl-H-pyrazol-5-yl)-2,9-dimethyl-4H,6H-thieno[2,3-e][1,2,4]triazolo[3,4-c][1,4]oxazepin-3-amine (Cpd. No. 7)

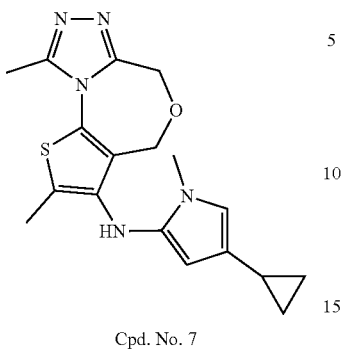

Cpd. No. 7

To a round-bottom flask was charged with Cpd. No. 2 (10 mg, 0.033 mmol), 3-cyclopropyl-1-methyl-1H-pyrazol-5-amine (9 mg, 2 eq), Pd$_2$(dba)$_3$(5.3 mg), a solution of P$^t$Bu$_3$(0.2 eq) in toluene, and NaO$^t$Bu (10 mg, 3 eq). Under N$_2$ atmosphere, toluene (1 mL) was added. The reaction mixture was heated at 100° C. for 12 h prior to being taken up in EtOAc and water. The organic layer was separated, evaporated to give a crude mixture which was purified via HPLC to provide the TFA salt of Cpd. No. 7 (40% yield). $^1$H NMR (400 MHz, MeOD) δ 5.36 (s, 1H), 4.82 (s, 2H), 4.73 (s, 2H), 3.83 (s, 3H), 2.78 (s, 3H), 2.39 (s, 3H), 1.94-1.87 (m, 1H), 1.19-1.09 (m, 2H), 0.86 (dt, J=6.9, 4.7 Hz, 2H). ESI-MS: 357.33.

Example 80

Synthesis of 3-(3-chlorobenzyl)-2,9-dimethyl-4H,6H-thieno[2,3-e][1,2,4]triazolo[3,4-c][1,4]oxazepine (Cpd. No. 8)

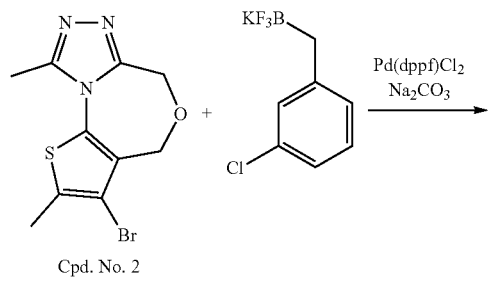

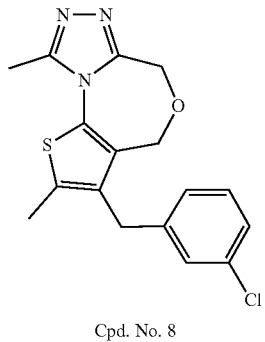

Cpd. No. 8

To a round-bottom flask was charged with Cpd. No. 2 (10 mg, 0.033 mmol), potassium (3-chlorobenzyl)trifluoroborane (14 mg, 2 eq), Pd(dppf)Cl$_2$ (3 mg). Under N$_2$ atmosphere, dioxane (1 mL) and a solution of Na$_2$CO$_3$ (2.0 M, 0.5 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 8 (45% yield). $^1$H NMR (400 MHz, MeOD) δ 7.30 (t, J=7.8 Hz, 1H), 7.23 (d, J=8.3 Hz, 1H), 7.14 (s, 1H), 7.08 (d, J=7.3 Hz, 1H), 4.72 (s, 2H), 4.67 (s, 2H), 3.96 (s, 2H), 2.77 (s, 3H), 2.50 (s, 3H). ESI-MS: 346.17.

Example 81

Synthesis of 3-(4-chlorobenzyl)-2,9-dimethyl-4H,6H-thieno[2,3-e][1,2,4]triazolo[3,4-c][1,4]oxazepine (Cpd. No. 9)

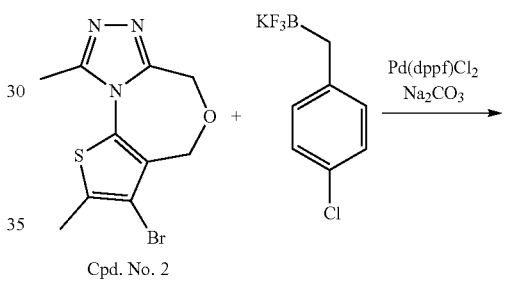

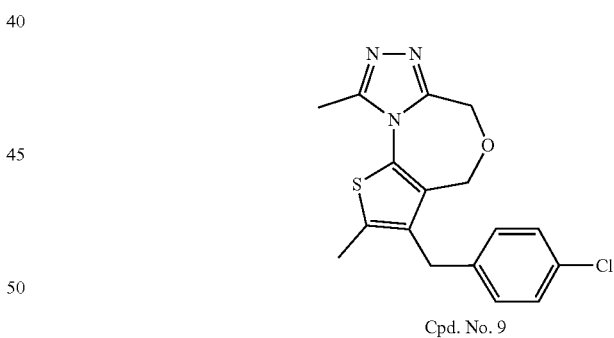

Cpd. No. 9

To a round-bottom flask was charged with Cpd. No. 2 (10 mg, 0.033 mmol), potassium (4-chlorobenzyl)trifluoroborate (14 mg, 2 eq), Pd(dppf)Cl$_2$(3 mg). Under N$_2$ atmosphere, dioxane (1 mL) and a solution of Na$_2$CO$_3$ (2.0 M, 0.5 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 9 (50% yield). $^1$H NMR (400 MHz, MeOD) δ 7.30 (d, J=8.4 Hz, 3H), 7.13 (d, J=8.3 Hz, 2H), 4.72 (s, 2H), 4.67 (s, 2H), 3.93 (s, 2H), 2.77 (s, 3H), 2.49 (s, 3H). ESI-MS: 346.22.

Example 82

Synthesis of 3-(2-chlorobenzyl)-2,9-dimethyl-4H,6H-thieno[2,3-e][1,2,4]triazolo[3,4-c][1,4]oxazepine (Cpd. No. 10)

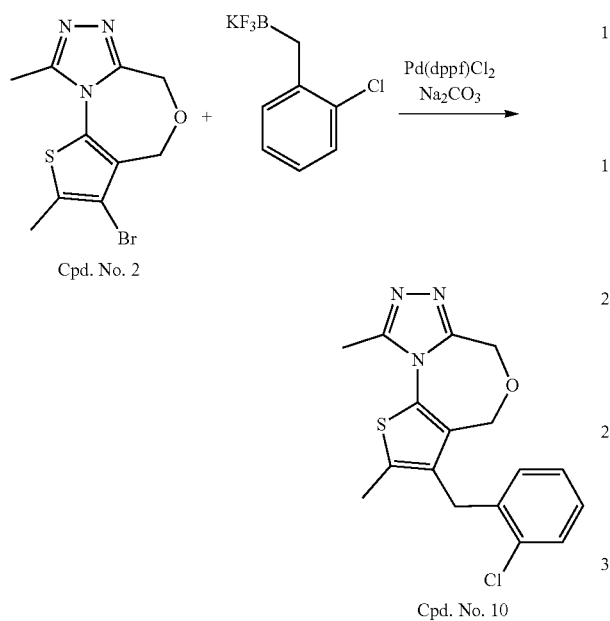

To a round-bottom flask was charged with Cpd. No. 2 (10 mg, 0.033 mmol), potassium (2-chlorobenzyl)trifluoroborane (14 mg, 2 eq), Pd(dppf)Cl$_2$(3 mg). Under N$_2$ atmosphere, dioxane (1 mL) and a solution of Na$_2$CO$_3$ (2.0 M, 0.5 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 10 (20% yield). $^1$H NMR (400 MHz, MeOD) δ 7.46 (d, J=6.3 Hz, 1H), 7.27-7.19 (m, 2H), 6.90 (d, J=6.3 Hz, 1H), 4.74 (s, 2H), 4.59 (s, 2H), 4.02 (s, 2H), 2.77 (s, 3H), 2.43 (s, 3H). ESI-MS: 346.21.

Example 83

Synthesis of 3-(3-fluorobenzyl)-2,9-dimethyl-4H,6H-thieno[2,3-e][1,2,4]triazolo[3,4-c][1,4]oxazepine (Cpd. No. 100)

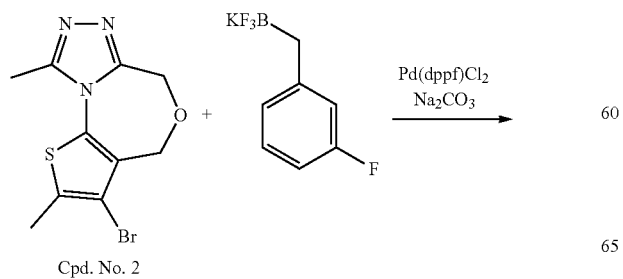

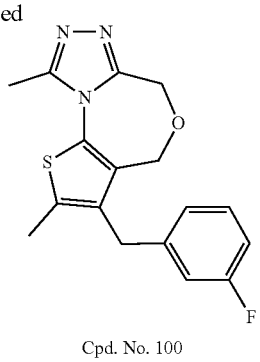

Cpd. No. 100

To a round-bottom flask was charged with Cpd. No. 2 (10 mg, 0.033 mmol), potassium (3-fluorobenzyl)trifluoroborane (13 mg, 2 eq), Pd(dppf)Cl$_2$(6 mg). Under N$_2$ atmosphere, dioxane (2 mL) and a solution of Na$_2$CO$_3$ (2.0 M, 1 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 100 (70% yield). H NMR (400 MHz, MeOD) δ 7.37-7.25 (m, 1H), 7.03-6.90 (m, 2H), 6.86 (d, J=10.1 Hz, 1H), 4.73 (s, 2H), 4.69 (s, 2H), 3.97 (s, 2H), 2.79 (s, 3H), 2.50 (s, 3H). ESI-MS: 330.11.

Example 84

Synthesis of 3-(3-cyanobenzyl)-2,9-dimethyl-4H,6H-thieno[2,3-e][1,2,4]triazolo[3,4-c][1,4]oxazepine (Cpd. No. 101)

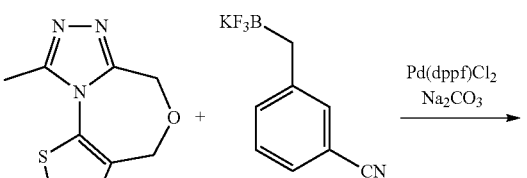

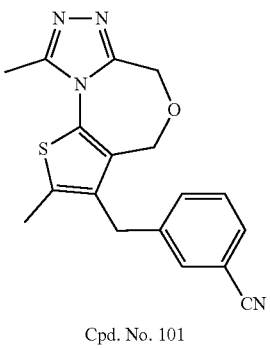

Cpd. No. 101

To a round-bottom flask was charged with Cpd. No. 2 (10 mg, 0.033 mmol), potassium (3-cyanobenzyl)trifluoroborate (14 mg, 2 eq), Pd(dppf)Cl₂(6 mg). Under N₂ atmosphere, dioxane (2 mL) and a solution of Na₂CO₃ (2.0 M, 1 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 101 (40% yield). ¹H NMR (400 MHz, MeOD) δ 7.58-7.45 (m, 4H), 4.71 (s, 2H), 4.64 (s, 2H), 4.02 (s, 2H), 2.75 (s, 3H), 2.49 (s, 3H). ESI-MS: 337.12.

Example 85

Synthesis of 3-(2-fluorobenzyl)-2,9-dimethyl-4H, 6H-thieno[2,3-e][1,2,4]triazolo[3,4-c][1,4]oxazepine (Cpd. No. 102)

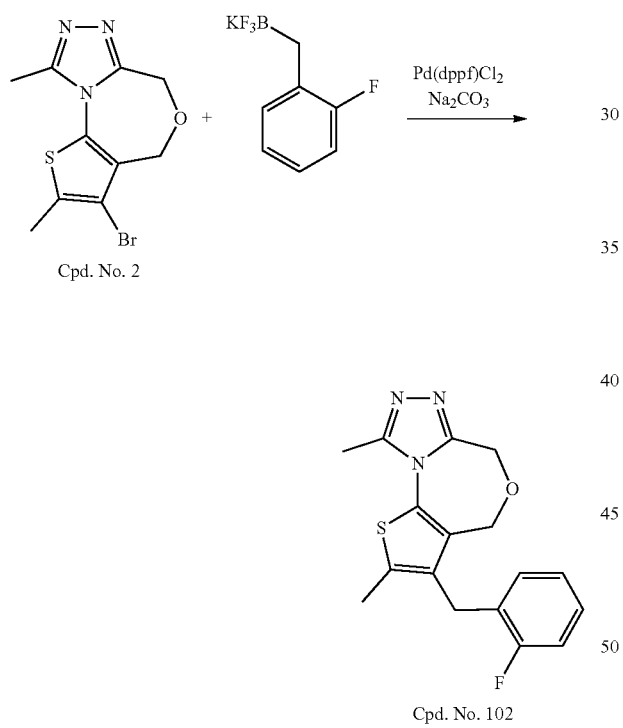

To a round-bottom flask was charged with Cpd. No. 2 (10 mg, 0.033 mmol), potassium (2-fluorobenzyl)trifluoroborate (13 mg, 2 eq), Pd(dppf)Cl₂(6 mg). Under N₂ atmosphere, dioxane (2 mL) and a solution of Na₂CO₃ (2.0 M, 1 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 102 (20% yield). ¹H NMR (400 MHz, MeOD) δ 7.34-7.20 (m, 1H), 7.15-7.05 (m, 2H), 7.02 (t, J=7.6 Hz, 1H), 4.72 (s, 2H), 4.70 (s, 2H), 3.95 (s, 2H), 2.76 (s, 3H), 2.47 (s, 3H). ESI-MS: 330.04.

Example 86

Synthesis of 3-(4-fluorobenzyl)-2,9-dimethyl-4H, 6H-thieno[2,3-e][1,2,4]triazolo[3,4-c][1,4]oxazepine (Cpd. No. 103)

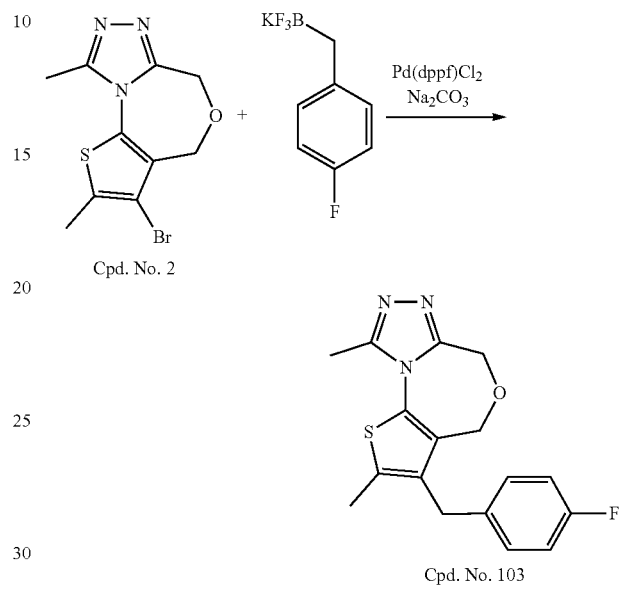

To a round-bottom flask was charged with Cpd. No. 2 (10 mg, 0.033 mmol), potassium (4-fluorobenzyl)trifluoroborate (13 mg, 2 eq), Pd(dppf)Cl₂(6 mg). Under N₂ atmosphere, dioxane (2 mL) and a solution of Na₂CO₃ (2.0 M, 1 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 103 (50% yield). ¹H NMR (400 MHz, MeOD) δ 7.15 (dd, J=8.5, 5.5 Hz, 2H), 7.09-6.96 (m, 2H), 4.72 (s, 2H), 4.68 (s, 2H), 3.93 (s, 2H), 2.77 (s, 3H), 2.49 (s, 3H). ESI-MS: 330.06.

Example 87

Synthesis of 3-(3,5-difluorobenzyl)-2,9-dimethyl-4H,6H-thieno[2,3-e][1,2,4]triazolo[3,4-c][1,4]oxazepine (Cpd. No. 104)

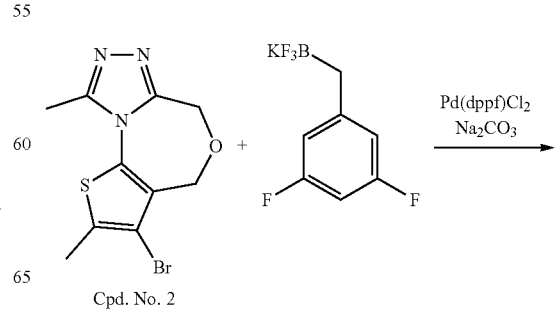

-continued

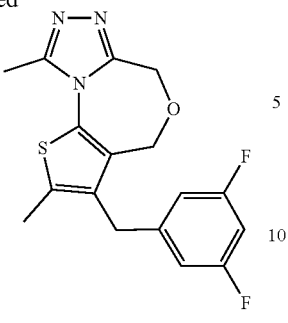

Cpd. No. 104

To a round-bottom flask was charged with Cpd. No. 2 (10 mg, 0.033 mmol), potassium (3,5-difluorobenzyl)trifluoroborate (13 mg, 2 eq), Pd(dppf)Cl₂ (6 mg). Under N₂ atmosphere, dioxane (2 mL) and a solution of Na₂CO₃ (2.0 M, 1 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 104 (20% yield). ¹H NMR (400 MHz, MeOD) δ 7.64-7.44 (m, 3H), 4.74 (s, 2H), 4.63 (s, 2H), 3.98 (s, 2H), 2.77 (s, 3H), 2.49 (s, 3H). ESI-MS: 348.10.

Example 88

Synthesis of 3-(3,4-difluorobenzyl)-2,9-dimethyl-4H,6H-thieno[2,3-e][1,2,4]triazolo[3,4-c][1,4]oxazepine (Cpd. No. 105)

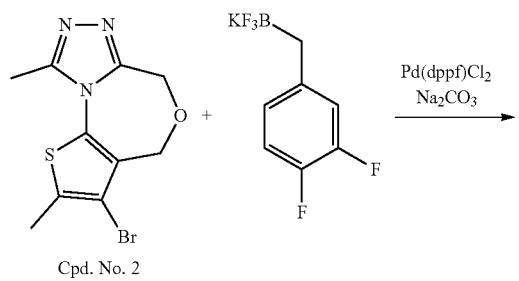

Cpd. No. 105

To a round-bottom flask was charged with Cpd. No. 2 (10 mg, 0.033 mmol), potassium (3,4-difluorobenzyl)trifluoroborate (13 mg, 2 eq), Pd(dppf)Cl₂ (6 mg). Under N₂ atmosphere, dioxane (2 mL) and a solution of Na₂CO₃ (2.0 M, 1 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 105 (15% yield). ¹H NMR (400 MHz, MeOD) δ 7.20 (dd, J=18.4, 8.9 Hz, 1H), 7.04 (d, J=9.3 Hz, 1H), 6.98 (d, J=18.7 Hz, 1H), 4.74 (s, 2H), 4.69 (s, 2H), 3.95 (s, 2H), 2.80 (s, 3H), 2.50 (s, 3H). ESI-MS: 348.02.

Example 89

Synthesis of 2,9-dimethyl-3-(1-phenylvinyl)-4H,6H-thieno[2,3-e][1,2,4]triazolo[3,4-c][1,4]oxazepine (Cpd. No. 24)

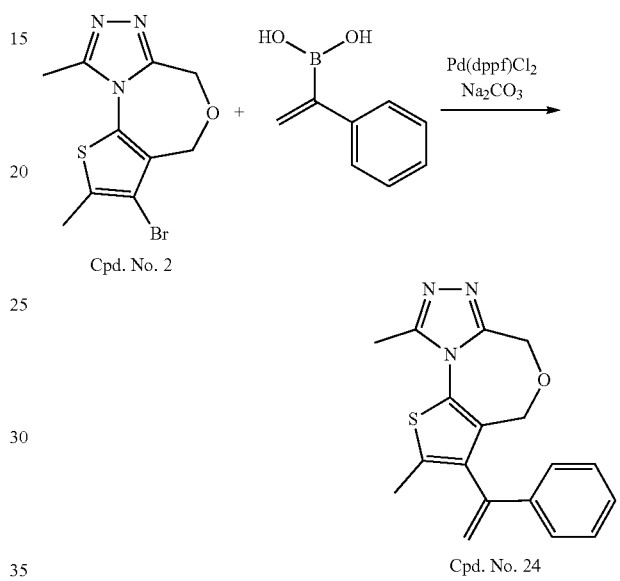

Cpd. No. 24

To a round-bottom flask was charged with Cpd. No. 2 (10 mg, 0.033 mmol), (1-phenylvinyl)boronic acid (10 mg, 2 eq), Pd(dppf)Cl₂ (3 mg). Under N₂ atmosphere, dioxane (1 mL) and a solution of Na₂CO₃ (2.0 M, 0.5 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 24 (90% yield). ¹H NMR (400 MHz, MeOD) δ 7.45-7.32 (m, 5H), 6.07 (s, 1H), 5.29 (s, 1H), 4.75 (s, 2H), 4.52 (s, 2H), 2.82 (s, 3H), 2.40 (s, 3H). ESI-MS: 324.23.

Example 90

Synthesis of 2,9-dimethyl-3-(1-phenylethyl)-4H,6H-thieno[2,3-e][1,2,4]triazolo[3,4-c][1,4]oxazepine (Cpd. No. 28)

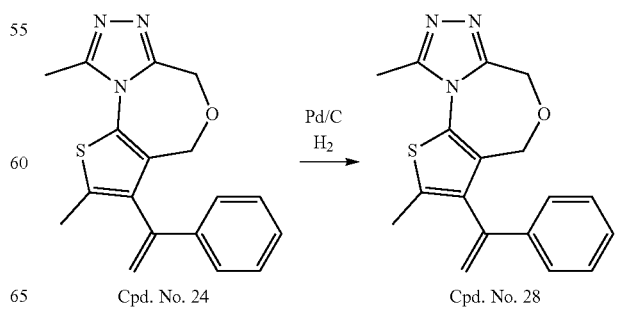

To a solution of Cpd. No. 24 (10 mg) in methanol (2 mL) was added 10% Pd/C (10 mg) and H$_2$ was bubbled into the solution for 20 min. The reaction was filtered and the crude was purified via HPLC to provide the TFA salt of Cpd. No. 28 (30% yield). $^1$H NMR (400 MHz, MeOD) δ 7.37-7.18 (m, 5H), 4.68 (d, J=13.8 Hz, 1H), 4.58 (d, J=13.8 Hz, 1H), 4.53 (d, J=14.2 Hz, 1H), 4.46 (q, J=7.3 Hz, 1H), 4.27 (d, J=14.2 Hz, 1H), 2.71 (s, 3H), 2.43 (s, 3H), 1.70 (d, J=7.3 Hz, 3H). ESI-MS: 326.20.

Example 91

Synthesis of 3-((1H-indol-1-yl)methyl)-2,9-dimethyl-4H,6H-thieno[2,3-e][1,2,4]triazolo[3,4-c][1,4]oxazepine (Cpd. No. 106)

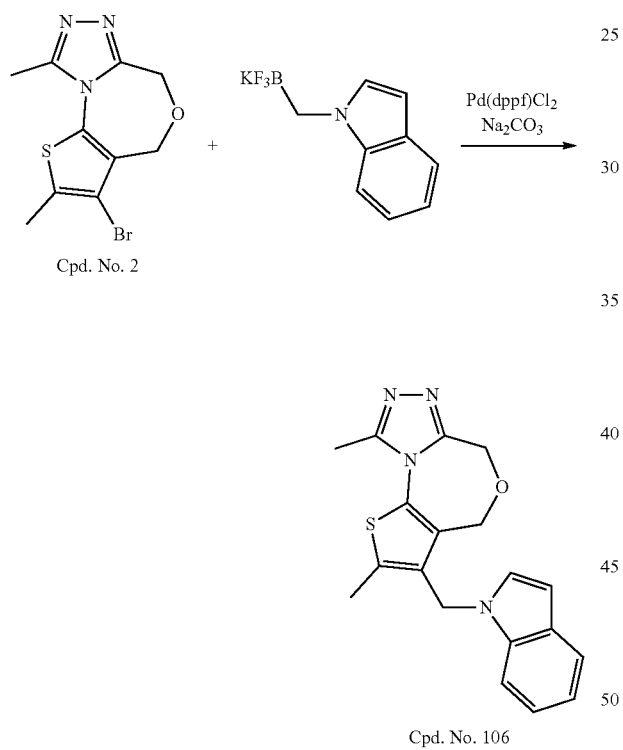

Cpd. No. 106

To a round-bottom flask was charged with Cpd. No. 2 (10 mg, 0.033 mmol), potassium 1H-indol-1-yl)methyltrifluoroborate (14 mg, 2 eq), Pd(dppf)Cl$_2$ (6 mg). Under N$_2$ atmosphere, dioxane (2 mL) and a solution of Na$_2$CO$_3$ (2.0 M, 1 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 106 (70% yield). $^1$H NMR (400 MHz, MeOD) δ 7.58 (d, J=7.9 Hz, 1H), 7.43 (d, J=8.2 Hz, 1H), 7.19 (t, J=7.7 Hz, 1H), 7.13-7.05 (m, 2H), 6.50 (d, J=3.2 Hz, 1H), 5.28 (s, 2H), 4.69 (s, 2H), 4.55 (s, 2H), 2.77 (s, 2H), 2.54 (s, 2H). ESI-MS: 351.02.

Example 92

Synthesis of 3-((1H-pyrrol-1-yl)methyl)-2,9-dimethyl-4H,6H-thieno[2,3-e][1,2,4]triazolo[3,4-c][1,4]oxazepine (Cpd. No. 107)

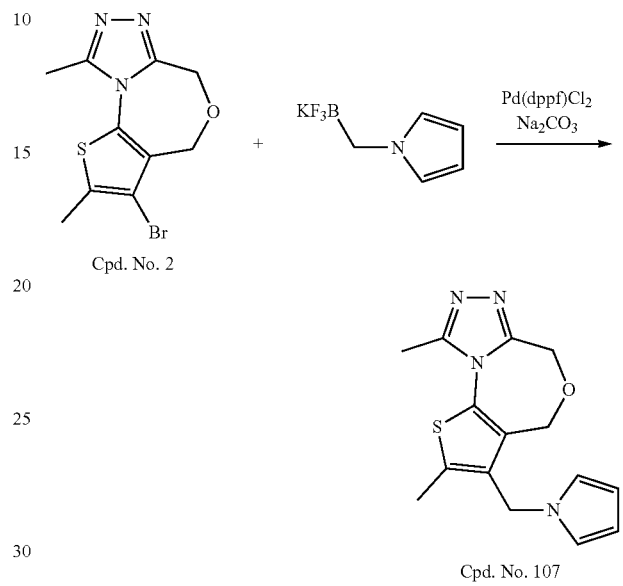

Cpd. No. 107

To a round-bottom flask was charged with Cpd. No. 2 (10 mg, 0.033 mmol), potassium 1H-pyrrol-1-yl)methyltrifluoroborate (11 mg, 2 eq), Pd(dppf)Cl$_2$ (6 mg). Under N$_2$ atmosphere, dioxane (2 mL) and a solution of Na$_2$CO$_3$ (2.0 M, 1 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 107 (65% yield). $^1$H NMR (400 MHz, MeOD) δ 6.65 (s, 2H), 6.09 (s, 2H), 5.04 (s, 2H), 4.72 (s, 2H), 4.64 (s, 2H), 2.74 (s, 3H), 2.55 (s, 3H). ESI-MS: 301.08.

Example 93

Synthesis of 3-((1H-pyrazol-1-yl)methyl)-2,9-dimethyl-4H,6H-thieno[2,3-e][1,2,4]triazolo[3,4-c][1,4]oxazepine (Cpd. No. 112)

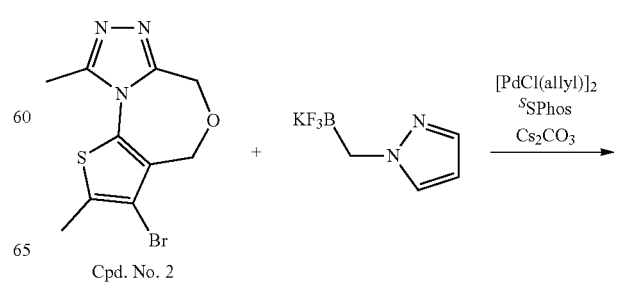

Cpd. No. 2

-continued

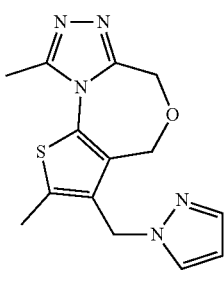

Cpd. No. 112

To a round-bottom flask was charged with Cpd. No. 2 (10 mg, 0.033 mmol), potassium 1H-pyrazol-1-yl)methyltrifluoroborate (11 mg, 2 eq), [PdCl(allyl)]$_2$ (2 mg), $^S$Sphos (3.4 mg), Cs$_2$CO$_3$ (32.6 mg, 3 eq). Under N$_2$ atmosphere, CPME (2 mL) and water (0.5 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 112 (20% yield). $^1$H NMR (400 MHz, MeOD) δ 7.64 (s, 1H), 7.51 (s, 1H), 6.33 (s, 1H), 5.28 (s, 2H), 4.78 (s, 2H), 4.75 (s, 2H), 2.75 (s, 3H), 2.57 (s, 3H). ESI-MS: 302.02.

Example 94

Synthesis of 2,9-dimethyl-3-((1-methyl-H-pyrazol-4-yl)methyl)-4H,6H-thieno[2,3-e][1,2,4]triazolo[3,4-c][1,4]oxazepine (Cpd. No. 127) and 2,3,9-trimethyl-4H,6H-thieno[2,3-e][1,2,4]triazolo[3,4-c][1,4]oxazepine (Cpd. No. 128)

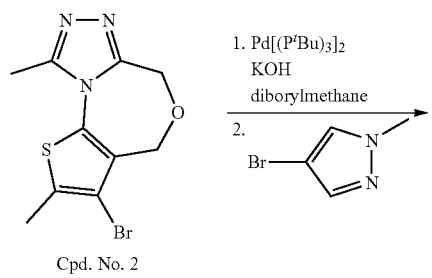

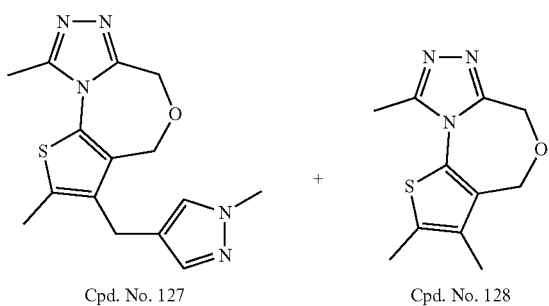

To a solution of diborylmethane (107 mg, 0.4 mmol, 2 eq), Cpd. No. 2 (60 mg, 0.2 mmol) and Pd[(P$^t$Bu)$_3$]$_2$ (11 mg, 0.1 eq) in dioxane (2 mL) was added 8 N KOH (0.05 mL, 0.4 mmol, 2 eq) at r.t. The mixture was stirred for 3 h. Then 8 N KOH (0.075 mL, 0.6 mmol, 3 eq) and 4-bromo-1-methyl-1H-pyrazole (97 mg, 3 eq) was added. The mixture was stirred at 60° C. for 24 h. The mixture was cooled and taken up in EtOAc and water. The organic layer was separated, evaporated to give a crude mixture which was purified via HPLC to provide the TFA salt of Cpd. No. 127 (30% yield). Major product Cpd. No. 127: $^1$H NMR (400 MHz, MeOD) δ 7.40 (s, 1H), 7.30 (s, 1H), 4.82 (s, 2H), 4.79 (s, 2H), 3.84 (s, 3H), 3.75 (s, 2H), 2.85 (s, 3H), 2.51 (s, 3H). Minor side product Cpd. No. 128: $^1$H NMR (400 MHz, MeOD) δ 4.89 (s, 2H), 4.82 (s, 2H), 2.79 (s, 3H), 2.43 (s, 3H), 2.07 (s, 3H).

Example 95

Synthesis of 3-(tert-butoxymethyl)-2,9-dimethyl-4H,6H-thieno[2,3-e][1,2,4]triazolo[3,4-c][1,4]oxazepine (Cpd. No. 108)

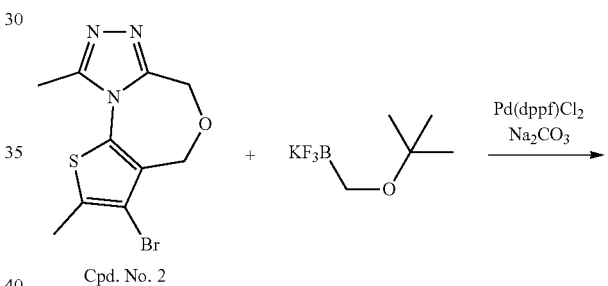

Cpd. No. 108

To a round-bottom flask was charged with Cpd. No. 2 (10 mg, 0.033 mmol), potassium tert-butoxymethyltrifluoroborate (20 mg), Pd(dppf)Cl$_2$ (6 mg). Under N$_2$ atmosphere, dioxane (2 mL) and a solution of Na$_2$CO$_3$ (2.0 M, 1 mL) was added. The reaction mixture was heated at 100° C. for 4 h prior to being taken up in EtOAc and water. The organic layer was separated, evaporated to give a crude mixture which was purified via HPLC to provide the TFA salt of Cpd. No. 108 (60% yield). $^1$H NMR (400 MHz, MeOD) δ 4.99 (s, 2H), 4.81 (s, 2H), 4.36 (s, 2H), 2.77 (s, 3H), 2.51 (s, 3H), 1.32 (s, 9H). ESI-MS: 308.09.

Example 96

Synthesis of 3-bromo-2,6,9-trimethyl-4H,6H-thieno[2,3-e][1,2,4]triazolo[3,4-c][1,4]oxazepine (Cpd. No. 130)

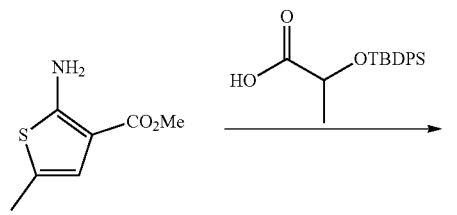

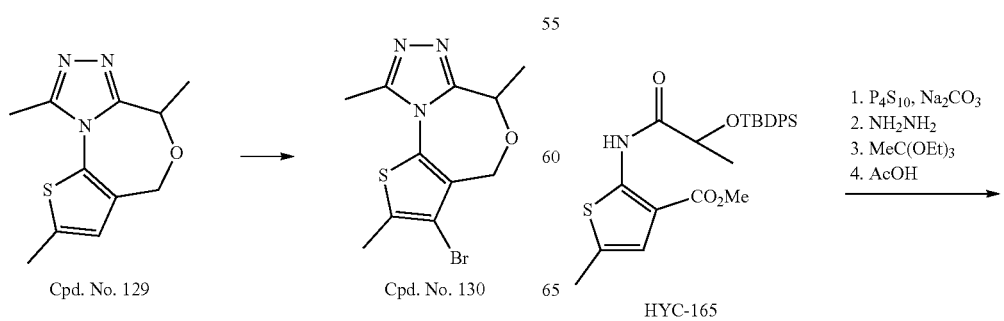

Example 96-A

Synthesis of methyl 2-(2-((tert-butyldiphenylsilyl)oxy)propanamido)-5-methylthiophene-3-carboxylate

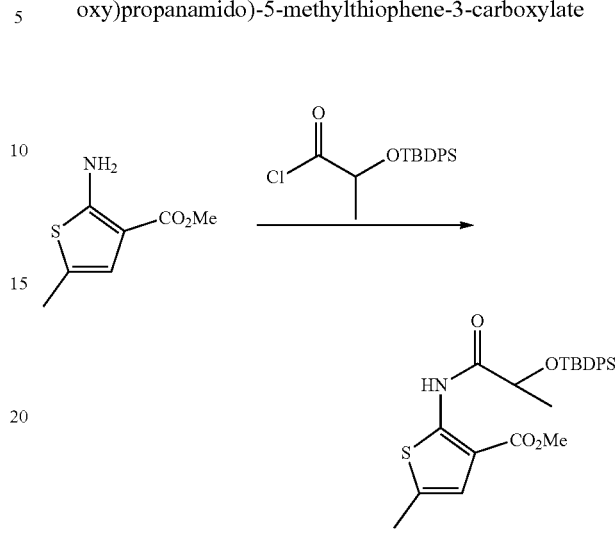

To a solution of 2-((tert-butyldipienylsilyl)oxy)propanoic acid (3 g, 9 mmol) in DCM (10 mL) was added oxallyl chloride (1 mL, 1.3 eq) at 0° C. A couple of drops of DMF were added and the reaction mixture was allowed to warm to r.t. and stirred for 1 h. Then all the volatiles were removed under vacuum and the residue was dissolved in DCM (4 mL). This solution was added dropwise at 0° C. to a solution of methyl 2-amino-thiophene-3-carboxylate (770 mg, 4.5 mmol) and DIPEA (2.35 mL, 13.5 mmol) in DCM (10 mL). The reaction mixture was allowed to warm to r.t. and stirred for 1 h prior to being quenched with saturated NaHCO$_3$ and extracted with DCM (3×20 mL). The combined organic layer was washed with water and then, dried (Na$_2$SO$_4$), filtered and then concentrated The oil was chromatographed on silica gel (1:8 ethyl acetate/hexanes) to give title compound as an oil: (2.3 g, 99%). $^1$H NMR (400 MHz, CDCl$_3$) δ 11.81 (s, 1H), 7.84-7.59 (m, 4H), 7.45-7.35 (m, 6H), 6.90 (s, 1H), 4.48-4.40 (m, 1H), 3.85 (s, 3H), 2.41 (s, 3H), 1.57 (br, 3H), 1.19 (s, 9H).

Example 96-B

Synthesis of methyl 2-(3-(1-((tert-butyldiphenylsilyl)oxy)ethyl)-5-methyl-4H-1,2,4-triazol-4-yl)-5-methylthiophene-3-carboxylate -continued

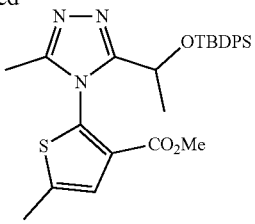

HYC-168

Step 1: To a solution of 2-(2-((tert-butyldiphenylsilyl)oxy)propanamido)-4-chlorothiophene-3-carboxylate (481 mg, 1 mmol) in dichloroethane (8 mL) was added Na₂CO₃ (212 mg, 2 mmol, 2 eq), P₄S₁₀ (444 mg, 2 mmol) and the reaction mixture was heated at reflux for 8 h. The reaction mixture was taken up in DCM and washed with saturated NaHCO₃. The organic layer was washed with brine, dried, and concentrated. The residue was chromatographed on silica gel (1:16 ethyl acetate/hexanes) to give methyl 2-(2-((tert-butyldiphenylsilyl)oxy)propanethioamido)-4-chlorothiophene-3-carboxylate as a crude oil (360 mg, 72%).

Step 2: To a solution of methyl 2-(2-((tert-butyldiphenylsilyl)oxy)propanethioamido)-4-chlorothiophene-3-carboxylate (360 mg, 0.72 mmol) in THF (4 mL) was added hydrazine monohydrate (0.07 mL, 1.44 mmol, 2 eq) at 0° C. and the reaction mixture was allowed to warm to r.t. The reaction mixture was stirred for 8 h prior to being concentrated in vacuum. The residue was taken up in DCM and washed with water and brine. The organic layer was separated, dried and concentrated. The residue was taken up in ethanol (8 mL) and triethyl orthoacetate (0.4 mL, 2 mmol, 3 eq) was added. The reaction mixture was heated at reflux for 12 h. All volatiles were removed under vacuum and the residue was dissolved in AcOH (2 mL). The solution was heated at reflux for 1 h prior to the removal of the solvent under vacuum. The residue was taken up in EtOAc and washed with 2 M Na₂CO₃. The organic layer was washed with brine, dried and concentrated. The residue was chromatographed on silica gel (ethyl acetate) to give title compound as a mixture of diastereoisomers (1:1 ratio by H-NMR):(130 mg, 35%). ¹H NMR (400 MHz, CDCl₃) δ 7.70-7.32 (m, 20H), 7.23 (s, 1H), 7.12 (s, 1H), 5.28-5.20 (m, 1H), 4.94-4.86 (m, 1H), 3.61 (s, 3H), 3.59 (s, 3H), 2.51 (s, 3H), 2.47 (s, 3H), 2.24 (br, 2H), 2.22 (br, 3H), 1.02 (s, 9H), 0.96 (s, 9H).

Example 96-C

Synthesis of 3-(1-((tert-butyldiphenylsilyl)oxy)ethyl)-4-(3-(chloromethyl)-5-methylthiophen-2-yl)-5-methyl-4H-1,2,4-triazole

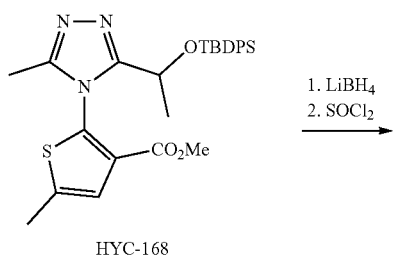

HYC-168

-continued

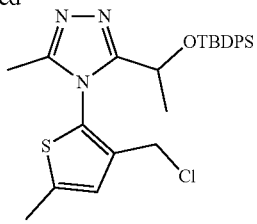

HYC-172

To a solution of methyl 2-(3-(1-((tert-butyldiphenylsilyl)oxy)ethyl)-5-methyl-4H-1,2,4-triazol-4-yl)-5-methylthiophene-3-carboxylate (130 mg, 0.25 mmol) in THF (4 mL) at 0° C. was added a solution of LiBH₄ (2 M in THF, 0.38 mL, 0.75 mmol, 3 eq). MeOH (0.4 mL) was added and the reaction mixture was allowed to warm to r.t. and stirred for 12 h. All volatiles were removed and the residue was taken up in EtOAc. The organic layer was washed with water and brine prior to being dried and concentrated. The residue was dissolved in DCM and cooled to 0° C. Thionyl chloride (0.07 mL, 1 mmol) was added and the reaction mixture was allowed to warm to r.t. After 1 h, all the volatiles were removed and the residue was taken up in EtOAc and washed with 2 M Na₂CO₃. The organic layer was washed with brine, dried and concentrated. The residue was chromatographed on silica gel (ethyl acetate) to give title compound as a mixture of diastereoisomers: (80 mg, 63%). ¹H NMR (400 MHz, CDCl₃) δ 7.64-7.32 (m, 20H), 6.81 (s, 1H), 6.75 (s, 1H), 5.10 (d, J=6.6 Hz, 1H), 5.06 (d, J=6.7 Hz, 1H), 3.96 (d, J=12.2 Hz, 1H), 3.78 (d, J=12.2 Hz, 1H), 2.50 (s, 3H), 2.49 (s, 3H), 2.30 (s, 3H), 2.30 (s, 3H), 1.40 (d, J=6.7 Hz, 3H), 1.28 (d, J=6.7 Hz, 3H), 1.03 (s, 9H), 1.02 (s, 9H).

Example 96-D

Synthesis of 2,6,9-trimethyl-4H,6H-thieno[2,3-e][1,2,4]triazolo[3,4-c][1,4]oxazepine (Cpd. No. 129)

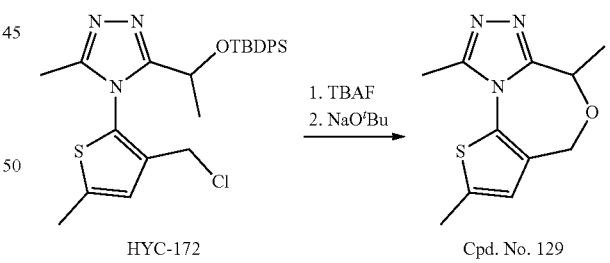

HYC-172      Cpd. No. 129

To a solution of 3-(1-((tert-butyldiphenylsilyl)oxy)ethyl)-4-(3-(chloromethyl)-5-methylthiophen-2-yl)-5-methyl-4H-1,2,4-triazole (160 mg, 0.3 mmol) in THF at 0° C. was added a solution of TBAF (0.3 mL, 0.3 mmol, 1M in THF). The solution was stirred for 1 h prior to being added to a solution of NaOtBu (86 mg, 0.9 mmol, 2 eq) in tBuOH (4 mL) at 80° C. The reaction mixture was stirred for 5 min prior to the removal of the solvent under vacuum. The residue was taken up in EtOAc and water. The organic layer was washed with brine, dried and concentrated. The residue was purified through HPLC to afford Cpd. No. 129 as a solid. (60 mg, 85%). ¹H NMR (400 MHz, CDCl₃) δ 6.56 (s, 1H), 5.00 (d, J=15.5 Hz, 1H), 4.93 (d, J=15.6 Hz, 1H), 4.67 (q, J=6.6 Hz, 1H), 2.91 (s, 3H), 2.54 (s, 3H), 1.84-1.74 (d, J=6.6 Hz, 3H). ESI: M+H 236.24.

Example 97

Synthesis of 3-bromo-2,6,9-trimethyl-4H,6H-thieno[2,3-e][1,2,4]triazolo[3,4-c][1,4]oxazepine (Cpd. No. 130)

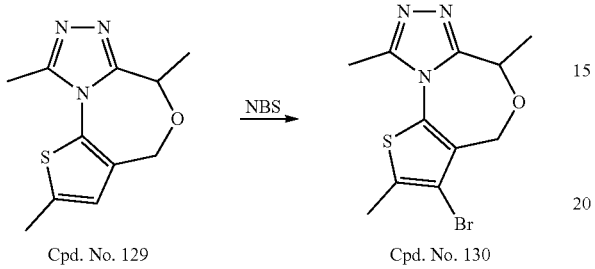

To a solution of 2,6,9-trimethyl-4H,6H-thieno[2,3-e][1,2,4]triazolo[3,4-c][1,4]oxazepine TFA salt (60 mg, 0.2 mmol) in AcOH (2 mL) was added NBS (44 mg, 1 eq). The reaction mixture was stirred for 1 h prior to being quenched with water. The reaction mixture was extracted with EtOAc and the organic layer was washed with 1M NaOH, saturated NaHCO₃ and brine. The residue was purified through HPLC to afford Cpd. No. 130 as a solid (16 mg, 25%). ¹H NMR (400 MHz, MeOD) δ 5.01 (d, J=15.9 Hz, 2H), 4.85 (d, J=15.9 Hz, 1H), 4.80 (q, J=6.6 Hz, 1H), 2.81 (s, 3H), 2.48 (s, 3H), 1.72 (d, J=6.6 Hz, 3H). ESI: M+H 314.02.

Example 98

Synthesis of 3-benzyl-2,6,9-trimethyl-4H,6H-thieno[2,3-e][1,2,4]triazolo[3,4-c][1,4]oxazepine (Cpd. No. 109)

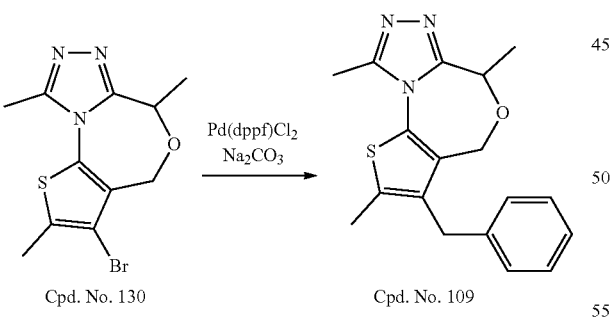

To a Shlenk tube was charged with 3-bromo-2,6,9-trimethyl-4H,6H-thieno[2,3-e][1,2,4]triazolo[3,4-c][1,4]oxazepine (16 mg, 0.05 mmol), potassium benzyltrifluoroborate (20 mg, 0.1 mmol), Pd(dppf)Cl₂ (10 mg), dioxane (2 mL) and Na₂CO₃ solution (2 M, 1 mL) under N₂. The tube was sealed and heated at 100° C. oil bath for 1 h. The reaction mixture was extracted with EtOAc and the organic layer was washed with brine, dried and concentrated. The residue was purified through HPLC to afford Cpd. No. 109 as a solid. (10 mg, 62%). ¹H NMR (400 MHz, MeOD) δ 7.29-7.14 (m, 5H), 4.81 (d, J=16.1 Hz, 1H), 4.65-4.57 (m, 2H), 3.98 (d, J=16.1 Hz, 1H), 3.90 (d, J=16.7 Hz, 1H), 2.79 (s, 3H), 2.50 (s, 3H), 1.65 (d, J=6.7 Hz 3H). ESI: M+H 326.10.

Example 99

Synthesis of (R)-3-benzyl-2,6,9-trimethyl-4H,6H-thieno[2,3-e][,2,4]triazolo[3,4-c][1,4]oxazepine (Cpd. No. 114)

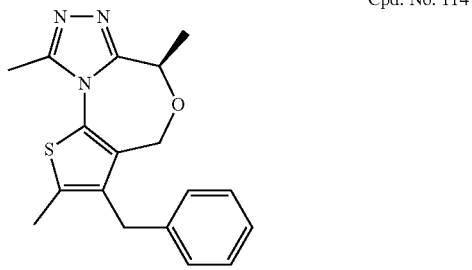

Cpd. No. 114

Cpd. No. 114 was synthesized following the same synthetic procedures as compound Cpd. No. 109 except for starting from chiral (R)-2-((tert-butyldiphenylsilyl)oxy)propanoic acid. ¹H NMR (400 MHz, MeOD) δ 7.29-7.14 (m, 5H), 4.81 (d, J=16.1 Hz, 1H), 4.65-4.57 (m, 2H), 3.98 (d, J=16.1 Hz, 1H), 3.90 (d, J=16.7 Hz, 1H), 2.79 (s, 3H), 2.50 (s, 3H), 1.65 (d, J=6.7 Hz 3H). ESI: M+H 326.08.

Example 100

Synthesis of tert-butyl 2-(3-benzyl-2,9-dimethyl-4H,6H-thieno[2,3-e][1,2,4]triazolo[3,4-c][1,4]oxazepin-6-yl)acetate (Cpd. No. 115)

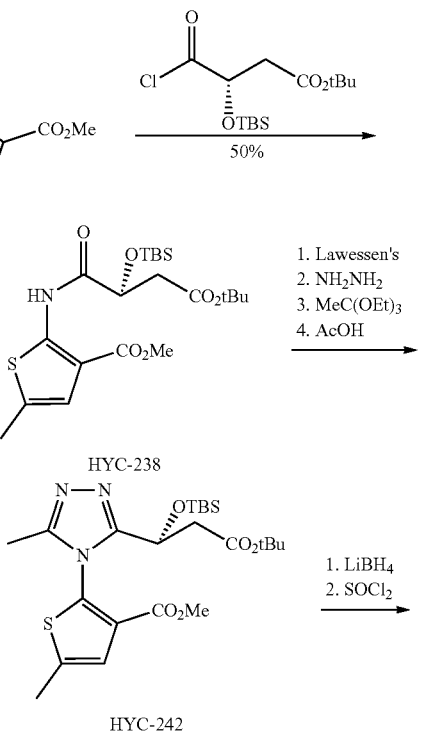

-continued

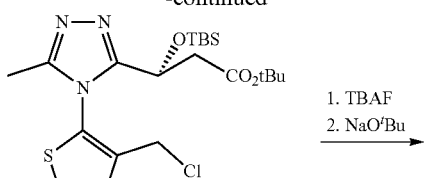

HYC-247

1. TBAF
2. NaO$^t$Bu

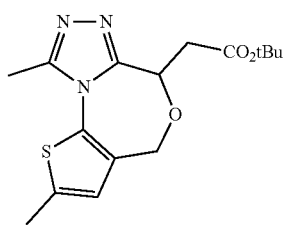

Cpd. No. 131

NBS

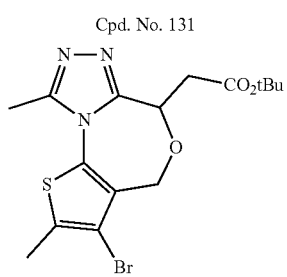

Cpd. No. 132

[Pd]

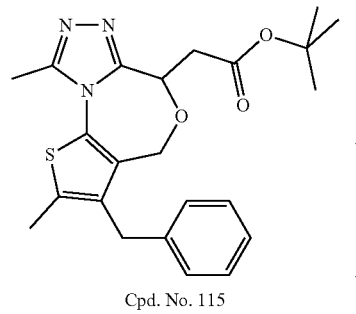

Cpd. No. 115

Example 100-A

Synthesis of methyl (S)-2-(4-(tert-butoxy)-2-((tert-butyldimethylsilyl)oxy)-4-oxobutanamido)-5-methylthiophene-3-carboxylate

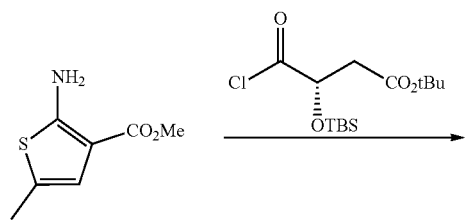

-continued

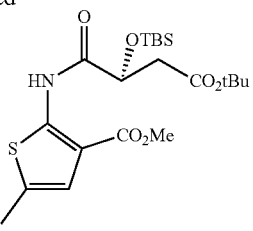

HYC-238

To a solution of (S)-4-(tert-butoxy)-2-((tert-butyldimethylsilyl)oxy)-4-oxobutanoic acid (3 g, 10 mmol) in DCM (20 mL) was added oxallyl chloride (0.85 mL, 1.3 eq) at 0° C. A couple of drops of DMF were added and the reaction mixture was allowed to warm to r.t. and stirred for 1 h. Then all the volatiles were removed under vacuum and the residue was dissolved in DCM (10 mL). This solution was added dropwise at 0° C. to a solution of methyl 2-amino-thiophene-3-carboxylate (850 mg, 5 mmol) and Et$_3$N (2 mL, 15 mmol) in DCM (20 mL). The reaction mixture was allowed to warm to r.t. and stirred for 1 h prior to being quenched with saturated NaHCO$_3$ and extracted with DCM (3×20 mL). The combined organic layer was washed with water and then, dried (Na$_2$SO$_4$), filtered and then concentrated. The oil was chromatographed on silica gel (1:8 ethyl acetate/hexanes) to give title compound as an oil: (1 g, 20%).

Example 100-B

Synthesis of methyl (S)-2-(3-(3-(tert-butoxy)-1-((tert-butyldimethylsilyl)oxy)-3-oxopropyl)-5-methyl-4H-1,2,4-triazol-4-yl)-5-methylthiophene-3-carboxylate

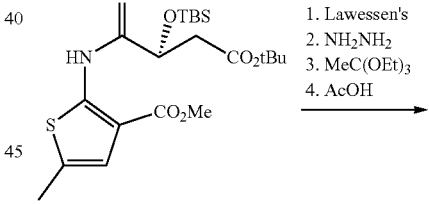

HYC-238

1. Lawessen's
2. NH$_2$NH$_2$
3. MeC(OEt)$_3$
4. AcOH

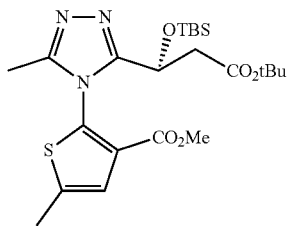

HYC-242

Step 1: To a solution of HYC-238 (1 g, 2 mmol) in dioxane (20 mL) was added Lawesson's reagent (484 mg, 0.1.2 mmol, 0.6 eq) and the reaction mixture was heated at reflux for 8 h. Another batch of Lawesson's reagent (484 mg, 0.12 mmol, 0.6 eq) was added and refluxed for 4 h The reaction was cooled, quenched with saturated solution of NaHCO$_3$, and extracted with EtOAc. The organic layers separated, dried, removed under vacuum and the residue was chromatographed on silica gel (1:16 ethyl acetate/hexanes) to give methyl (S)-2-(4-(tert-butoxy)-2-((tert-butyldimethylsilyl)oxy)-4-oxobutanethioamido)-5-methylthiophene-3-carboxylate as an oil: (530 mg, 60%).

Step 2: To a solution of methyl (S)-2-(4-(tert-butoxy)-2-((tert-butyldimethylsilyl)oxy)-4-oxobutanethioamido)-5-methylthiophene-3-carboxylate (510 mg, 1.1 mmol) in THF (4 mL) was added hydrazine monohydrate (0.12 mL, 2.4 mmol, 2 eq) at 0° C. and the reaction mixture was allowed to warm to r.t. The reaction mixture was stirred for 1 h prior to being concentrated in vacuum. The residue was taken up in DCM and washed with water and brine. The organic layer was separated, dried and concentrated.

Step 3: The residue was taken up in ethanol (4 mL) and triethyl orthoacetate (0.54 mL, 3.3 mmol, 3 eq) was added. The reaction mixture was heated at reflux for 12 h.

Step 4: All volatiles were removed under vacuum and the residue was dissolved in AcOH (4 mL). The solution was heated at reflux for 1 h prior to the removal of the solvent under vacuum. The residue was taken up in EtOAc and washed with 2 M $Na_2CO_3$. The organic layer was washed with brine, dried and concentrated. The residue was chromatographed on silica gel (ethyl acetate) to give a pair of diastereoisomers (ratio 2:1), (260 mg, 56%). $^1$H NMR (400 MHz, $CDCl_3$) δ Major isomer: 7.21 (s, 1H), 5.51-5.40 (m, 1H), 3.69 (s, 3H), 2.65 (dd, J=15.8, 4.8 Hz, 1H), 2.54 (s, 3H), 2.45 (dd, J=15.8, 8.5 Hz, 1H), 2.22 (s, 3H), 1.42 (s, 9H), 0.83 (s, 9H), 0.11 (s, 3H), −0.13 (s, 3H)).: Minor 7.21 (s, 1H), 5.20 (t, J=6.9 Hz, 1H), 3.67 (s, 3H), 2.90-2.85 (m, 2H), 2.54 (s, 3H), 2.26 (s, 3H), 1.41 (s, 9H), 0.80 (s, 9H), −0.04 (s, 3H), −0.05 (s, 3H).

Example 100-C

Synthesis of tert-butyl (S)-3-((tert-butyldimethylsilyl)oxy)-3-(4-(3-(chloromethyl)-5-methylthiophen-2-yl)-5-methyl-4H-1,2,4-triazol-3-yl)propanoate

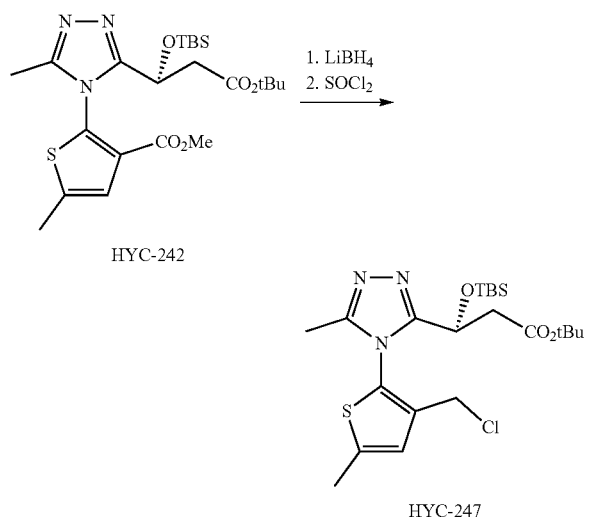

Step 1: To a solution of HYC-242 (300 mg, 0.6 mmol) in THF (10 mL) at 0° C. was added a solution of $LiBH_4$ (2 M in THF, 0.45 mL, 0.9 mmol). MeOH (1 mL) was added and the reaction mixture was allowed to warm to r.t. and stirred for 12 h. All volatiles were removed and the residue was taken up in EtOAc. The organic layer was washed with water and brine prior to being dried and concentrated.

Step 2: The residue was dissolved in DCM and cooled to 0° C. Thionyl chloride (0.13 mL, 1.8 mmol, 3 eq) was added and the reaction mixture was allowed to warm to r.t. After 1 h, all the volatiles were removed and the residue was taken up in EtOAc and washed with 2 M $Na_2CO_3$. The organic layer was washed with brine, dried and concentrated. The residue was chromatographed on silica gel (ethyl acetate) to give HYC-247 as a mixture of diastereoisomers: (229 mg, 64%). $^1$H NMR (400 MHz, $CDCl_3$) δ 6.86 (s, 1H), 6.85 (s, 1H), 5.37 (t, J=7.2 Hz, 1H), 5.18 (dd, J=8.5, 6.3 Hz, 1H), 4.31 (dd, J=12.1, 10.8 Hz, 1H), 4.21 (d, J=12.2 Hz, 1H), 4.12 (d, J=12.2 Hz, 1H), 3.03 (dd, J=15.7, 8.5 Hz, 1H), 2.78-2.67 (m, 2H), 2.63-2.56 (m, 1H), 2.53 (s, 3H), 2.53 (s, 3H), 2.34 (s, 3H), 2.32 (s, 3H), 1.41 (s, 9H), 1.39 (s, 9H), 0.84 (s, 9H), 0.83 (s, 9H), 0.10 (s, 3H), 0.01 (s, 3H), −0.00 (s, 3H), −0.08 (s, 3H).

Example 100-D

Synthesis of tert-butyl 2-(2,9-dimethyl-4H,6H-thieno[2,3-e][1,2,4]triazolo[3,4-c][1,4]oxazepin-6-yl)acetate (Cpd. No. 131)

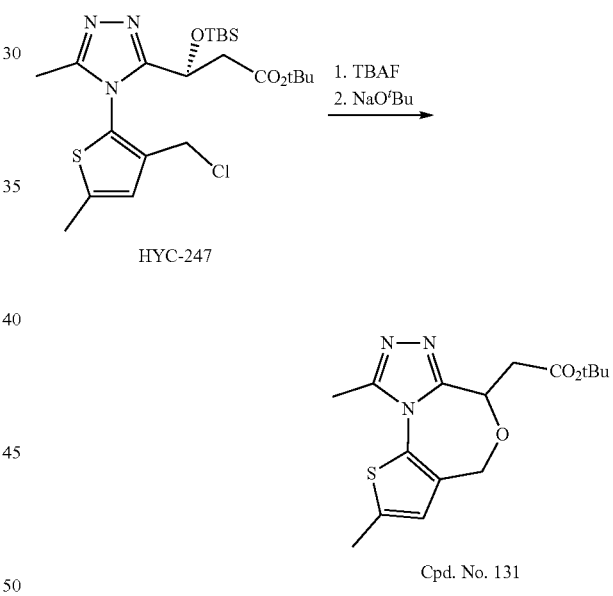

To a solution of HYC-247 (57 mg, 0.1 mmol) in THF (2 mL) at 0° C. was added a solution of TBAF (0.1 mL, 0.1 mmol, 1M in THF). The solution was stirred for 1 h prior to being added to a hot solution of $NaO^tBu$ (9.6 mg, 0.1 mmol, 1 eq) in $^tBuOH$ (2 mL) at 80° C. The reaction mixture was stirred for 5 min prior to the removal of the solvent under vacuum. The residue was taken up in EtOAc and water. The organic layer was washed with brine, dried and concentrated. The residue was purified through HPLC to afford TFA salt of Cpd. No. 131 (8 mg, 20%). $^1$H NMR (400 MHz, MeOD) δ 6.68 (s, 1H), 5.05 (d, J=15.7 Hz, 1H), 5.02-4.98 (m, 1H), 4.96 (d, J=15.7 Hz, 1H), 3.20 (dd, J=16.7, 4.2 Hz, 1H), 2.94 (dd, J=16.7, 9.4 Hz, 1H), 2.76 (s, 3H), 2.53 (s, 3H), 1.50 (s, 9H). ESI-MS: 336.06.

Example 100-E

Synthesis of tert-butyl 2-(3-bromo-2,9-dimethyl-4H,6H-thieno[2,3-e][1,2,4]triazolo[3,4-c][1,4]oxazepin-6-yl)acetate (Cpd. No. 132)

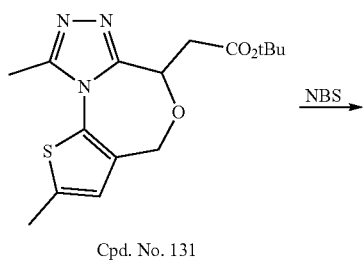

Cpd. No. 131

Cpd. No. 132

To a solution of Cpd. No. 131 (23 mg, 0.05 mmol) in acetic acid (1 mL) was added NBS (9 mg, 0.05 mmol) and the reaction was stirred for 20 min. The mixture was purified through HPLC to afford TFA salt of Cpd. No. 132 (13 mg, 50%). $^1$H NMR (400 MHz, MeOD) δ 5.05-4.91 (m, 3H), 3.22 (dd, J=16.8, 3.9 Hz, 1H), 2.95 (dd, J=16.8, 9.6 Hz, 1H), 2.74 (s, 2H), 2.48 (s, 2H), 1.52 (s, 7H). ESI-MS: 414.18.

Example 100-F

Synthesis of tert-butyl 2-(3-benzyl-2,9-dimethyl-4H,6H-thieno[2,3-e][1,2,4]triazolo[3,4-c][1,4]oxazepin-6-yl)acetate (Cpd. No. 115)

Cpd. No. 132

Cpd. No. 115

To a Shlenk tube was charged with Cpd. No. 132 (5 mg), potassium benzyltrifluoroborate (10 mg), Pd(dppf)Cl$_2$ (5 mg), dioxane (1 mL) and Na$_2$CO$_3$ solution (2 M, 0.5 mL) under N$_2$. The tube was sealed and heated at 100° C. oil bath for 1 h. The reaction mixture was extracted with EtOAc and the organic layer was washed with brine, dried and concentrated. The residue was purified through I-PLC to afford Cpd. No. 115 (20% yield). $^1$H NMR (400 MHz, MeOD) δ 7.30 (t, J=7.6 Hz, 2H), 7.21 (t, J=7.0 Hz, 1H), 7.14 (d, J=7.7 Hz, 2H), 4.93-4.88 (m, 1H), 4.82 (d, J=15.7 Hz, 1H), 4.67 (d, J=15.7 Hz, 1H), 3.93 (s, 2H), 3.15 (dd, J=16.3, 3.5 Hz, 1H), 2.88 (dd, J=16.8, 9.2 Hz, 1H), 2.78 (s, 3H), 2.50 (s, 3H), 1.42 (d, J=0.7 Hz, 9H). ESI-MS: 426.36.

Example 101

Synthesis of 3'-benzyl-2',9'-dimethyl-4'H-spiro[cyclopropane-1,6'-thieno[2,3-e][1,2,4]triazolo[3,4-c][1,4]oxazepine] (Cpd. No. 136)

HYC-258

HYC-276

-continued

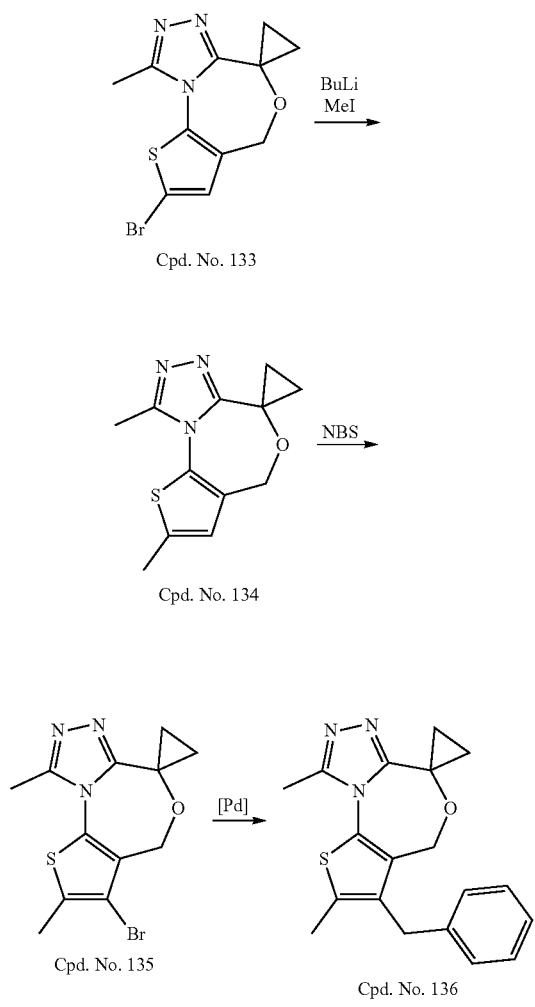

Cpd. No. 133

Cpd. No. 134

Cpd. No. 135    Cpd. No. 136

Example 101-A

Synthesis of methyl 1-(thiophen-3-ylmethoxy)cyclopropane 1-carboxylate

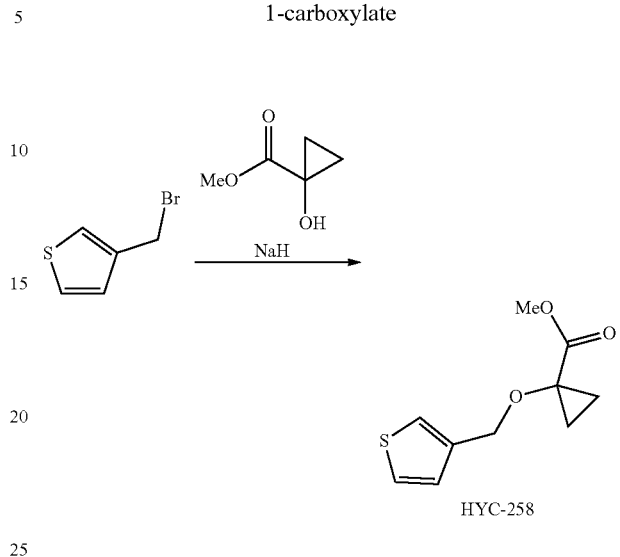

HYC-258

To a suspension of NaH (960 mg, 24 mmol) in TI-F (20 mL) at ° C. was added dropwise a solution of methyl 1-hydroxycyclopropane-1-carboxylate (2.32 g, 20 mmol, 1.25 eq) in THF (4 mL) and stirred for 10 min. Then 3-(bromomethyl)thiophene (2.83 g, 16 mmol) was added followed by the addition of TBAI (590 mg, 1.6 mmol). The reaction mixture was allowed to warm to r.t. and stirred for overnight. The reaction mixture was quenched by the addition of water and extracted with EtoAc (3×40 mL). The organic layer was washed with brine, dried over $Na_2SO_4$ and concentrated. The residue was purified on silica gel (1:8 ethyl acetate/hexanes) to give HYC-258 as colorless oil. (2.1 g, 63%). $^1$H NMR (400 MHz, $CDCl_3$) δ 7.35-7.29 (m 1H), 7.27-7.23 (m, 1H), 7.12 (d, J=4.9 Hz, 1H), 4.68 (s, 2H), 3.80 (s, 3H), 1.40-1.33 (m, 2H), 1.28-1.21 (m, 2H).

Example 101-B

Synthesis of 1-((2-bromothiophen-3-yl)methoxy) cyclopropane-1-carboxamide

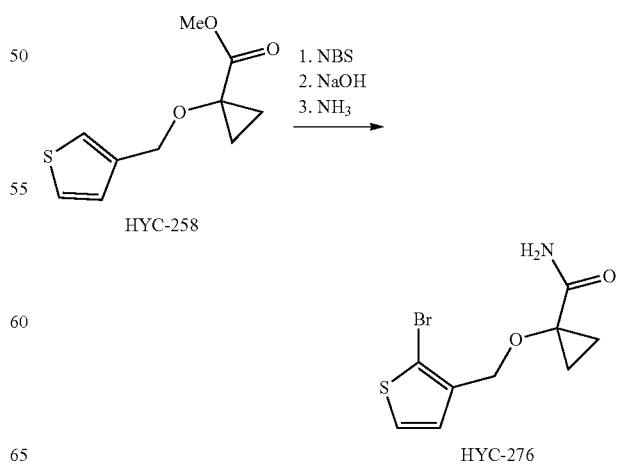

HYC-258    HYC-276

Step 1: To a solution of methyl 1-(thiophen-3-ylmethoxy) Cyclopropane-1-carboxylate (1.65 g, 7.8 mmol) in DCM (5 mL) and AcOH (5 mL) was added NBS (138 g, 7.8 mmol) and the reaction mixture was stirred overnight. The reaction mixture was poured into mixture of ice-water and extracted with Et₂O (3×20 mL). The combined organic layer was washed with 1 M NaOH (2×10 mL), saturated NaHCO₃ (2×20 mL), and brine, dried, filtered and then concentrated The oil was used directly in the next step without further purification.

Step 2: To a solution of methyl 1-((2-bromothiophen-3-yl)methoxy)cyclopropane-1-carboxylate (2.24 g, 7.8 mmol) in THF (15.6 mL) and EtOH (15.6 mL) was added at 0° C. 1 M NaOH (15.6 mL, 2 eq). The mixture was allowed to warm to r.t. and stirred overnight. The volatiles are evaporated and the residue was added water and extracted with Et₂O. The aqueous layer was separated and cooled to 0° C. prior to being neutralized with HCl (1 M, 16 mL). The solution was extracted with EtOAc, washed with brine, dried, and concentrated to provide the crude for the next step.

Step 3: The above crude was dissolved in DCM and cooled to 0° C. Oxallyl chloride (0.87 mL, 10 mmol, 1.3 eq) was added slowly followed by several drops of DMF. The reaction mixture was allowed to warm to rt. and stirred for 1 h prior to being concentrated under vacuum. The residue was dissolved in DCM and added slowly at 0° C. to a solution of NH₃ in methanol (7 M, 5 mL). The reaction mixture was stirred overnight prior to being filtered over Celite. The filtrate was concentrated and the residue was chromatographed on silica gel (ethyl acetate) to give HYC-276 as a solid. (1.38 g, 64%.). ¹H NMR (400 MHz, CDCl₃) δ 7.29 (d, J=5.6 Hz, 1H), 6.95 (d, J=5.6 Hz, 1H), 6.68 (s, 1H), 6.12 (s, 1H), 4.53 (s, 2H), 1.45-1.34 (m, 2H), 1.26-1.15 (m, 2H).

Example 101-C

Synthesis of 1',5'-dihydro-2'H-spiro[cyclopropane-1,3'-thieno[2,3-e][1,4]oxazepin]-2 one

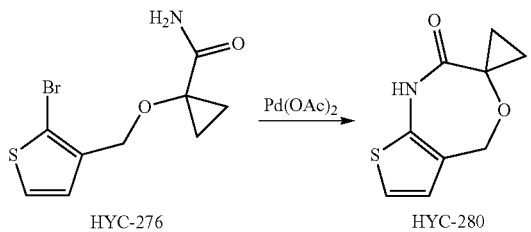 [SMILES: NC(=O)C1(OCc2ccsc2Br)CC1 ; O=C1Nc2sccc2COC12CC2 ; "Pd(OAc)2"]

To a flask under N was charged with HYC-276 (1.23 g, 4.5 n ol), Pd(OAc); (56 mg, 0.25 mmol), Xantphos (289 mg 0.5 mmol), Cs₂CO₃ (3.2 g, 10 mmol), and dioxane (25 mL). The reaction mixture was stirred at 100° C. overnight. The reaction mixture was cooled, quenched with water, extracted with EtOAc. The combined organic layer was washed with brine, dried (Na₂SO₄), filtered and concentrated. The oil was chromatographed on silica gel (1:2 ethyl acetate/hexanes) to give HYC-280 as a solid. (140 mg, 16%).

Example 101-D

Synthesis of 7'-bromo-1',5'-dihydro-2'H-spiro[cyclopropane-1,3'-thieno[2,3-e][1,4]oxazepin]-2'-one

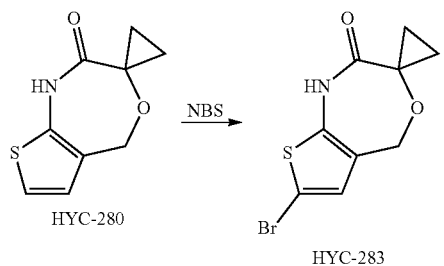

To a solution of HYC-280 (140 mg, 0.72 mmol) in DCM (4 mL) and AcOH (1 mL) was added NBS (128 mg, 0.75 mmol) and the reaction mixture was stirred overnight. The reaction mixture was diluted with DCM and washed with brine. The combined organic layer was dried, filtered and then concentrated The oil was chromatographed on silica gel (1:15 ethyl acetate/DCM) to give HYC-283 as a solid. (140 mg, 73%). ¹H NMR (400 MHz, CDCl₃) δ 6.54 (s, 1H), 4.57 (s, 2H), 1.49 (s, 2H), 1.17 (s, 2H).

Example 101-F

Synthesis of 2'-bromo-9'-methyl-4'H-spiro[cyclopropane-1,6'-thieno[2,3-e][1,2,4]triazolo[3,4-c][1,4]oxazepine] (Cpd. No. 133)

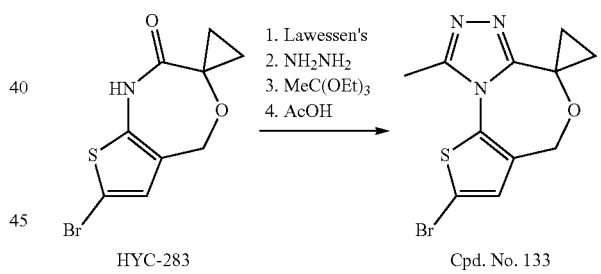

Step 1: To a solution of HYC-283 (110 mg, 0.4 mmol) in dioxane (6 mL) was added Lawesson's reagent (97.7 mg, 0.24 mmol, 0.6 eq) and the reaction mixture was heated at 80° C. for 4 h. The reaction was cooled, quenched with saturated solution of NaHCO₃, and extracted with EtOAc. The organic layers separated, dried, removed under vacuum and the residue was chromatographed on silica gel (1:16 ethyl acetate/hexanes) to give Cpd. No. 133 as an oil.

Step 2: To a solution of 7'-bromo-1',5'-dihydro-2'H-spiro[cyclopropane-1,3'-thieno[2,3-e][1,4]oxazepine]-2'-thione in THF (2 mL) was added hydrazine monohydrate (0.038 mL, 0.8 mmol, 2 eq) at 0° C. and the reaction mixture was allowed to warm to r.t. The reaction mixture was stirred for 1 h prior to being concentrated in vacuum. The residue was taken up in DCM and washed with water and brine. The organic layer was separated, dried and concentrated.

Step 3: The residue was taken up in ethanol (2 mL) and triethyl orthoacetate (0.22 mL, 1.2 mmol, 3 eq) was added. The reaction mixture was heated at reflux for 12 h.

Step 4: All volatiles were removed under vacuum and the residue was dissolved in AcOH (1 mL). The solution was heated at reflux for 1 h prior to being purified via HPLC to give Cpd. No. 133 (110 mg, 65%). ¹H NMR (400 MHz, CDCl₃) δ 6.54 (s, 1H), 4.57 (s, 2H), 1.52-1.47 (m, 2H), 1.21-1.17 (m, 2H).

Example 101-G

Synthesis of 2',9'-dimethyl-4'H-spiro[cyclopropane-1,6'-thieno[2,3-e][1,2,4]triazolo[3,4-c][1,4]oxazepine] (Cpd. No. 134)

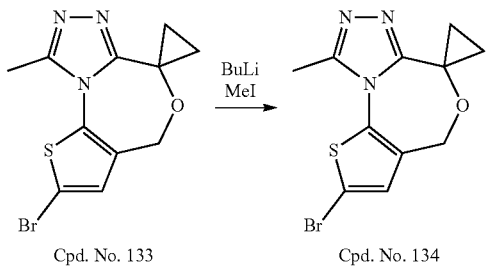 [SMILES: Cc1nnc2n1-c1sc(Br)cc1COC21CC1 ; Cc1nnc2n1-c1sc(Br)cc1COC21CC1]

Cpd. No. 133      Cpd. No. 134

A solution of Cpd. No. 133 (80 mg, 0.26 mmol) in THF (5 mL) was cooled to −78° C. under N₂. A solution of BuLi (1.6 M in THF, 0.16 mL, 0.26 mmol) was added dropwise and the reaction mixture was stirred for 20 min. Then MeI (0.024 mL, 0.4 mmol) was added and the reaction mixture was allowed to warm to r.t. After stirring overnight, the reaction mixture was quenched with the addition of water. The mixture was extracted with EtOAc and the combined organic layer was washed with brine, dried (Na₂SO₄), filtered and concentrated. The oil was purified via HPLC to give Cpd. No. 134 as a solid. (47 mg, 50%). ¹H NMR (400 MHz, MeOD) δ 6.68 (s, 1H), 4.91 (s, 2H), 2.81 (s, 3H), 2.52 (s, 3H), 1.37 (t, J=6.8 Hz, 2H), 1.31 (t, J=6.9 Hz, 2H). ESI-MS: 248.15.

Example 101-H

Synthesis of 3'-bromo-2',9'-dimethyl-4'H-spiro[cyclopropane-1,6'-thieno[2,3-e][1,2,4]triazolo[3,4-c][1,4]oxazepine] (Cpd. No. 135)

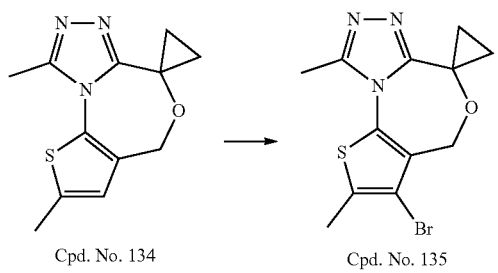 [SMILES: Cc1cc2c(s1)-n1c(C)nnc1C1(CC1)OC2 ; Cc1sc2c(c1Br)COC1(CC1)c1nnc(C)n1-2]

Cpd. No. 134      Cpd. No. 135

To a solution of Cpd. No. 134 (45 mg, 0.125 mmol) in AcOH (1 mL) was added NBS (23 mg, 0.125 mmol) and the reaction mixture was stirred for 1 h. The reaction mixture was purified via HPLC to give Cpd. No. 135 as a solid. (13 mg, 30%). ESI-MS: 326.02.

Example 101-I

Synthesis of 3'-benzyl-2',9'-dimethyl-4'H-spiro[cyclopropane-1,6'-thieno[2,3-e][1,2,4]triazolo[3,4-c][1,4]oxazepine] (Cpd. No. 136)

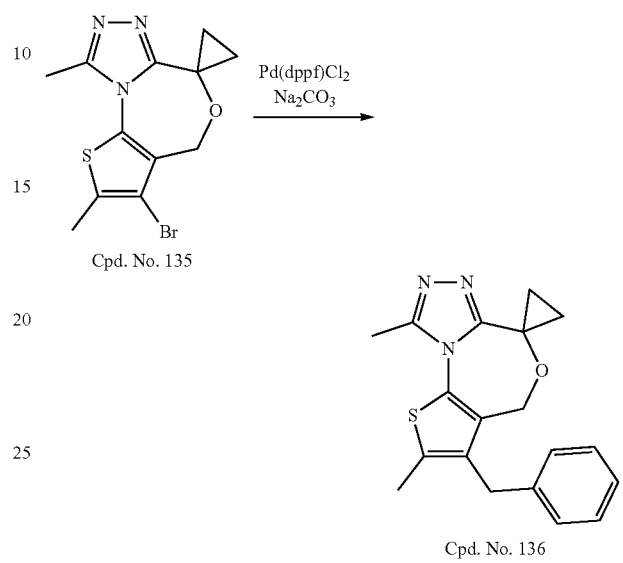

To a Shlenk tube was charged with Cpd. No. 135 (13 mg), potassium benzyltrifluoroborate (16 mg), Pd(dppf)Cl₂ (6 mg), dioxane (2 mL) and Na₂CO₃ solution (2 M, 1 mL) under N₂. The tube was sealed and heated at 100° C. oil bath for 1 h. The reaction mixture was extracted with EtOAc and the organic layer was washed with brine, dried and concentrated. The residue was purified through HPLC to afford Cpd. No. 136 (90% yield)¹H NMR (400 MHz, MeOD) δ 7.30 (t, J=7.5 Hz, 2H), 7.21 (t, J=7.2 Hz, 1H), 7.12 (d, J=7.5 Hz, 2H), 4.65 (s, 2H), 3.95 (s, 2H), 2.79 (s, 3H), 2.50 (s, 3H), 1.28-1.17 (m, 2H), 1.17-1.09 (m, 2H). ESI-MS: 338.12.

Example 102

Synthesis of 5-(3-benzyl-9-methyl-4H,6H-thieno[2,3-e][1,2,4]triazolo[3,4-c][1,4]oxazepin-2-yl)pyridin-2-amine (Cpd. No. 32)

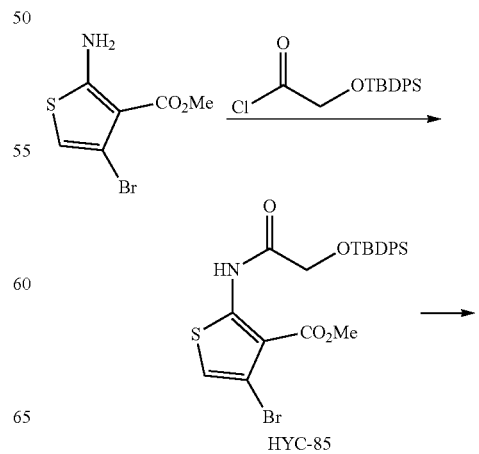

HYC-85

195
-continued

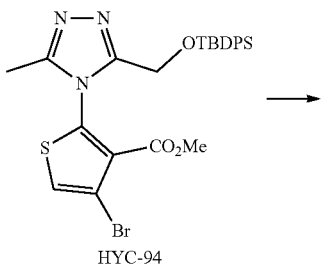
HYC-94

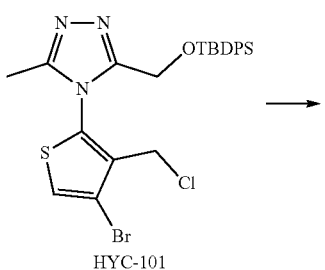
HYC-101

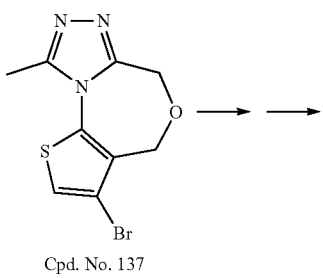
Cpd. No. 137

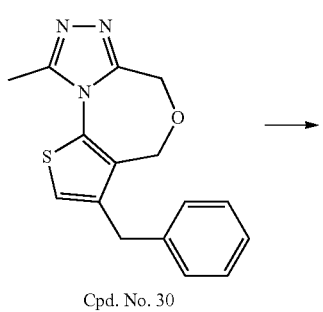
Cpd. No. 30

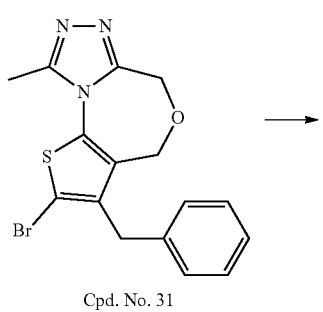
Cpd. No. 31

196
-continued

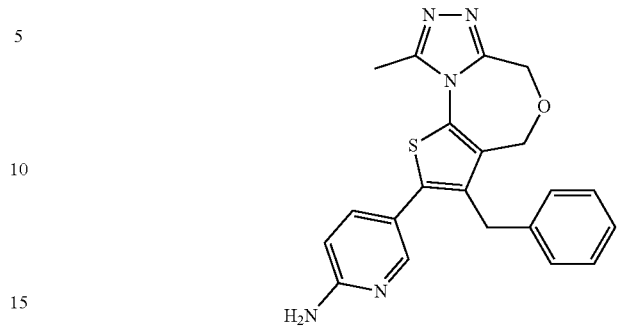
Cpd. No. 32

Example 102-A

Synthesis of methyl 4-bromo-2-(2-((tert-butyldiphenylsilyl)oxy)acetamido)thiophene-3-carboxylate

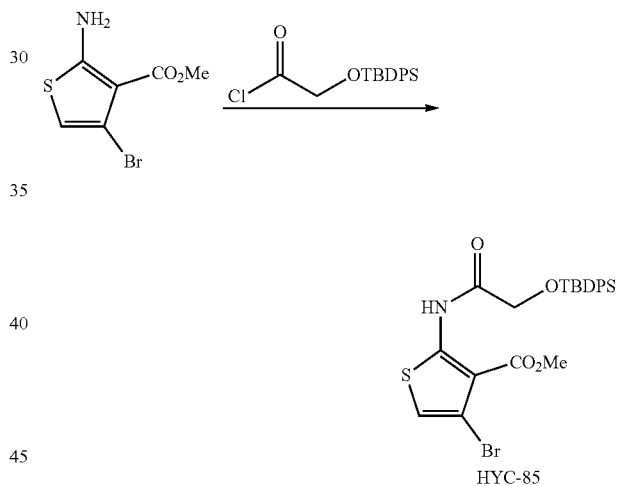
HYC-85

To a solution of 2-((tert-butyldiphenylsilyl)oxy)acetic acid (8 g, 25.4 mmol) in DCM (40 mL) was added oxallyl chloride (30 mmol, 2.6 mL, 1.2 eq) at 0° C. A couple of drops of DMF were added and the reaction mixture was allowed to warm to r.t. and stirred for 1 h. Then all the volatiles were removed under vacuum and the residue was dissolved in DCM (10 mL). This solution was added dropwise at 0° C. to a solution of methyl 2-amino-4-bromothiophene-3-carboxylate (2.9 g, 12.7 mmol) and DIPEA (6.6 mL, 38 mmol) in DCM (40 mL). The reaction mixture was allowed to warm to r.t. and stirred for 1 h prior to being quenched with saturated $NaHCO_3$ and extracted with DCM (3×40 mL). The combined organic layer was washed with water and then, dried ($Na_2SO_4$), filtered and then concentrated. The oil was chromatographed on silica gel (1:8 ethyl acetate/hexanes) to give title compound as an oil: (6.6 g, 90%.). $^1$H NMR (400 MHz, $CDCl_3$) δ 12.30 (s, 1H), 7.83-7.72 (m, 4H), 7.54-7.38 (m, 6H), 6.87 (s, 1H), 4.35 (s, 2H), 3.94 (s, 3H), 1.24 (s, 9H).

Example 102-B

Synthesis of methyl 4-bromo-2-(3-(((tert-butyldiphenylsilyl)oxy)methyl)-5-methyl-4H-1,2,4-triazol-4-yl)thiophene-3-carboxylate

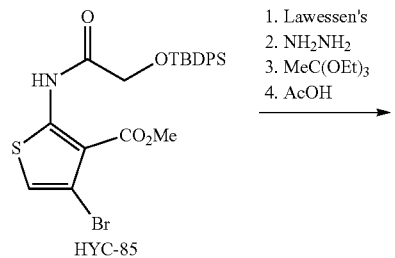

HYC-85

1. Lawessen's
2. NH₂NH₂
3. MeC(OEt)₃
4. AcOH

HYC-94

Step 1: To a solution of HYC-85 (394 mg, 0.74 mmol) in dioxane (8 mL) was added Lawesson's reagent (300 mg, 0.74 mmol, 1 eq) and the reaction mixture was heated at reflux for 8 h. The reaction was cooled, quenched with saturated solution of NaHCO₃, and extracted with EtOAc. The organic layers separated, dried, removed under vacuum and the residue was chromatographed on silica gel (1:16 ethyl acetate/hexanes) to a crude oil (230 mg, 57%).

Step 2: To a solution of the above crude in THF (4 mL) was added hydrazine monohydrate (42 mg, 0.84 mmol, 2 eq) at 0° C. and the reaction mixture was allowed to warm to r.t. The reaction mixture was stirred for 1 h prior to being concentrated in vacuum. The residue was taken up in DCM and washed with water and brine. The organic layer was separated, dried and concentrated.

Step 3: The residue was taken up in ethanol (4 mL) and triethyl orthoacetate (0.23 mL, 1.26 mmol, 3 eq) was added. The reaction mixture was heated at reflux for 12 h.

Step 4: All volatiles were removed under vacuum and the residue was dissolved in AcOH (4 mL). The solution was heated at reflux for 1 h prior to the removal of the solvent under vacuum. The residue was taken up in EtOAc and washed with 2 M Na₂CO₃. The organic layer was washed with brine, dried and concentrated. The residue was chromatographed on silica gel (ethyl acetate) to give title compound (175 mg, 42%). $^1$H NMR (400 MHz, CDCl₃) δ 7.57-7.32 (m, 10H), 4.78 (d, J=12.8 Hz, 1H), 4.62 (d, J=12.8 Hz, 1H), 3.64 (s, 3H), 2.36 (s, 3H), 0.96 (s, 9H).

Example 102-C

Synthesis of 4-(4-bromo-3-(chloromethyl)thiophen-2-yl)-3-(((tert-butyldiphenylsilyl)oxy)methyl)-5-methyl-4H-1,2,4-triazole

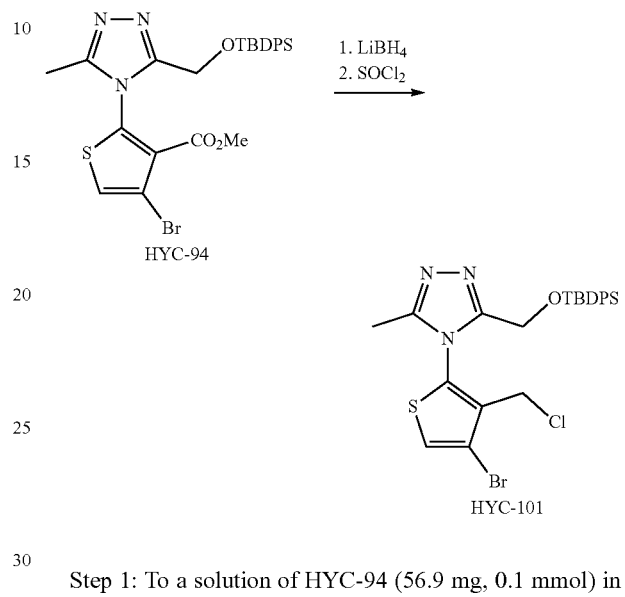

Step 1: To a solution of HYC-94 (56.9 mg, 0.1 mmol) in THF (4 mL) at 0° C. was added a solution of LiBH₄ (2 M in THF, 0.075 mL, 0.15 mmol). MeOH (0.4 mL) was added and the reaction mixture was allowed to warm to r.t. and stirred for 12 h. All volatiles were removed and the residue was taken up in EtOAc. The organic layer was washed with water and brine prior to being dried and concentrated.

Step 2: The residue was dissolved in DCM and cooled to 0° C. Thionyl chloride (0.3 mmol, 3 eq) was added and the reaction mixture was allowed to warm to r.t. After 1 h, all the volatiles were removed and the residue was taken up in EtOAc and washed with 2 M Na₂CO₃. The organic layer was washed with brine, dried and concentrated. The residue was chromatographed on silica gel (ethyl acetate) to give HYC-101 (90% yield). H NMR (400 MHz, CDCl₃) δ 7.55-7.33 (m, 10H), 4.73 (d, J=12.6 Hz, 1H), 4.66 (d, J=12.6 Hz, 1H), 4.24 (s, 2H), 2.40 (s, 3H), 0.99 (s, 9H).

Example 102-D

Synthesis of 3-bromo-9-methyl-4H,6H-thieno[2,3-e][1,2,4]triazolo[3,4-c][1,4]oxazepine (Cpd. No. 137)

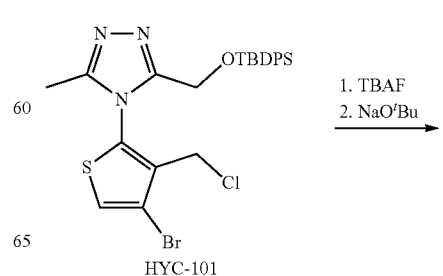

HYC-101

1. TBAF
2. NaO$^t$Bu

-continued

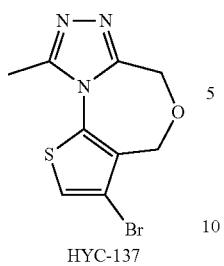

HYC-137

To a solution of HYC-101 (800 mg, 1.6 mmol) in THF (8 mL) at 0° C. was added a solution of TBAF (1.6 mL, 1.6 mmol, 1M in THF). The solution was stirred for 1 h prior to being added to a hot solution of NaO'Bu (307 mg, 3.2 mmol, 2 eq) in 'BuOH (30 mL) at 80° C. The reaction mixture was stirred for 5 min prior to the removal of the solvent under vacuum. The residue was taken up in EtOAc and water. The organic layer was washed with brine, dried and concentrated. The residue was purified through HPLC to afford TFA salt of Cpd. No. 137 (210 mg, 46%).

Example 102-F

Synthesis of 3-benzyl-9-methyl-4H,6H-thieno[2,3-e][1,2,4]triazolo[3,4-c][1,4]oxazepine (Cpd. No. 30)

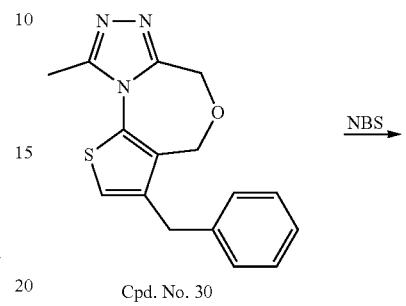

To a flask was charged with Cpd. No. 137 (210 mg, 0.74 mmol), potassium benzyltrifluoroborate (293 mg, 1.48 mmol), Pd(dppf)Cl₂ (60 mg, 0.07 mmol), dioxane (6 mL) and Na₂CO₃ solution (2 M, 3 mL) under N₂. The reaction mixture was heated at 100° C. oil bath for 1 b. The reaction mixture was extracted with EtOAc and the organic layer was washed with brine, dried and concentrated. The residue was purified through HPLC to afford Cpd. No. 30 (166 mg, 76% yield). ¹H NMR (400 MHz, CDCl₃) δ 7.40-7.30 (m, 3H), 7.20 (d, J=7.2 Hz, 2H), 6.82 (s, 1H), 4.79 (s, 2H), 4.73 (s, 2H), 3.88 (s, 2H), 2.75 (s, 3H).

Example 102-G

Synthesis of 3-benzyl-2-bromo-9-methyl-4H,6H-thieno[2,3-e][1,2,4]triazolo[3,4-c][1,4]oxazepine (Cpd. No. 31)

To a solution of Cpd. No. 30 TFA salt (166 mg, 0.53 mmol) in DCM (4 mL) and AcOH (1 mL) was added NBS (94 mg, 0.6 mmol) and the reaction mixture was stirred for 1 h. The reaction mixture was purified via HPLC to give Cpd. No. 31 as a solid. (126 mg, 63%). ESI-MS:375.94.

Example 102-F

Synthesis of 5-(3-benzyl-9-methyl-4H,6H-thieno[2,3-e][1,2,4]triazolo[3,4-c][1,4]oxazepin-2-yl)pyridin-2-amine (Cpd. No. 32)

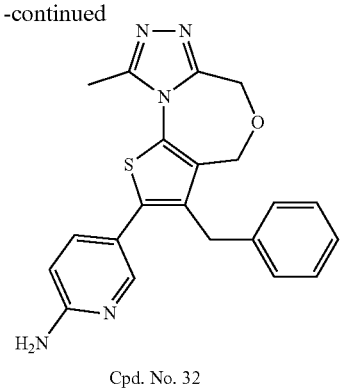

Cpd. No. 32

To a flask was charged with Cpd. No. 31 (10 mg, 0.03 mmol), (6-aminopyridin-3-yl)boronic acid (10 mg, 2 eq), Pd(dppf)Cl$_2$ (3 mg), dioxane (1 mL) and Na$_2$CO$_3$ solution (2 M, 0.5 mL) under N$_2$. The reaction mixture was heated at 100° C. oil bath for 1 h. The reaction mixture was extracted with EtOAc and the organic layer was washed with brine, dried and concentrated. The residue was purified through HPLC to afford Cpd. No. 32 (40% yield). $^1$H NMR (400 MHz, MeOD) δ 7.94 (d, J=9.2 Hz, 1H), 7.89 (s, 1H), 7.32 (t, J=7.4 Hz, 2H), 7.24 (t, J=7.3 Hz, 1H), 7.12 (d, J=7.3 Hz, 2H), 7.05 (s, 1H), 4.78 (s, 2H), 4.71 (s, 2H), 4.02 (s, 2H), 2.79 (s, 3H). ESI-MS: 390.38.

Example 103

Synthesis of 3-benzyl-2-ethynyl-9-methyl-4H,6H-thieno[2,3-e][1,2,4]triazolo[3,4-c][1,4]oxazepine (Cpd. No. 33)

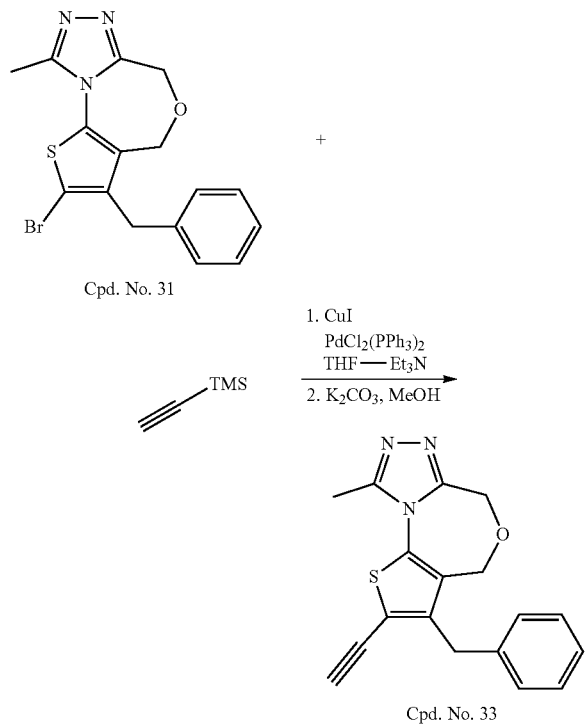

Step 1: To a flask was charged with Cpd. No. 31 (10 mg, 0.03 mmol), ethynyltrimethylsilane (6 mg, 2 eq), Pd(PPh$_3$)$_2$Cl$_2$ (2.1 mg), CuI (1 mg), THF (1 mL) and Et$_3$N (1 mL) under N$_2$. The reaction mixture was stirred at r.t. for 18 h. The reaction mixture was extracted with EtOAc and the organic layer was washed with brine, dried and concentrated.

Step 2: The residue was dissolved in MeOH (1 mL) and K$_2$CO$_3$ (13.8 mg) was added and stirred for 1 h. The reaction mixture was extracted with EtOAc and the organic layer was washed with brine, dried and concentrated. The residue was purified through HPLC to afford Cpd. No. 33 (20% yield). $^1$H NMR (400 MHz, MeOD) δ 7.37-7.16 (m, 5H), 4.72 (s, 2H), 4.69 (s, 2H), 4.22 (s, 1H), 4.10 (s, 2H), 2.76 (s, 3H). ESI-MS: 322.20.

Example 104

Synthesis of 3-benzyl-9-methyl-2-(morpholinomethyl)-4H,6H-thieno[2,3-][1,2,4]triazolo[3,4-c][1,4]oxazepine (Cpd. No. 90)

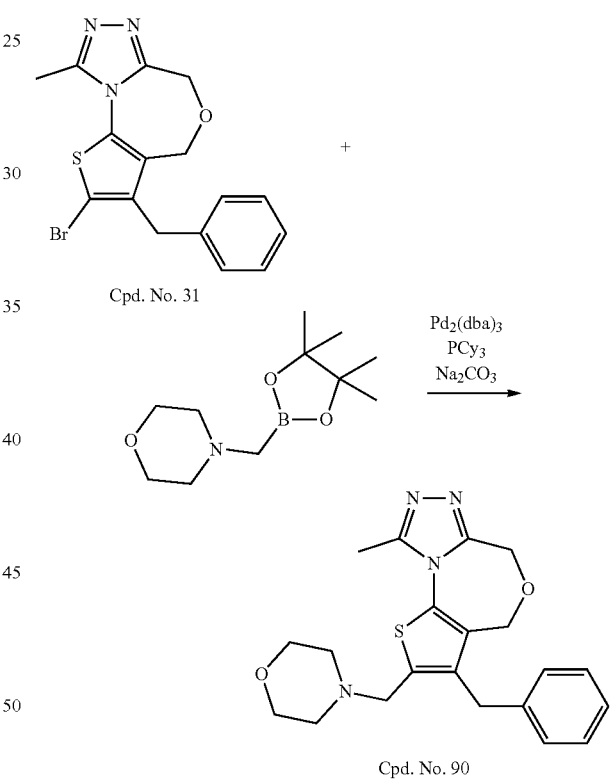

To a Shlenk tube was charged with Cpd. No. 31 (10 mg), 4-((4,4,5,5-tetramethyl-1,3,2-dioxaborolan-2-yl)methyl)morpholine (14 mg, 2 eq), Pd$_2$(dba)$_3$ (2.7 mg), PCy$_3$ (1.7 mg), dioxane (1 mL) and Na$_2$CO$_3$ solution (2 M, 0.5 mL) under N$_2$. The tube was sealed and heated at 100° C. oil bath for 4 h. The reaction mixture was extracted with EtOAc and the organic layer was washed with brine, dried and concentrated. The residue was purified through HPLC to afford Cpd. No. 90 (45% yield). $^1$H NMR (400 MHz, MeOD) δ 7.34 (t, J=7.6 Hz, 2H), 7.26 (t, J=7.2 Hz, 1H), 7.13 (d, J=7.7 Hz, 2H), 4.74 (s, 2H), 4.72 (s, 2H), 4.67 (s, 2H), 4.17 (s, 2H), 3.92 (s, 4H), 3.36 (s, 4H), 2.80 (s, 3H). ESI-MS: M+H 397.10.

Example 105

Synthesis of 3-benzyl-9-methyl-2-(1H-pyrazol-4-yl)-4H,6H-thieno[2,3-e][1,2,4]triazolo[3,4-c][1,4]oxazepine (Cpd. No. 91)

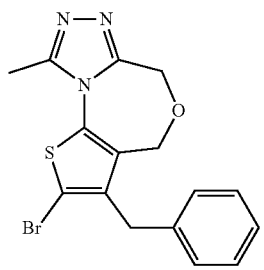

Cpd. No. 31

+

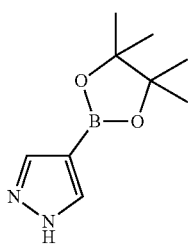

Pd(dppf)Cl₂
Na₂CO₃
→

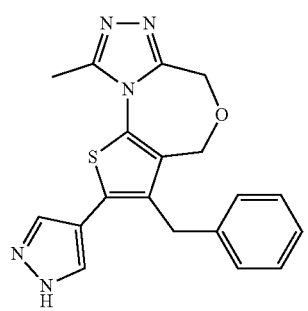

Cpd. No. 91

To a flask was charged with Cpd. No. 31 (37.5 mg, 0.1 mmol), 4-(4,4,5,5-tetramethyl-1,3,2-dioxaborolan-2-yl)-1H-pyrazole (38.8 mg, 2 eq), Pd(dppf)Cl₂ (8 mg), dioxane (4 mL) and Na₂CO₃ solution (2 M, 2 mL) under N₂. The reaction mixture was heated at 100° C. oil bath for 1 h. The reaction mixture was extracted with EtOAc and the organic layer was washed with brine, dried and concentrated. The residue was purified through HPLC to afford Cpd. No. 91 (25% yield). ¹H NMR (400 MHz, MeOD) δ 7.77 (s, 2H), 7.32 (t, J=7.5 Hz, 2H), 7.23 (t, J=7.3 Hz, 1H), 7.14 (d, J=7.5 Hz, 2H), 4.78 (s, 2H), 4.73 (s, 2H), 4.05 (s, 2H), 2.85 (s, 3H). ESI-MS: M+H 364.09.

Example 106

Synthesis of 3-benzyl-9-methyl-2-(1-methyl-H-pyrazol-4-yl)-4H,6H-thieno[2,3-e][1,2,4]triazolo[3,4-c][1,4]oxazepine (Cpd. No. 92)

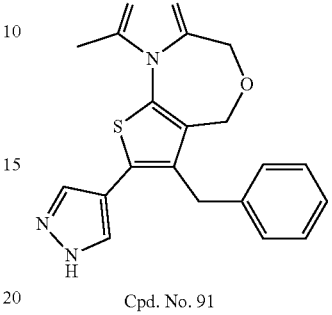

Cpd. No. 91

K₂CO₃
18-crown-ehter
MeI
→

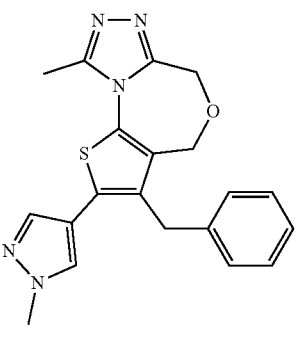

Cpd. No. 92

To a flask was charged with Cpd. No. 91 (7 mg, 0.02 mmol), K₂CO₃ (27 mg), MeI (0.025 mL), acetonitrile (2 mL) and 18-crown-ether (10 mg). The reaction mixture was stirred for 4 h. The reaction mixture was extracted with EtOAc and the organic layer was washed with brine, dried and concentrated. The residue was purified through HPLC to afford Cpd. No. 92 (50% yield). ¹H NMR (400 MHz, MeOD) δ 7.81 (s, 1H), 7.59 (s, 1H), 7.32 (t, J=7.6 Hz, 2H), 7.23 (t, J=7.0 Hz, 1H), 7.13 (d, J=7.7 Hz, 2H), 4.77 (s, 2H), 4.70 (s, 2H), 4.05 (s, 2H), 3.93 (s, 3H), 2.83 (s, 3H). ESI-MS: M+H 378.00.

Example 107

Synthesis of 3-benzyl-2-cyclopropyl-9-methyl-4H,6H-thieno[2,3-e][1,2,4]triazolo[3,4-c][1,4]oxazepine (Cpd. No. 93)

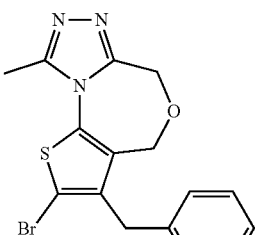

Cpd. No. 31

+

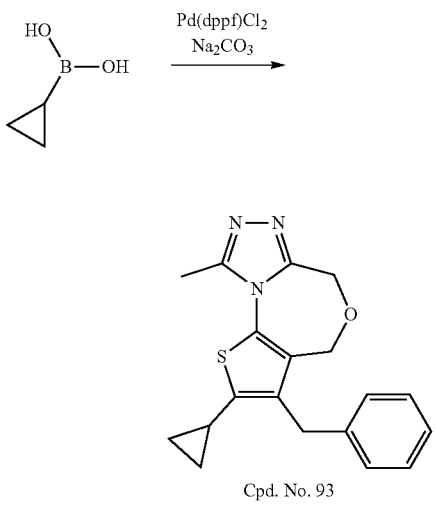

Cpd. No. 93

To a flask was charged with Cpd. No. 31 (10 mg, 0.03 mmol), cyclopropylboronic acid (5 mg, 2 eq), Pd(dppf)Cl₂ (3 mg), dioxane (1 mL) and Na₂CO₃ solution (2 M, 0.5 mL) under N₂. The reaction mixture was heated at 100° C. oil bath for 1 h. The reaction mixture was extracted with EtOAc and the organic layer was washed with brine, dried and concentrated. The residue was purified through HPLC to afford Cpd. No. 93 (30% yield). ¹H NMR (400 MHz, MeOD) δ 7.30 (t, J=7.6 Hz, 3H), 7.22 (d, J=6.8 Hz, 1H), 7.18 (d, J=7.7 Hz, 2H), 4.73 (s, 2H), 4.68 (s, 2H), 4.09 (s, 2H), 2.79 (d, J=0.6 Hz, 3H), 2.22-2.10 (m, 1H), 1.11 (q, J=5.0 Hz, 2H), 0.79 (q, J=4.9 Hz, 2H). ESI-MS: M+H 338.18.

Example 108

Synthesis of 3-benzyl-9-methyl-2-(prop-1-en-2-yl)-4H,6H-thieno[2,3-e][1,2,4]triazolo[3,4-c][1,4]oxazepine (Cpd. No. 94)

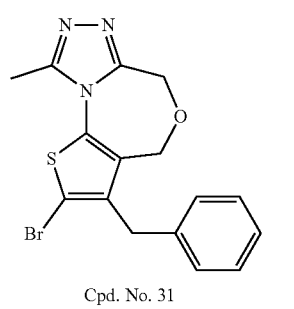

Cpd. No. 31

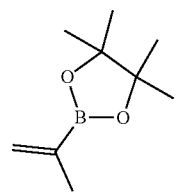

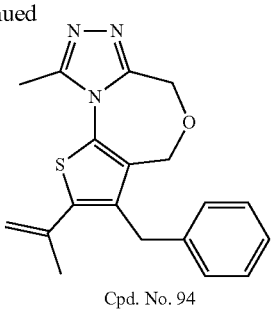

Cpd. No. 94

To a Shlenk tube was charged with Cpd. No. 31 (20 mg), 4,4,5,5-tetramethyl-2-(prop-1-en-2-yl)-1,3,2-dioxaborolane (20 mg, 2 eq), Pd(dppf)Cl₂ (6 mg), dioxane (2 mL) and Na₂CO₃ solution (2 M, 1 mL) under N₂. The tube was sealed and heated at 100° C. oil bath for 1 h. The reaction mixture was extracted with EtOAc and the organic layer was washed with brine, dried and concentrated. The residue was purified through HPLC to afford Cpd. No. 94 (75% yield). ¹H NMR (400 MHz, MeOD) δ 7.30 (t, J=7.3 Hz, 2H), 7.21 (t, J=7.1 Hz, 1H), 7.11 (d, J=7.4 Hz, 2H), 5.36 (s, 1H), 5.20 (s, 1H), 4.73 (s, 2H), 4.63 (s, 2H), 4.07 (s, 2H), 2.80 (s, 3H), 2.17 (s, 3H). ESI-MS: M+H 338.05.

Example 109

Synthesis of 3-benzyl-2-(3,6-dihydro-2H-pyran-4-yl)-9-methyl-4H,6H-thieno[2,3-e][1,2,4]triazolo[3,4-c][1,4]oxazepine (Cpd. No. 95)

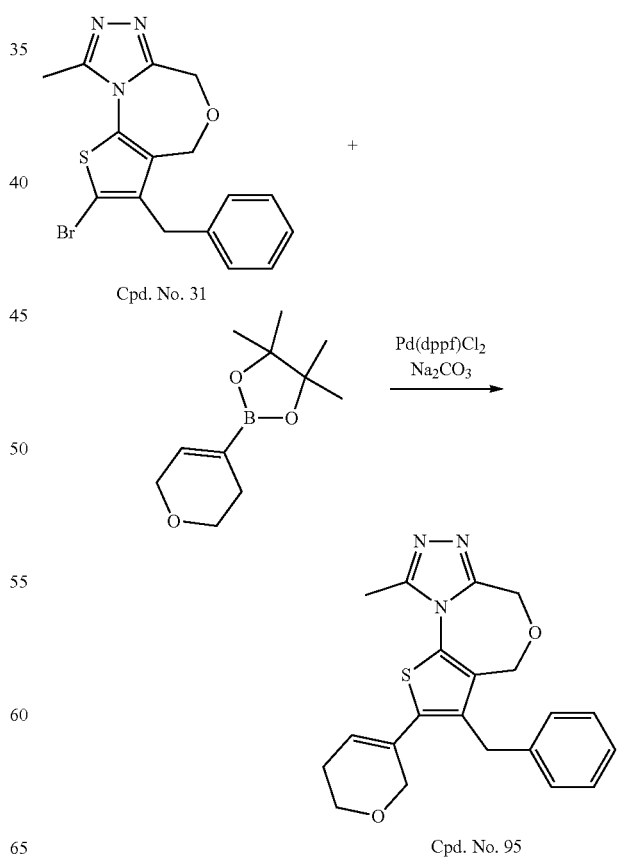

To a Shlenk tube was charged with Cpd. No. 31 (20 mg), 2-(3,6-dihydro-2H-pyran-4-yl)-4,4,5,5-tetramethyl-1,3,2-dioxaborolane (25 mg, 2 eq), Pd(dppf)Cl$_2$ (6 mg), dioxane (2 mL) and Na$_2$CO$_3$ solution (2 M, 1 mL) under N$_2$. The tube was sealed and heated at 100° C. oil bath for 1 h. The reaction mixture was extracted with EtOAc and the organic layer was washed with brine, dried and concentrated. The residue was purified through HPLC to afford Cpd. No. 95 (95% yield). $^1$H NMR (400 MHz, MeOD) δ 7.31 (t, J=7.4 Hz, 2H), 7.22 (t, J=7.3 Hz, 1H), 7.12 (d, J=7.2 Hz, 2H), 6.05-5.97 (m, 1H), 4.75 (s, 2H), 4.66 (s, 2H), 4.23 (dd, J=5.5, 2.8 Hz, 2H), 4.06 (s, 2H), 3.87 (t, J=5.4 Hz, 2H), 2.83 (s, 3H), 2.48-2.42 (m, 2H). ESI-MS: 380.10.

Example 110

Synthesis of 4-(3-benzyl-9-methyl-4H,6H-thieno[2,3-e][1,2,4]triazolo[3,4-c][1,4]oxazepin-2-yl)but-3-yn-1-ol (Cpd. No. 96)

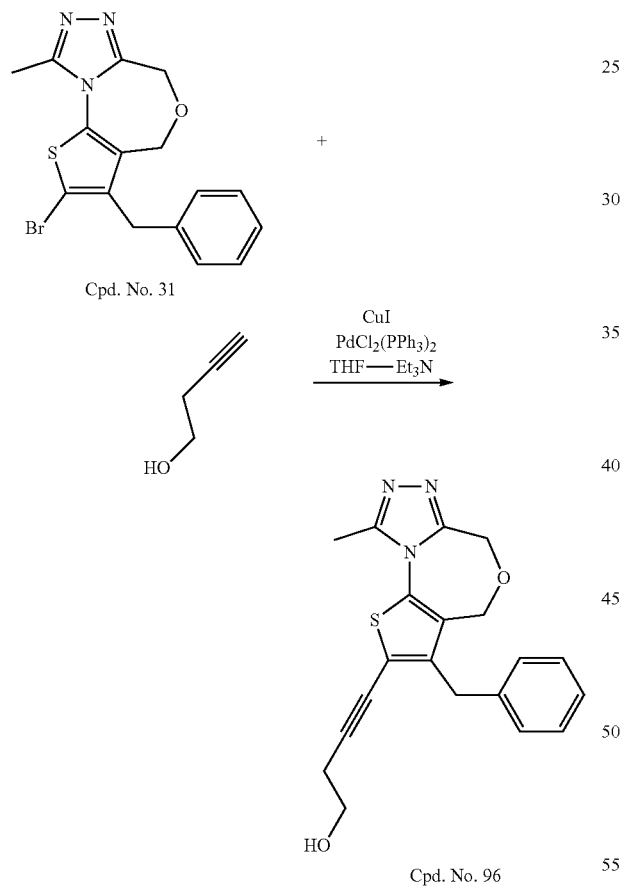

To a flask was charged with Cpd. No. 31 (20 mg, 0.05 mmol), but-3-yn-1-ol (8.4 mg, 2 eq), Pd(PPh$_3$)$_2$Cl$_2$ (4.2 mg), CuI (2.3 mg), THF (1 mL) and Et$_3$N (1 mL) under N$_2$. The reaction mixture was stirred at 60° C. for 18 h. The reaction mixture was extracted with EtOAc and the organic layer was washed with brine, dried and concentrated. The residue was purified through HPLC to afford Cpd. No. 96 (80% yield). $^1$H NMR (400 MHz, MeOD) δ 7.29 (t, J=7.5 Hz, 2H), 7.25-7.15 (m, 3H), 4.72 (s, 2H), 4.69 (s, 2H), 4.06 (s, 2H), 3.75 (t, J=6.5 Hz, 2H), 2.75-2.70 (m, 5H). ESI-MS: 366.11.

Example 111

Synthesis of 3-benzyl-9-methyl-4H,6H-thieno[2,3-e][1,2,4]triazolo[3,4-c][1,4]oxazepine-2-carbonitrile (Cpd. No. 110)

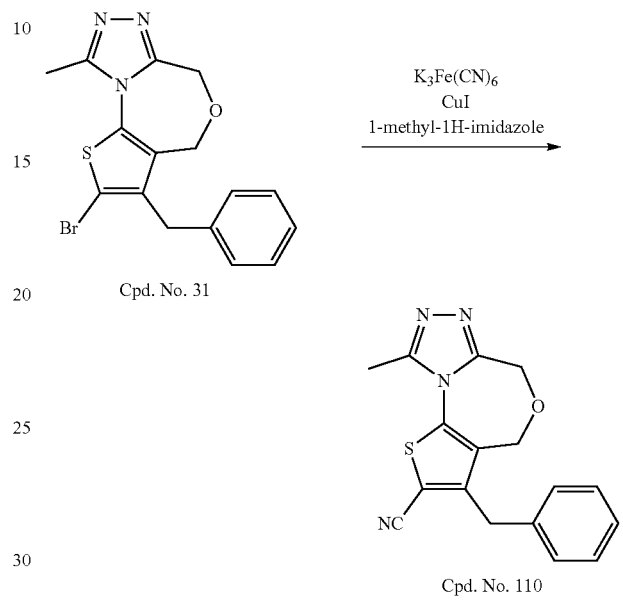

To a flask was charged with Cpd. No. 31 (20 mg, 0.05 mmol), K$_3$Fe(CN)$_6$ (7 mg), CuI (2 mg), 1-methyl-1H-imidazole (0.5 mL) under N$_2$. The reaction mixture was stirred at 140° C. for 18 h. The reaction mixture was extracted with EtOAc and the organic layer was washed with brine, dried and concentrated. The residue was purified through HPLC to afford Cpd. No. 110 (45% yield). $^1$H NMR (400 MHz, MeOD) δ 7.35 (t, J=7.3 Hz, 2H), 7.28 (d, J=7.3 Hz, 1H), 7.27-7.20 (m, 2H), 4.77 (s, 2H), 4.76 (s, 2H), 4.18 (s, 2H), 2.79 (s, 3H). ESI-MS: 323.20.

Example 112

Synthesis of 3-benzyl-9-methyl-2-(tetrahydro-2H-pyran-4-yl)-4H,6H-thieno[2,3-e][1,2,4]triazolo[3,4-c][1,4]oxazepine (Cpd. No. 97)

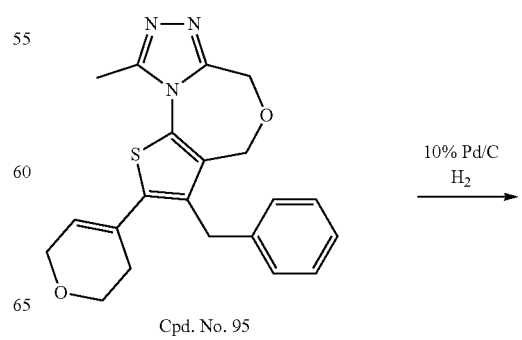

209

-continued

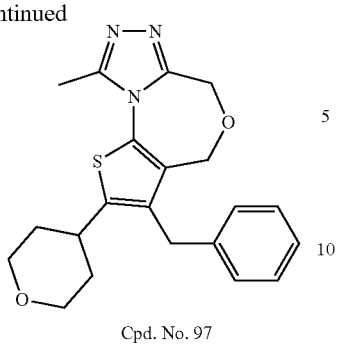

Cpd. No. 97

To a solution of Cpd. No. 95 (20 mg) in methanol (4 mL) was added 10% Pd/C (20 mg) and $H_2$ was bubbled into the solution for 20 min. The reaction was filtered and the crude was purified via HPLC to provide the TFA salt of Cpd. No. 97 (30% yield). $^1$H NMR (400 MHz, MeOD) δ 7.30 (t, J=7.4 Hz, 2H), 7.22 (t, J=7.3 Hz, 1H), 7.13 (d, J=7.1 Hz, 2H), 4.71 (s, 2H), 4.66 (s, 2H), 4.03 (s, 2H), 4.01-3.95 (m, 1H), 3.65-3.42 (m, 3H), 3.40-3.35 (m, 1H), 2.78 (s, 3H), 1.97-1.69 (m, 4H). ESI-MS: 382.09.

Example 113

Synthesis of 3-benzyl-2-isopropyl-9-methyl-4H,6H-thieno[2,3-e][1,2,4]triazolo[3,4-c][1,4]oxazepine (Cpd. No. 98)

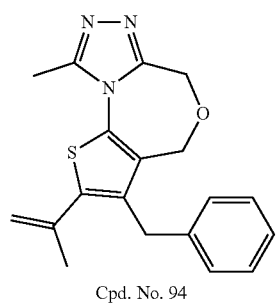

Cpd. No. 94

10% Pd/C
$H_2$

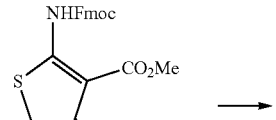

Cpd. No. 98

To a solution of Cpd. No. 94 (10 mg) in methanol (3 mL) was added 10% Pd/C (20 mg) and $H_2$ was bubbled into the solution for 20 min. The reaction was filtered and the crude was purified via HPLC to provide the TFA salt of Cpd. No. 98 (50% yield). $^1$H NMR (400 MHz, MeOD) δ 7.30 (d, J=7.4 Hz, 2H), 7.21 (t, J=7.4 Hz, 1H), 7.13 (d, J=7.1 Hz, 2H), 4.72 (s, 2H), 4.66 (s, 2H), 4.00 (s, 2H), 3.50-3.43 (m, 1H), 2.81 (s, 3H), 1.34 (d, J=6.8 Hz, 6H). ESI-MS: 340.02.

210

Example 114

Synthesis of 4-(3-benzyl-9-methyl-4H,6H-thieno[2,3-e][1,2,4]triazolo[3,4-c][1,4]oxazepin-2-yl)butan-1-ol (Cpd. No. 99)

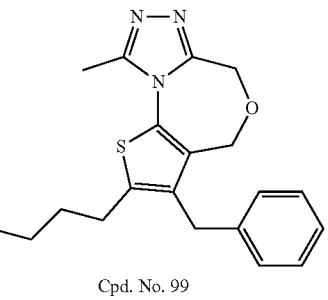

Cpd. No. 96

10% Pd/C
$H_2$

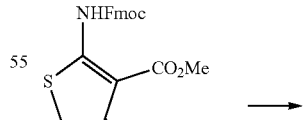

Cpd. No. 99

To a solution of Cpd. No. 96 (18 mg) in methanol (4 mL) was added 10% Pd/C (20 mg) and $H_2$ was bubbled into the solution for 20 min. The reaction was filtered and the crude was purified via HPLC to provide the TFA salt of Cpd. No. 99 (60% yield). $^1$H NMR (400 MHz, MeOD) δ 7.30 (t, J=7.4 Hz, 2H), 7.21 (t, J=7.0 Hz, 1H), 7.13 (d, J=7.6 Hz, 2H), 4.73 (s, 2H), 4.68 (s, 2H), 3.98 (s, 2H), 3.57 (t, J=6.3 Hz, 2H), 2.93 (t, J=6.3 Hz, 2H), 2.80 (s, 3H), 1.80-1.69 (m, 2H), 1.69-1.56 (m, 2H). ESI-MS: 370.11.

Example 115

Synthesis of 2-bromo-3-(4-fluorobenzyl)-9-methyl-4H,6H-thieno[2,3-e][1,2,4]triazolo[3,4-c][1,4]oxazepine (Cpd. No. 140)

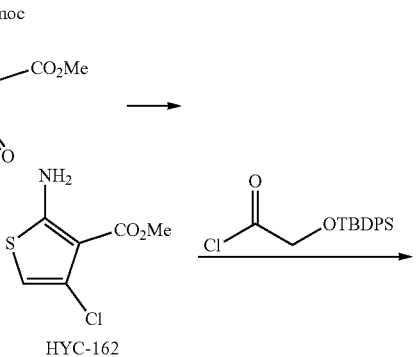

HYC-162

Example 115-A

Synthesis of methyl 2-amino-4-chlorothiophene-3-carboxylate

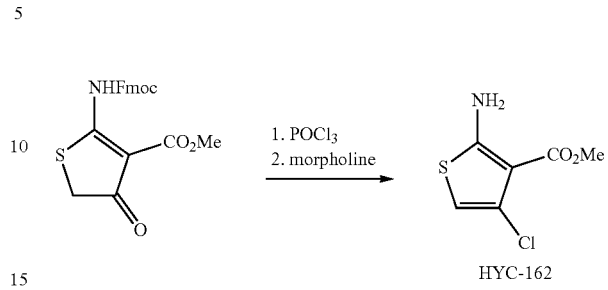

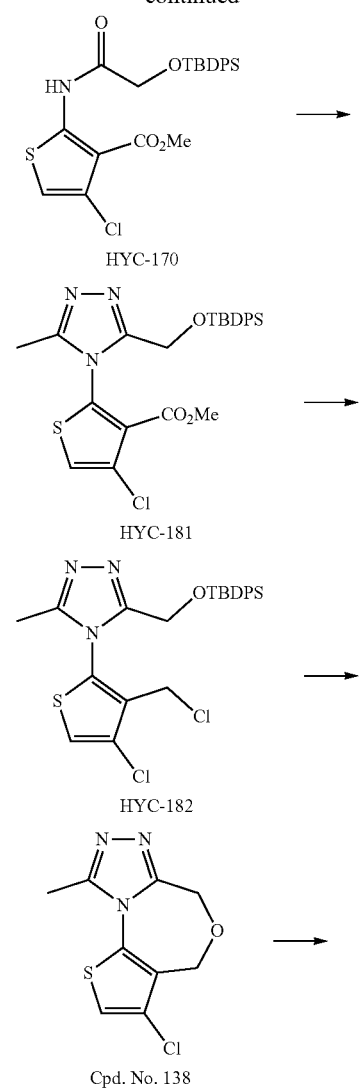

Step 1: To a suspension of methyl 2-(((((9H-fluoren-9-yl)methoxy)carbonyl)amino)-4-oxo-4,5-dihydrothiophene-3-carboxylate (36.6 g, 92 mmol) in dioxane (100 mL) was added POCl$_3$(19 mL, 184 mmol, 2 eq) and the reaction mixture was heated to reflux for 1 hour. The reaction mixture was cooled and poured into the mixture of ice-water. The reaction mixture was extracted with EtOAc (3×200 mL). The combined organic layers were washed with brine, dried over Na$_2$SO$_4$ and concentrated. The crude was purified on silica gel (pure DCM to DCM/EtOAc 15:1) to give methyl 2-(((((9H-fluoren-9-yl)methoxy)carbonyl)amino)-4-chlorothiophene-3-carboxylate as white solid. (8 g, 22%).

Step 2: To a solution of methyl 2-(((((9H-fluoren-9-yl)methoxy)carbonyl)amino)-4-chlorothiophene-3-carboxylate (5.6 g, 13.5 mmol) in DCM (11.8 mL) was added morpholine (11.8 mL, 135 mmol) and the reaction mixture was stirred overnight. The reaction mixture was filtered and rinsed with small amount of Et$_2$O. The filtrate was evaporated under vacuum and the residue was chromatographed on silica gel (pure DCM) to afford title compound as a white solid (2.6 g, 99%). $^1$H NMR (400 MHz, CDCl$_3$) δ 6.22 (s, 2H), 6.12 (s, 1H), 3.87 (s, 3H).

Example 115-B

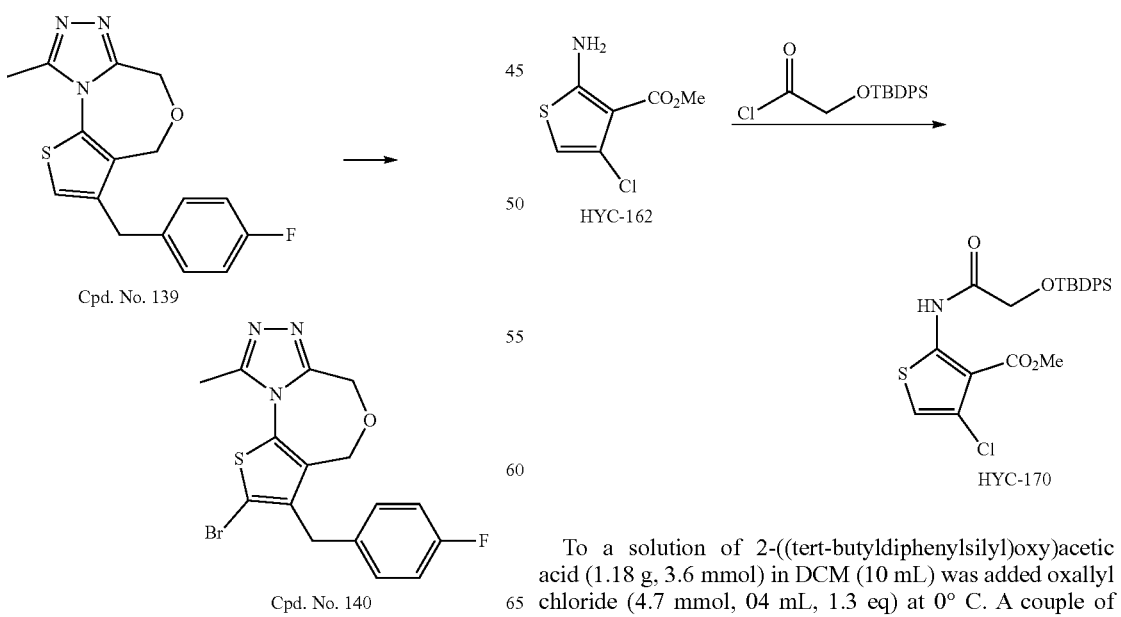

To a solution of 2-((tert-butyldiphenylsilyl)oxy)acetic acid (1.18 g, 3.6 mmol) in DCM (10 mL) was added oxallyl chloride (4.7 mmol, 04 mL, 1.3 eq) at 0° C. A couple of drops of DMF were added and the reaction mixture was allowed to warm to r.t. and stirred for 1 h. Then all the volatiles were removed under vacuum and the residue was dissolved in DCM (4 mL). This solution was added dropwise at 0° C. to a solution of methyl 2-amino-4-chlorothiophene-3-carboxylate (360 mg, 1.8 mmol) and DIPEA (0.94 mL, 5.4 mmol) in DCM (8 mL). The reaction mixture was allowed to warm to r.t. and stirred for 1 h prior to being quenched with saturated NaHCO₃ and extracted with DCM (3×20 mL). The combined organic layer was washed with water and then, dried (Na₂SO₄), filtered and then concentrated. The oil was chromatographed on silica gel (1:8 ethyl acetate/hexanes) to give title compound as an oil: (0.6 g, 68%).

Example 115-C

Synthesis of methyl 2-(3-(((tert-butyldiphenylsilyl)oxy)methyl)-5-methyl-4H-1,2,4-triazol-4-yl)-4-chlorothiophene-3-carboxylate Step 4: All volatiles were removed under vacuum and the residue was dissolved in AcOH (2 mL). The solution was heated at reflux for 1 h prior to the removal of the solvent under vacuum. The residue was taken up in EtOAc and washed with 2 M Na₂CO₃. The organic layer was washed with brine, dried and concentrated. The residue was chromatographed on silica gel (ethyl acetate) to give title compound as an oil: (360 mg, 72%.). $^1$H NMR (400 MHz, CDCl₃) δ 7.64-7.36 (m, 10H), 7.33 (s, 1H), 4.78 (d, J=12.8 Hz, 1H), 4.62 (d, J=12.8 Hz, 1H), 3.64 (s, 3H), 2.33 (s, 3H), 0.96 (s, 9H).

Example 115-D

Synthesis of 3-(((tert-butyldiphenylsilyl)oxy)methyl)-4-(4-chloro-3-(chloromethyl)thiophen-2-yl)-5-methyl-4H-1,2,4-triazole

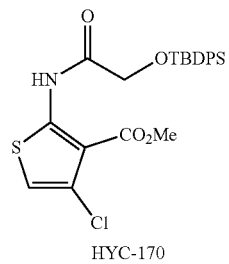
HYC-170

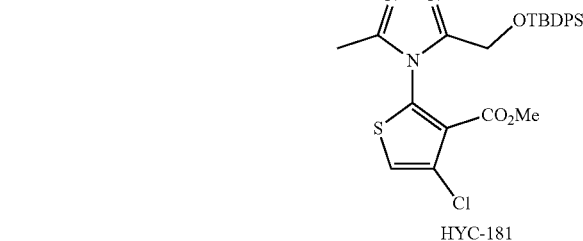
HYC-181

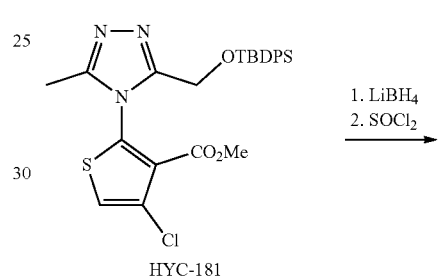
HYC-181

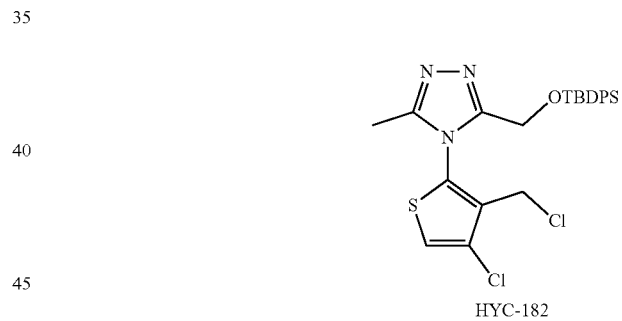
HYC-182

Step 1: To a solution of methyl 2-(2-((tert-butyldiphenylsilyl)oxy)acetamido)-4-chlorothiophene-3-carboxylate (0.6 g, 1.23 mmol) in dioxane (7 mL) was added Lawesson's reagent (299 mg, 0.74 mmol, 0.6 eq) and the reaction mixture was heated at reflux for 8 h. The volatiles were removed under vacuum and the residue was chromatographed on silica gel (1:16 ethyl acetate/hexanes) to give title compound as an oil: (480 mg, 80%).

Step 2: To a solution of methyl 2-(2-((tert-butyldiphenylsilyl)oxy)ethanethioamido)-4-chlorothiophene-3-carboxylate (480 mg, 0.95 mmol) in THF (4 mL) was added hydrazine monohydrate (0.1 mL, 2 mmol, 2 eq) at 0° C. and the reaction mixture was allowed to warm to r.t. The reaction mixture was stirred for 1 h prior to being concentrated in vacuum. The residue was taken up in DCM and washed with water and brine. The organic layer was separated, dried and concentrated.

Step 3: The residue was taken up in ethanol (4 mL) and triethyl orthoacetate (0.52 mL, 2.85 mmol, 3 eq) was added. The reaction mixture was heated at reflux for 12 h.

To a solution of methyl 2-(3-(((tert-butyldiphenylsilyl)oxy)methyl)-5-methyl-4H-1,2,4-triazol-4-yl)-4-chlorothiophene-3-carboxylate (360 mg, 0.68 mmol) in THF (10 mL) at 0° C. was added a solution of LiBH₄(2 M in THF, 1 mL, 2 mmol). MeOH (1 mL) was added and the reaction mixture was allowed to warm to r.t. and stirred for 12 h. All volatiles were removed and the residue was taken up in EtOAc. The organic layer was washed with water and brine prior to being dried and concentrated. The residue was dissolved in DCM and cooled to 0° C. Thionyl chloride (0.1 mL, 1.4 mmol, 2 eq) was added and the reaction mixture was allowed to warm to r.t. After 1 h, all the volatiles were removed and the residue was taken up in EtOAc and washed with 2 M Na₂CO₃. The organic layer was washed with brine, dried and concentrated. The residue was chromatographed on silica gel (ethyl acetate) to give title compound as an oil: (350 mg, 99%). $^1$H NMR (400 MHz, CDCl₃) δ 7.58-7.33 (m, 10H), 4.73 (d, J=12.6 Hz, 1H), 4.67 (d, J=12.6 Hz, 1H), 4.22 (s, 2H), 2.40 (s, 3H), 0.99 (s, 9H).

Example 115-E

Synthesis of 3-chloro-9-methyl-4H,6H-thieno[2,3-e][1,2,4]triazolo[3,4-c][1,4]oxazepine (Cpd. No. 138)

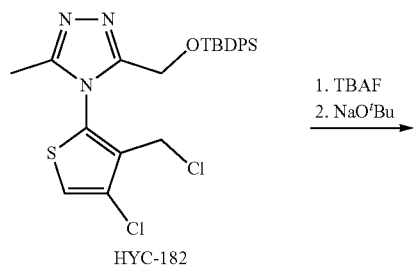

HYC-182

1. TBAF
2. NaO$^t$Bu

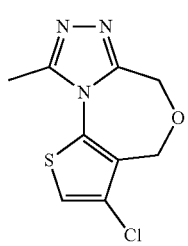

Cpd. No. 138

To a solution of 3-(((tert-butyldiphenylsilyl)oxy)methyl)-4-(4-chloro-3-(chloromethyl)thiophen-2-yl)-5-methyl-4H-1,2,4-triazole (350 mg, 0.68 mmol) in THF at 0° C. was added a solution of TBAF (0.7 mL, 0.7 mmol, 1M in THF). The solution was stirred for 1 h prior to being added to a solution of NaO$^t$Bu (134 mg, 1.4 mmol, 2 eq) in tBuOH (6 mL) at 80° C. The reaction mixture was stirred for 5 min prior to the removal of the solvent under vacuum. The residue was taken up in EtOAc and water. The organic layer was washed with brine, dried and concentrated. The residue was purified through HPLC to afford Cpd. No. 138 as a solid (100 mg, 61%). ESI: M+H 242.17.

Example 115-F

Synthesis of 3-(4-fluorobenzyl)-9-methyl-4H,6H-thieno[2,3-e][1,2,4]triazolo[3,4-c][1,4]oxazepine (Cpd. No. 139)

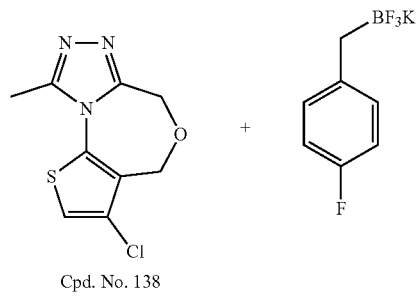

Cpd. No. 138

Pd(allyl)Cl$_2$
$^S$SPhos
Na$_2$CO$_3$

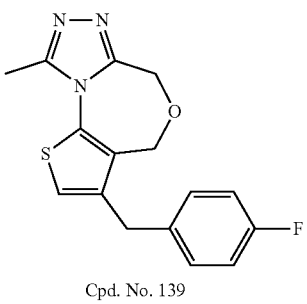

Cpd. No. 139

To a Shlenk tube was charged with 3-chloro-9-methyl-4H,6H-thieno[2,3-e][1,2,4]triazolo[3,4-c][1,4]oxazepine (100 mg, 0.4 mmol), potassium 4-fluorobenzyltrifluoroborate (250 mg, 1.1 mmol), [Pd(allyl)Cl]$_2$ (22 mg, 0.058 mmol), $^S$Sphos (60 mg, 0.12 mmol), toluene (5 mL) and Na$_2$CO$_3$ solution (2 M, 5 mL) under N$_2$. The tube was sealed and heated at 100° C. oil bath for 4 h. The reaction mixture was extracted with EtOAc and the organic layer was washed with brine, dried and concentrated. The residue was purified through HPLC to afford Cpd. No. 139 as a solid (70 mg, 56%). ESI: M+H 316.20.

Example 115-G

Synthesis of 2-bromo-3-(4-fluorobenzyl)-9-methyl-4H,6H-thieno[2,3-e][1,2,4]triazolo[3,4-c][1,4]oxazepine (Cpd. No. 140)

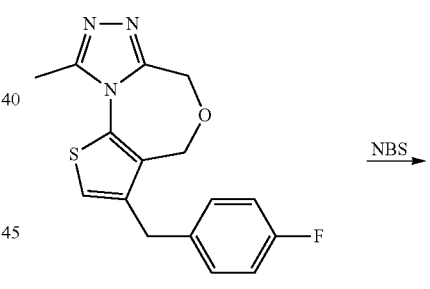

Cpd. No. 139

NBS

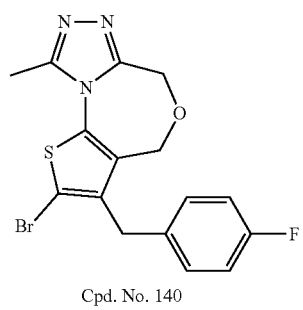

Cpd. No. 140

To a solution of 3-(4-fluorobenzyl)-9-methyl-4H,6H-thieno[2,3-e][1,2,4]triazolo[3,4-c][1,4]oxazepine (70 mg, 0.22 mmol) in AcOH (1 mL) was added NBS (39.5 mg, 1 eq). The reaction mixture was stirred for 1 h prior to being purified through HPLC to afford Cpd. No. 140 as a solid (25 mg, 29%). ESI: M+H 394.10.

Example 116

Synthesis of 3-(4-fluorobenzyl)-9-methyl-2-((1-methyl-H-pyrazol-4-yl)ethynyl)-4H,6H-thieno[2,3-e][1,2,4]triazolo[3,4-c][1,4]oxazepine (Cpd. No. 111)

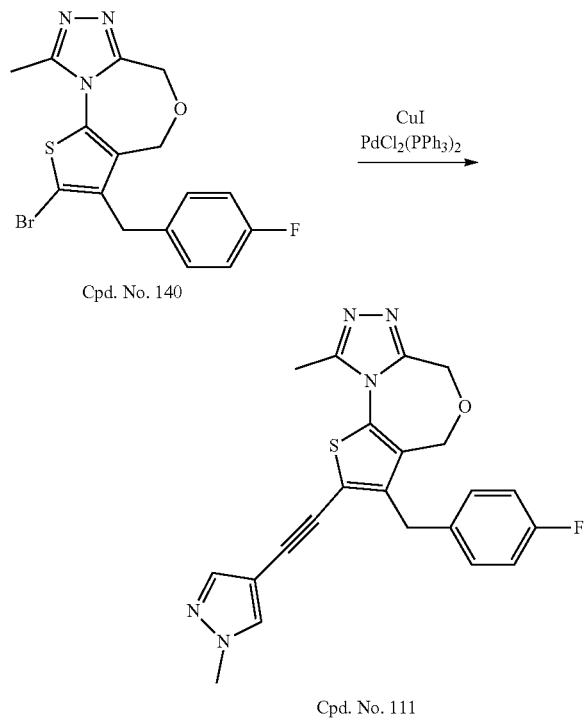

To a Shlenk tube was charged with 3-(4-fluorobenzyl-2-bromo-9-methyl-4H,6H-thieno[2,3-e][1,2,4]triazolo[3,4-c][1,4]oxazepine (10 mg, 0.03 mmol), 4-ethynyl-1-methyl-1H-pyrazole (6 mg, 0.06 mmol, 2 eq), [PdCl$_2$(PPh$_3$)$_2$] (2.1 mg), CuI (1.1 mg), THF (1 mL) and Et$_2$NH (0.5 mL) under N$_2$. The tube was sealed and heated at 70° C. oil bath for 12 h. The reaction mixture was extracted with EtOAc and the organic layer was washed with brine, dried and concentrated. The residue was purified through HPLC to afford Cpd. No. 111 as a solid (7 mg, 56%). $^1$H NMR (400 MHz, MeOD) δ 7.90 (s, 1H), 7.76-7.65 (m, 5H), 4.74 (s, 2H), 4.72 (s, 2H), 4.09 (s, 2H), 3.92 (s, 3H), 2.77 (s, 3H). ESI: M+H 420.16.

Example 117

Synthesis of (S)-3-benzyl-2-bromo-6,9-dimethyl-4H,6H-thieno[2,3-e][1,2,4]triazolo[3,4-c][1,4]oxazepine (Cpd. No. 119)

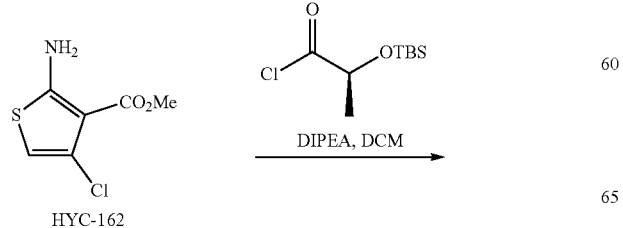

Example 117-A

Synthesis of Methyl(S)-2-(2-((tert-butyldimethylsilyl)oxy)propanamido)-4-chlorothiophene-3-carboxylate

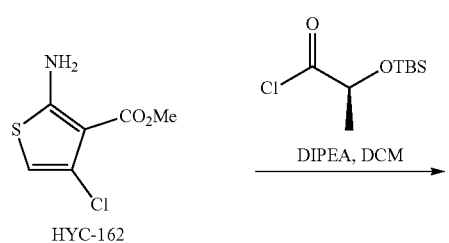

(S)-2-((tert-butyldimethylsilyl)oxy)propanoyl chloride was prepared based on the modification of the reported procedure (Organic Letters, 16(9), 2322-2325; 2014). To a solution of lithium (S)-2-hydroxypropanoate (2.88 g, 30 mmol) in DMF (30 mL) at 0° C. under $N_2$ was added TBSCl (9 g, 60 mmol) and imidazole (8.2 g, 120 mmol). The reaction mixture was allowed to warm to r.t. and stirred overnight. The reaction mixture was partitioned between hexanes (300 mL) and saturated $NaHCO_3$ solution (300 mL). The organic layer was separated, washed with brine (30 mL×5). The organic layer was dried and concentrated to provide a crude oil (9.2 g). The crude was dissolved in DCM (60 mL) and the solution was cooled to 0° C. under $N_2$. DMF (0.43 mL) was added followed by the dropwise addition of a solution of oxalyl chloride (1.3 eq, 39 mmol, 3.3 mL) in DCM (10 mL). The reaction mixture was allowed to warm to r.t. and stirred for another. All the volatiles were removed under vacuum and the residue was dissolved in DCM (10 mL). This solution was added to a solution of HYC-162 (1.92 g, 10 mmol) in DCM (90 mL) and DIPEA (7 mL, 40 mmol) at 0° C. under $N_2$. The reaction mixture was allowed to warm to r.t. and stirred for 1 h prior to being quenched with saturated $NaHCO_3$ and extracted with DCM (3×50 mL). The combined organic layer was washed with water and then, dried ($Na_2SO_4$), filtered and then concentrated The oil was chromatographed on silica gel (1:16 to 1:8 ethyl acetate/hexanes) to give title compound as an oil: (3.1 g, 82%.). $^1$H NMR (400 MHz, $CDCl_3$) δ 11.99 (s, 1H), 6.68 (s, 1H), 4.47 (q, J=6.7 Hz, 1H), 3.94 (s, 3H), 1.51 (d, J=6.7, 3H), 1.00 (s, 9H), 0.20 (s, 6H).

Example 117-B

Synthesis of Methyl (S)-2-(3-(1-((tert-butyldimethylsilyl)oxy)ethyl)-5-methyl-4H-1,2,4-triazol-4-yl)-4-chlorothiophene-3-carboxylate

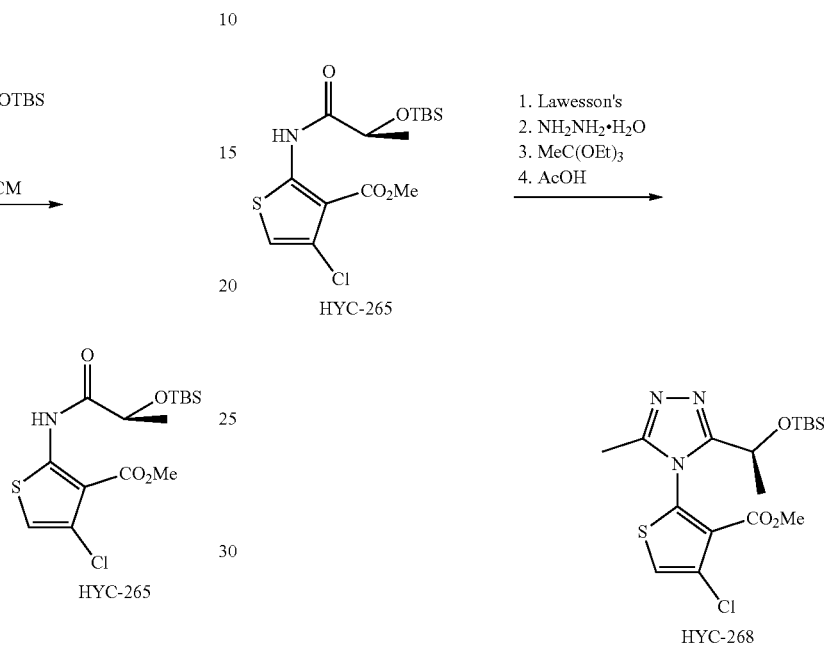

Step 1: To a solution of 6 (3 g, 8 mmol) in dioxane (20 mL) was added Lawesson's reagent (1.93 g, 4.8 mmol, 0.6 eq) and the reaction mixture was heated at reflux for 12 h. The volatiles were removed under vacuum and the residue was chromatographed on silica gel (1:16 ethyl acetate/hexanes) to Methyl (S)-2-(2-((tert-butyldimethylsilyl)oxy)propanethioamido)-4-chlorothiophene-3-carboxylate as an oil: (1.8 g, 57%).

Step 2: To a solution of above compound (3.6 g, 9.2 mmol) in THF (10 mL) was added hydrazine monohydrate (0.89 mL, 18.4 mmol, 2 eq) at 0° C. and the reaction mixture was allowed to warm to r. The reaction mixture was stirred for 1 h prior to being concentrated in vacuum. The residue was taken up in DCM and washed with water and brine. The organic layer was separated, dried and concentrated.

Step 3: The residue was taken up in ethanol (10 mL) and triethyl orthoacetate (5 mL, 27.6 mmol, 3 eq) was added. The reaction mixture was heated at reflux for 1 h.

Step 4: All volatiles were removed under vacuum and the residue was dissolved in AcOH (10 mL). The solution was heated at reflux for 1 h prior to the removal of the solvent under vacuum. The residue was chromatographed on silica gel (1:2 ethyl acetate/hexanes followed by ethyl acetate/triethylamine 25:1) to give title compound as a mixture of non-consequential diastereoisomers. (1.8 g, 47%). $^1$H NMR (400 MHz, $CDCl_3$) Major isomer: δ 7.33 (s, 1H), 5.20 (q, J=6.7 Hz, 1H), 3.67 (s, 3H), 2.22 (s, 3H), 1.29 (d, J=6.7 Hz, 3H), 0.81 (s, 6H), 0.04 (s, 3H), −0.05 (s, 3H); Minor isomer: 7.31 (s, 1H), 5.07 (q, J=6.7 Hz, 1H), 3.66 (s, 3H), 2.23 (d, J=1.2 Hz, 3H), 1.57 (d, J=6.7 Hz, 3H), 0.75 (s, 9H), 0.02 (s, 3H), −0.11 (s, 3H).

Example 117-C

Synthesis of (S)-3-(1-((tert-butyldimethylsilyl)oxy)ethyl)-4-(4-chloro-3-(chloromethyl)thiophen-2-yl)-5-methyl-4H-1,2,4-triazole

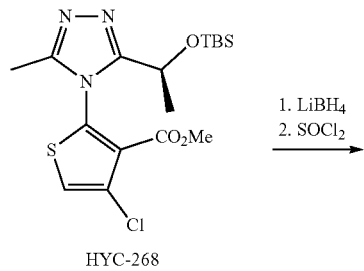

HYC-268

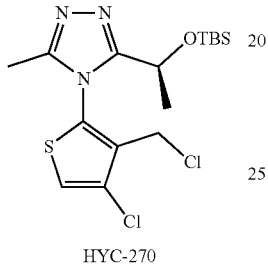

HYC-270

To a solution of HYC-268 (1.8 g, 4.3 mmol) in THF (30 mL) at 0° C. was added a solution of LiBH$_4$(2 M in THF, 3.3 mL, 6.5 mmol, 1.5 eq). MeOH (3 mL) was added and the reaction mixture was allowed to warm to r.t. and stirred for 12 h. All volatiles were removed and the residue was taken up in EtOAc. The organic layer was washed with water and brine prior to being dried and concentrated. The residue was dissolved in DCM (20 mL) and cooled to 0° C. Thionyl chloride (0.94 mL, 12.9 mmol, 3 eq) was added and the reaction mixture was allowed to warm to r.t. After 1 h, all the volatiles were removed and the residue was taken up in EtOAc and washed with 1 M Na$_2$CO$_3$. The organic layer was washed with brine, dried and concentrated. The residue was chromatographed on silica gel (ethyl acetate/triethylamine 25:1) to give title compound as a mixture of diastereoisomers (1.34 g, 75%).

Example 117-D

Synthesis of (S)-3-chloro-6,9-dimethyl-4H,6H-thieno[2,3-e][1,2,4]triazolo[3,4-c][1,4]oxazepine (Cpd. No. 141)

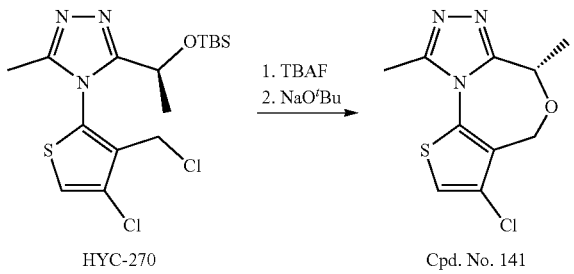

To a solution of HYC-270 (1.34 g, 3.3 mmol) in THF (10 mL) at 0° C. was added a solution of TBAF (3.6 mL, 3.6 mmol, 1M in THF). The solution was stirred for 1 h prior to being added to a hot solution of NaO$^t$Bu (634 mg, 6.6 mmol, 2 eq) in $^t$BuOH (40 mL) at 80° C. The reaction mixture was stirred for 5 min prior to the removal of the solvent under vacuum. The residue was taken up in EtOAc and water. The organic layer was washed with brine, dried and concentrated. The residue was purified through HPLC to afford TFA salt of Cpd. No. 141) (575 mg, 52%). $^1$H NMR (400 MHz, MeOD) δ 7.52 (s, 1H), 5.05 (d, J=15.8 Hz, 2H), 4.89 (d, J=15.8 Hz, 2H), 4.79 (q, J=6.7 Hz, 1H), 2.79 (s, 3H), 1.73 (d, J=6.6 Hz, 3H). ESI: M+H 256.2.

Example 117-E

Synthesis of (S)-3-benzyl-6,9-dimethyl-4H,6H-thieno[2,3-e][1,2,4]triazolo[3,4-c][1,4]oxazepine (Cpd. No. 118)

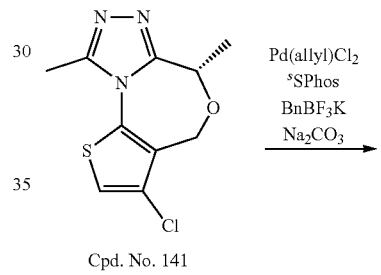

Cpd. No. 141

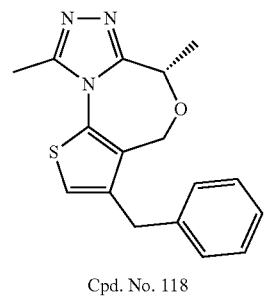

Cpd. No. 118

To a flask under N$_2$ was charged with TFA salt of (S)-3-chloro-6,9-dimethyl-4H,6H-thieno[2,3-e][1,2,4]triazolo[3,4-c][1,4]oxazepine (152 mg, 0.4 mmol), potassium benzyltrifluoroborate (158 mg, 0.8 mmol, 2 eq), [Pd(allyl)Cl]$_2$ (15 mg, 0.04 mmol), $^S$Sphos (41 mg, 0.08 mmol), toluene (5 mL) and Na$_2$CO$_3$ solution (2 M, 2 mL), water (2 mL). The reaction mixture was heated at 100-110° C. oil bath for 2 h. The reaction mixture was extracted with EtOAc and the organic layer was washed with brine, dried and concentrated. The residue was purified through HPLC to afford Cpd. No. 118 as a solid (150 mg, 88%). ESI: M+H 312.08.

Example 117-F

Synthesis of (S)-3-benzyl-2-bromo-6,9-dimethyl-4H,6H-thieno[2,3-e][1,2,4]triazolo[3,4-c][1,4]oxazepine (Cpd. No. 119)

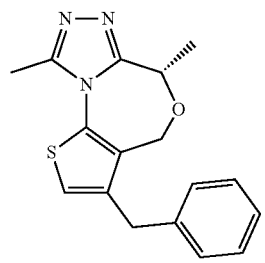

Cpd. No. 118

NBS
AcOH
→

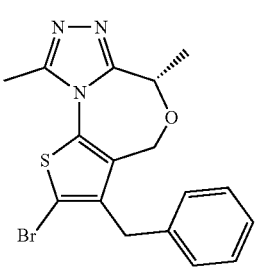

Cpd. No. 119

To a solution TFA salt of (S)-3-benzyl-6,9-dimethyl-4H,6H-thieno[2,3-e][1,2,4]triazolo[3,4-c][1,4]oxazepine (240 mg, 0.57 mmol) in AcOH (4 mL) was added NBS (101 mg, 0.57 mmol, 1 eq). The reaction mixture was stirred for 1 h prior to the addition of water (2 mL) and methanol (2 mL). All volatiles were removed under vacuum and the residue was purified by HPLC to afford Cpd. No. 119 as a solid (240 ng, 84%). ESI: M+H 390.03.

Example 118

Synthesis of (S)-4-(3-benzyl-6,9-dimethyl-4H,6H-thieno[2,3-e][1,2,4]triazolo[3,4-c][1,4]oxazepin-2-yl)but-3-yn-1-ol (Cpd. No. 113)

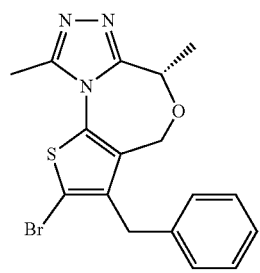

Cpd. No. 119

+

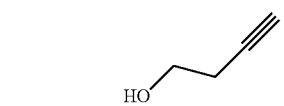

CuI
PdCl$_2$(PPh$_3$)$_2$
→

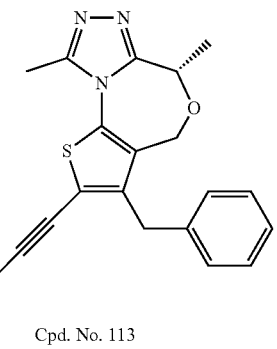

Cpd. No. 113

To a Shlenk tube was charged with (S)-3-benzyl-2-bromo-6,9-dimethyl-4H,6H-thieno[2,3-e][1,2,4]triazolo[3,4-c][1,4]oxazepine (36 mg, 0.09 mmol), but-3-yn-1-ol (14 mg, 0.2 mmol, 2 eq), [PdCl$_2$(PPh$_3$)$_2$](8.4 mg, 0.01 mmol), CuI (4.6 mg, 0.02 mmol), THF (1 mL) and Et$_3$N (1 mL) under N$_2$. The tube was sealed and heated at 70° C. oil bath for 12 h. The reaction mixture was extracted with EtOAc and the organic layer was washed with brine, dried and concentrated. The residue was purified through HPLC to afford Cpd. No. 113 as a solid (21 ng, 62%). $^1$H NMR (400 MHz, MeOD) δ 7.34-7.27 (m, 2H), 7.27-7.16 (m, 3H), 4.83 (d, J=15.2 Hz, 1H), 4.72-4.63 (m, 1H), 4.59 (d, J=15.3 Hz, 1H), 4.11 (d, J=15.6 Hz, 1H), 4.00 (d, J=15.5 Hz, 1H), 3.74 (t, J=6.6 Hz, 2H), 2.72 (t, J=6.5 Hz, 4H), 1.64 (d, J=5.8 Hz, 3H). ESI: M+H 312.08.

Example 119

Synthesis of(S)-3-(3-benzyl-6,9-dimethyl-4H,6H-thieno[2,3-e][1,2,4]triazolo[3,4-c][1,4]oxazepin-2-yl)-N,N-dimethylprop-2-yn-1-amine (Cpd. No. 144)

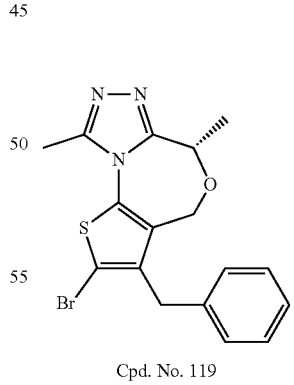

Cpd. No. 119

+

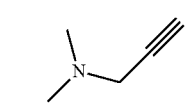

CuI
PdCl$_2$(PPh$_3$)$_2$
→

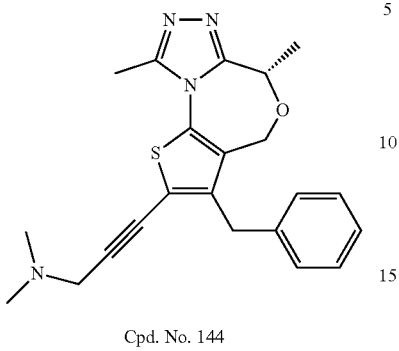

Cpd. No. 144

To a Shlenk tube was charged with (S)-3-benzyl-2-bromo-6,9-dimethyl-4H,6H-thieno[2,3-e][1,2,4]triazolo[3,4-c][1,4]oxazepine (20 mg, 0.05 mmol), N,N-dimethylprop-2-yn-1-amine (8.3 mg, 0.1 mmol, 2 eq), [PdCl$_2$(PPh$_3$)$_2$] (7 mg), CuI (3.8), THF (2 mL) and Et$_3$N (0.5 mL) under N$_2$. The tube was sealed and heated at 70° C. oil bath for 12 h. The reaction mixture was extracted with EtOAc and the organic layer was washed with brine, dried and concentrated. The residue was purified through HPLC to afford Cpd. No. 144 as a solid (90%). $^1$H NMR (400 MHz, MeOD) δ 7.32 (t, J=7.3 Hz, 2H), 7.24 (d, J=7.3 Hz, 1H), 7.20 (d, J=6.7 Hz, 2H), 4.86 (d, J=15.4 Hz, 1H), 4.69 (q, J=6.4 Hz, 1H), 4.63 (d, J=15.4 Hz, 1H), 4.42 (s, 2H), 4.18 (d, J=15.9 Hz, 1H), 4.09 (d, J=15.9 Hz, 1H), 2.96 (s, 6H), 2.80 (s, 3H), 1.65 (d, J=6.5 Hz, 3H). ESI: M+H 392.99.

Example 120

Synthesis of (S)-3-benzyl-2-(3-methoxyprop-1-yn-1-yl)-6,9-dimethyl-4H,6H-thieno[2,3-e][1,2,4]triazolo[3,4-c][1,4]oxazepine (Cpd. No. 145)

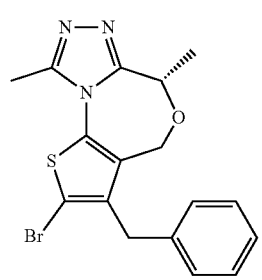

Cpd. No. 119

+

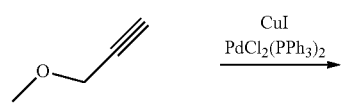

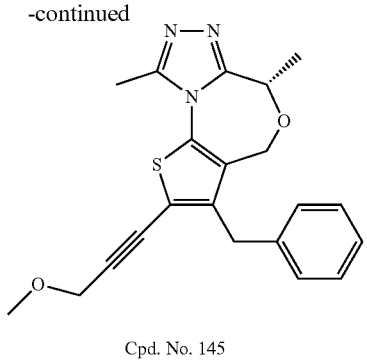

Cpd. No. 145

To a Shlenk tube was charged with (S)-3-benzyl-2-bromo-6,9-dimethyl-4H,6H-thieno[2,3-e][1,2,4]triazolo[3,4-c][1,4]oxazepine (20 mg, 0.05 mmol), 3-methoxyprop-1-yne (7 mg, 0.1 mmol, 2 eq), [PdCl$_2$(PPh$_3$)$_2$] (7 mg), CuI (3.8), THF (2 mL) and Et$_3$N (0.5 mL) under N$_2$. The tube was sealed and heated at 70° C. oil bath for 12 h. The reaction mixture was extracted with EtOAc and the organic layer was washed with brine, dried and concentrated. The residue was purified through HPLC to afford Cpd. No. 145 as a solid (75%). $^1$H NMR (400 MHz, MeOD) δ 7.35-7.27 (m, 2H), 7.26-7.15 (m, 3H), 4.84 (d, J=15.4 Hz, 1H), 4.66 (q, J=6.5 Hz, 1H), 4.60 (d, J=15.4 Hz, 1H), 4.40 (s, 2H), 4.13 (d, J=15.6 Hz, 1H), 4.03 (d, J=15.6 Hz, 1H), 3.41 (s, 3H), 2.78 (s, 3H), 1.64 (d, J=6.5 Hz, 3H). ESI: M+H 380.33.

Example 121

Synthesis of 3-benzyl-2,9-dimethyl-5,6-dihydro-4H-thieno[3,2-f][1,2,4]triazolo[4,3-a][1,4]diazepine (Cpd. No. 15)

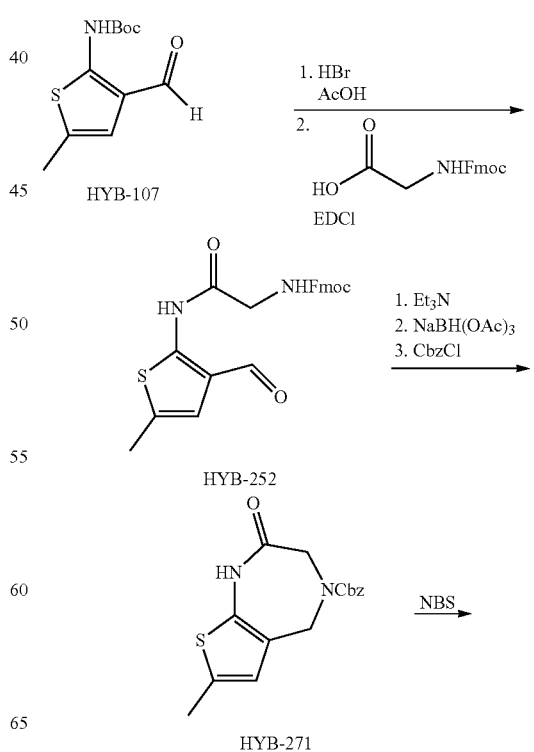

-continued

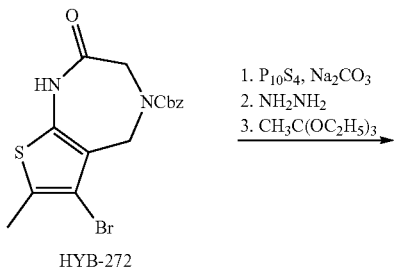
HYB-272

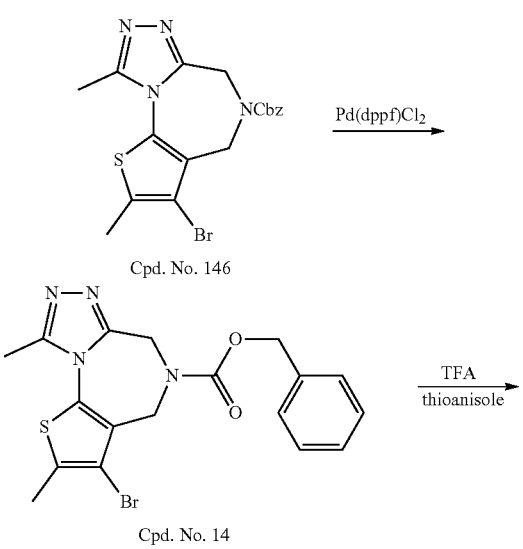
Cpd. No. 146

Cpd. No. 14

Cpd. No. 15

Example 121-A

Synthesis of (9H-fluoren-9-yl)methyl (2-((3-formyl-5-methylthiophen-2-yl)amino)-2-oxoethyl)carbamate

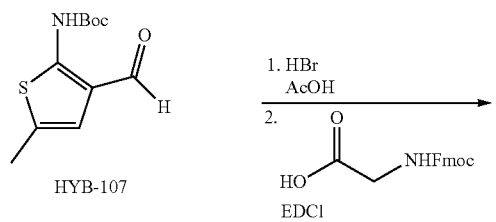
HYB-107

-continued

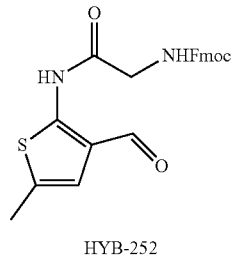
HYB-252

Step 1: A solution of 33% HBr in acetic acid (7.3 mL) was cooled to 0° C. A cold solution of HYB-107 (1 g, 4 mmol) in DCM (1 mL) was added and the reaction mixture turned red immediately. The reaction mixture was immediately poured into ice-water (50 g each) and was taken up in ethyl acetate. The organic layer was separated, washed successively with 10% NaOH (40 mL), NaHCO$_3$ (40 mL), and brine (40 mL). After drying, the organic solution was passed through a short pad of silica gel, then concentrated. The residue was dissolved in dichloromethane for next step.

Step 2: The above solution was cooled to 0° C., and (((9H-fluoren-9-yl)methoxy)carbonyl)glycine (1.5 eq) and EDCI (1.5 eq) were successively added. The reaction mixture was allowed to warm to r.t. and stirred overnight. The reaction mixture was directly poured onto a pad of silica gel. Elution (1:15 ethyl acetate/DCM) to give HYB-252 (900 mg, 53%) as a crude red solid, which was triturated in Et$_2$O to give yellow solid. $^1$H NMR (400 MHz, CDCl$_3$) δ 11.70 (s, 1H), 9.66 (s, 1H), 7.76-7.65 (m, 4H), 7.39-7.28 (m, 4H), 6.75 (s, 1H), 5.87 (s, 1H), 4.48 (d, J=6.9 Hz, 2H), 4.29-4.20 (m, 1H), 4.19-4.09 (m, 2H), 2.39 (s, 3H).

Example 121-B

Synthesis of benzyl 7-methyl-2-oxo-1,2,3,5-tetrahydro-4H-thieno[2,3-e][1,4]diazepine-4-carboxylate

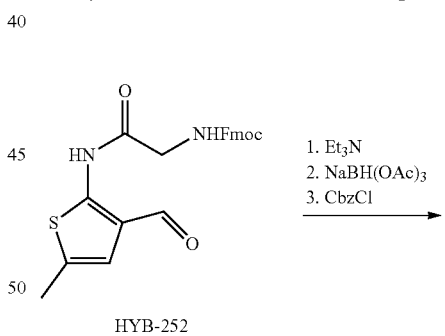
HYB-252

HYB-271

To a solution of HYB-252 (900 mg, 2.1 mmol)) in THF (20 mL) was added Et$_3$N (2 mL) and the reaction mixture was heated to 60° C. for 4 hours. The volatiles were removed under vacuum and the residue was dissolved in THF (20 mL) and NaBH(OAc)$_3$ (1.7 g, 8 mmol) was added. The reaction mixture was stirred for 4 h prior to being quenched with Na$_2$CO$_3$ solution (2 M). The reaction mixture was extracted with EtOAc, washed with saturated NaHCO$_3$ solution. The organic solvent was removed. The residue was dissolved in DCM (10 mL) and saturated NaHCO$_3$(10 mL). CbzCl (2 mmol, 0.3 mL) was added and the reaction mixture was stirred for overnight. The organic layer was separated, dried, and concentrated. The residue was purified by chromatography on silica gel (1:2 ethyl acetate/hexanes) to give HYB-271 (200 mg, 30% yield). $^1$H NMR (400 MHz, DMSO) δ 10.26 (s, 1H), 7.35 (s, 5H), 6.41 (s, 1H), 5.12 (s, 2H), 4.56 (s, 2H), 4.23-4.15 (m, 2H), 2.28 (s, 3H). ESI-MS: 339.19.

Example 121-C

Synthesis of benzyl 6-bromo-7-methyl-2-oxo-1,2,3,5-tetrahydro-4H-thieno[2,3-e][1,4]diazepine-4-carboxylate

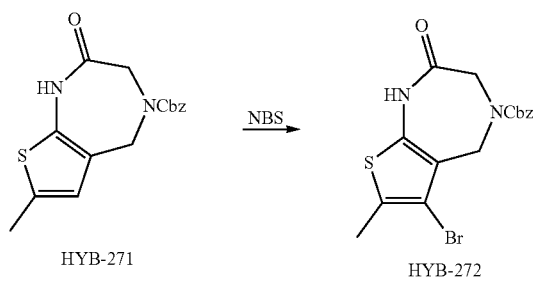 [SMILES: Cc1cc2c(s1)NC(=O)CN(C(=O)OCc1ccccc1)C2 ; "NBS" ; Cc1sc2c(c1Br)CN(C(=O)OCc1ccccc1)CC(=O)N2]

The HYB-271(100 mg, 0.3 mmol) was dissolved in a mixture of AcOH/DCM (4 mL/4 mL). NBS (50 mg, 0.9 eq) was added and the reaction was stirred for 10 minute prior to being poured into the ice/water. The mixture was extracted with EtOAc, washed with NaOH (1 M, 10 mL), NaHCO$_3$ solution (10 mL), and brine. The organic layer was separated, dried, and concentrated. The residue was purified by chromatography on silica gel (1:2 ethyl acetate/hexanes) to give HYB-272 (110 mg, 93% yield). ESI-MS: 395.03.

Example 121-D

Synthesis of benzyl 3-bromo-2,9-dimethyl-4H-thieno[3,2-f][1,2,4]triazolo[4,3-a][1,4]diazepine-5(6H)-carboxylate (Cpd. No. 146)

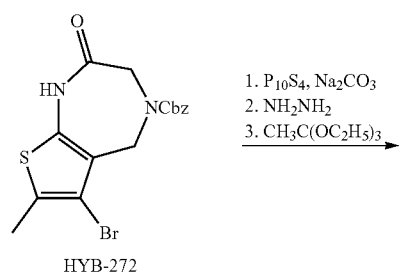

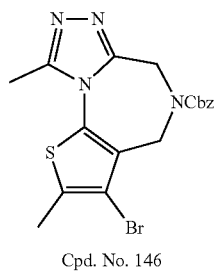

Cpd. No. 146

Step 1: To a suspension of P$_4$S$_{10}$ (124 mg, 0.56 mmol) and Na$_2$CO$_3$ (59 mg, 0.56 mmol) in 1,2-DCE (4 mL) was added HYB-272 (110 mg, 0.28 mmol). The reaction mixture was heated to 65° C. for 4 h until the reaction is completed. The reaction mixture was cooled, taken up in saturated NaHCO$_3$, and extracted with DCM. The organic layer was washed with saturated NaHCO$_3$ and brine prior to being dried.

Step 2: The solvent was removed and the residue was dissolved in THF (4 mL). NH$_2$NH$_2$.H$_2$O (27 μL, 0.56 mmol) was added and the reaction was stirred for 1 h. The volatiles were removed under vacuum and the residue was taken up in saturated NaHCO$_3$, and extracted with DCM. The organic layer was separated and dried prior to being removed.

Step 3: The residue was dissolved in ethanol (4 mL) and triethyl orthoacetate (0.9 mmol, 0.16 mL) was added. The reaction mixture was heated at 60° C. for 1 h. The volatile was removed to give a crude mixture which was purified via HPLC (30 mg, 25%). $^1$H NMR (400 MHz, CDCl$_3$) δ 7.45-7.36 (m, 5H), 5.20 (s, 2H), 4.79 (s, 2H), 4.78 (s, 2H), 2.77 (s, 3H), 2.49 (s, 3H). ESI-MS: 433.22.

Example 121-E

Synthesis of benzyl 3-benzyl-2,9-dimethyl-4H-thieno[3,2-f][1,2,4]triazolo[4,3-a][1,4]diazepine-5(6H)-carboxylate (Cpd. No. 14)

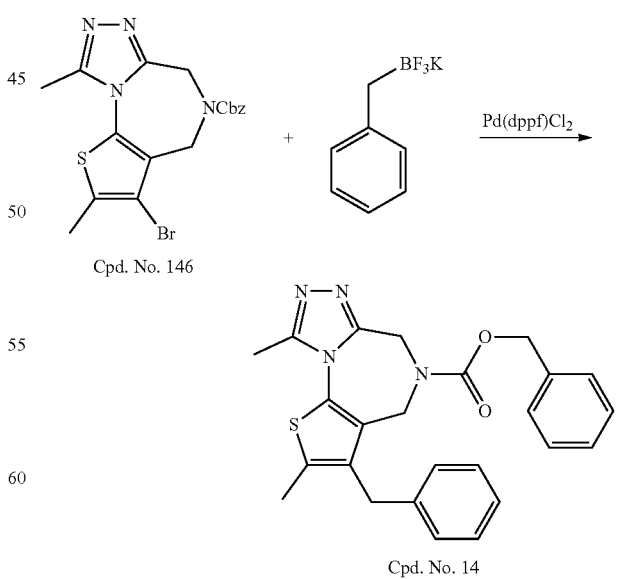

To a Shlenk tube was charged with Cpd. No. 146 (30 mg, 0.07 mmol), potassium benzyltrifluoroborate (28 mg, 2 eq), Pd(dppf)Cl₂ (8 mg), dioxane (2 mL) and Na₂CO₃ solution (2 M, 1 mL) under N₂. The tube was sealed and heated at 100° C. oil bath for 1 h. The reaction mixture was extracted with EtOAc and the organic layer was washed with brine, dried and concentrated. The residue was purified through HPLC to afford Cpd. No. 14 (84% yield). ESI-MS: 445.21

Example 121-F

Synthesis of 3-benzyl-2,9-dimethyl-5,6-dihydro-4H-thieno[3,2-f][1,2,4]triazolo[4,3-a][1,4]diazepine (Cpd. No. 15)

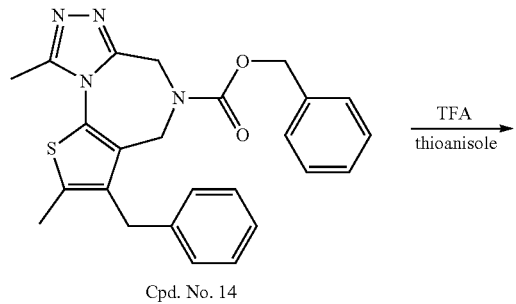

Cpd. No. 14

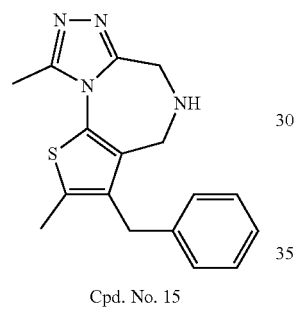

Cpd. No. 15

Cpd. No. 14 (26 mg) was dissolved in a mixture of TFA-thioanisole (2 mL-0.2 mL) and stirred at r.t. for 24 h. The volatiles was evaporated to give a crude mixture which was purified via HPLC to give Cpd. No. 15 (12 mg, 67%). ¹H NMR (400 MHz, MeOD) δ 7.30 (t, J=7.5 Hz, 2H), 7.21 (t, J=7.3 Hz, 1H), 7.13 (d, J=7.5 Hz, 2H), 4.42 (s, 2H), 4.14 (s, 2H), 4.04 (s, 2H), 2.68 (s, 3H), 2.53 (s, 3H). ESI-MS: 311.07.

Example 122

Synthesis of 3-benzyl-2,5,9-trimethyl-5,6-dihydro-4H-thieno[3,2-f][1,2,4]triazolo[4,3-a][1,4]diazepine (Cpd. No. 35)

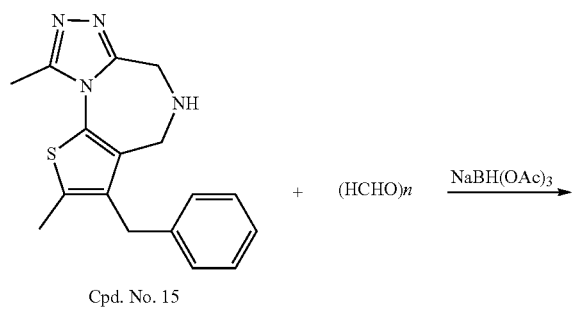

Cpd. No. 15

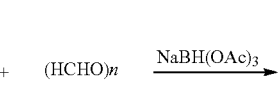

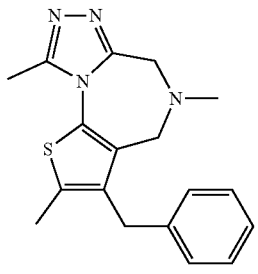

Cpd. No. 35

Cpd. No. 15 (10 mg) was dissolved in THF and formaldehyde (37% solution, 10 mg) was added. NaBH(OAc)₃ (25 mg) was added in one portion and the reaction was stirred at r.t. for 24 h prior to being quenched with Na₂CO₃ solution (2 M). The reaction mixture was extracted with EtOAc, washed with saturated NaHCO₃ solution. The organic solvent was removed. The residue was purified via HPLC to give Cpd. No. 35 (90%). ¹H NMR (400 MHz, MeOD) δ 7.32 (t, J=7.4 Hz, 2H), 7.23 (t, J=7.3 Hz, 1H), 7.16 (d, J=7.5 Hz, 2H), 4.45 (s, 2H), 4.15 (s, 2H), 4.12 (s, 2H), 2.84 (s, 3H), 2.69 (s, 3H), 2.54 (s, 3H).

Example 123

Synthesis of S)-3-benzyl-2,6,9-trimethyl-5,6-dihydro-4H-thieno[3,2-f][1,2,4]triazolo[4,3-a][1,4]diazepine (Cpd. No. 13)

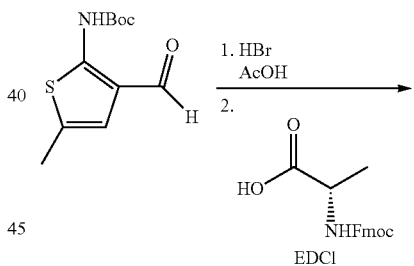

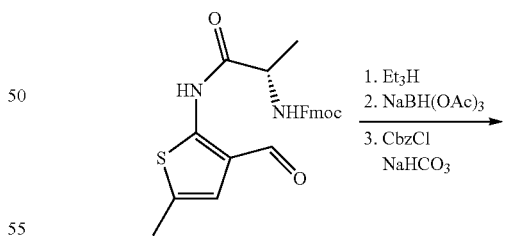

HYB-240

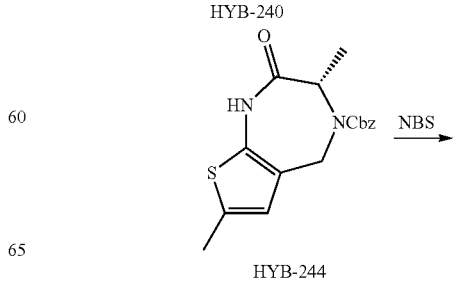

HYB-244

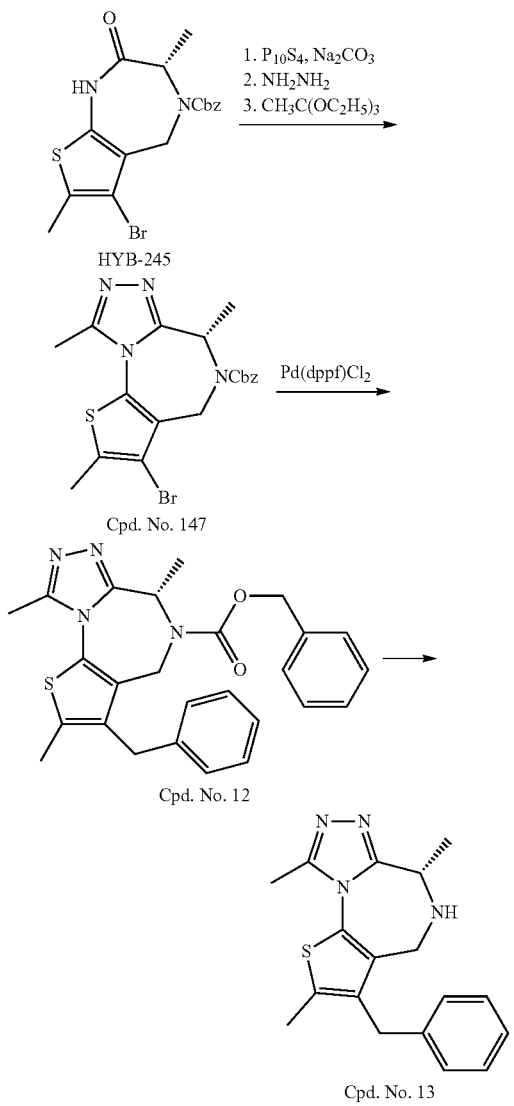

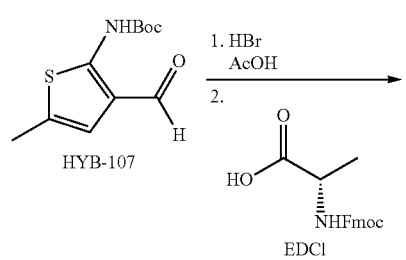

Example 123-A

Synthesis of (9H-fluoren-9-yl)methyl (S)-(1-((3-formyl-5-methylthiophen-2-yl)amino)-1-oxopropan-2-yl)carbamate

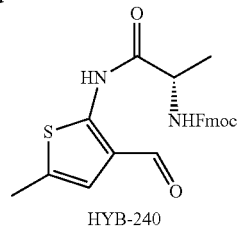

Step 1: A solution of 33% HBr in acetic acid (7.3 mL) was cooled to 0° C. A cold solution of HYB-107 (1 g, 4 mmol) in DCM (1 mL) was added and the reaction mixture turned red immediately. The reaction mixture was immediately poured into ice-water (50 g each) and was taken up in ethyl acetate. The organic layer was separated, washed successively with 10% NaOH (40 mL), NaHCO₃ (40 mL), and brine (40 mL). After drying, the organic solution was passed through a short pad of silica gel, then concentrated. The residue was dissolved in dichloromethane for next step.

Step 2: The above solution was cooled to 0° C., and (((9H-fluoren-9-yl)methoxy)carbonyl)-L-alanine (2 g, 1.5 eq) and EDCI (1.15 g, 1.5 eq) were successively added. The reaction mixture was allowed to warm to r.t. and stirred overnight. The reaction mixture was take up in EtOAc and washed with water and brine. The organic layer was separated, dried, and evaporated to give a crude mixture which was purified on silica gel (elution 1:15 ethyl acetate/DCM) to give HYB-240 (580 mg, 33%). ¹H NMR (400 MHz, CDCl₃) δ 11.78 (s, 1H), 9.75 (s, 1H), 7.97-7.33 (m, 8H), 6.83 (s, 1H), 5.38 (s, 1H), 4.58-4.48 (m, 2H), 4.46-4.38 (m, 1H), 4.35-4.26 (m, 1H), 2.44 (s, 3H), 1.57 (br, 3H).

Example 123-B

Synthesis of benzyl(S)-3,7-dimethyl-2-oxo-1,2,3,5-tetrahydro-4H-thieno[2,3-e][1,4]diazepine-4-carboxylate

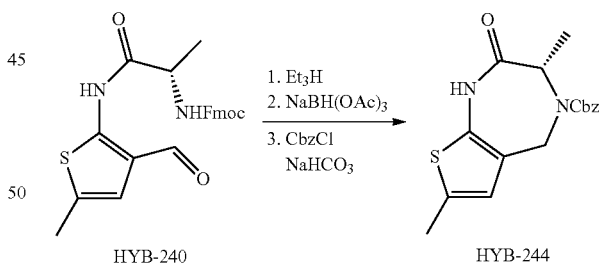

To a solution of HYB-240 (1 g, 2.3 mmol) in THF (20 mL) was added Et₃N (2 mL) and the reaction mixture was heated to 60° C. for 4 hours. Then another portion of Et₃N (2 mL) was added and heated 4 more hours. The volatiles were removed under vacuum and the residue was dissolved in THF (40 mL) and NaBH(OAc)₃ (1.95 g, 4 eq) was added. The reaction mixture was stirred for 4 h prior to being quenched with Na₂CO₃ solution (2 M). The reaction mixture was extracted with EtOAc, washed with saturated NaHCO₃ solution. The organic solvent was removed. The residue was dissolved in DCM (10 mL) and saturated NaHCO₃ (10 mL). CbzCl (4.6 mmol, 0.65 mL) was added and the reaction mixture was stirred for overnight. The organic layer was separated, dried, and concentrated. The residue was purified by chromatography on silica gel (1:2 ethyl acetate/hexanes) to give HYB-244 (500 mg, 65% yield). $^1$H NMR (400 MHz, CDCl$_3$) δ 8.46 (s, 1H), 7.67-7.30 (m, 5H), 6.30 (s, 1H), 5.20 (s, 2H), 5.02-4.69 (m, 2H), 4.44 (d, J=17.2 Hz, 1H), 2.35 (s, 3H), 1.54 (d, J=6.8 Hz, 3H). ESI-MS: 331.12.

Example 123-C

Synthesis of benzyl(S)-6-bromo-3,7-dimethyl-2-oxo-1,2,3,5-tetrahydro-4H-thieno[2,3-e][1,4]diazepine-4-carboxylate

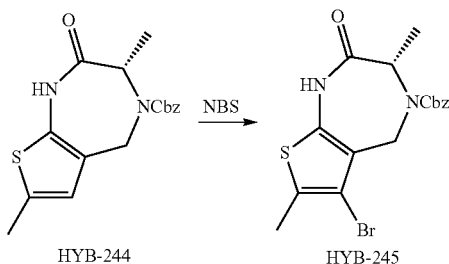

HYB-244 (500 mg, 1.5 mmol) was dissolved in AcOH (6 mL). NBS (269 mg, 1.5 mmol) was added and the reaction mixture was stirred for 10 minute prior to being poured into the ice/water. The mixture was extracted with EtOAc, washed with NaOH (1 M, 10 mL), NaHCO$_3$ solution (10 mL), and brine. The organic layer was separated, dried, and concentrated. The residue was purified by chromatography on silica gel (1:2 ethyl acetate/hexanes) to give HYB-245 (394 mg, 64% yield). $^1$H NMR (400 MHz, CDCl$_3$) δ 7.49-7.32 (m, 5H), 5.20 (s, 2H), 4.93 (d, J=18.0 Hz, 1H), 4.78-4.70 (m, 1H), 4.37 (d, J=17.5 Hz, 1H), 2.31 (s, 3H), 1.55 (d, J=6.1 Hz, 3H). (HPLC: 5.2 min, ESI-MS: 409.02).

Example 123-D

Synthesis of benzyl (S)-3-bromo-2,6,9-trimethyl-4H-thieno[3,2-f][1,2,4]triazolo[4,3-a][1,4]diazepine-5(6H)-carboxylate (Cpd. No. 147)

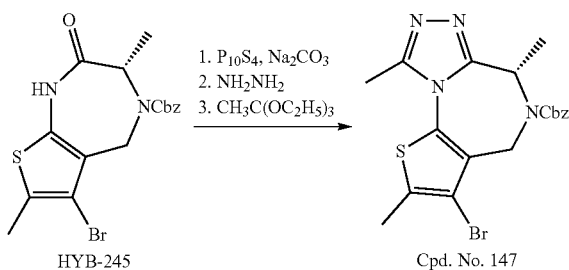

Step 1: To a suspension of P$_4$S$_{10}$ (444 mg, 2 mmol) and Na$_2$CO$_3$ (212 mg, 2 mmol) in 1,2-DCE (10 mL) was added HYB-245 (394 mg, 0.95 mmol). The reaction mixture was heated to 65° C. for 4 h until the reaction is completed. The reaction mixture was cooled, taken up in saturated NaHCO$_3$, and extracted with DCM. The organic layer was washed with saturated NaHCO$_3$ and brine prior to being dried.

Step 2: The solvent was removed and the residue was dissolved in THF (4 mL). NH$_2$NH$_2$—H$_2$O (0.1 mL, 2 mmol) was added and the reaction was stirred for 1 h. The volatiles were removed under vacuum and the residue was taken up in saturated NaHCO$_3$, and extracted with DCM. The organic layer was separated and dried prior to being removed.

Step 3: The residue was dissolved in ethanol (4 mL) and triethyl orthoacetate (3 mmol, 0.55 mL) was added. The reaction mixture was heated at 60° C. for 1 h. The volatile was removed to give a crude mixture which was purified via HPLC to give Cpd. No. 147 (270 mg, 60%). $^1$H NMR (400 MHz, CDCl$_3$) δ 7.51-7.33 (m, 5H), 5.82-5.76 (m, 1H), 5.21 (s, 2H), 5.06 (d, J=15.4 Hz, 1H), 4.24 (br, 1H), 2.65 (s, 3H), 2.49 (s, 3H), 1.27 (d, J=7.0 Hz, 3H). ESI-MS: 447.10.

Example 123-E

Synthesis of benzyl (S)-3-benzyl-2,6,9-trimethyl-4H-thieno[3,2-f][1,2,4]triazolo[4,3-a][1,4]diazepine-5(6H)-carboxylate (Cpd. No. 12)

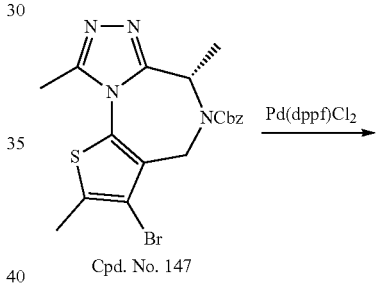

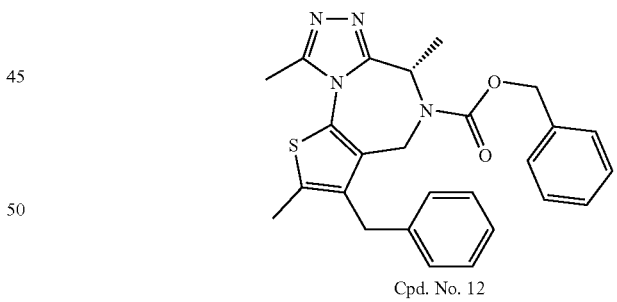

To a Shlenk tube was charged with Cpd. No. 147 (270 mg, 0.6 mmol), potassium benzyltrifluoroborate (238 mg, 2 eq), Pd(dppf)Cl$_2$ (49 mg), dioxane (4 mL) and Na$_2$CO$_3$ solution (2 M, 1 mL) under N$_2$. The tube was sealed and heated at 100° C. oil bath for 1 h. The reaction mixture was extracted with EtOAc and the organic layer was washed with brine, dried and concentrated. The residue was purified through HPLC to afford Cpd. No. 12 (73% yield). $^1$H NMR (400 MHz, MeOD) δ 7.42-7.32 (m, 5H), 7.21-7.12 (m, 4H), 6.97 (br,s, 1H), 5.56 (br,s, 1H), 5.22-4.95 (m, 3H), 4.02-3.90 (m, 2H), 3.88 (d, J=15.0 Hz, 1H), 2.67 (s, 3H), 2.53 (s, 3H), 1.12 (br,s, 3H). ESI-MS: 459.20.

Example 123-F

Synthesis of (S)-3-benzyl-2,6,9-trimethyl-5,6-di-hydro-4H-thieno[3,2-f][1,2,4]triazolo[4,3-a][1,4]diazepine (Cpd. No. 13)

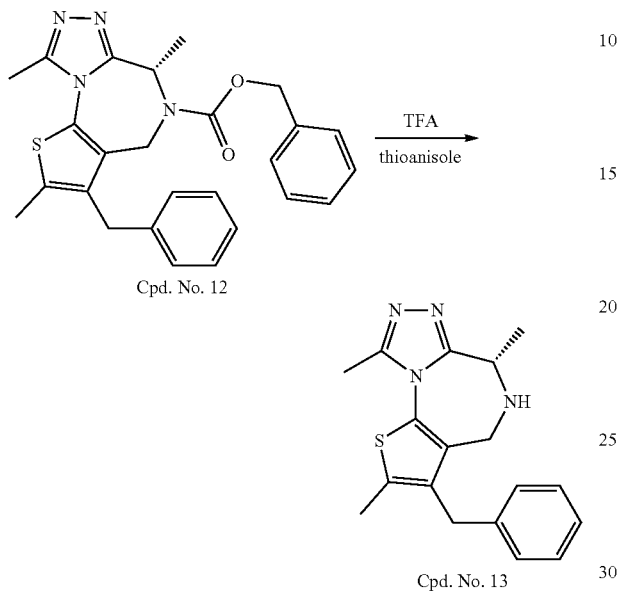

Cpd. No. 12 (50 mg) was dissolved in a mixture of TFA-thioanisole (2 mL-0.2 mL) and stirred at r.t. for 24 h. The volatiles was evaporated to give a crude mixture which was purified via HPLC to give Cpd. No. 13. (25 mg, 77%). $^1$H NMR (400 MHz, MeOD) δ 7.30 (t, J=6.8 Hz, 2H), 7.22 (t, J=7.4 Hz, 1H), 7.13 (d, J=7.7 Hz, 2H), 4.44-4.36 (m, 1H), 4.21 (t, J=14.3 Hz, 2H), 4.04 (d, J=16.4 Hz, 1H), 3.82 (d, J=14.4 Hz, 1H), 2.68 (s, 3H), 2.52 (s, 3H), 1.85 (d, J=6.9 Hz, 3H). ESI-MS: 325.11.

Example 124

Synthesis of benzyl (R)-3-benzyl-2,6,9-trimethyl-4H-thieno[3,2-f][1,2,4]triazolo[4,3-a][1,4]diazepine-5(6H)-carboxylate (Cpd. No. 16)

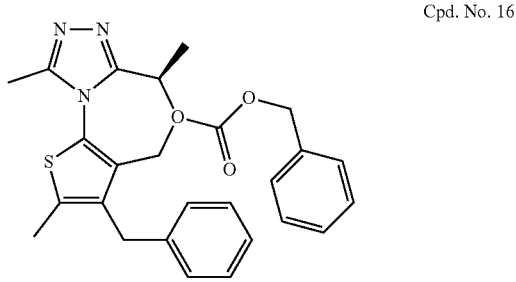

Cpd. No. 16 was synthesized following the same synthetic procedures as compound Cpd. No. 12 except for starting from chiral (((9H-fluoren-9-yl)methoxy)carbonyl)-D-alanine. ESI-MS: 459.11.

Example 125

Synthesis of (R)-3-benzyl-2,6,9-trimethyl-5,6-di-hydro-4H-thieno[3,2-f][1,2,4]triazolo[4,3-a][1,4]diazepine (Cpd. No. 17)

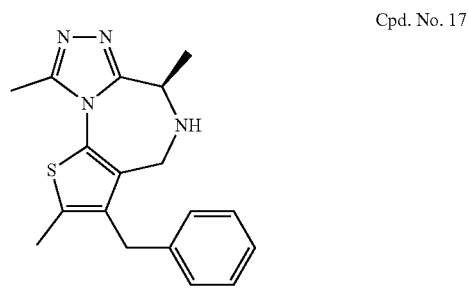 [SMILES: Cc1sc2c(c1Cc1ccccc1)CN[C@H](C)c1nnc(C)n1-2]

Cpd. No. 17 was synthesized following the same synthetic procedure as compound Cpd. No. 13. ESI-MS: 325.10.

Example 126

Synthesis of ethyl (S)-3-benzyl-2,6,9-trimethyl-4H-thieno[3,2-f][1,2,4]triazolo[4,3-a][1,4]diazepine-5(6H)-carboxylate (Cpd. No. 18)

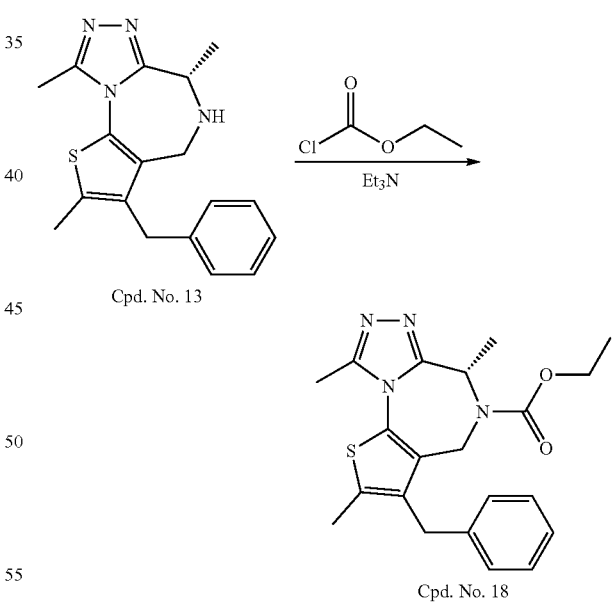

To a solution of Cpd. No. 13 (14 mg, 0.043 mmol) in DCM (1 mL) at 0° C. was added Et$_3$N (0.1 mL) and ethyl chloroformate (0.05 mL). The reaction mixture was extracted with EtOAc and the organic layer was washed with brine, dried and concentrated. The residue was purified through HPLC to afford Cpd. No. 18 (76% yield). $^1$H NMR (400 MHz, CDCl$_3$) δ 7.02-7.35 (m, 5H), 5.69 (br, 1H), 4.84 (br, 1H), 4.10 (br, 2H), 4.01 (s, 2H), 3.96 (br, 1H), 2.78 (s, 3H), 2.53 (s, 3H), 1.25 (s, 3H), 1.16 (d, J=6.7 Hz, 3H).

Example 127

Synthesis of (S)-1-(3-benzyl-2,6,9-trimethyl-4H-thieno[3,2-f][1,2,4]triazolo[4,3-a][1,4]diazepin-5(6H)-yl)propan-1-one (Cpd. No. 19)

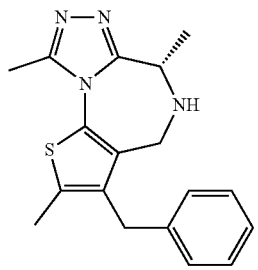

Cpd. No. 13

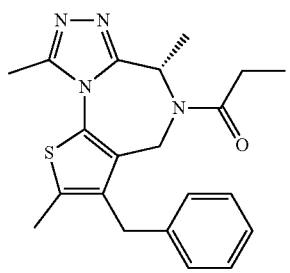

Cpd. No. 19

To a solution of Cpd. No. 13 (30 mg) in DCM (1 mL) at 0° C. was added Et$_3$N (0.1 mL) and propionic anhydride (0.05 mL). The reaction mixture was extracted with EtOAc and the organic layer was washed with brine, dried and concentrated. The residue was purified through HPLC to afford Cpd. No. 19 (90% yield). $^1$H NMR (400 MHz, MeOD) δ 7.35-7.08 (m, 5H), 5.88 (q, J=7.2 Hz, 1H), 4.59 (d, J=15.0 Hz, 1H), 4.19 (d, J=17.1 Hz, 1H), 4.10 (d, J=17.0 Hz, 1H), 3.98 (d, J=15.4 Hz, 1H), 2.70 (s, 3H), 2.55 (s, 2H), 2.18-2.04 (m, 1H), 1.71-1.56 (m, 1H), 1.10 (d, J=7.2 Hz, 3H), 0.85 (t, J=7.2 Hz, 3H).

Example 128

Synthesis of (S)-3-benzyl-2,5,6,9-tetramethyl-5,6-dihydro-4H-thieno[3,2-f][1,2,4]triazolo[4,3-a][1,4] diazepine (Cpd. No. 20)

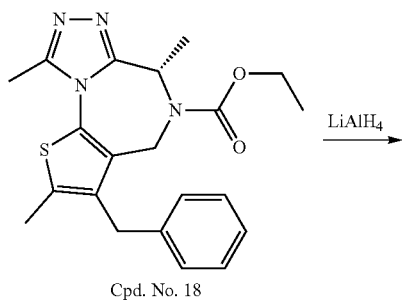

Cpd. No. 18

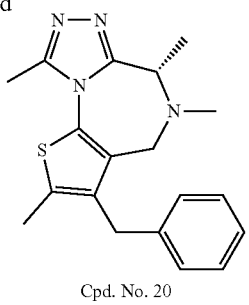

Cpd. No. 20

To a solution of Cpd. No. 18 (10 mg) in THF (1 mL) at 0° C. was added LiAlH$_4$ (10 mg). The reaction mixture was extracted with EtOAc and the organic layer was washed with brine, dried and concentrated. The residue was purified through HPLC to afford Cpd. No. 20 (6 mg). $^1$H NMR (400 MHz, MeOD) δ 7.37-7.27 (m, 2H), 7.23 (t, J=7.3 Hz, 1H), 7.16 (d, J=7.1 Hz, 2H), 4.44-4.33 (m, 1H), 4.29 (d, J=14.5 Hz, 1H), 4.19 (d, J=17.0 Hz, 1H), 4.13 (d, J=16.7 Hz, 1H), 3.98 (d, J=14.4 Hz, 1H), 2.82 (s, 3H), 2.68 (s, 3H), 2.53 (s, 3H), 1.84 (d, J=6.9 Hz, 3H).

Example 129

Synthesis of (R)-3-benzyl-2,5,6,9-tetramethyl-5,6-dihydro-4H-thieno[3,2-f][1,2,4]triazolo[4,3-a][1,4] diazepine (Cpd. No. 34)

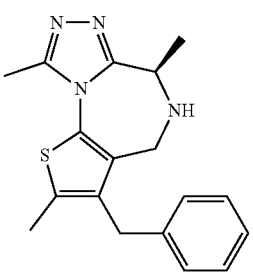

Cpd. No. 17

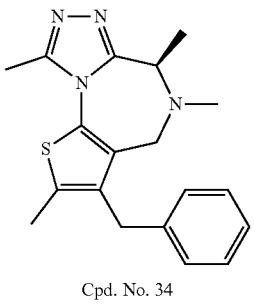

Cpd. No. 34

The Cpd. No. 17 (20 mg) was dissolved in THF and formaldehyde (37% solution, 10 mg) was added. NaBH(OAc)$_3$ (51 mg) was added in one portion and the reaction was stirred at r.t. for 24 h prior to being quenched with Na$_2$CO$_3$ solution (2 M). The reaction mixture was extracted with EtOAc, washed with saturated NaHCO$_3$ solution. The organic solvent was removed. The residue was purified via HPLC to give Cpd. No. 34 (17 mg).

Example 130

Synthesis of (S)-3-benzyl-N-ethyl-2,6,9-trimethyl-4H-thieno[3,2-f][1,2,4]triazolo[4,3-a][1,4]diazepine-5(6H)-carboxamide (Cpd. No. 22)

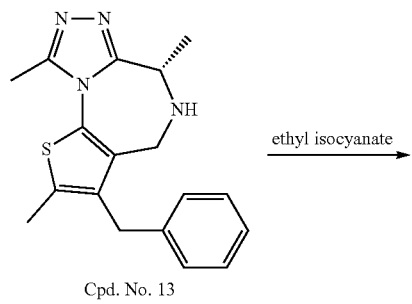

Cpd. No. 13 ethyl isocyanate

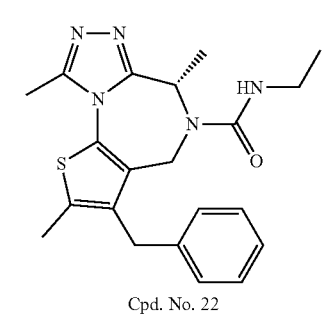

Cpd. No. 22

To a solution of Cpd. No. 13 (10 mg) in DCM (1 mL) was added Et₃N (20 mg) at 0° C. and ethyl isocyanate (3 eq). The volatiles were removed and the residue was purified through HPLC to afford Cpd. No. 22 (90% yield). ¹H NMR (400 MHz, MeOD) δ 7.26 (t, J=7.5 Hz, 2H), 7.23-7.13 (m, 3H), 5.55 (q, J=7.1 Hz, 1H), 4.81 (d, J=14.7 Hz, 1H), 4.10 (d, J=16.2 Hz, 1H), 4.02 (d, J=16.1 Hz, 1H), 3.86 (d, J=14.7 Hz, 1H), 3.19-3.03 (m, 2H), 2.69 (s, 3H), 2.54 (s, 3H), 1.09 (t, J=7.2 Hz, 3H), 1.03 (d, J=7.0 Hz, 3H).

Example 131

Synthesis of ethyl (S)-2-(3-benzyl-2,6,9-trimethyl-4H-thieno[3,2-f][1,2,4]triazolo[4,3-a][1,4]diazepin-5(6H)-yl)acetate (Cpd. No. 25)

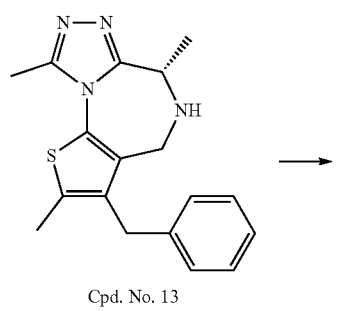

Cpd. No. 13

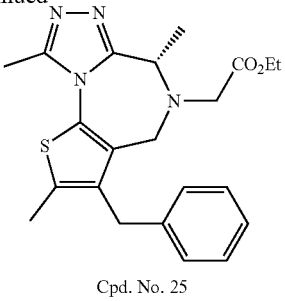

Cpd. No. 25

To a solution of Cpd. No. 13 (32 mg, 0.1 mmol) in DCE (1 mL) was added AcOH (0.3 mL) and ethyl oxoacetate (102 mg, 0.5 mmol, 50% in toluene). After stirring for 30 min, NaBH(OAc)₃ (212 mg) was added in one portion and the reaction was stirred for 2 h prior to being quenched with saturated NaHCO₃ solution. The reaction mixture was extracted with EtOAc and the organic layer was washed with brine, dried and concentrated. The residue was purified via HPLC to give Cpd. No. 25) (3 mg). ¹H NMR (400 MHz, MeOD) δ 7.28 (t, J=7.6 Hz, 2H), 7.20 (t, J=7.1 Hz, 1H), 7.14 (d, J=7.8 Hz, 2H), 4.25-4.08 (m, 3H), 4.06 (d, J=16.2 Hz, 1H), 3.98 (d, J=11.4 Hz, 1H), 3.94 (d, J=10.7 Hz, 1H), 3.73 (d, J=15.0 Hz, 1H), 3.50-3.42 (m, 2H), 2.71 (d, J=1.0 Hz, 3H), 2.51 (s, 3H), 1.43 (d, J=7.0 Hz, 3H), 1.23 (t, J=7.1, 3H).

Example 132

Synthesis of (S)-3-benzyl-2,6,9-trimethyl-5-(phenethylsulfonyl)-5,6-dihydro-4H-thieno[3,2-f][1,2,4]triazolo[4,3-a][1,4]diazepine (Cpd. No. 26)

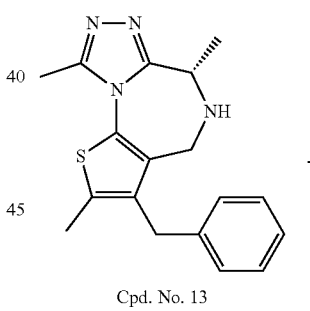

Cpd. No. 13

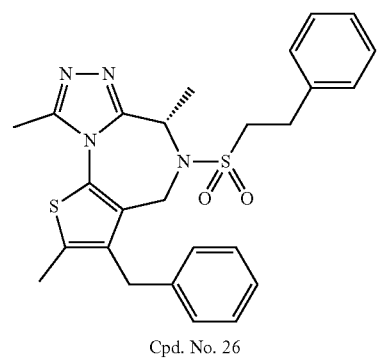

Cpd. No. 26

To a solution of Cpd. No. 13 (10 mg) in DCM (1 mL) at 0° C. was added 2-phenylethane-1-sulfonyl chloride (20 mg). The reaction mixture was extracted with EtOAc and the organic layer was washed with brine, dried and concentrated. The residue was purified through HPLC to afford Cpd. No. 26 (10 mg). $^1$H NMR (400 MHz, MeOD) δ 7.35-7.25 (m, 4H), 7.23-7.15 (m, 6H), 5.40 (q, J=7.1 Hz, 1H), 4.56 (d, J=14.1 Hz, 1H), 4.10 (d, J=16.2 Hz, 1H), 3.98 (d, J=16.1 Hz, 1H), 3.82 (d, J=14.1 Hz, 1H), 3.28 (t, J=7.6 Hz, 1H), 3.09-2.91 (m, 2H), 2.65 (s, 3H), 2.54 (s, 3H), 1.14 (d, J=7.1 Hz, 3H).

Example 133

Synthesis of (S)-3-benzyl-5-(cyclopropylmethyl)-2, 6,9-trimethyl-5,6-dihydro-4H-thieno[3,2-f][1,2,4]triazolo[4,3-a][1,4]diazepine (Cpd. No. 27)

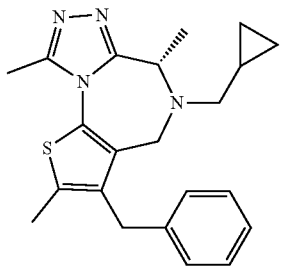
Cpd. No. 27

To a solution of Cpd. No. 13 (20 mg, 0.06 mmol) in THF (1 mL) was added cyclopropanecarbaldehyde (10 mg). After stirring for 10 min, NaBH(OAc)$_3$ (51 mg) was added in one portion and the reaction was stirred for 2 h prior to being quenched with saturated NaHCO$_3$ solution. The reaction mixture was extracted with EtOAc and the organic layer was washed with brine, dried and concentrated. The residue was purified via HPLC to give Cpd. No. 27 (24 mg). $^1$H NMR (400 MHz, MeOD) δ 7.33 (t, J=7.6 Hz, 2H), 7.24 (t, J=7.2 Hz, 1H), 7.17 (d, J=7.8 Hz, 2H), 4.56 (q, J=7.0 Hz, 1H), 4.39 (d, J=14.5 Hz, 1H), 4.22 (s, 1H), 4.15 (d, J=16.8 Hz, 1H), 3.98 (d, J=14.6 Hz, 1H), 3.14 (dd, J=13.3, 6.1 Hz, 1H), 2.82 (dd, J=13.3, 8.5 Hz, 1H), 2.69 (d, J=0.7 Hz, 3H), 2.57 (s, 3H), 1.78 (d, J=6.9 Hz, 3H), 1.14-0.93 (m, 1H), 0.75-0.65 (m, 2H), 0.43-0.20 (m, 2H).

Example 134

Synthesis of benzyl(S)-3-benzyl-6-(2-methoxy-2-oxoethyl)-2,9-dimethyl-4H-thieno[3,2-f][1,2,4]triazolo[4,3-a][1,4]diazepine-5(6H)-carboxylate (Cpd. No. 21)

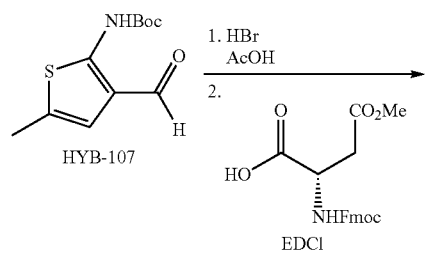

-continued

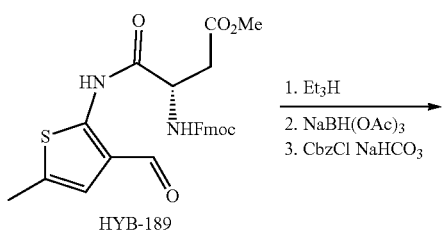
HYB-189

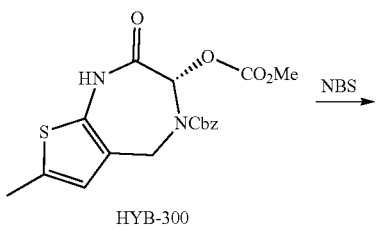
HYB-300

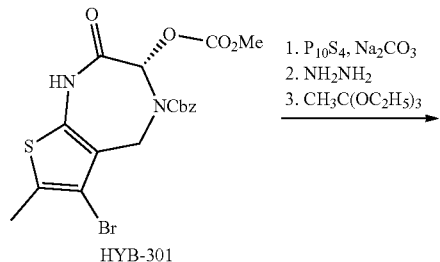
HYB-301

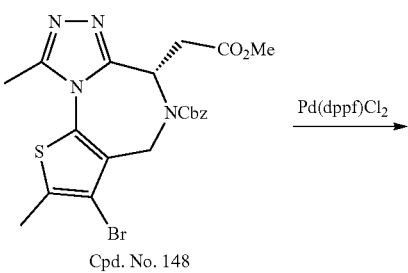
Cpd. No. 148

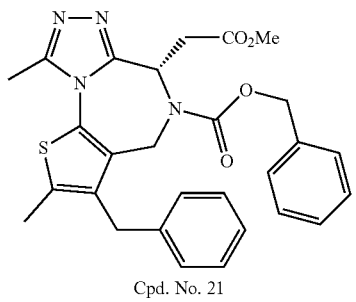
Cpd. No. 21

Example 134-A

Synthesis of methyl (S)-3-((((9H-fluoren-9-yl)methoxy)carbonyl)amino)-4-((3-formyl-5-methylthiophen-2-yl)amino)-4-oxobutanoate

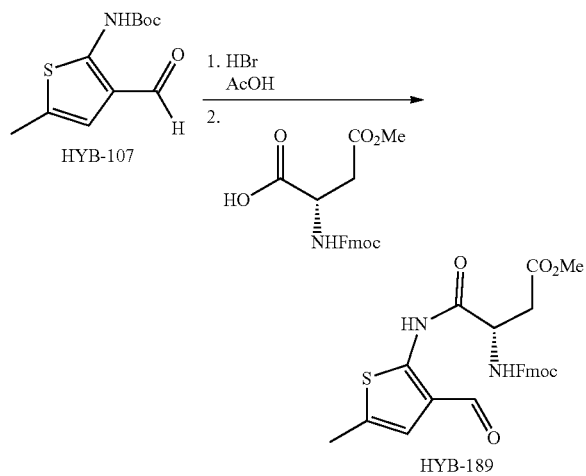

Step 1: A solution of 33% HBr in acetic acid (7.3 mL) was cooled to 0° C. A cold solution of HYB-107 (1 g, 4 mmol) in DCM (1 mL) was added and the reaction mixture turned red immediately. The reaction mixture was immediately poured into ice-water (50 g each) and was taken up in ethyl acetate. The organic layer was separated, washed successively with 10% NaOH (40 mL), NaHCO$_3$(40 mL), and brine (40 mL). After drying, the organic solution was passed through a short pad of silica gel, then concentrated. The residue was dissolved in dichloromethane for next step.

Step 2: The above solution was cooled to 0° C., (S)-2-((((9H-fluoren-9-yl)methoxy)carbonyl)amino)-4-methoxy-4-oxobutanoic acid (2.2 g, 1.5 eq) and EDCI (1.2 g, 1.5 eq) were successively added. The reaction mixture was allowed to warm to r.t. and stirred overnight. The reaction mixture was take up in EtOAc and washed with water and brine. The organic layer was separated, dried, and evaporated to give a crude mixture which was purified on silica gel (elution 1:15 ethyl acetate/DCM) to give HYB-189 (1.5 g, 76%). $^1$H NMR (400 MHz, CDCl$_3$) δ 12.10 (s, 1H), 9.76 (s, 1H), 7.88-7.60 (m, 4H), 7.51-7.31 (m, 4H), 6.83 (s, 1H), 6.18-6.12 (m, 1H), 4.92-4.85 (m, 1H), 4.63 (dd, J=10.3, 6.6 Hz, 1H), 4.42-4.36 (m, 2H), 3.75 (s, 3H), 3.32-3.25 (m, 1H), 2.88-2.82 (m, 1H), 2.43 (s, 3H).

Example 134-B

Synthesis of benzyl (S)-3-(2-methoxy-2-oxoethyl)-7-methyl-2-oxo-1,2,3,5-tetrahydro-4H-thieno[2,3-e][1,4]diazepine-4-carboxylate

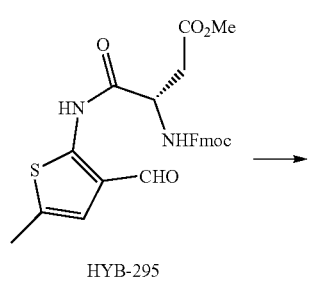

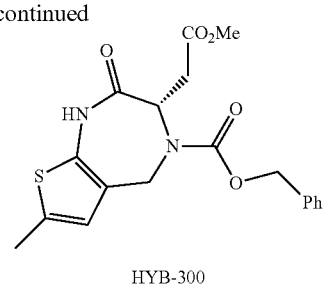

To a solution of HYB-295 (1.3 g, 2.6 mmol) in THF (20 mL) was added Et$_3$N (2 mL) and the reaction mixture was heated to 60° C. for 8 hours. The volatiles were removed under vacuum and the residue was dissolved in THF (40 mL) and NaBH(OAc)$_3$ (2.12 g, 4 eq) was added. The reaction mixture was stirred for 4 h prior to being quenched with Na$_2$CO$_3$ solution (2 M). The reaction mixture was extracted with EtOAc, washed with saturated NaHCO$_3$ solution. The organic solvent was removed. The residue was dissolved in DCM (10 mL) and saturated NaHCO$_3$(10 mL). CbzCl (5.2 mmol, 0.74 mL) was added and the reaction mixture was stirred for overnight. The organic layer was separated, dried, and concentrated. The residue was purified by chromatography on silica gel (1:2 ethyl acetate/hexanes) to give HYB-300 (270 mg, 27% yield).

Example 134-C

Synthesis of benzyl(S)-6-bromo-3-(2-methoxy-2-oxoethyl)-7-methyl-2-oxo-1,2,3,5-tetrahydro-4H-thieno[2,3-e][1,4]diazepine-4-carboxylate

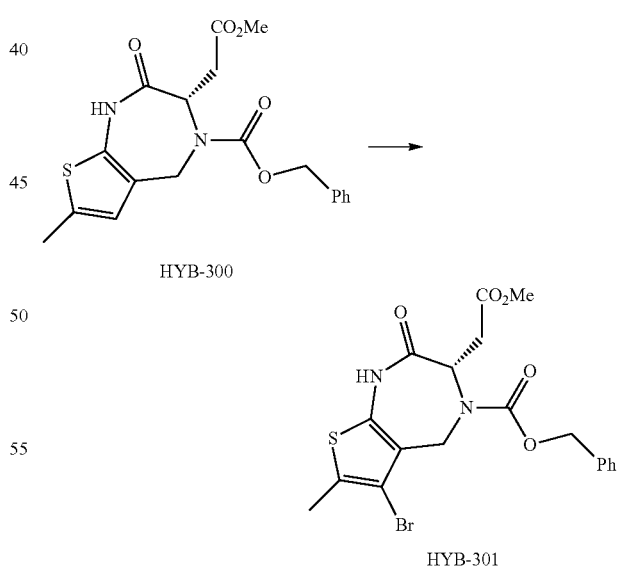

HYB-300 (270 mg, 0.7 mmol) was dissolved in AcOH (6 mL). NBS (124 mg) was added and the reaction mixture was stirred for 10 minute prior to being poured into the ice/water. The mixture was extracted with EtOAc, washed with NaOH (1 M, 10 mL), NaHCO$_3$ solution (10 mL), and brine. The organic layer was separated, dried, and concentrated. The

247 residue was purified by chromatography on silica gel (1:2 ethyl acetate/hexanes) to give HYB-301 (180 mg, 55% yield).

Example 134-D

Synthesis of benzyl (S)-3-bromo-6-(2-methoxy-2-oxoethyl)-2,9-dimethyl-4H-thieno[3,2-f][1,2,4]triazolo[4,3-a][1,4]diazepine-5(6H-carboxylate (Cpd. No. 148)

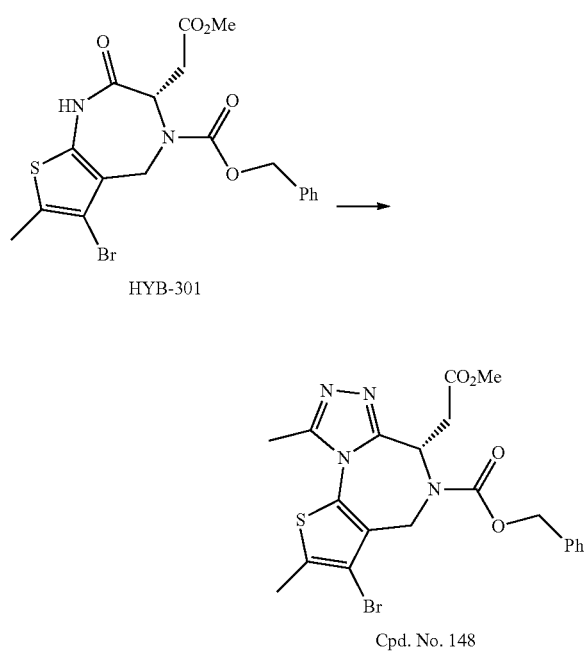

HYB-301

Cpd. No. 148

Step 1: To a suspension of P$_4$S$_{10}$ (172 mg, 0.77 mmol) and Na$_2$CO$_3$ (81 mg, 0.77 mmol) in 1,2-DCE (10 mL) was added HYB-301 (180 mg, 0.38 mmol). The reaction mixture was heated to 65° C. for 4 h until the reaction is completed. The reaction mixture was cooled, taken up in saturated NaHCO$_3$, and extracted with DCM. The organic layer was washed with saturated NaHCO$_3$ and brine prior to being dried.

Step 2: The solvent was removed and the residue was dissolved in THF (4 mL). NH$_2$NH$_2$.H$_2$O (38 mg) was added and the reaction was stirred for 1 h. The volatiles were removed under vacuum and the residue was taken up in saturated NaHCO$_3$, and extracted with DCM. The organic layer was separated and dried prior to being removed.

Step 3: The residue was dissolved in ethanol (4 mL) and triethyl orthoacetate (1.2 mmol, 0.21 mL) was added. The reaction mixture was heated at 60° C. for 1 h. The volatile was removed to give a crude mixture which was purified via HPLC to give Cpd. No. 148 (20 mg). $^1$H NMR (400 MHz, MeOD) δ 7.45-7.27 (m, 5H), 5.72 (t, J=7.3 Hz, 1H), 5.20 (d, J=16.0 Hz, 1H), 5.16 (d, J=16.0 Hz, 1H), 5.06 (d, J=16.4 Hz, 1H), 4.41 (d, J=16.3 Hz, 1H), 3.61 (s, 3H), 3.05 (dd, J=15.9, 6.7 Hz, 1H), 2.74 (dd, J=14.8, 8.7 Hz, 1H), 2.69 (s, 3H), 2.51 (s, 3H).

248

Example 134-E

Synthesis of benzyl (S)-3-benzyl-6-(2-methoxy-2-oxoethyl)-2,9-dimethyl-4H-thieno[3,2-f][1,2,4]triazolo[4,3-a][1,4]diazepine-5(6H)-carboxylate (Cpd. No. 21)

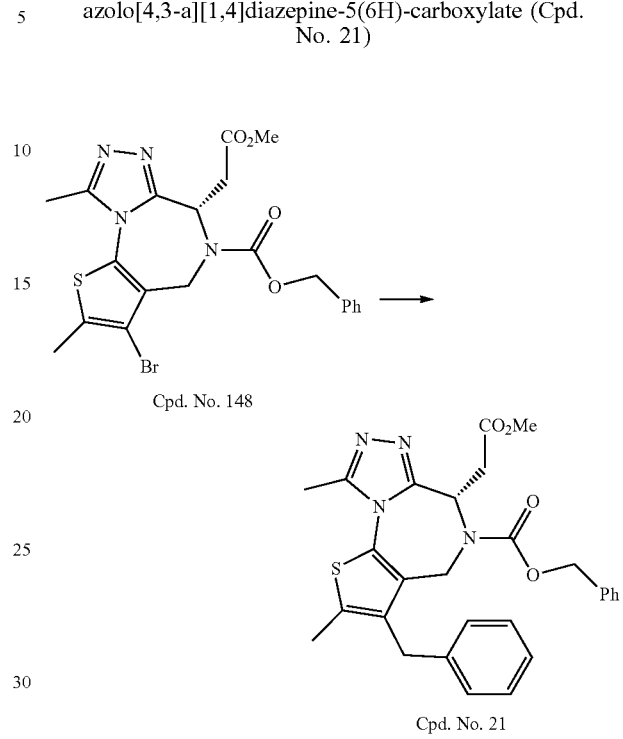

Cpd. No. 148

Cpd. No. 21

To a Shlenk tube was charged with Cpd. No. 148 (20 mg, 0.04 mmol), potassium benzyltrifluoroborate (16 mg, 2 eq), Pd(dppf)Cl$_2$ (3.3 mg), dioxane (1 mL) and Na$_2$CO$_3$ solution (2 M, 0.5 mL) under N$_2$. The tube was sealed and heated at 100° C. oil bath for 1 h. The reaction mixture was extracted with EtOAc and the organic layer was washed with brine, dried and concentrated. The residue was purified through HPLC to afford Cpd. No. 21 (50% yield). $^1$H NMR (400 MHz, MeOD) δ 7.46-7.30 (m, 5H), 7.26-7.10 (m, 4H), 7.00-6.95 (m, 1H), 5.77 (dd, J=9.1, 5.5 Hz, 1H), 5.94-5.06 (m, 2H), 4.02-3.92 (m, 2H), 3.40-3.52 (m, 2H), 2.73-2.68 (m, 1H), 2.65 (s, 3H), 2.54 (s, 3H), 2.32-2.25 (m, 1H).

Example 135

Synthesis of methyl(S)-2-(3-benzyl-2,9-dimethyl-5,6-dihydro-4H-thieno[3,2-f][1,2,4]triazolo[4,3-a][1,4]diazepin-6-yl)acetate (Cpd. No. 23)

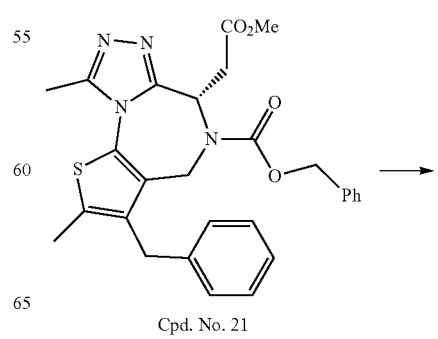

Cpd. No. 21

Example 137

Synthesis of (S)-3-benzyl-5-cyclobutyl-2,6,9-trimethyl-5,6-dihydro-4H-thieno[3,2-f][1,2,4]triazolo[4,3-a][1,4]diazepine (Cpd. No. 29)

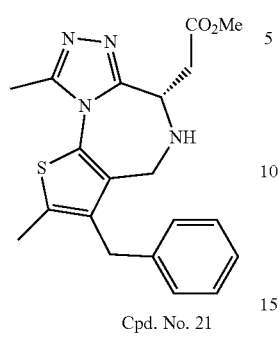

Cpd. No. 21

Cpd. No. 21 (7 mg) was dissolved in a mixture of TFA-thioanisole (2 mL-0.2 mL) and stirred at r.t. for 24 h. The volatiles was evaporated to give a crude mixture which was purified via HPLC to give HYB-312 (4 mg). $^1$H NMR (400 MHz, MeOD) δ 7.31 (t, J=7.4 Hz, 2H), 7.22 (t, J=7.3 Hz, 1H), 7.13 (d, J=7.2 Hz, 2H), 4.68 (t, J=6.8 Hz, 1H), 4.24 (d, J=4.5 Hz, 1H), 4.20 (d, J=6.6 Hz, 1H), 4.10 (d, J=16.6 Hz, 1H), 3.88 (d, J=14.6 Hz, 1H), 3.77 (s, 3H), 3.55-3.49 (m, 1H), 3.30-3.22 (m, 1H), 2.69 (s, 3H), 2.54 (s, 3H).

Example 136

Synthesis of 1-methyl-7-phenoxy-4H,6H-benzo[e][1,2,4]triazolo[3,4-c][1,4]oxazepine (Cpd. No. 40)

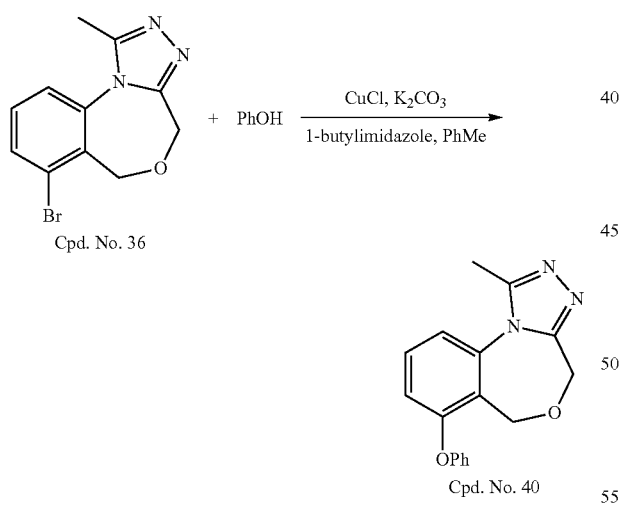

Cpd. No. 36 (28 mg), copper(I) chloride (2 mg), potassium carbonate (30 mg), PhOH (14 mg), 13 μL 1-butylimidazole, and 1 mL of toluene were added to an Ace pressure tube under argon and heated to 120° C. for 16 h. After cooling, water and EtOAc were added. The organic phase was washed with brine, dried over Na$_2$SO$_4$, and concentrated on a rotary evaporator. The residues were purified by reverse phase HPLC. Cpd. No. 40 was isolated in 0.4 mg as a salt of CF$_3$CO$_2$H. ESI-MS calculated for C$_{17}$H$_{16}$N$_3$O$_2$ [M+H]$^+$=294.1; Observed: 294.3.

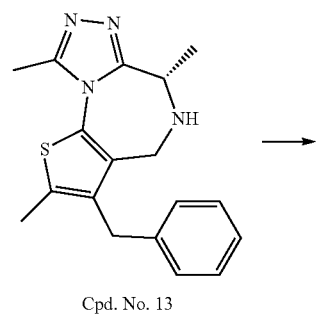

Cpd. No. 13

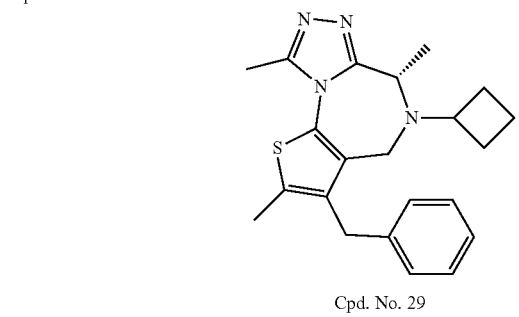

Cpd. No. 29

To a solution of Cpd. No. 13 (20 mg, 0.06 mmol) in THF (1 mL) was added cyclobutanone (10 mg). After stirring for 10 min, NaBH(OAc)$_3$ (51 mg) was added in one portion and the reaction was stirred for 2 h prior to being quenched with saturated NaHCO$_3$ solution. The reaction mixture was extracted with EtOAc and the organic layer was washed with brine, dried and concentrated. The residue was purified via HPLC to give Cpd. No. 29 (18 mg, 80%). $^1$H NMR (400 MHz, MeOD) δ 7.33 (t, J=7.5 Hz, 2H), 7.24 (t, J=7.3 Hz, 1H), 7.15 (d, J=7.3 Hz, 2H), 4.73 (q, J=7.2 Hz, 1H), 4.22-4.11 (m, 2H), 3.97 (t, J=15.1 Hz, 1H), 3.85 (d, J=14.5 Hz, 1H), 3.81-3.68 (m, 1H), 2.71 (d, J=15.4 Hz, 3H), 2.56 (d, J=15.4 Hz, 3H), 2.32 (dt, J=29.5, 10.2 Hz, 4H), 1.85 (dd, J=20.0, 9.9 Hz, 1H), 1.73-1.65 (m, 1H), 1.62 (d, J=7.2 Hz, 3H). ESI-MS: 379.02.

Example 138

Synthesis of 4-(5-((3-benzyl-9-methyl-4H,6H-thieno[2,3-e][1,2,4]triazolo[3,4-c][1,4]oxazepin-2-yl)ethynyl)pyridin-2-yl)butanal (Cpd. No. 151)

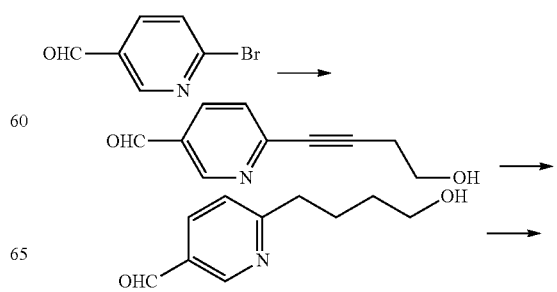

-continued

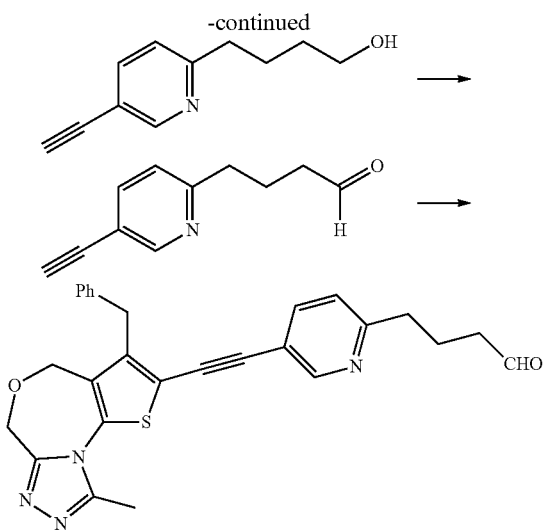

Cpd. No. 151

Step 1: To a flask was added CuI (19 mg, 0.1 mmol), Pd(Ph₃P)₂Cl₂ (70 mg, 0.1 mmol), 6-bromonicotinaldehyde (1.86 g, 10 mmol), and but-3-yn-1-ol (1.1 mL, 15 mmol), THF(25 mL) and Et₃N (3 mL). The reaction mixture was heated at 60° C. for 12 hours. The reaction mixture was cooled and treated with EtOAc and brine. The organic layer was separated, dried, and evaporated. The residue was purified by chromatography (EtOAc) to afford 6-(4-hydroxybut-1-yn-1-yl)nicotinaldehyde (1.7 g, 99% yield).

Step 2: To a solution of 6-(4-hydroxybut-1-yn-1-yl)nicotinaldehyde (1.7 g, 10 mmol) in MeOH (50 mL) was added 10% Pd/C (200 mg). The reaction was stirred under H₂ balloon for 4 h prior to being filtered. The organic solvent was removed and the residue was purified by chromatography (EtOAc) to afford 6-(4-hydroxybutyl)nicotinaldehyde (927 mg, 52%). $^1$H NMR (400 MHz, CDCl₃) δ 10.04 (s, 1H), 8.93 (d, J=1.9 Hz, 1H), 8.07 (dd, J=8.0, 2.1 Hz, 1H), 7.33 (d, J=8.0 Hz, 1H), 3.66 (t, J=6.4 Hz, 2H), 3.02-2.63 (m, 4H), 1.93-1.73 (m, 2H), 1.68-1.52 (m, 2H).

Step 3: To a solution of 6-(4-hydroxybutyl)nicotinaldehyde (627 mg, 3.5 mmol) and dimethyl (1-diazo-2-oxopropyl)phosphonate (807 mg, 4.2 mmol) in methanol (50 mL) was added K₂CO₃ (966 mg, 7 mmol). The reaction mixture was stirred for 12 hours. The reaction mixture was evaporated and treated with EtOAc and brine. The organic layer was separated, dried, and evaporated. The residue was purified by chromatography (Hexanes:EtOAc 2:1) to give 4-(5-ethynylpyridin-2-yl)butan-1-ol (500 mg, 80%). $^1$H NMR (400 MHz, CDCl₃) δ 8.59 (s, 1H), 7.67 (dd, J=8.0, 1.9 Hz, 1H), 7.12 (d, J=7.9 Hz, 1H), 3.65 (t, J=6.4 Hz, 2H), 3.18 (s, 1H), 2.87 (s, 1H), 2.84-2.68 (m, 2H), 1.80 (dt, J=15.3, 7.5 Hz, 2H), 1.61 (dt, J=13.4, 6.5 Hz, 2H).

Step 4: 4-(5-ethynylpyridin-2-yl)butan-1-ol (400 mg, 2.3 mmol) was dissolved in DMSO (9 mL) and Et₃N (6 mL). SO₃.pyridine complex (1.08 g, 6.8 mmol) was then added. The reaction mixture was stirred for 3 h prior to being quenched with water. The reaction mixture was extracted with EtOAc. The organic layer was separated, washed with brine, dried, and evaporated. The residue was purified by chromatography (EtOAc/Hexanes: 1:2) to afford 4-(5-ethynylpyridin-2-yl)butanal. (350 mg, 87%). $^1$H NMR (400 MHz, CDCl₃) δ 9.74 (s, 1H), 8.61 (d, J=1.7 Hz, 1H), 7.67 (dd, J=8.0, 2.2 Hz, 1H), 7.10 (d, J=8.0 Hz, 1H), 3.18 (s, 1H), 2.81 (t, J=7.2 Hz, 2H), 2.48 (t, J=7.2 Hz, 2H), 2.03-1.98 (m, 2H).

Step 5: To a Schlenk tube was added CuI (9.5 mg), Pd(Ph₃P)₂Cl₂ (35 mg), 4-(5-ethynylpyridin-2-yl)butanal (170 mg, 1 mmol), and L12 (180 mg, 0.5 mmol), THF (6 mL) and Et₃N (1.5 mL). The reaction mixture was heated at 60° C. for 12 hours. The reaction mixture was cooled and treated with EtOAc and brine. The organic layer was separated, dried, and evaporated. The residue was purified by HPLC to afford Cpd. No. 151 (231 mg, 92% yield). $^1$H NMR (400 MHz, MeOD) δ 9.14 (s, 1H), 8.80 (s, 1H), 8.48 (dd, J=8.3, 1.8 Hz, 1H), 8.29 (td, J=8.1, 2.0 Hz, 1H), 7.92 (d, J=8.4 Hz, 1H), 7.74 (t, J=7.6 Hz, 1H), 7.38-7.30 (m, 3H), 7.27-7.20 (m, 2H), 4.80-4.73 (m, 4H), 4.22 (s, 2H), 3.10-2.97 (m, 2H), 2.80 (s, 3H), 2.21-2.07 (m, 2H), 1.86-1.80 (m, 2H), 1.67-1.60 (m, 2H). ESI-MS: 468.92.

Example 139

Synthesis of 3-benzyl-9-methyl-2-((1-methyl-H-pyrazol-4-yl)ethynyl)-4H,6H-thieno[2,3-e][1,2,4]triazolo[3,4-c][1,4]oxazepine (Cpd. No. 152)

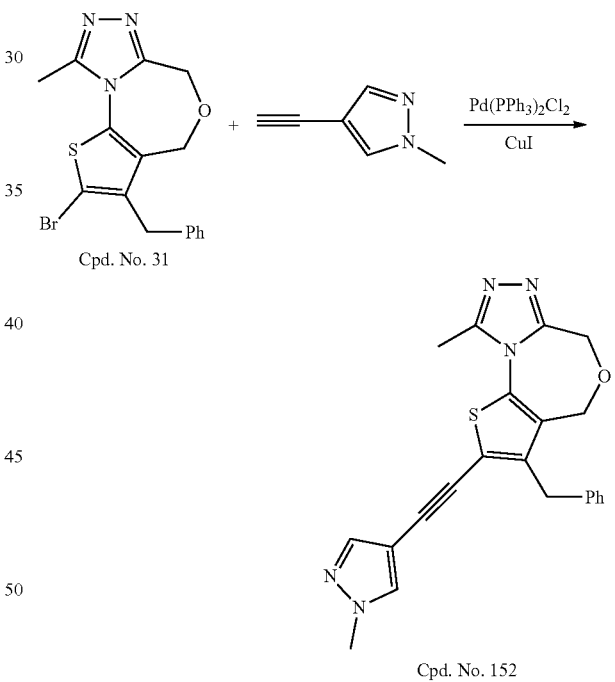

Cpd. No. 152

To a round-bottom flask containing Cpd. No. 31 (25 mg), 4-ethynyl-1-methyl-1H-pyrazole (16 mg), Pd(PPh₃)Cl₂ (13.5 mg) and CuI (7.3 mg), Et₃N (0.5 mL) and THF (1 mL) was added under N₂ atmosphere. The reaction mixture was heated at 60° C. for 10 h. The reaction was cooled, taken up with saturated NaHCO₃, and extracted with EtOAc. The organic layers were combined and washed with brine, dried over anhydrous sodium sulfate, and concentrated on a rotary evaporator. The residues were purified by reverse phase HPLC. Cpd. No. 152 was isolated (13 mg) as a salt of CF₃CO₂H. ESI-MS calculated for C₂₃H₁₉N₄OS [M+H]⁺=402.14; Observed: 402.1.

Example 140

Synthesis of (S)-3-benzyl-2,6,9-trimethyl-4H,6H-thieno[2,3-e][1,2,4]triazolo[3,4-c][1,4]oxazepine (Cpd. No. 154)

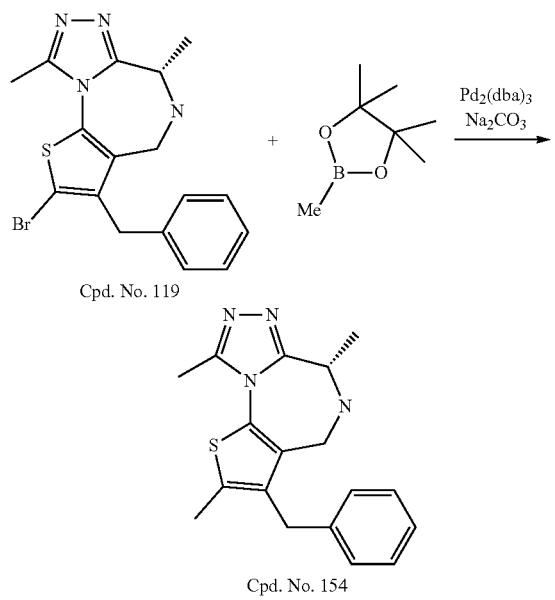

To a Shlenk tube was charged with Cpd. No. 119 (50 mg), 2,4,4,5,5-pentamethyl-1,3,2-dioxaborolane (36 mg, 2 eq), $Pd_2(dba)_3$ (13 mg), $PCy_3$ (8.5 mg), dioxane (2 mL) and $Na_2CO_3$ solution (2 M, 1.0 mL) under $N_2$. The tube was sealed and heated at 100° C. in an oil bath for 4 h. The reaction mixture was extracted with EtOAc and the organic layer was washed with brine, dried and concentrated. The residue was purified by HPLC to afford Cpd. No. 154 (30% yield). 1H NMR (400 MHz, MeOD) δ 7.33-7.10 (m 5H), 4.79 (d, J=16.0 Hz, 1H), 4.67-4.55 (m 2H), 4.00 (d, J=16.1 Hz, 1H), 3.89 (d, J=16.6 Hz, 1H), 2.81 (s, 3H), 2.52 (s, 3H), 1.67 (d, J=6.7 Hz 3H). ESI: M+H 326.12.

Example 141

Competitive Fluorescence-Polarization (FP) Assays

Fluorescence Polarization (FP) competitive binding studies were carried out using a FAM labeled fluorescent probe, see Cpd. No. 350 of US 2014/0256706, to determine binding affinities of representative Compounds of the Disclosure for recombinant BRD4 BD1 and BRD4 BD2 proteins. See Table 2. Equilibrium dissociation constants ($K_d$) values of the fluorescent probe to BRD4 BD1 and BD2 proteins were determined from protein saturation experiments by monitoring the total fluorescence polarization of mixtures composed with the fluorescent probe at a fixed concentration and proteins with increasing concentrations up to full saturation. Serial dilutions of testing proteins were mixed with the fluorescent probe to a final volume of 200 µl in the assay buffer (100 mM phosphate buffer, pH=6.5, 0.01% Triton X-100 (Sigma, 282103) being added right before assays). Final fluorescent probe concentration was 1.5 nM for both proteins. Plates were incubated at room temperature for 30 minutes with gentle shaking to assure equilibrium. FP values in millipolarization units (mP) were measured using the Infinite M-1000 plate reader (Tecan U.S., Research Triangle Park, N.C.) in Microfluor 1 96-well, black, round-bottom plates (Thermo Scientific, Waltham, Mass.) at an excitation wavelength of 485 nm and an emission wavelength of 530 nm. $K_d$ values of the fluorescent probe, which were calculated by fitting the sigmoidal dose-dependent FP increases as a function of protein concentrations using Graphpad Prism 6.0 software (Graphpad Software, San Diego, Calif.), are 5.5 and 3.0 nM to BDR4 BD1 and 2, respectively.

The $IC_{50}$ and $K_i$ values of compounds were determined in a competitive binding experiment. See US 2014/0256706. Mixtures of 10 µl of the tested compounds in assay buffer with 40% Ethylene Glycol and 190 µl of preincubated protein/probe complex solution in the assay buffer (100 mM potassium phosphate, pH 6.5, 0.01% Triton X-100) were added into assay plates which were incubated at room temperature for 30 minutes with gentle shaking. Final concentrations of proteins were 10 and 6 nM in assays for BRD4 BD1 and BD2, respectively. Final probe concentration is 1.5 nM in both assays. Negative controls containing protein/probe complex only (equivalent to 0% inhibition), and positive controls containing only free probes (equivalent to 100% inhibition), were included in each assay plate. FP values were measured as described above. $IC_{50}$ values were determined by nonlinear regression fitting of the competition curves. Instead of being calculated from $IC_{50}$ values as described before. Ki values of competitive inhibitors were obtained directly by nonlinear regression fitting as well, based upon the Kd values of the probe to different proteins, and concentrations of the proteins and probes in the competitive assays (US 2014/0256706; Wang, FEBS Lett. 360; 111 (1995); Zhang et al., Analytical Biochemistry, 331; 138 (2004)).

TABLE 2

| Cpd. No. | $IC_{50}$ (nM) | |
| --- | --- | --- |
| | BRD4 BD1 | BRD4 BD2 |
| 1 | 66880 | |
| 2 | 23161 | |
| 3 | 13335 | |
| 4 | 84.9, 63.4, 90.2 | 133, 164, 134 |
| 5 | 1369 | 1067 |
| 6 | 317, 629 | 346, 457 |
| 7 | 171, 311 | 1162, 1262 |
| 8 | 311 | 285 |
| 9 | 88.4 | 271 |
| 10 | 263 | 312 |
| 12 | 371 | 328, 379 |
| 13 | 1073, 1203 | 1206, 1352 |
| 14 | 85, 112 | 118, 145 |
| 15 | 531, 751 | 102, 111 |
| 16 | 229 | 326 |
| 17 | 1084 | 622 |
| 18 | 532 | 601 |
| 19 | 2428 | 3212 |
| 20 | 235, 340 | 636, 1212 |
| 21 | 23763 | 17688 |
| 22 | 6061 | 5921 |
| 23 | 2498 | 9006 |
| 24 | 491 | 492 |
| 25 | 942 | 1103 |
| 26 | 9596 | 4457 |
| 27 | 611 | 2615 |
| 28 | 772 | 749 |
| 29 | 1465 | 5862 |
| 30 | 1390 | |
| 31 | 209, 265, 352 | |
| 32 | 294 | |
| 33 | 74.6 | |

TABLE 2-continued

| Cpd. No. | IC$_{50}$ (nM) BRD4 BD1 | IC$_{50}$ (nM) BRD4 BD2 |
|---|---|---|
| 35 | 602 | |
| 36 | >10000 | >10000 |
| 37 | 14488 | 1457 |
| 38 | 1424, 1257 | 367 |
| 39 | 5451 | 1061 |
| 41 | 17957 | 16630 |
| 42 | 10315 | 5016 |
| 43 | 3525 | 328 |
| 44 | 4402 | 238 |
| 45 | 1546 | 1368 |
| 46 | 807 | 268 |
| 47 | 1197 | 303 |
| 48 | 454, 696 | 71.6, 137 |
| 49 | 2348, 1817 | 271, 175 |
| 50 | 425, 585 | 146, 247 |
| 51 | 256 | 207 |
| 52 | >10000 | >10000 |
| 53 | 244 | |
| 54 | 210 | 127 |
| 55 | 288 | |
| 56 | 134 | |
| 57 | 198 | |
| 58 | 289 | |
| 59 | 966 | |
| 60 | 1146 | |
| 70 | >10000 | |
| 71 | 864 | |
| 72 | 2073, 1979 | |
| 73 | 234, 366 | |
| 74 | 1784 | |
| 75 | 923 | |
| 76 | 937 | |
| 77 | 13208 | |
| 78 | 1322 | |
| 79 | 18117 | |
| 80 | 532 | |
| 81 | 5419 | |
| 82 | 500 | |
| 83 | 150 | |
| 85 | 7.3, 8.1 | 48.3, 60.3 |
| 86 | 14.4 | 111 |
| 87 | 11.6 | 174 |
| 88 | 11.0 | 105 |
| 89 | 8.7 | 315 |
| 90 | 6514 | |
| 91 | 153 | |
| 92 | 211 | |
| 93 | 551 | |
| 94 | 1053 | |
| 95 | 1818 | |
| 96 | 48.8, 37.8 | 232 |
| 97 | 6712 | |
| 98 | 8999 | |
| 99 | 367 | |
| 100 | 208 | |
| 101 | 832 | |
| 102 | 222 | |
| 103 | 115, 70.4 | 213 |
| 104 | 313 | |
| 105 | 279 | |
| 106 | 283 | |
| 107 | 494 | |
| 108 | 5000 | |
| 109 | 99.6, 93.8 | 125, 120 |
| 110 | 634 | 2320 |
| 111 | 5.4, 10.5, 12.9 | 112, 142, 127 |
| 112 | 1373, 2615, 1764 | 3229, 3850, 3955 |
| 113 | 26.9, 40.0 | 146, 149 |
| 114 | 249 | 297 |
| 115 | 170 | 338 |
| 117 | 118 | |
| 147 | 48560 | 83706 |

Binding affinities to BRD2 BD1 and BD2, BRD3 BD1 and BD2, and BRD4 BD1 and BD2 can also be determined by a label free binding assay using the OctetRED label free biolayer interferometry (BLI) binding assay.

Example 142

Cell Growth Inhibition

The effect of representative Compounds of the Disclosure on cell viability was determined in a 4-day proliferation assay. See Table 3. Cells were maintained in the appropriate culture medium with 10% FBS at 37° C. and an atmosphere of 5% $CO_2$. All the cell lines were used within three months of thawing fresh vials.

Cells were seeded in 96-well flat bottom (Corning COSTAR, Corning, N.Y., cat #3595) or white opaque cell culture plates (BD Falcon, cat #353296) at a density of 3,000-10,000 cells/well in 75 µl of culture medium. Compounds were serially diluted in the appropriate medium, and 75 µl of the diluted compounds were added to the appropriate wells of the cell plate. After the addition of compounds, the cells were incubated at 37° C. in an atmosphere of 5% $CO_2$ for 4 days. Cell viability was determined using the CellTiter-Glo® Luminescent Cell Viability Assay Kit (Promega, Madison, Wis.) for leukemia cells and WST (2-(2-methoxy-4-nitrophenyl)-3-(4-nitrophenyl)-5-(2,4-disulfophenyl)-2H-tetrazolium, monosodium salt) Cell Counting-8 Kit (Dojindo Molecular Technologies, Inc., Rockville, Md.) for adhenrent cells according to the manufacturers' instructions.

For WST assay (adherent cells), WST-8 reagent was added to each well at a final concentration of 10% (v/v), and then the plates were incubated at 37° C. for 1-2 hours for color development. The absorbance was measured at 450 nm using a SPECTRAmax PLUS plate reader (Molecular Devices, Sunnyvale, Calif.). The readings were normalized to the DMSO-treated cells and the half maximal inhibitory concentration (IC$_{50}$) was calculated by nonlinear regression (four parameters sigmoid fitted with variable slope, least squares fit, and no constraint) analysis using the GraphPad Prism 5 software (GraphPad Software, La Jolla, Calif.).

For CellTiter-Glo assay (suspension cells), 100 µl of CellTiter-Glo® Reagent was added to each well, and then the plates were incubated at room temperature for 10-20 minutes. The luminescent signal was measured using a Tecan Infinite M1000 multimode microplate reader (Tecan, Morrisville, N.C.). The readings were normalized to the DMSO-treated cells and the IC$_{50}$ was calculated by nonlinear regression (four parameters sigmoid fitted with variable slope, least squares fit, and no constraint) analysis using the GraphPad Prism 5 software. See US 2014/0256706.

TABLE 3

| | Cell Viability (IC$_{50}$, µM) | |
|---|---|---|
| Cpd No. | RS4-11 | MOLM-13 |
| 4 | 1.7 | 0.8, 0.9 |
| 5 | >5 | |
| 6 | 4.5 | >5 |
| 7 | 4.2 | 2.8 |
| 8 | | 2.5 |
| 9 | | 1.0 |
| 10 | | 3.4 |
| 12 | 4.7 | 4.0 |
| 14 | 2.4 | 1.9 |
| 15 | 2.7 | 2.0 |
| 16 | | 2.8 |
| 18 | | 4.3 |

TABLE 3-continued

| Cpd No. | Cell Viability (IC$_{50}$, µM) | |
|---|---|---|
| | RS4-11 | MOLM-13 |
| 20 | | 1.3 |
| 24 | | 3.4 |
| 27 | | >5 |
| 28 | | 4.7 |
| 31 | | 1.4, 1.7 |
| 32 | | 1.9 |
| 33 | | 1.0 |
| 34 | | 1.0 |
| 35 | | 2.2 |
| 46 | | 2.9 |
| 48 | | 1.4 |
| 49 | | >5 |
| 50 | | 2.7 |
| 71 | | 3.8 |
| 73 | | 1.1 |
| 84 | 1.0 | 0.7 |
| 85 | 0.14, 0.12 | 0.16, 0.10 |
| 86 | 0.20 | 0.14 |
| 87 | 0.21 | 0.14 |
| 88 | 0.25 | 0.12 |
| 89 | 0.62 | 0.28 |
| 91 | 1.2 | 1.2 |
| 92 | 1.6 | 1.6 |
| 93 | >5 | >5 |
| 96 | 0.4, 0.34 | 0.3, 0.25 |
| 99 | 2.2 | 2.9 |
| 100 | 2.3 | 2.4 |
| 101 | 3.6 | >5 |
| 102 | 2.6 | 3.9 |
| 103 | 1.0, 0.95 | 1.1, 0.67 |
| 106 | 1.5 | 2.6 |
| 109 | 1.0, 1.0 | 1.1, 0.81 |
| 110 | 3.5 | 3.8 |
| 111 | 0.18, 0.25 | 0.15, 0.38 |
| 113 | 0.24, 0.45 | 0.19, 0.67 |

Example 143

In Vivo Efficacy Studies Using the MDA-MB-231 (Human Breast Cancer) Xenograft Model For in vivo efficacy experiments for MDA-MB-231, see FIG. 1, 5×10$^6$ tumor cells with 50% Matrigel were subcutaneously injected on the dorsal side of SCID mice from Charles River, one tumor per mouse. When xenograft tumors reached a mean of 100-200 mm$^3$, mice were randomized into groups of 6-8 mice. Vehicle Control (PEG200) or experimental compound was administered orally (p.o.) once per day for indicated dose and duration. Tumor sizes and animal weights were measured 2-3 times per week. Data are represented as mean tumor volumes. Tumor volume (mm$^3$)=(A×B$^2$)/2 where A and B are the tumor length and width (in mm), respectively. Statistical analyses were done by two-way ANOVA and unpaired two-tailed t test, using Prism (version 6.1, GraphPad). P<0.05 was considered statistically significant. Animal weight was also measured. See FIG. 2. All animal experiments were performed under the guidelines of the University of Michigan Committee for Use and Care of Animals.

Having now fully described the methods, compounds, and compositions of matter provided herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications, and publications cited herein are fully incorporated by reference herein in their entirety.

What is claimed is:

1. A compound having Formula II:

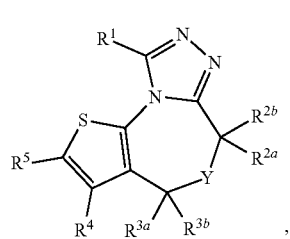

or a pharmaceutically acceptable salt or hydrate thereof, wherein:

$R^1$ is $C_{1-4}$ alkyl;

$R^{2a}$ and $R^{2b}$ are each independently selected from the group consisting of hydrogen and $C_{1-4}$ alkyl, or $R^{2a}$ and $R^{2b}$ together with the carbon atom to which they are attached form a 3- to 6-membered cycloalkyl;

$R^{3a}$ and $R^{3b}$ are each independently selected from the group consisting of hydrogen and $C_{1-4}$ alkyl;

$R^4$ is selected from the group consisting of aralkyl and optionally substituted $C_{3-7}$ cycloalkyl;

$R^5$ is selected from the group consisting of hydrogen, halogen, $C_{1-4}$ alkyl, optionally substituted $C_{2-4}$ alkynyl, and substituted 5- to 14-membered heteroaryl; and Y is —O—.

2. The compound of claim 1 having Formula V:

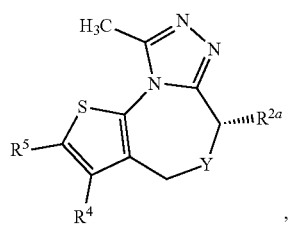

or a pharmaceutically acceptable salt or hydrate thereof.

3. The compound of claim 2, wherein:

$R^{21}$ is $C_{1-4}$ alkyl;

$R^4$ is selected from the group consisting of aralkyl and optionally substituted $C_{3-7}$ cycloalkyl; and $R^5$ is selected from the group consisting of hydrogen, halogen, $C_{1-4}$ alkyl, optionally substituted $C_{2-4}$ alkynyl, and substituted 5- to 14-membered heteroaryl, or a pharmaceutically acceptable salt or hydrate thereof.

4. The compound of claim 1, wherein $R^4$ is aralkyl, or a pharmaceutically acceptable salt or hydrate thereof.

5. The compound of claim 1 having Formula VIII:

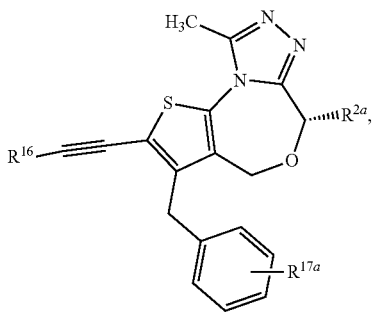

or a pharmaceutically acceptable salt or hydrate thereof, wherein:
  $R^{2a}$ is selected from the group consisting of hydrogen and $C_{1-3}$ alkyl;
  $R^{16}$ is selected from the group consisting of hydroxyalkyl, optionally substituted aryl, and optionally substituted heteroaryl; and
  $R^{17a}$ is selected from the group consisting of hydrogen and halo.

6. The compound of claim 5, or a pharmaceutically acceptable salt or hydrate thereof, wherein $R^{16}$ is optionally substituted heteroaryl.

7. A compound having Formula XI:

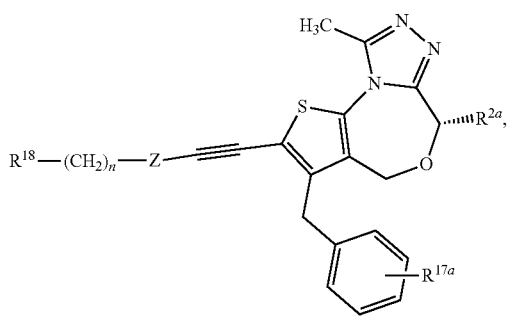

or pharmaceutically acceptable salts or hydrates thereof, wherein:
  $R^{2a}$ is selected from the group consisting of hydrogen and $C_{1-3}$ alkyl;
  Z is heteroarylenyl;
  $R^{17a}$ is selected from the group consisting of hydrogen and halo;
  $R^{18}$ is selected from the group consisting of —CHO, —CO$_2$H, —OH, and halo; and
  n is 0, 1, 2, 3, 4, 5, or 6.

8. A compound, or a pharmaceutically acceptable salt or hydrate thereof, selected from the group consisting of:
  2,9-dimethyl-4H,6H-thieno[2,3-e][1,2,4]triazolo[3,4-c][1,4]oxazepine;
  3-bromo-2,9-dimethyl-4H,6H-thieno[2,3-e][1,2,4]triazolo[3,4-c][1,4]oxazepine;
  2,9-dimethyl-3-phenyl-4H,6H-thieno[2,3-e][1,2,4]triazolo[3,4-c][1,4]oxazepine;
  3-benzyl-2,9-dimethyl-4H,6H-thieno[2,3-e][1,2,4]triazolo[3,4-c][1,4]oxazepine;
  2,9-dimethyl-3-(quinolin-4-yl)-4H,6H-thieno[2,3-e][1,2,4]triazolo[3,4-c][1,4]oxazepine;
  2,9-dimethyl-N-phenyl-4H,6H-thieno[2,3-e][1,2,4]triazolo[3,4-c][1,4]oxazepin-3-amine;
  N-(3-cyclopropyl-1-methyl-1H-pyrazol-5-yl)-2,9-dimethyl-4H,6H-thieno[2,3-e][1,2,4]triazolo[3,4-c][1,4]oxazepin-3-amine;
  3-(3-chlorobenzyl)-2,9-dimethyl-4H,6H-thieno[2,3-e][1,2,4]triazolo[3,4-c][1,4]oxazepine;
  3-(4-chlorobenzyl)-2,9-dimethyl-4H,6H-thieno[2,3-e][1,2,4]triazolo[3,4-c][1,4]oxazepine;
  3-(2-chlorobenzyl)-2,9-dimethyl-4H,6H-thieno[2,3-e][1,2,4]triazolo[3,4-c][1,4]oxazepine;
  benzyl (S)-3-bromo-2,6,9-trimethyl-4H-thieno[3,2-f][1,2,4]triazolo[4,3-a][1,4]diazepine-5(6H)-carboxylate;
  benzyl (S)-3-benzyl-2,6,9-trimethyl-4H-thieno[3,2-f][1,2,4]triazolo[4,3-a][1,4]diazepine-5(6H)-carboxylate;
  (S)-3-benzyl-2,6,9-trimethyl-5,6-dihydro-4H-thieno[3,2-f][1,2,4]triazolo[4,3-a][1,4]diazepine;
  benzyl 3-benzyl-2,9-dimethyl-4H-thieno[3,2-f][1,2,4]triazolo[4,3-a][1,4]diazepine-5(6H)-carboxylate;
  3-benzyl-2,9-dimethyl-5,6-dihydro-4H-thieno[3,2-f][1,2,4]triazolo[4,3-a][1,4]diazepine;
  benzyl (R)-3-benzyl-2,6,9-trimethyl-4H-thieno[3,2-f][1,2,4]triazolo[4,3-a][1,4]diazepine-5(6H)-carboxylate;
  (R)-3-benzyl-2,6,9-trimethyl-5,6-dihydro-4H-thieno[3,2-f][1,2,4]triazolo[4,3-a][1,4]diazepine;
  ethyl (S)-3-benzyl-2,6,9-trimethyl-4H-thieno[3,2-f][1,2,4]triazolo[4,3-a][1,4]diazepine-5(6H)-carboxylate;
  (S)-1-(3-benzyl-2,6,9-trimethyl-4H-thieno[3,2-f][1,2,4]triazolo[4,3-a][1,4]diazepin-5(6H)-yl)propan-1-one;
  (S)-3-benzyl-2,5,6,9-tetramethyl-5,6-dihydro-4H-thieno[3,2-f][1,2,4]triazolo[4,3-a][1,4]diazepine;
  benzyl (S)-3-benzyl-6-(2-methoxy-2-oxoethyl)-2,9-dimethyl-4H-thieno[3,2-f][1,2,4]triazolo[4,3-a][1,4]diazepine-5(6H)-carboxylate;
  (S)-3-benzyl-N-ethyl-2,6,9-trimethyl-4H-thieno[3,2-f][1,2,4]triazolo[4,3-a][1,4]diazepine-5(6H)-carboxamide;
  methyl (S)-2-(3-benzyl-2,9-dimethyl-5,6-dihydro-4H-thieno[3,2-f][1,2,4]triazolo[4,3-a][1,4]diazepin-6-yl)acetate;
  2,9-dimethyl-3-(1-phenylvinyl)-4H,6H-thieno[2,3-e][1,2,4]triazolo[3,4-c][1,4]oxazepine;
  ethyl (S)-2-(3-benzyl-2,6,9-trimethyl-4H-thieno[3,2-f][1,2,4]triazolo[4,3-a][1,4]diazepin-5(6H)-yl)acetate;
  (S)-3-benzyl-2,6,9-trimethyl-5-(phenethylsulfonyl)-5,6-dihydro-4H-thieno[3,2-f][1,2,4]triazolo[4,3-a][1,4]diazepine;
  (S)-3-benzyl-5-(cyclopropylmethyl)-2,6,9-trimethyl-5,6-dihydro-4H-thieno[3,2-f][1,2,4]triazolo[4,3-a][1,4]diazepine;
  2,9-dimethyl-3-(1-phenylethyl)-4H,6H-thieno[2,3-e][1,2,4]triazolo[3,4-c][1,4]oxazepine;
  (S)-3-benzyl-5-cyclobutyl-2,6,9-trimethyl-5,6-dihydro-4H-thieno[3,2-f][1,2,4]triazolo[4,3-a][1,4]diazepine;
  3-benzyl-9-methyl-4H,6H-thieno[2,3-e][1,2,4]triazolo[3,4-c][1,4]oxazepine;
  3-benzyl-2-bromo-9-methyl-4H,6H-thieno[2,3-e][1,2,4]triazolo[3,4-c][1,4]oxazepine;
  5-(3-benzyl-9-methyl-4H,6H-thieno[2,3-e][1,2,4]triazolo[3,4-c][1,4]oxazepin-2-yl)pyridin-2-amine;
  3-benzyl-2-ethynyl-9-methyl-4H,6H-thieno[2,3-e][1,2,4]triazolo[3,4-c][1,4]oxazepine;
  (R)-3-benzyl-2,5,6,9-tetramethyl-5,6-dihydro-4H-thieno[3,2-f][1,2,4]triazolo[4,3-a][1,4]diazepine;
  3-benzyl-2,5,9-trimethyl-5,6-dihydro-4H-thieno[3,2-f][1,2,4]triazolo[4,3-a][1,4]diazepine;

7-bromo-1-methyl-4H,6H-benzo[e][1,2,4]triazolo[3,4-c][1,4]oxazepine;
1-methyl-N-phenyl-4H,6H-benzo[e][1,2,4]triazolo[3,4-c][1,4]oxazepin-7-amine;
7-benzyl-1-methyl-4H,6H-benzo[e][1,2,4]triazolo[3,4-c][1,4]oxazepine;
1-methyl-7-(phenylthio)-4H,6H-benzo[e][1,2,4]triazolo[3,4-c][1,4]oxazepine;
1-methyl-7-phenoxy-4H,6H-benzo[e][1,2,4]triazolo[3,4-c][1,4]oxazepine;
7-((λ1-oxidanyl)(phenyl)-λ3-sulfanyl)-1-methyl-4H,6H-benzo[e][1,2,4]triazolo[3,4-c][1,4]oxazepine;
1-methyl-7-(phenylsulfonyl)-4H,6H-benzo[e][1,2,4]triazolo[3,4-c][1,4]oxazepine;
1-methyl-7-(1-phenylvinyl)-4H,6H-benzo[e][1,2,4]triazolo[3,4-c][1,4]oxazepine;
7-(1H-inden-3-yl)-1-methyl-4H,6H-benzo[e][1,2,4]triazolo[3,4-c][1,4]oxazepine;
1-methyl-7-(4-(trifluoromethoxy)benzyl)-4H,6H-benzo[e][1,2,4]triazolo[3,4-c][1,4]oxazepine;
1-methyl-7-(1-phenylethyl)-4H,6H-benzo[e][1,2,4]triazolo[3,4-c][1,4]oxazepine;
7-(2,3-dihydro-1H-inden-1-yl)-1-methyl-4H,6H-benzo[e][1,2,4]triazolo[3,4-c][1,4]oxazepine;
1-methyl-7-(1-phenylcyclopropyl)-4H,6H-benzo[e][1,2,4]triazolo[3,4-c][1,4]oxazepine;
7-(3,4-dihydronaphthalen-1-yl)-1-methyl-4H,6H-benzo[e][1,2,4]triazolo[3,4-c][1,4]oxazepine;
1-methyl-7-(1,2,3,4-tetrahydronaphthalen-1-yl)-4H,6H-benzo[e][1,2,4]triazolo[3,4-c][1,4]oxazepine;
3-(3,4-dihydronaphthalen-1-yl)-2,9-dimethyl-4H,6H-thieno[2,3-e][1,2,4]triazolo[3,4-c][1,4]oxazepine;
(1-methyl-4H,6H-benzo[e][1,2,4]triazolo[3,4-c][1,4]oxazepin-7-yl)(phenyl)methanone;
3-(1H-inden-3-yl)-2,9-dimethyl-4H,6H-thieno[2,3-e][1,2,4]triazolo[3,4-c][1,4]oxazepine;
2,9-dimethyl-3-(1,2,3,4-tetrahydronaphthalen-1-yl)-4H,6H-thieno[2,3-e][1,2,4]triazolo[3,4-c][1,4]oxazepine;
3-(2,3-dihydro-1H-inden-1-yl)-2,9-dimethyl-4H,6H-thieno[2,3-e][1,2,4]triazolo[3,4-c][1,4]oxazepine;
3-(6,7-dihydro-5H-benzo[7]annulen-9-yl)-2,9-dimethyl-4H,6H-thieno[2,3-e][1,2,4]triazolo[3,4-c][1,4]oxazepine;
3-(6-fluoro-3,4-dihydronaphthalen-1-yl)-2,9-dimethyl-4H,6H-thieno[2,3-e][1,2,4]triazolo[3,4-c][1,4]oxazepine;
3-(7-fluoro-3,4-dihydronaphthalen-1-yl)-2,9-dimethyl-4H,6H-thieno[2,3-e][1,2,4]triazolo[3,4-c][1,4]oxazepine;
7-(6,7-dihydro-5H-benzo[7]annulen-9-yl)-1-methyl-4H,6H-benzo[e][1,2,4]triazolo[3,4-c][1,4]oxazepine;
1-methyl-7-(6,7,8,9-tetrahydro-5H-benzo[7]annulen-5-yl)-4H,6H-benzo[e][1,2,4]triazolo[3,4-c][1,4]oxazepine;
7-(6-fluoro-1,2,3,4-tetrahydronaphthalen-1-yl)-1-methyl-4H,6H-benzo[e][1,2,4]triazolo[3,4-c][1,4]oxazepine;
7-(7-fluoro-1,2,3,4-tetrahydronaphthalen-1-yl)-1-methyl-4H,6H-benzo[e][1,2,4]triazolo[3,4-c][1,4]oxazepine;
2,9-dimethyl-3-(6,7,8,9-tetrahydro-5H-benzo[7]annulen-5-yl)-4H,6H-thieno[2,3-e][1,2,4]triazolo[3,4-c][1,4]oxazepine;
3-(6-fluoro-1,2,3,4-tetrahydronaphthalen-1-yl)-2,9-dimethyl-4H,6H-thieno[2,3-e][1,2,4]triazolo[3,4-c][1,4]oxazepine;
3-(7-fluoro-1,2,3,4-tetrahydronaphthalen-1-yl)-2,9-dimethyl-4H,6H-thieno[2,3-e][1,2,4]triazolo[3,4-c][1,4]oxazepine;
2',9'-dimethyl-3'-(1,2,3,4-tetrahydronaphthalen-1-yl)-4'H-spiro[cyclopropane-1,6'-thieno[2,3-e][1,2,4]triazolo[3,4-c][1,4]oxazepine;
8-chloro-1-methyl-7-(1,2,3,4-tetrahydronaphthalen-1-yl)-4H,6H-benzo[e][1,2,4]triazolo[3,4-c][1,4]oxazepine;
1-methyl-8-(1-methyl-1H-pyrazol-4-yl)-7-(1,2,3,4-tetrahydronaphthalen-1-yl)-4H,6H-benzo[e][1,2,4]triazolo[3,4-c][1,4]oxazepine;
5-(1-methyl-7-(1,2,3,4-tetrahydronaphthalen-1-yl)-4H,6H-benzo[e][1,2,4]triazolo[3,4-c][1,4]oxazepin-8-yl)pyridin-2-amine;
7-bromo-8-chloro-1-methyl-4H,6H-benzo[e][1,2,4]triazolo[3,4-c][1,4]oxazepine;
7-benzyl-8-chloro-1-methyl-4H,6H-benzo[e][1,2,4]triazolo[3,4-c][1,4]oxazepine;
5-(7-benzyl-1-methyl-4H,6H-benzo[e][1,2,4]triazolo[3,4-c][1,4]oxazepin-8-yl)pyridin-2-amine;
7-benzyl-1-methyl-8-(1-methyl-1H-pyrazol-4-yl)-4H,6H-benzo[e][1,2,4]triazolo[3,4-c][1,4]oxazepine;
8-chloro-7-(3,4-dihydronaphthalen-1-yl)-1-methyl-4H,6H-benzo[e][1,2,4]triazolo[3,4-c][1,4]oxazepine;
7-benzyl-1-methyl-8-(1H-pyrazol-4-yl)-4H,6H-benzo[e][1,2,4]triazolo[3,4-c][1,4]oxazepine;
2-(4-(7-benzyl-1-methyl-4H,6H-benzo[e][1,2,4]triazolo[3,4-c][1,4]oxazepin-8-yl)-1H-pyrazol-1-yl)acetamide;
7-benzyl-8-(3,6-dihydro-2H-pyran-4-yl)-1-methyl-4H,6H-benzo[e][1,2,4]triazolo[3,4-c][1,4]oxazepine;
7-benzyl-8-(4,5-dihydrofuran-3-yl)-1-methyl-4H,6H-benzo[e][1,2,4]triazolo[3,4-c][1,4]oxazepine;
7-benzyl-1-methyl-8-(tetrahydro-2H-pyran-4-yl)-4H,6H-benzo[e][1,2,4]triazolo[3,4-c][1,4]oxazepine;
7-benzyl-8-(furan-3-yl)-1-methyl-4H,6H-benzo[e][1,2,4]triazolo[3,4-c][1,4]oxazepine;
7-benzyl-1-methyl-8-(tetrahydrofuran-3-yl)-4H,6H-benzo[e][1,2,4]triazolo[3,4-c][1,4]oxazepine;
7-benzyl-1-methyl-8-((trimethylsilyl)ethynyl)-4H,6H-benzo[e][1,2,4]triazolo[3,4-c][1,4]oxazepine;
7-benzyl-8-ethynyl-1-methyl-4H,6H-benzo[e][1,2,4]triazolo[3,4-c][1,4]oxazepine;
4-(7-benzyl-1-methyl-4H,6H-benzo[e][1,2,4]triazolo[3,4-c][1,4]oxazepin-8-yl)but-3-yn-1-ol;
(S)-3-benzyl-6,9-dimethyl-2-((1-methyl-1H-pyrazol-4-yl)ethynyl)-4H,6H-thieno[2,3-e][1,2,4]triazolo[3,4-c][1,4]oxazepine;
3-benzyl-9-methyl-2-((1-methyl-1H-imidazol-5-yl)ethynyl)-4H,6H-thieno[2,3-e][1,2,4]triazolo[3,4-c][1,4]oxazepine;
3-benzyl-9-methyl-2-(pyridin-4-ylethynyl)-4H,6H-thieno[2,3-e][1,2,4]triazolo[3,4-c][1,4]oxazepine;
3-benzyl-9-methyl-2-(pyridin-3-ylethynyl)-4H,6H-thieno[2,3-e][1,2,4]triazolo[3,4-c][1,4]oxazepine;
5-((3-benzyl-9-methyl-4H,6H-thieno[2,3-e][1,2,4]triazolo[3,4-c][1,4]oxazepin-2-yl)ethynyl)pyridin-2-amine;
3-benzyl-9-methyl-2-(morpholinomethyl)-4H,6H-thieno[2,3-e][1,2,4]triazolo[3,4-c][1,4]oxazepine;
3-benzyl-9-methyl-2-(1H-pyrazol-4-yl)-4H,6H-thieno[2,3-e][1,2,4]triazolo[3,4-c][1,4]oxazepine;
3-benzyl-9-methyl-2-(1-methyl-1H-pyrazol-4-yl)-4H,6H-thieno[2,3-e][1,2,4]triazolo[3,4-c][1,4]oxazepine;
3-benzyl-2-cyclopropyl-9-methyl-4H,6H-thieno[2,3-e][1,2,4]triazolo[3,4-c][1,4]oxazepine;
3-benzyl-9-methyl-2-(prop-1-en-2-yl)-4H,6H-thieno[2,3-e][1,2,4]triazolo[3,4-c][1,4]oxazepine;
3-benzyl-2-(3,6-dihydro-2H-pyran-4-yl)-9-methyl-4H,6H-thieno[2,3-e][1,2,4]triazolo[3,4-c][1,4]oxazepine;

4-(3-benzyl-9-methyl-4H,6H-thieno[2,3-e][1,2,4]triazolo[3,4-c][1,4]oxazepin-2-yl)but-3-yn-1-ol;
3-benzyl-9-methyl-2-(tetrahydro-2H-pyran-4-yl)-4H,6H-thieno[2,3-e][1,2,4]triazolo[3,4-c][1,4]oxazepine;
3-benzyl-2-isopropyl-9-methyl-4H,6H-thieno[2,3-e][1,2,4]triazolo[3,4-c][1,4]oxazepine;
4-(3-benzyl-9-methyl-4H,6H-thieno[2,3-e][1,2,4]triazolo[3,4-c][1,4]oxazepin-2-yl)butan-1-ol;
3-(3-fluorobenzyl)-2,9-dimethyl-4H,6H-thieno[2,3-e][1,2,4]triazolo[3,4-c][1,4]oxazepine;
3-((2,9-dimethyl-4H,6H-thieno[2,3-e][1,2,4]triazolo[3,4-c][1,4]oxazepin-3-yl)methyl)benzonitrile;
3-(2-fluorobenzyl)-2,9-dimethyl-4H,6H-thieno[2,3-e][1,2,4]triazolo[3,4-c][1,4]oxazepine;
3-(4-fluorobenzyl)-2,9-dimethyl-4H,6H-thieno[2,3-e][1,2,4]triazolo[3,4-c][1,4]oxazepine;
3-(3,5-difluorobenzyl)-2,9-dimethyl-4H,6H-thieno[2,3-e][1,2,4]triazolo[3,4-c][1,4]oxazepine;
3-(3,4-difluorobenzyl)-2,9-dimethyl-4H,6H-thieno[2,3-e][1,2,4]triazolo[3,4-c][1,4]oxazepine;
3-((1H-indol-1-yl)methyl)-2,9-dimethyl-4H,6H-thieno[2,3-e][1,2,4]triazolo[3,4-c][1,4]oxazepine;
3-((1H-pyrrol-1-yl)methyl)-2,9-dimethyl-4H,6H-thieno[2,3-e][1,2,4]triazolo[3,4-c][1,4]oxazepine;
3-(tert-butoxymethyl)-2,9-dimethyl-4H,6H-thieno[2,3-e][1,2,4]triazolo[3,4-c][1,4]oxazepine;
3-benzyl-2,6,9-trimethyl-4H,6H-thieno[2,3-e][1,2,4]triazolo[3,4-c][1,4]oxazepine;
3-benzyl-9-methyl-4H,6H-thieno[2,3-e][1,2,4]triazolo[3,4-c][1,4]oxazepine-2-carbonitrile;
3-(4-fluorobenzyl)-9-methyl-2-((1-methyl-1H-pyrazol-4-yl)ethynyl)-4H,6H-thieno[2,3-e][1,2,4]triazolo[3,4-c][1,4]oxazepine;
3-((1H-pyrazol-1-yl)methyl)-2,9-dimethyl-4H,6H-thieno[2,3-e][1,2,4]triazolo[3,4-c][1,4]oxazepine;
(S)-4-(3-benzyl-6,9-dimethyl-4H,6H-thieno[2,3-e][1,2,4]triazolo[3,4-c][1,4]oxazepin-2-yl)but-3-yn-1-ol;
(R)-3-benzyl-2,6,9-trimethyl-4H,6H-thieno[2,3-e][1,2,4]triazolo[3,4-c][1,4]oxazepine;
tert-butyl 2-(3-benzyl-2,9-dimethyl-4H,6H-thieno[2,3-e][1,2,4]triazolo[3,4-c][1,4]oxazepin-6-yl)acetate;
1-(1-methyl-4H,6H-benzo[e][1,2,4]triazolo[3,4-c][1,4]oxazepin-7-yl)-1-phenylethane-1,2-diol;
(S)-3-bromo-6,9-dimethyl-4H,6H-thieno[2,3-e][1,2,4]triazolo[3,4-c][1,4]oxazepine;
(S)-3-benzyl-6,9-dimethyl-4H,6H-thieno[2,3-e][1,2,4]triazolo[3,4-c][1,4]oxazepine;
(S)-3-benzyl-2-bromo-6,9-dimethyl-4H,6H-thieno[2,3-e][1,2,4]triazolo[3,4-c][1,4]oxazepine;
(S)-3-benzyl-6,9-dimethyl-2-((1-methyl-1H-imidazol-5-yl)ethynyl)-4H,6H-thieno[2,3-e][1,2,4]triazolo[3,4-c][1,4]oxazepine;
(S)-3-benzyl-6,9-dimethyl-2-(pyridin-4-ylethynyl)-4H,6H-thieno[2,3-e][1,2,4]triazolo[3,4-c][1,4]oxazepine;
(S)-3-benzyl-6,9-dimethyl-2-(pyridin-3-ylethynyl)-4H,6H-thieno[2,3-e][1,2,4]triazolo[3,4-c][1,4]oxazepine;
(S)-5-((3-benzyl-6,9-dimethyl-4H,6H-thieno[2,3-e][1,2,4]triazolo[3,4-c][1,4]oxazepin-2-yl)ethynyl)pyridin-2-amine;
(S)-3-(4-fluorobenzyl)-6,9-dimethyl-4H,6H-thieno[2,3-e][1,2,4]triazolo[3,4-c][1,4]oxazepine;
(S)-2-bromo-3-(4-fluorobenzyl)-6,9-dimethyl-4H,6H-thieno[2,3-e][1,2,4]triazolo[3,4-c][1,4]oxazepine;
(S)-3-(4-fluorobenzyl)-6,9-dimethyl-2-((1-methyl-1H-pyrazol-4-yl)ethynyl)-4H,6H-thieno[2,3-e][1,2,4]triazolo[3,4-c][1,4]oxazepine;
2,9-dimethyl-3-((1-methyl-1H-pyrazol-4-yl)methyl)-4H,6H-thieno[2,3-e][1,2,4]triazolo[3,4-c][1,4]oxazepine;
2,3,9-trimethyl-4H,6H-thieno[2,3-e][1,2,4]triazolo[3,4-c][1,4]oxazepine;
2,6,9-trimethyl-4H,6H-thieno[2,3-e][1,2,4]triazolo[3,4-c][1,4]oxazepine;
3-bromo-2,6,9-trimethyl-4H,6H-thieno[2,3-e][1,2,4]triazolo[3,4-c][1,4]oxazepine;
tert-butyl 2-(2,9-dimethyl-4H,6H-thieno[2,3-e][1,2,4]triazolo[3,4-c][1,4]oxazepin-6-yl)acetate;
tert-butyl 2-(3-bromo-2,9-dimethyl-4H,6H-thieno[2,3-e][1,2,4]triazolo[3,4-c][1,4]oxazepin-6-yl)acetate;
2'-bromo-9'-methyl-4'H-spiro[cyclopropane-1,6'-thieno[2,3-e][1,2,4]triazolo[3,4-c][1,4]oxazepine];
2',9'-dimethyl-4'H-spiro[cyclopropane-1,6'-thieno[2,3-e][1,2,4]triazolo[3,4-c][1,4]oxazepine];
3'-bromo-2',9'-dimethyl-4'H-spiro[cyclopropane-1,6'-thieno[2,3-e][1,2,4]triazolo[3,4-c][1,4]oxazepine];
3'-benzyl-2',9'-dimethyl-4'H-spiro[cyclopropane-1,6'-thieno[2,3-e][1,2,4]triazolo[3,4-c][1,4]oxazepine];
3-bromo-9-methyl-4H,6H-thieno[2,3-e][1,2,4]triazolo[3,4-c][1,4]oxazepine;
3-chloro-9-methyl-4H,6H-thieno[2,3-e][1,2,4]triazolo[3,4-c][1,4]oxazepine;
3-(4-fluorobenzyl)-9-methyl-4H,6H-thieno[2,3-e][1,2,4]triazolo[3,4-c][1,4]oxazepine;
2-bromo-3-(4-fluorobenzyl)-9-methyl-4H,6H-thieno[2,3-e][1,2,4]triazolo[3,4-c][1,4]oxazepine;
(S)-3-chloro-6,9-dimethyl-4H,6H-thieno[2,3-e][1,2,4]triazolo[3,4-c][1,4]oxazepine;
(S)-3-(3-benzyl-6,9-dimethyl-4H,6H-thieno[2,3-e][1,2,4]triazolo[3,4-c][1,4]oxazepin-2-yl)-N,N-dimethylprop-2-yn-1-amine;
(S)-3-benzyl-2-(3-methoxyprop-1-yn-1-yl)-6,9-dimethyl-4H,6H-thieno[2,3-e][1,2,4]triazolo[3,4-c][1,4]oxazepine;
benzyl 3-bromo-2,9-dimethyl-4H,6H-thieno[3,2-f][1,2,4]triazolo[4,3-a][1,4]diazepine-5(6H)-carboxylate;
benzyl (S)-3-bromo-6-(2-methoxy-2-oxoethyl)-2,9-dimethyl-4H-thieno[3,2-f][1,2,4]triazolo[4,3-a][1,4]diazepine-5(6H)-carboxylate;
3-benzyl-9-methyl-2-(pyridin-2-ylethynyl)-4H,6H-thieno[2,3-e][1,2,4]triazolo[3,4-c][1,4]oxazepine;
(S)-3-benzyl-6,9-dimethyl-2-(pyridin-2-ylethynyl)-4H,6H-thieno[2,3-e][1,2,4]triazolo[3,4-c][1,4]oxazepine;
4-(5-((3-benzyl-9-methyl-4H,6H-thieno[2,3-e][1,2,4]triazolo[3,4-c][1,4]oxazepin-2-yl)ethynyl)pyridin-2-yl)butanal;
3-benzyl-9-methyl-2-((1-methyl-1H-pyrazol-4-yl)ethynyl)-4H,6H-thieno[2,3-e][1,2,4]triazolo[3,4-c][1,4]oxazepine;
2-((1H-pyrazol-4-yl)ethynyl)-3-benzyl-9-methyl-4H,6H-thieno[2,3-e][1,2,4]triazolo[3,4-c][1,4]oxazepine; and
(S)-3-benzyl-2,6,9-trimethyl-4H,6H-thieno[2,3-e][1,2,4]triazolo[3,4-c][1,4]oxazepine.

9. A pharmaceutical composition comprising the compound of claim 1, or a pharmaceutically acceptable salt or hydrate thereof, and a pharmaceutically acceptable carrier.

10. A method of treating a patient, the method comprising administering to the patient a therapeutically effective amount of the compound of claim 1, or a pharmaceutically acceptable salt or hydrate thereof, wherein the patient has breast cancer.

11. The method of claim 10 further comprising administering a therapeutically effective amount of a second therapeutic agent useful in the treatment of breast cancer.

12. A kit comprising the compound of claim 1, or a pharmaceutically acceptable salt or hydrate thereof, and instructions for administering the compound, or a pharmaceutically acceptable salt, hydrate, or solvate thereof, to a patient having cancer, a chronic autoimmune disorder, an inflammatory condition, a proliferative disorder, sepsis, or a viral infection.

13. The kit of claim 12, wherein the patient has cancer.

14. The kit of claim 12 further comprising one or more additional therapeutic agents.

15. The compound of claim 1, wherein $R^{2a}$ and $R^{2b}$ are each independently selected from the group consisting of hydrogen and $C_{1-4}$ alkyl, and $R^{3a}$ and $R^{3b}$ are hydrogen, or a pharmaceutically acceptable salt or hydrate thereof.

16. The compound of claim 1, wherein $R^4$ is optionally substituted $C_{3-7}$ cycloalkyl selected from the group consisting of:

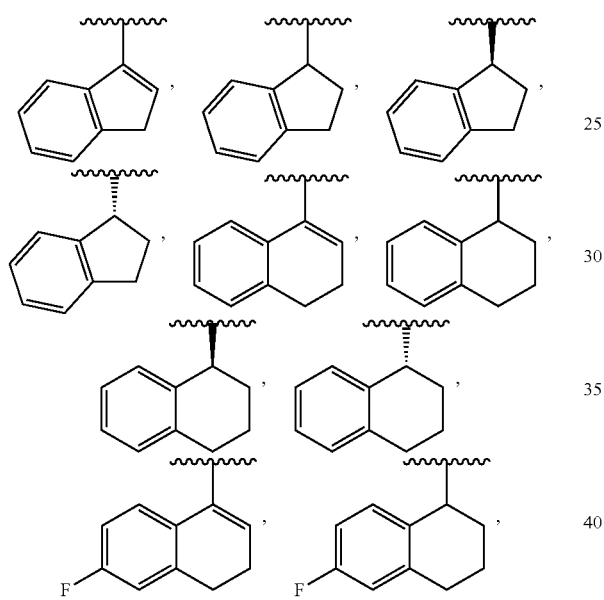

or a pharmaceutically acceptable salt or hydrate thereof.

* * * * *